(12) United States Patent
Klein et al.

(10) Patent No.: US 11,702,701 B2
(45) Date of Patent: Jul. 18, 2023

(54) MEANS AND METHODS FOR STAGING, TYPING AND TREATING A CANCEROUS DISEASE

(71) Applicants: Fraunhofer-Gesellschaft zur Förderung der angewandten Forschung e.V., Munich (DE); Universität Regensburg, Regensburg (DE)

(72) Inventors: Christoph Klein, Regensburg (DE); Sebastian Scheitler, Regensburg (DE); Melanie Werner-Klein, Regensburg (DE); Martin Hoffmann, Regensburg (DE); Isabelle Hodak, Munich (DE)

(73) Assignees: FRAUNHOFER-GESELLSCHAFT ZUR FÖRDERUNG DER ANGEWANDTEN FORSCHUNG E.V., Munich (DE); UNIVERSITÄT REGENSBURG, Regensburg (DE)

(*) Notice: Subject to any disclaimer, the term of this patent is extended or adjusted under 35 U.S.C. 154(b) by 206 days.

(21) Appl. No.: 16/073,271

(22) PCT Filed: Jan. 27, 2017

(86) PCT No.: PCT/EP2017/051789
§ 371 (c)(1),
(2) Date: Jul. 26, 2018

(87) PCT Pub. No.: WO2017/129753
PCT Pub. Date: Aug. 3, 2017

(65) Prior Publication Data
US 2019/0062845 A1 Feb. 28, 2019

(30) Foreign Application Priority Data
Jan. 27, 2016 (EP) ..................... 16152883

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/118* (2013.01); *C12Q 2600/156* (2013.01)

(58) Field of Classification Search
CPC .. C12Q 1/6806; C12Q 1/6827; C12Q 1/6881; C12Q 1/6883; C12Q 1/6886;
(Continued)

(56) References Cited

U.S. PATENT DOCUMENTS

2013/0149704 A1    6/2013   Jewell et al.

FOREIGN PATENT DOCUMENTS

EP          2503009         9/2012
WO       WO 0237113         5/2002
(Continued)

OTHER PUBLICATIONS

Picard, M. et al. British Journal of Dermatology 171:108 (Jul. 2014). (Year: 2014).*
(Continued)

*Primary Examiner* — Diana B Johannsen
(74) *Attorney, Agent, or Firm* — Parker Highlander PLLC

(57) ABSTRACT

The present invention relates to methods for diagnosing, staging and treating cancer, in particular melanoma. In particular, the present invention provides methods for determining the stage/type of a cancerous disease, comprising detecting somatic alterations of the DNA of one or more disseminated cancer cells (DCCs), obtained after homing to a distant organ, such as lymph node; and determining the somatic evolution of the DCC(s) based on the detected
(Continued)

Figure 1:
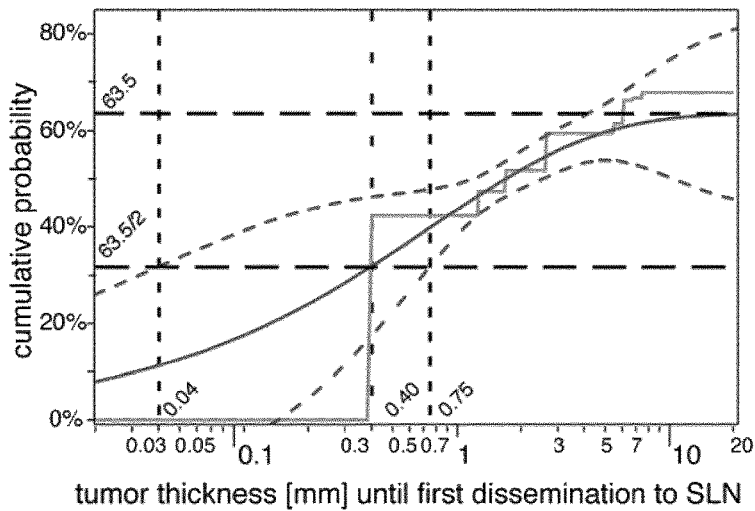
Figure 1:
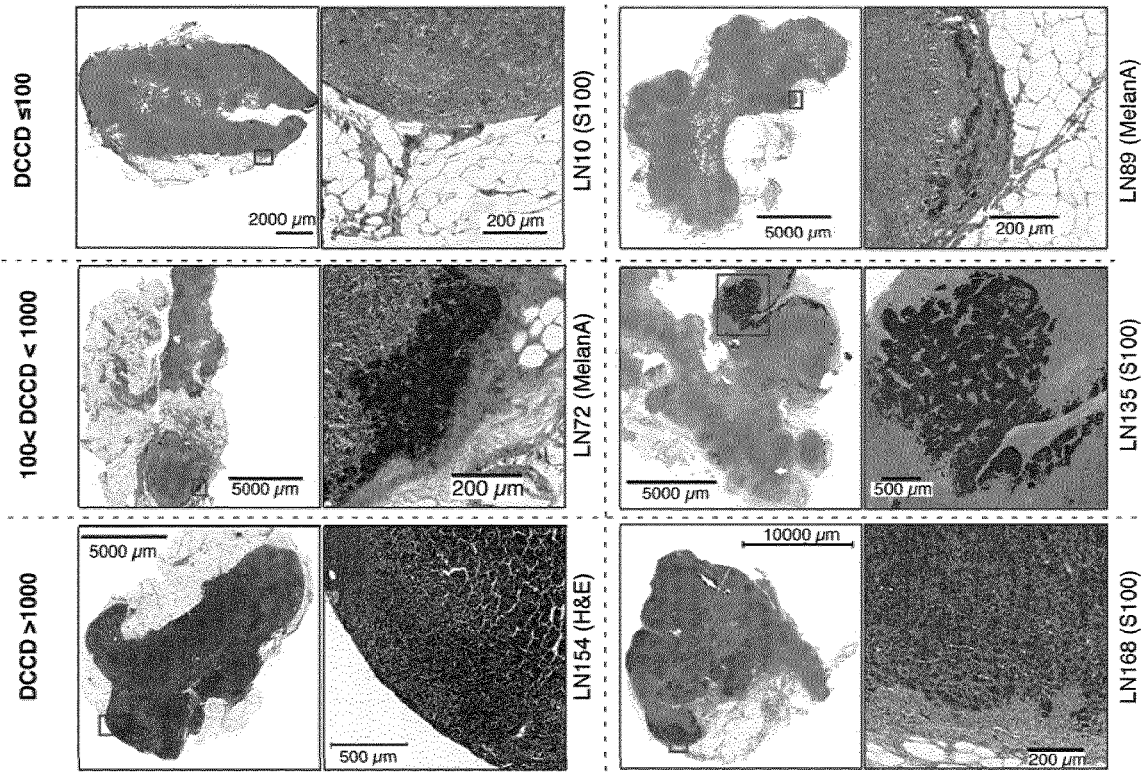
Figure 1:
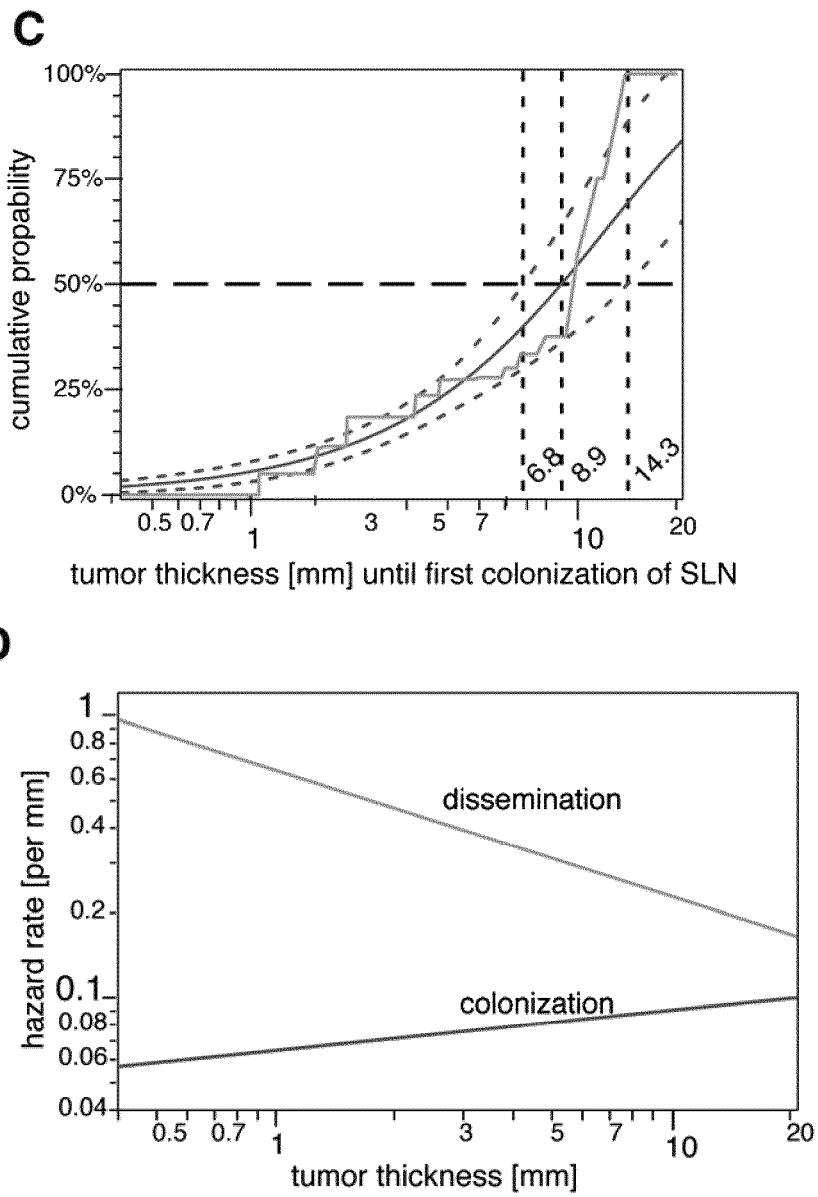
Figure 1:
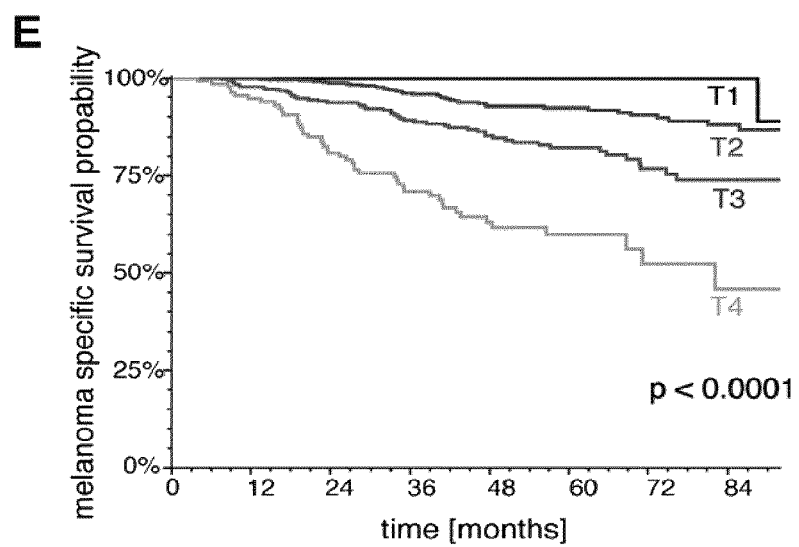

somatic alterations, wherein the somatic evolution is indicative of the stage/type of the cancerous disease.

12 Claims, 50 Drawing Sheets

Specification includes a Sequence Listing.

(58) Field of Classification Search
CPC .......... C12Q 2600/16; C12Q 2600/106; C12Q 2600/112; C12Q 2600/118; C12Q 2600/136; C12Q 2600/156; C12Q 2600/158; C12Q 2600/178
See application file for complete search history.

(56) References Cited

FOREIGN PATENT DOCUMENTS

| WO | WO 2013/009632 | 1/2013 |
|---|---|---|
| WO | WO 2015/023553 | 2/2015 |

OTHER PUBLICATIONS

Harbst, K. et al. Journal of Pathology 233:39 (Jan. 2014). (Year: 2014).*

Crespi B., et al., "Evolutionary Biology of Cancer", *Trends in Ecology and Evolution*, vol. 20, No. 10, pp. 545-552, Oct. 2005.

European Application No. 16152883.1, European Search Report and Search Opinion, pp. 1-10, dated Jul. 15, 2016.

International Application No. PCT/EP2017/051789 International Search Report and Written Opinion, pp. 1-18, dated Apr. 7, 2017.

International Application No. PCT/EP2017/051789 International Preliminary Report on Patentability, pp. 1-11, dated Aug. 9, 2018.

Nguyen, D.X., et al., "Metastasis : From Dissemination to Organ-Specific Colonization", *Nature*, Reviews/Cancer, vol. 9, pp. 274-285, Apr. 2009.

Rinner, B., et al., "Molecular Evidence for the Bi-Clonal Origin of Neuroendocrine Tumor Derived Metastases", *BMC Genomics*, pp. 1-9, Nov. 5, 2012.

Trinh, V.A., et al., "Chemoprevention for Brain Metastases", *Curr Oncol. Rep, Neuro-Oncology*, pp. 63-69, Oct. 18, 2011.

Ulmer, A., et al., "Quantitative Measurement of Melanoma Spread in Sentinel Lymph Nodes and Survival", *PLOS Medicine*, vol. 11, No. 2, pp. 1-17, Feb. 2014.

Office Action issued in European Application No. 16152883.1, dated Mar. 20, 2019.

Sanborn et al., "Phylogenetic analyses of melanoma reveal complex patterns of metastatic dissemination," *PNAS*, 112(35):10995-11000, 2015.

Leong and Tseng, "Micrometastatic Cancer Cells in Lymph Nodes, Bone Marrow, and Blood", *CA Cancer J. Clin.*, 2014; 64:195-206.

Search Report for Singapore Application No. 11201805990X dated Nov. 23, 2022, 6 pages.

* cited by examiner

A

B

C

Figure 5 cont.

D

| Ki-67 staining pattern | Group A (DCCD≤100) n cells | Group B (DCCD>100) n cells |
|---|---|---|
| Mitosis | 3 (1.4%) | 46 (6.3%) |
| Early G1 | 8 (3.8%) | 68 (9.4%) |
| G2 | 13 (6.2%) | 46 (6.3%) |
| G0 | 186 (88.6%) | 567 (78.0%) |
| n MelanA+ cells | 210 (100%) | 727 (100%) |
| n lymphnodes (cells/lymphnode) | 37 (1-28) | 21 (10-50) |

2316 KMN1

2349 KMN1

2337 KMN1

2349 KMN2

2436 KMN1

2436 LKN1

2436 KMN2

2501 KMN1

3214 LKN1

3425 KMN1

3596 KMN1

778 NZ1

3641 KMN2

778 NZ2

1032 NZ1

1032 NZ2

1077 NZ2

LK 16 N2

LK 16 N1

LK 16 N3

RPC 94 N

114 N

856-3b

983-9SMb16

741-9SMb

PBL SC 1

PBL SC 2

PBL SC 3

PBL SC 4

PBL SC 5

A

B B

C

| patient ID | sample | TH01 | D21S11 | D5S818 | D13S317 | D16S538 | vWA |
|---|---|---|---|---|---|---|---|
| LN125 | DCC | 7 | 29, 30 | 10,13 | 11,12 | 9,13 | 11,14,21 |
| | PDX | 7 | 29, 30 | 10,13 | 11,12 | 9,13 | 11,14 |
| LN135 | DCC | 8,9 | 29,30,32.2,33.2 | 12,13 | 9,11 | 12,13 | 12,14,15 |
| | PDX | 8,9 | 29,30,32.2,33.2 | 13 | 9,11 | 12,13 | 12,14,15 |
| LN154 | DCC | 7,9 | 28,29 | 11,12 | 11,12 | n.d. | 12,13,17,21 |
| | sphere | 7,9 | 28,29,30.2,31.2 | 11,12 | 11,12 | 11,12 | 13,17,21 |
| | PDX | n.d. | n.d. | n.d. | n.d. | n.d. | n.d. |
| LN155 | DCC | 7,9 | 29,32.2 | 12,13 | 11,12 | 9,10,11 | 14,17,21 |
| | sphere | 7,9 | 29,32.2 | 12,13 | 11,12 | 9,10,11 | 14,17,21 |
| | PDX | 7,9 | 29,32.2 | 12,13 | 11,12 | 9,10,11 | 14,17,21 |

A

B cont.

SEQUENCE LISTING

```
<160> NUMBER OF SEQ ID NOS: 6

<210> SEQ ID NO 1
<211> LENGTH: 12431
<212> TYPE: DNA
<213> ORGANISM: Homo sapiens

<400> SEQUENCE: 1
gaaacgtccc gtgtgggagg ggcgggtctg ggtgcggcct gccgcatgac tcgtggttcg      60
gaggcccacg tggccgggc ggggactcag gcgcctgggg cgccgactga ttacgtagcg     120
ggcggggccg gaagtgccgc tccttggtgg gggctgttca tggcggttcc ggggtctcca     180 acattttcc cggctgtggt cctaaatctg tccaaagcag aggcagtgga gcttgaggta     240
agtttatctc atgcatagtg ttcggctttg ggctgtggaa tgttcaggcg tttcactgat     300
gccagaaatg gagcagaatc tatcagctgg agacaaaggc cttgggcggg ggtccttcca     360
tttggtgcct acgtggggag atctttggag acagaaggga gaatgggaag gagttgcggc     420
ctggaggctt cctgctagag ctgagaagcc ttcggggagt aataggaagg gggatttcca     480
ttgcttaggc tgagggcggg gcccaaggac tgttgaaaaa tagctaagga tggggggttgc     540 tagaaaacta ctccagaagt gtgaggccga tattaatccg gtgtttttgc gttctctagt     600
cactttaaga accaaatgga aggtcacact agggttttca tttccattga ttatagaaag     660
ctttaaagta ctgtagatgt ggctcgccaa ttaaccctga ttactggttt ccaacaggtt     720
cttgctggtg tgaaatgact gagtacaaac tggtggtggt tggagcaggt ggtgttggga     780
aaagcgcact gacaatccag ctaatccaga accactttgt agatgaatat gatcccacca     840
```

```
tagaggtgag gcccagtggt agcccgctga cctgatcctg tctctcactt gtcggatcat    900
ctttacccat attctgtatt aaaggaataa gaggagagaa agtaaaaagt tattttgggt    960
atacattcag ttatgcaata agcttaacgt gtttatagag aacagttcat ttttattagc   1020
tgctgaagtt tctaaaacct gtccagtttt taacagttct gtaaactatt gcaaactcag   1080
tgttgagttc attcatgagt ttcttcatat ataacagctc tattacatga gaaacacagg   1140
ccatagtagc gagactgtct gattgtatgg gagataatag gatggagata aaggattcag   1200
agatgagtgt tcttcaatat ttatttatta gctagttgaa gcagctgaga ccagatgatt   1260
ggagtagcaa gaacttgaga ttttagtct ttatgcctag gattttggtc cctgtttgca    1320
gtttatttag ttgtgtgata ttgagcaact gaatctctcc caacctcatt ttcctcatgt   1380
tttaaattac cataaacttg tcctgcctac cacacaggga tgttatggaa agttaaataa   1440
tatatttaag ttatttatga atggtaaagc actatgtaat agtacttagg gattctattg   1500
ttattatgag agttcatggt acagattgtc ttcagtaagt ggcacctaag gctctttaaa   1560
taaagggttt tgccggacac ggtggctcac gcctgtaatc ccagcacttt gggaggctga   1620
ggcaggcgga tcacaaggtc aggagttcaa gaccagcctg atcaacatgg tgaaaccccg   1680
tctctactaa aaatacaaaa attagctggg tgtggtggca ggcacctgta atcccagcta   1740
ctcaggaggc tgaggcagga gaatcgcttg aaccagaggc agagggtgca gtgagccgag   1800
atcacaccac agacctccag cctgggcaac agagcgagac ttcgtctcaa aaataaata    1860
aatagataaa taaataaagg gttttgtaat tttgttcagt ttagaaatgc ctaactttag   1920
agattatttt aatcaacacc tggcctccct accatctggc tactcgtgtt taattgatga   1980
aaactaactc taatgtagcc actataaaaa attggttgct aacccttggc aaaatcttta   2040
ttttgagctt aacagcttta atattttaca tgaaatgttt aatattttaa ttaaatattt   2100
ttaaatgttt gatttattga gcaatttaca taagtaaaat acataaattt tatgtctaca   2160
gcccagtgct ttttgcgttt ctatatagtc atgtagctac cacccagata acagtataga   2220
gcacttccag tactccagag agttctccaa gtgtgatgac attaaaatac aagtaaaagt   2280
cctgttgcca taaaaccaaa atgaaagtat tttttatatg atctatgcat gtttgtcttc   2340
ctgagaaatt aaacataact ataccttgtt tggaaccttt aagaatttga ttcaggaata   2400
tttcccaaag gtacatctgt catgataaaa aaaaaacctt ctctgaaaca aaggtatttg   2460
tatatttagt cataaacaca aatgatgtat atagggccag gttataattg gtggaggtat   2520
gtttagattt cttaagtaa aataaacagc acaaataaaa cagtccagtt catagcttag    2580
tgaaatacac tgggtactta atctgtagcc tcctggctgc agtagagttg tcatttgagt   2640
tactgtgttt tcttaatctt ttccaggaac acagtgacca tatttctttt ctgcaggcat   2700
atagaatttg gtgggttttc ttttatgtag ggtgatattg gatactttt gtttgtgatt    2760
atatattagc aatttgaggg acaaaccaga taggcagaaa tgggcttgaa tagttagatg   2820
cttatttaac cttggcaata gcattgcatt ccctgtggtt tttaataaaa attgaacttc   2880
cctccctccc tgcccccctta ccctccacac ccccaggatt cttacagaaa acaagtggtt   2940
atagatggtg aaacctgttt gttggacata ctggatacag ctggacaaga agagtacagt   3000
gccatgagag accaatacat gaggacaggc gaaggcttcc tctgtgtatt tgccatcaat   3060
aatagcaagt catttgcgga tattaacctc tacaggtact aggagcatta ttttctctga   3120
aaggatgatc tttgtgttct gaatctttat ggggaaatga ggttaccaca ctagggaaga   3180
tagagctttt taattatggg aagagttggt tttaggttgt ttgacattga gaatctaggg   3240
```

```
taattactga aagttaatac tggaatttat tttacataat atactgttac tataaagttt    3300
gataatacat aagtgaagct tgctactggg aatgacttgg aaccagagtt gttgtaatta    3360
gagatcacga aggaatttca gagaggaaaa catctccaag aaacatcttt cagtatgtaa    3420
tggaaaagat aggccaggca cagtggctca cacctgaat  gtcagtgctt gggaggcca    3480 aggcgggagg atcactttca gcccaggagt tggagaccag cctgggcaac agagcaagac    3540
cctgtctcta caaaaataaa aataaaaaaa ttagtcacac atggtggcag ctactcggga    3600
ggcagaggtg ggaggatcac gtgagctcag gaggtcgagg catgctcact ccactgcact    3660
gctgcactcc agcctaatca acagagcaag attctgtctc caaaaaaaat aaaaaataaa    3720
atgataggag taagcaaata ggaagtccat aaagatgaaa acaaagcaag gaacataaa    3780 gatagacttt gtccatagaa ccataaagtt tcaaagctag atttggaccat aaaaattcta    3840 gtacaatatt cttattttgc agaatcagaa acagagttca gaatgtcgtt tgttaggttt    3900
tggagtcagg attgttatta gtagcagagc caggaccaaa aacccaaagc tcctttttct    3960
tagcacagtg ttcttaaaca gaataatata atggttaaga atgagaactc tgcctggatt    4020
gaaacctagc tctgtttatt agcgacgtga ctcaggggct atgtggcttt cctaacctat    4080
aatatggaaa taataatacc tacctcatag agttgtgaag attacagttt taataaatac    4140
gcaaatcact cagaatagtg cctggcacac agtaaatgct acttaagtgt tctgcctaaa    4200
ggcttgagtc ttggcttatt ttctatccat gtgaagatgt ctgctctcaa aagcagattg    4260
gtccaacact gaattcaagt gttcttttcc taacctgttg tacttcccat ttttttttg    4320 tctaaaagta atagcagtac ttaataaaat gcccacactt ggcatgcatc taataaatgt    4380
tttttgaatt tctagaagtc attttttcttc tttcttacaa gaaatttatt cattttcta    4440 tatgccttag ctcaaaccaa agagtattta aaacatctta tgaaaatgca tatagtagag    4500
caagataaga ttaatgaaaa ataggcttaa gtgagaccaa aaaaataagg gtaaaataaa    4560
caaatttagg agtgagcata ttctgtgatt gtgcatgaag ttccagtggc tttctaaagg    4620
tggactacaa atttggtcac tgttgtgaaa aggaaagtag ccagctgaaa gattcagtat    4680
ctgtatgctg aaagccgtta agttgctcgg actagaagga aattttccca tggatcctca    4740
aagaggcttg tttaatgtaa aaatcagtag taacctgaca gtgacatggt ccaggtactt    4800
taggctgtct tatcccttaa tgtaggctat taccatcaag cacagttttg caaatagcca    4860
gtggaatgta gttcagatac atgactttgt gggtaatcca ggggtagaga ctaaaacagt    4920
actgtgcagt atgtggttat ttacagttaa ttaagattaa ataaaattta aaaattagtt    4980
ccttgactac caaatgctca atagccacta gtaggtacca tgttgaacag tacagatata    5040
gaccatttcc atcatcacat aaagtactgt tggattgtgt tggtcaagac aatctaaagc    5100 aattgttttcc caggtgtgct gtgtggtgtg ccttacatgt cattgaaagg ggtgctgtca    5160
ggagttctag atgcttcagc ctccctttac taagagcagt tcttatgttt tctattttat    5220
cgcttgggct tccagataca atgttttgtt ttaggtttgt ttttttgtt tgtttgtttt    5280 tttttttttg agacggagtt ttgctctggt tgcccaagct ggatggagta cggtggtgcg    5340
atcgcggctc actgcaacct ccgcctcccg ggttcgagag attctcctgc ctcagcttcc    5400
cgagtagctg gaattacagg cgtccaccac catgcctgac taattttttt tgtattttta    5460
gtagacttgg ggtttcacca tgttggccgg ctggtttca  aactcctgac ctcaggtgat    5520
ccacccgcct cggcctccca gagggctggg attacaggtg tgaaccaccg tgcccggcct    5580
```

-continued

```
gttttagttt tttagagatg gagtctccct ctgttgccca agccagagtg cggtggcatg    5640
acactctcag ggttcaacct ctcagggatc aagggatcct cccacctcag cttcctgagt    5700
agctggaacc acaggcacat gtgccaccat gcccagctaa ttttttgtatt ttttgtagaa   5760 gcaaggtttc accatgttgc ccaggctggt ctcggactcc taggtcaagt gatcctccca    5820
cctcaatctc ctagagtgct aagactatag gcgggagtca ccatgcccag cttcatctac   5880
aatttatttg aagaaaatgt tgagcacca cccatcttga aaagtgatag actgccttcc     5940
attaaatact gtcacaccta gttatttagc agcagtgagc ttcactttttt atactttaga  6000 ccttaatcta aagggtgatt tctagttgcc agttaaatcc agagccaagc tctttggaga   6060
atccaggagc ctcactaggt catgtatcag gataaaatac ccatccactc ccattagaag   6120
gtgagcttgt acttatggct tcctgatggc tgctgcaaca agtctaaagc agtctcctta   6180
gtatacaatg tcttctctaa gtggtagaaa aaagcaaaaa tactacaagt taatagggct   6240
acataaaatt tgctagtttc ttttttgccc tagccattta ttccttcctg aaatcttgtc   6300
tctctctcgc tctctctttc tctcgctctc actttctttc tctttttctt ttctcttttc    6360
ttttctttct tcccttttctt ttcttttcttt tttcctgttg cccaggctgg agtgcagtgg 6420
aacaattatg gctcactgca gccttgacct ttctggaccc aggtgatcct cccacctcag   6480
tctcccaatt agctgggact acaggcatgc gccaccacac ccagctataa tatatattgt   6540
atatatattt tttatttata aatatatata aatatatatt tatatgtgta aattatatat    6600
atttatatat tataaattat ataaaatat atatttatat ataatatata taatatatat     6660
ttatttttat atatttttata tatttttttt ggggggggtt gggggggatg gagtctcact   6720
ctgtcgccca ggctagagtg tagtggcgtg atcttggctc actgcaatct cgcctccca    6780 ggttcaagcg attctcctgc ctcagcttcc cgagtagctg ggactatagg cgcctgccac    6840
cacacctggc taattttttgt atttttagta gagatggggt ttcaccatat tggccaggct  6900
ggtcttcaac tcctgacctt gtgatctgcc cacctcaacc tcccaaagtg ctgggaatac   6960
aggcatgagc cactgcaccc agcctaatct ttgtattttt ttgtagagac cgggttttgc    7020
catgttgccc aggctaatct caaactcctg ggttcaagca gtctgccctc tcagcctcc    7080 caaagtgctg agattgcagg catgagccac tgtacccagc ctaatcttgt ttttcttatg   7140
ttctgataat atattcccgt ttttagggag cagattaagc gagtaaaaga ctcggatgat   7200
gtacctatgg tgctagtggg aaacaagtgt gatttgccaa caaggacagt tgatacaaaa   7260
caagcccacg aactggccaa gagttacggg attccattca ttgaaacctc agccaagacc   7320
agacaggtat ggtacagctt tcagcatttg tgcaagagtt tgcatcagtt gattaactct   7380
ggtagagatg tgatccatat tcatattctt tgttgttatg cattttttc atttttattt     7440 tttatttttt tatttttttt taggcagagt ctcactctat cttctaagct ggagtgcagt    7500
ggtgtgatct cagctcactg cagcctctgt ctcttgggtt caagtgattc tcctgcctca   7560
gcctcccaag tagctgggac tacgggcaca tcatcatgcc cggctaattt ttgtactttt    7620
agtagagaca gggttttacc atgttgccca ggctggtctc gaactcctgg cctcaagcaa   7680
tcctcccacc tgggcctccc agagtgctgg gattacaggt gtgagccacc acgcccagcc   7740
tgttgttagg cattttttagt agtgttcttt tcttaacgc ttgtttaaac ccaaaatgaa    7800
cttactaata ttctgttatg gcatgtttac tcctgcatta acatccacaa atatttcttg   7860
ggaagatcct tgactaaaaa tatttataaa cattagttat ttctctgtca acaccagccc   7920
gtttatggct taagcctcct gaatggagtc tttagtttaa tgtagttttg ttccgtgttt   7980
```

```
ctcacattac cctttccctt tgcatgaatg tttatttggc aaaatgtgcc atttttatat      8040
cagcctgttc ttgtgattca ataggaatgt gaaatttagt gttctcttcc ttaaatcacc      8100
atatttatt ttatcagcta ttcgtttagt aattggaatc ttatgtccac ataaagagat      8160
acaaatgcaa gagagcttat aatttggatt gtgtccgttg agctagctct ctcatttttt      8220
ttcattttt cctttatag ggtgttgaag atgcttttta cacactggta agagaaatac        8280
gccagtaccg aatgaaaaaa ctcaacagca gtgatgatgg gactcagggt tgtatgggat      8340
tgccatgtgt ggtgatgtaa caaggtgagc atatggtttc ttggcataat tacaaatctt      8400
agtatatagt attgggcaat ttggaggagt gctggtgtta ttgtctatat gttttttgag      8460
tttctgccta tcctcttctg cacattttcc atatgacacc ctttctgaaa gtactgaggt      8520
ctaaagtgtt taaaacattt gattattcca caggtatctt tatattttg gtaacattag       8580
aaattataag acattattta tgaaatgtag gcatacccta ttcctggcaa tgaccaggaa      8640
tttgaaggat cactactttg aaactagtta ataaggacat ggtttctgtt cttttttac       8700
agatactttt aaagttttgt cagaaagag ccactttcaa ggtaggacaa gtttggaaat       8760
gtattctcat tcctgttaat tttgtatatt tgttttct atactctgaa tgtgtcactt        8820
atacaaattc tgtttctat tcagctgcac tgacaccctg gtcctgactt ccctggagga       8880
gaagtattcc tgttgctgtc ttcagtctca cagagaagct cctgctactt ccccagctct      8940
cagtagttta gtacaataat ctctatttga gaagttctca gaataactac ctcctcactt      9000
ggctgtctga ccagagaatg cacctcttgt tactccctgt tattttctg ccctgggttc       9060
ttccacagca caaacacacc tctgccaccc caggttttc atctgaaaag cagttcatgt       9120
ctgaaacaga gaaccaaacc gcaaacgtga aattctattg aaaacagtgt cttgagctct      9180
aaagtagcaa ctgctggtga tttttttt cttttactg ttgaacttag aactatgcta         9240
atttttggag aaatgtcata aattactgtt ttgccaagaa tatagttatt attgctgttt      9300
ggtttgttta taatgttatc ggctctattc tctaaactgg catctgctct agattcataa      9360
atacaaaaat gaatactgaa ttttgagtct atcctagtct tcacaacttt gacgtaatta      9420
aatccaactt tcacagtgaa gtgccttttt cctagaagtg gtttgtagac ttcctttata     9480
atatttcagt ggaatagatg tctcaaaaat ccttatgcat gaaatgaatg tctgagatac      9540
gtctgtgact tatctaccat tgaaggaaag ctatatctat ttgagagcag atgccatttt     9600
gtacatgtat gaaattggtt ttccagaggc ctgttttggg gctttcccag gagaaagatg      9660
aaactgaaag cacatgaata atttcactta ataatttta cctaatctcc acttttca         9720
taggttacta cctatacaat gtatgtaatt tgtttcccct agcttactga taaacctaat      9780
attcaatgaa cttccatttg tattcaaatt tgtgtcatac cagaaagctc tacatttgca     9840
gatgttcaaa tattgtaaaa ctttggtgca ttgttattta atagctgtga tcagtgattt     9900
tcaaacctca aatatagtat attaacaaat tacatttca ctgtatatca tggtatctta      9960
atgatgtata taattgcctt caatcccctt ctcacccac cctctacagc ttcccccaca      10020
gcaatagggg cttgattatt tcagttgagt aaagcatggt gctaatggac cagggtcaca     10080
gtttcaaaac ttgaacaatc cagttagcat cacagagaaa gaaattcttc tgcatttgct     10140
cattgcacca gtaactccag ctagtaattt tgctaggtag ctgcagttag ccctgcaagg     10200
aaagaagagg tcagttagca caaaccctt accatgactg gaaaactcag tatcacgtat     10260
ttaaacattt ttttttcttt tagccatgta gaaactctaa attaagccaa tattctcatt    10320
```

```
tgagaatgag gatgtctcag ctgagaaacg tttaaattc tctttattca taatgttctt    10380
tgaagggttt aaaacaagat gttgataaat ctaagctgat gagtttgctc aaaacaggaa    10440
gttgaaattg ttgagacagg aatggaaaat ataattaatt gatacctatg aggatttgga    10500
ggcttggcat tttaatttgc agataatacc ctggtaattc tcatgaaaaa tagacttgga    10560
taacttttga taaaagacta attccaaaat ggccactttg ttcctgtctt taatatctaa    10620
atacttactg aggtcctcca tcttctatat tatgaatttt catttattaa gcaaatgtca    10680
tattaccttg aaattcagaa gagaagaaac atatactgtg tccagagtat aatgaacctg    10740
cagagttgtg cttcttactg ctaattctgg gagctttcac agtactgtca tcatttgtaa    10800
atggaaattc tgcttttctg tttctgctcc ttctggagca gtgctactct gtaattttcc    10860
tgaggcttat cacctcagtc atttctttt taaatgtctg tgactggcag tgattctttt    10920
tcttaaaaat ctattaaatt tgatgtcaaa ttagggagaa agatagttac tcatcttggg    10980
ctcttgtgcc aatagccctt gtatgtatgt acttagagtt ttccaagtat gttctaagca    11040
cagaagtttc taaatggggc caaaattcag acttgagtat gttctttgaa taccttaaga    11100
agttacaatt agccgggcat ggtggcccgt gcctgtagtc ccagctactt gagaggctga    11160
ggcaggagaa tcacttcaac ccaggaggtg gaggttacag tgagcagaga tcgtgccact    11220
gcactccagc ctgggtgaca agagagactt gtctccaaaa aaaagttac acctaggtgt    11280 gaattttggc acaaaggagt gacaaactta tagttaaaag ctgaataact tcagtgtggt    11340
ataaaacgtg gttttaggc tatgtttgtg attgctgaaa agaattctag tttacctcaa    11400
aatccttctc tttccccaaa ttaagtgcct ggccagctgt cataaattac atattccttt    11460
tggttttttt aaaggttaca tgttcaagag tgaaaataag atgttctgtc tgaaggctac    11520
catgccggat ctgtaaatga acctgttaaa tgctgtattt gctccaacgg cttactatag    11580
aatgttactt aatacaatat catacttatt acaatttta ctataggagt gtaataggta    11640
aaattaatct ctatttagt gggcccatgt ttagtctttc accatccttt aaactgctgt    11700 gaatttttt gtcatgactt gaaagcaagg atagagaaac actttagaga tatgtggggt    11760
ttttttacca ttccagagct tgtgagcata atcatatttg ctttatattt atagtcatga    11820
actcctaagt tggcagctac aaccaagaac caaaaaatgg tgcgttctgc ttcttgtaat    11880
tcatctctgc taataaatta taagaagcaa ggaaaattag ggaaaatatt ttatttggat    11940
ggtttctata acaagggac tataattctt gtacattatt tttcatcttt gctgtttctt    12000
tgagcagtct aatgtgccac acaattatct aaggtatttg ttttctataa gaattgtttt    12060
aaaagtattc ttgttaccag agtagttgta ttatatttca aaacgtaaga tgatttttaa    12120
aagcctgagt actgacctaa gatggaattg tatgaactct gctctggagg gaggggagga    12180
tgtccgtgga agttgtaaga cttttatttt tttgtgccat caaatatagg taaaaataat    12240
tgtgcaattc tgctgtttaa acaggaacta ttggcctcct tggccctaaa tggaagggcc    12300
gatattttaa gttgattatt ttattgtaaa ttaatccaac ctagttcttt ttaatttggt    12360
tgaatgtttt ttcttgttaa atgatgttta aaaaataaaa actggaagtt cttggcttag    12420
tcataattct t                                                        12431
```

<210> SEQ ID NO 2
<211> LENGTH: 208814
<212> TYPE: DNA
<213> ORGANISM: Homo sapiens

<400> SEQUENCE: 2

```
cgcctcccctt cccccctcccc gcccgacagc ggccgctcgg gccccggctc tcggttataa    60
gatggcggcg ctgagcggtg gcggtggtgg cggcgcggag ccgggccagg ctctgttcaa    120
cggggacatg gagcccgagg ccggcgccgg cgccggcgcc gcggcctctt cggctgcgga    180
ccctgccatt ccggaggagg tgagtgctgg cgccacctg ccgcccctccc gactccgggc    240 tcggcggctg gctggtgttt attttggaaa gaggcggcgg tggggcttg atgccctcag    300 ccaccttctc gggccagctc cgcgggctgg gaggtgggca tcgcccccgt gtccctctcc    360
gtcatgcagc gccttcctac gtaaacacac acaatggccc ggggggtttc cctggccccc    420 acccccagatg tggggattgg ggcagcgtg gttgagcggg aggctatcaa taggggggcga    480 aactcagggt tggtccgaga aggtcacgat tggctgaagt atccagctct gcatctctgt    540
ggggtggggg cggcggcggc ctcgacgtgg aggatatagg ttagttgctg gggctgagac    600
aacagcccga gttactgtcg cgtgtaattc ttacatggtc gtggggatga tggggctcat    660
catttcctct ctcctctccc ggactgcccc ccttctcagt ccgctgccct ttttcacttt    720
tctatttggg gatttctctt cacctgtttt acccagcaaa ttattttgat ttagtctttta    780 ctttttcaat cctaaatcgc agtttccgat gccttttctg gtctctggtc ctctgttcct    840
aatgtttgtc agcgctctgt cgctgattgg taacccccat tctattccca tctaccgccc    900
gctcattttc cagttgtcgg acctgcctgc cttctaaccc cagctcccac ttaagagcat    960
ttttgcactt ctcttaccct ggtcctcttg aggctctgta cttgatctca ccactcccta    1020
acattgttgt ctgttgttat cttcacaaat cctcctggac actttggagc tacttgtttt    1080
ctgagcccag aagctgtcaa gattccatca ggtttcactt ggctcttttc gcgcttgcac    1140
tactggcact ttttggctag tcgtccattg tgcattcaca cctctttatt cctacccatt    1200
tttataggtc tgattgattt cttagtgttg tcctcctttt tgtcctattt ttttcctttt    1260 ccttttttcct ctccagtcct tgcttctctc agcctgtttt tgcattagtc agcctcttag    1320
cactgtgtca aattatttac gtttttttat tacataaaat ttattacaaa tatttggtat    1380
tttattacag aaaataatac tttattatgc tttacaaata agatatggta taataattgt    1440
ggtttacagt tattgattag gtaatgtgac ttactctgtt gactttgctc gaagttctct    1500
ttgctactta ctattaacat ctaatttctc aattctcata acatctcatt ctctctgcaa    1560
tttttttttt gcatcatcat cttttggaaat tcatccaata tgcttgcttt attcagcatc    1620
agcttgttta tgataatgtt tgttttctac tctttatatc atctttgtta catgcccaaa    1680
atgtgttctg taccatcatt tgatctgttc taaaatttct catttttaag tttcttaaaa    1740
tcattccact tttcagtatg cattttttgct tagatcagtt tcctctcata tctgttcctt    1800
tcccccagct tcttgatttc taaggagaaa gctcttctct acttcaattt cctagtttat    1860
tctgtttccc ttgtttccag ttaccattca ttttgccttg tttcctggct tttggtactt    1920
aactttctga agcttcctct tttcttctcc acacctccac gttccttctt atttataaac    1980
atctttgttt cctttgacat ggaaatttat ttttaggata cattgttttt aatggataaa    2040
tactaggggt cacatctgct gtctgttttc tccaggaatc ggatatgcct tgtcttaac    2100 caggcacagg tgcctctgga ttttattttta ctctgtaata gatgtgtagt tttgttgaat    2160
tgtatcttgt ttgaagacta ctacagagtg gaacaatgag tgaagtaata agtaggggtt    2220 atgaaaattgt aattctctga ttataaaatt gtttatcttg ggaactttgc tgcagagtta    2280
ttagaaccgt ttgcaattct gtaaagaagg cttttgtgaa gtaaaatctc taccccttcta    2340
```

```
tttatttga aagggccaga ttgtttggaa ctgtaccccc tgaagagtct gatttagtaa    2400
gtgagagcga gggccatgga tttctgtatt tggcacatgt cttgagcagt tcccatgtac    2460
caatccttga gaacctctag gctagctgaa tttaagtata aattgccagt aattggaaag    2520
catattcata tcttctgaaa ctataaggat actctcattt tacttggtta aaaacaagt     2580 gtttcctact gtcctctttta cccaggtttt aatgtttagt ggtgaacagt agttttccct   2640 ctacatttt ttctgaactg ataataaatg tatttggctg ggagggtgac attgattaaa     2700
aaatgtatct cttgaatgta aatatcagta ttacagatga taaaataaat tcctccaaga    2760 aataattta aatttgaagt tgatattcag tggaaactga aatgtgctgt ggtcttttat     2820
ttgaagtctt ccttacattc acttaaaggg atcttttact gcaaattaca tggaaagaat    2880
gaaaaggttt gcttgtgtgt aatgacacat tttattctga agatttattt tacctaacag    2940
taaaatgtag gttttttttt tttaaataaa agtttcccag agggaaattt catctaaaaa    3000
aaaagtctga tttcaaaggg aaagcaagtc attatcaaaa attagaaaac tataagtaca    3060
aaaagtaaaa aatcatcagt aatttgtgcca ctaagatatt attactatag acattttggt   3120
gtattccatc tgttcttttt taatgctttt ataacactat gtagttttgt attttaaaaa    3180
acttaaagca aaaatttcta cgtattatta gacatactgt gatttattta actaatcatt    3240 tttttgggt gttaggttgt ttttaatttt ttactgccat caaacatctt gaacatagga     3300
tgtagatttt agtctttaaa atatgttggg gaatgaacaa atttcacatc ctgtatttgt    3360
agtattaata ctttgtaggt gctcaaaata gaatattctg gtaaatgatt agtgcttatt    3420
aaatatttat caaatgaatg tacttgtact tttggcatta aacattaaca tctgaccatt    3480
tatatttacc tgatttttttt tctatggcca tatggtatga aatagtgtat ggtataaatt   3540
aaccatatgg tataataaat acattttttt aagtgtgata ccagagtgat atttattaac    3600
tgttcttcct gtgctgtttc tgtagaaggg agcttctcac aattgcatta gaattacaat    3660
tttattatgt tctgttttca agatctctga tcgtcagtct taaactgttt aattataata    3720
atgtattgac tagggaatat tctgggatat aatctccttt ataatgaggt ccactgtatt    3780
aaaatacatc tttgcaagcc acaccaggtt ggattgcatc ataaccctga aaagtggtat    3840
tctcattaat gcaggtgctt gtgcagtttt ggctattgct gttaatactt atacagatat    3900
attcacaggt gcccttgtgg caaaaatcat aaaatagttg tttgtctttg gtatttctag    3960
tgttcacttt ctatattctt ttctctctcc ttatttactg aactcccttc tttaggcatc    4020
cactcactcc ttttttctgtt tagaatatta tctgtcagtc attttatatg ttggccatta    4080
aaggaataaa ctgtcagtaa acagctaaga aaggaatgtt ggactgggtg cttgaatcct    4140
tgaatgtagt aaatgtgagt gcaaacttga tttaattgta catgtatttg gataataggc    4200
cagaaaaatt acattagggt aacaggctag aacagtctga cttttcttgt ttttctatcc    4260
cttgctttct tgattagaat gaataggagg tgggtctgga tatagcagct ggaaacctgt    4320
gttccatgag tgatggggaa gagagggagg gaataggttc ctctgatttt tggcatttc     4380 taagacctga tgcccaccctt gtcagagaat gcgatgacta cttttgtgtt cttccttttc    4440 ccttttctc ccaattataa aattgttttc tcttcagaa ctgcagaagt gcattttgtt     4500
tctttgacac tttgatgttg ttaatttagc tgaataccta gtgaacattt tgtgtcataa    4560
tccccttgtt ttatgaaatc cagtatggtc tagtcacctt acatttctgc ctcatattgt    4620
ccttaagcct ttttttgtca gtagctctta ctagattttg tcttcatcag aagttaaagt    4680
gttttaagtc ctttactcat tctgtttctc tattttaact tacattggtt attctgtaaa   4740
```

```
gtcagatgtg gcagtagggc tggtcgtggt ggctcacacc tgtagtccca gctacttggg    4800
aagctgagat gggagcatca cttgagccct gaagttcgag gctgcagtga gccatgatcg    4860
caccactgca ctctagcctg gcaacagagt gagaccctgc ctcaaaacaa acaaacaaac    4920
aaacaaaaaa aaaacaaaaa aacttgcttg tagaacttct gaattcaaaa taggtgggcc    4980
tatttgggag cttttctgtt tttaaggtgt caagtactgc ttttttaaaat cataaggtta    5040 tggataactt catgttagtg taagaagaaa aatatagcct catttgttcc atttctttct    5100
taaatttttt gttttcattg ccatgttttt attttttcgat ttcaattttt ccagcctaaa   5160
tcactaacat acttaattag catggtaatc agaagatact ctttaataca gtctccaccc    5220
taacattaag caattatttt tcccccctac cctctgagat tattttttgtg tccatgtttt   5280 ctcttgggct taaaaaaaaa aactattatt ctaattcctt cctgtatcaa gactatgcat    5340
atagagggaa ctcaatgccc agtaacttct ttttctgggc cctggtgatg tagaatataa    5400
aaattgcttt gaactcaatt aactttatat cttctggaag ctctgtaaca tcggataaag    5460
cgtcgttttc attcttgtaa tgtagctgca gttcctgaca gcacgtttgg gacaaatgta    5520
ctgtgggacg gtggttttca aagtacgcca gagctctagg agaattttc gaaaacattc    5580 tatcattgta aataataatt ttttttttt ttttttttga gacggagtct cgctctgtct    5640
cgcagactgg agtgcagtgg cgcgatctca gctcactgca agctctgcct cccgggttca    5700
cgcctttctg cctttctcct gcctcagcct ccccagtagc tgggactaca ggcgcctgcc    5760
accacgccca gctaattttt tgtattttta gtagagacgg ggtttcaccg tgttggccag    5820
gatggtctca atctcctgac ctcgtgatct gcccgcctca gcctcccaaa gtgctgggat    5880
tacaggcgtg agccaccaca cctggccaga ataaaaattc caaattgcac taatgcatat    5940
gtgaaactgt ttttgtctgt tttgtagttt taaaatcttc atctataata gtacctggca    6000
cataggtact aaaatatttg gtgaaagaat tagtgaataa aaccttactg gatatgaggt    6060
gatctgattt tctgtaacat tctattcttt ttttctgccg gtcacaaaat caccttatga    6120
aattgacagc caaattggct gcaacaggca gtttgaaaaa cactgttttg gggtttcaag    6180
gaccttcttc agaggttacc ccagggctct gtttagtgcc tctataccag ggccccccaa    6240
cccctgggcc acagcctcgt atctaccagt ccgtgacctg ttaggaacct gactacaccg    6300
caggaggtga gtggcaggca agtgagcatt accgccaaag ctccacctcc tgtcagatca    6360
gcggcaggag cgtgaaccct atcagaaact gtgcatgtga gggatctaga ttgtgtgctt    6420
cttgtgagaa tctaatgcct gatgatctga ggtggaacaa tttcatcctg aaacccctc    6480 taccctgtc catggaaaaa ttgtcttcca tgaaattggt cactggtccc aaaaaggttg    6540
gggagtgctg ccctatacca taactattga agttcttcat ttatctgctt tacatgttag    6600
tttccttgaa aaagggttt tatggctgta aaaatttag agctactatg tatggaagag    6660
aggtttgtgc tggcataaat cttctcaggt atcatctgtg tagaaaattt caacaacttg    6720
tgtcttaagg cagaggtcag caatcttaag ggtcagatgg caaatatttt aggcattgtg    6780
ggacatacag ttcctctcac aattcctcaa caatactgta gtagctcaga agtagctaat    6840
agacaatatt taaacaaatg agtttgactc tgttccagta gtcattttca ggacactgaa    6900
atttgaattt catatcattt tcatgtgtca tgaaaatctt cttttgattt tttttctacc    6960
acttaaacat gtaaaaagta ttcttagctt gtgagctata caaaagcaga tagtgggcca    7020
gttcatgggc tgaactgttc tgactcctgg tctaagggag actatatatg ttatatttga    7080
```

```
ggttctcaaa gtaagatgta ggttagaggt ctatagaaag ttcataattg cttttgtaaa    7140
aactagattg atttatttga gagggagaga gaggtggagt ttcactgtat tgcccaggct    7200
ggacttgaac tctgggctca agcaatcttc cagcctcagc ctcccaagta gctaggacta    7260
caggcatgca ccaagcccag ctcctagttc tctttgcac tcagtttcat cttctaccct     7320
cagcccctgg caaacactgg tctgatctct gtgcccttc cagaaagtca tataaatgga     7380
gtcatataaa agtcatatca gtggggccgg gcatggtggc tcacacctgt aatttcagca    7440
cttggggagg ctgaggaggg cagatcacct gaggtcagga gtttgagact ggcctggcca    7500
acatggtgaa accccctctc tactaaaaat acaaaaatta gccgagcatg gtggtgggca    7560
cctgcaatcc cagctacctg ggaggctgag gcaggagaaa cacttgaacc cgggagaggg    7620
aggttgtagt gagccgagat cgcgtcattg cactccagca attgtgaagc agtggttaag    7680
gttcattcat tattttacat atggatgtcc agttgtttca catttatcaa atttcttttg    7740
aatcaccttg gcacttttat tgaaatcaat tgcttatgtt tgtgagtttt ggattctact    7800
gttttattga tctgtgtgtg ttttcttagg ctaatacccc actaccttag ttatgatagc    7860
tttatagtta aatttaaaat caggtaggtc cagttgagaa gattttaga actttgactt     7920 tttaatttct tgttaccata cttttggaag agaagactc ataattttat tcaggttttc      7980
aaaggtgtct tctaccccca aatacttaag acttcagtat atagttaata tatctctgtc    8040
ttgaattatg tggtggtgag gttcatgaaa agtgacaggg aaaagttgca accaaaatta    8100
atttccttat aagaaaggac atattttagt aggttgcaca gaaaagtcaa tcacgtcctt    8160
tttaccgtgt tgcattatga ggtgtaatca aaatgtgtat aggggaaaat gaatatgtta    8220
agatgtttat tcaccaaaaa agtcaccga aagtgtcaat taggttgtga aagatactag      8280
tttacaatgt gttattctcc atcttcatta gaagagttct tccatttgaa acctatgtca    8340
tgttctgtga tatttcagag ttagtatctt tatgaatctt agggcatca ttaaatcatt      8400 atgtttcttc taaggaaagg catatggtag tagttggtca tatttctacc ttttcagtg     8460 gggcctatag ggcccctta ctttgtttta aactgcactg atagctttt actggttagc       8520 ccagggaatt atccctacag tgtaaaatga tgtttctcat catgattttc atttaataat    8580
ttaaaaacaa aataacagga aacacatgtt tctagagagg aagtgtggaa tacctgacta    8640
gtagagggtc aggtgacaat tgcgaaggta gaaactgact aagttttgac catgttgcaa    8700
ggagtatcgt tccagttttg ttgggtcacc ttgcagagtt ttttaaaaaa atccttgggt    8760
tttttttgtt tgtttgtttg tttgttttgg tagagatgct gtgttgctca ggctagtctc    8820
gaaatcctgg gctcaagcag tccttcccag agtgctggga ttacaggcat gagccaccgc    8880
acccagcatc accttgccga ttttgaaact acacttccag ggagagagta atacaatatc    8940
ttggcagact atttttaact attgttccaa aattaatctg tttttaaaaa gtaaagaagt     9000
gtggatatct ttaaaagata ctttaattag gctggtcacg gtggctcatg cctgtaatcc    9060
cagcactttg ggaggccagg atgggtggat cacctgaggt caggagttcg agaccaacct    9120
gaccaacatg gagacactcc gtctctacta aaaatgcaaa aaattagccg gcatggtgg    9180 cgcatgtctg taatcccagc tacttgggag gctgaggcag gagaattgct tgaacctggg    9240
aggcggaggt tgcagtgagc cgatattgcg ccattgcact ccagcctggg caacaagagt    9300
gagggaaact ccgtgtcaaa aaaaaaaaaa aagatacttt aattatattt aagttgggga    9360
atacttttgt tttatatttt ttcttgcact aaatatgtaa cctttaagtt aataacacca    9420
gaaaattttt actttatagt tttagaactg cttaattgaa ataaaatgtt aggatacttt    9480
```

```
gaattagtca cttatttttgg catatttttaa acagtttaat gtactgcttg gggttgtttc   9540
tcaattgact tgatattttt aaactgtatt ttttaccttg taccatttat tttgcaaaat   9600
aaatttctat tttggcttat agatgtattt ttaatattaa aggggattat tggtgtcagc   9660
cataaaattg taattaagtc ttaagtaggt atggttttt tttttttttt tttttggaga   9720
cggagtctcg ctctatcatc catgctggag tgcagtggtg tgatctcggc tcattgcaac   9780
ctccgccccc cccccccccc gggttcaagt gattctcctg cctcagcctc cagagtagct   9840
ggcactacag gcgcatgcca ccatgcccgg ctaatttttt tgtattttttg gtagagatgg   9900 gatttcacca tgttagctag gatggtctcg atctcctgac ctcatgatcc gtccgcctca   9960
gcctcccaaa gtgctgggat tacaggcatg agccaccgtg cctggctgat tatttttata  10020
gagctcttgt tagcgtaatt tctggtaatg ttttatggag gtgacttaat tcccatcata  10080
aaaatatccc atcttttctg tgactagcaa gcagttattg cctttataac ttttttttac  10140
cataaaaaga taaagtacta ttgataatta ctcctaatta actcagaact ttttttgtttt  10200 acacacatta atatatactt ccatgggaat agtgtcagag aacatcaaat agggaagaga  10260
ttatgattca gagtggtctt tatattccta ttctagagcc acagaaaatg ttcatctccc  10320
tttagttttt gcaggattgc ctctaacact gatgatattc cactcatatt cttcctgcac  10380
atgccttctc atactaacag taagtcacac aatctcaaat aagtttcatt atacatgaga  10440
actcagttga atgcttgcct ttcactggca tctcttgatc ctcctccccc tccttatggt  10500
atgcactgaa cttctagtag gccatatgtg ttaagtagat cataggagtg ctatgaaaat  10560
aaagtgaaat gatgaatatg taaaagcctt cacaaaatta tagtagtgtt ttctgttgat  10620
ttttaagaca aaagataaat actatgtatg taaaaatttc ctttcagaaa tctttgttct  10680 ttttttttgtt ttgaatgttc aatatgctta gcacagggct ctagttaaca cttttggcag  10740
ttcttaatgt gggactgact gatgattgtc ctagaactgt ttcagtgtta actacattct  10800
attaatgtta ctttaaaaca ttatttaatt aaagaaacat gaagtggcaa catactgatt  10860
catgtgttca gtaagcaatt catgggaaag aggtaagctt tcttaataac agtagaaaga  10920
ctgttccatt tataggaaaa ctggtaatta tgacttgtgt tttggtatttt aaaagctgtg  10980 gttggccggg cgcagtggct cacgcctgta atcccagcac tttgaaaggc cctggcgggt  11040
ggatcatgag gtcaggagat tgagaccatc ctggccaaca tggtgaaacc ccgtctctac  11100
taaatataca aaaaattagc tgggcctggt ggcatgtgcc tgtaatccca gctactctgg  11160
aggctgaggc aagagaatcg cttcaatcag ggagtcggag gttgcagtga gccaagatcg  11220
cgccactgca ctccagcctg gctacagagc gagactctgt ctcaaaaaa aaaaaaaaaa  11280 aaaaaaaaa aaaagctgt gattaacatt tgctttgtca ttcatccaaa actacattgg  11340
tgacttttgt attgagtcat ttcttagggc aacaggtatt catgtattca gtaaatattt  11400
gagtgcctac tatatgccag gtagtgatct aggtgcttag tagtacactt gaaaacaaaa  11460
caaaggtctc taccccttatg tagctgctgt ccagtggagg ggtgtgtgtg tattggggga  11520 tgggggctgag aaaccttaga catacagaaa ggaaattatg tagtatgttc aaaggtaata  11580
agtgctgtgg agcaatgaaa gttaaacagt ttagggctgg gatgggggta ggtagcaatt  11640
taaataggga ggtcagggta ggcctcactt gagaaggggg tatttgaaca aaaatttgag  11700
aaaggaggag gaggcatttc agataaaacca attagttcaa agattctgtg tcgggaatgt  11760
gccttgccta tttaagaaac agcaggaggc caaagttgct ggggcaaggt agagactagg  11820
```

```
ggattaggga aggatctctt tcagttatct aggccatatt ggtgatagca gaaatactga    11880
gaagtagtca gattttggat gttttgaaag tagattcatc ggggcttggt ggctcacgcc    11940
tgtaatccca gcactttggg aggccgaggc gggcagatca cccgaggtga ggagttcgag    12000
accagcctga ccaacatggt gaaaccctgt ctctactaaa aatacaaaaa ttaggtgaaa    12060
tattgaagga gatgttttga ttgaagtgat tttaagagag aagaggaggg gaagtaaaga    12120
tggtgaggaa ttatcctgta aaggggaaca gagaaatggg gccagagcta gtgaggaaag    12180
tggggtcaat aaattttttaa tgataagaaa aagaagagcg tatgatgata ggaatgagcc    12240
attagagagt aaaacgtttc aggagggaga gagaagaatt gctgaagcac tgtcttagaa    12300
gaggtaagag ggaaagggat ttagtgtata aataggaagg attggctttc ataggagca    12360 tctatacttt atgataatag gccattaagc agagtatgtg gttagaaatg ctgctaggaa    12420
ggtcgacgtg attggtggag tctgtacacg ttctgttgca gttgctttgg ttttttcag    12480 tgaagtaaga cttgaggtta tcagccgaga atgaggattg gggatatgtg aaagtagctc    12540
cgcagcagta tgggagcata aatgaactgg agacaaaatag taaaattaat gggcaatttt    12600
ttttccttta agatgggg gtctcactct gctacccagg ctggggtgca gtggcacagt    12660
catagctcac tgcagcctcc aactcctggg ctcaagtgat tttctcacct cagcttcccg    12720
agtagccagg actataggct aatggcaata ttaagttatt ttatgagttg tctagacagc    12780
attatgagtc tcctaactt ttggtactga tcttcagatc agagttaaat gtaacttgcc    12840
caggcaattt aaacactcaa tatgagtcat tttcatttgg actcaaacat ggaatcattg    12900
ggaaatagaa catgaattta ttactcctta atgaagtacc tgccactatc ctgccatgaa    12960
tgtaggctaa atttggagtg gtctggtaac tgcttttctt ttaaaaaaat tttcttcatc    13020
ttttctgtat caaatactta ctggttttc tatgtagaat aacataatct catcattact    13080 ttcttcaaa cactctccaa atttgacttg tctttgctca tgttttttcct accacctgaa    13140 atacagattt cctccccat cccacccctcc aaaccttcca gacttacctc acctaccgtt    13200
tattgtagga agcttttctt aacctctttc caagtcctag tttgatgcct ctgctttgtg    13260
cttttgtaga atcccagagt ttaccttgtt ttactcacta tatcgtattg tggggttttt    13320
ttgttaatag gtatttcttt ttcctctaga cctgcactgt tcagtcatac tttctgtgat    13380
gatgaaaatg ttcagtgtcg tcttaatatg gtagacagta gccgtatcta tgtggctact    13440
gtgcacttca aatttgcata gcaggactga ggaactaaat tttatttcat tttaattaat    13500
ttaaaaataa ctagcctgat ggctagtggc tgctttaatc agtgcagttc tagacccctt    13560
caaagtcaag agtgtgtggg attcatactt attctctcgt tgcttaacaa taatactgtc    13620
taatacttaa atgactgaat tcttttttcgg tactcttagt ctgcatagtt ataactcacc    13680
tagaatatgg cagttttgtt ctctagattt ctgtctttaa ccatggcttt tcagtttgtt    13740
ttcaagatta tgttgattta cacagcactg agttcttcag tcctgcgaag ttagcgtttt    13800
ggttggatgt ggtggctggc atctgtaatc ccagcaatat gggaggctga ggcgggacga    13860
ctgcttgaag ccaggacttt gagatcagcc tgggcaacat agcgagcccc tgtctctaca    13920
aaaaattagc tgagtgtggt ggcatccaca tgtagtccca gctacttggg aggctgaggg    13980
cgggaggatt gcttgaaccc agttcacggc tgcagtgagc tatgatcaca ccactgcact    14040
cctgcctggg tgacagagca ggagtcaccc tctcaaaaaa aaagtgtatt ttttccctt    14100 taggactgaa aaaattgggt gttacaagat tacctcaagg actggtctga gaactgggga    14160
tggtaaggaa gaaactcaag tggccagcct ctggtttgtg ggggtaggtg ggcaatttct    14220
```

```
gtttcaacca aagcagttct acttcataaa ttaatatatt ggaattgtgc ttgggatttc   14280
atttggaggg gaaaaaagtc ttctaaacaa taacactgtt aattgaagag acaaagcatg   14340
catatggcag cacgtgatta accaccaaag tggataacag atcaagaaga catgggaagt   14400
tgttatgggc tagtgaggtc ttgatggaag ttaaggttta atttaggtag gtagaaggaa   14460
gacaaaagga tgtaataggc agtgggaata gaatttgcaa agaattggag ttggaaatac   14520
atatgttagt tttggttaag aaacaatgag ctgattatag ttgagcaaat tgtatgaaat   14580
aaaatttgac aaaattagat gggactggat tgtaggaaaa agtgataggc tgacaaaaag   14640
tgcactttat attgcatgca atgagatgaa atactcggag gtattttggt tgttacaaag   14700
atggaggaag aggacactat tagcatttaa tgagaaagga tcagggaagt cagccatccc   14760
acaatgttca ggacagtttg cacatttaag aattgttcca aatcaccaca tgacctagaa   14820
tgacttgctg gactttgatg atgtaggtta aaaaaaaaaa gtgatcataa tgatgtgagc   14880
atagacagta actccatttt gtgtatgagg cacttttttg ttgttgttgt tgttgttgtt   14940
gttgttgttg ttgttttgag acggagtttc gctcttgttg cccaggctga aatgcagtgg   15000
caccatctag gctcactgta actgaggcac ctttaatata cactaagatt ttcaggaatt   15060
cagttaccac aatattggag gaatgttaaa gttttgttc agaactttat caggagtact   15120
ccaccccttt agaaaatcac gtaattgatg gcagtgtcac ttgtgctgta ttggtgacgc   15180
aaatactctt cagtctgcag ttgtaactgc cacagtcaca gtgcttgttg tatatatgta   15240
caaagtacca tcagtgtgtt atttattata gtaatagcct aaatattata aaattgcact   15300
aaggtagatt atctctgaat tacatttatt ttttatttt atttttgtga cggagttttg   15360
ctcttattgc ccagggtgga gtacaatggc gtgctcacca aaaccttcgc ctcccgggtt   15420
caagcgattc tcctgcctca gcctcccaag tagctgggat tacaggcatg tgccaccatg   15480
cccggctaat tttgtatttt tattagagac ggggtttttc catgttggtc aggcttgtct   15540
tgaactcccg acctcaggtg atctgcccgc ctcggcctcc caaagtgctg ggattacagg   15600
catgaaccac tgtgcccagc ctctgaatta catttaaggg tagtatagag aatgtacaaa   15660
atagttgttg taaaaaggag aaattgattt ctgttttcag tattgaaaga ctgggttatt   15720
cagatgaaaa caattaaaat tcttggaaac agtattaaaa aaaaaaaaa aaaaagaaaa   15780 cgtagagcag ttgcagagct gaaaagatag tggggagctg ccaggccaaa ttctaggaat   15840
aaacaagaat ccaaataaat aagtggatga agtagctttt gccctaaagg cagttgccaa   15900
tctgtacaag ttgggcttg gttttggtgg accattgggg tgaagaggac agaaatcaag   15960
tcctagagtt catctaaagt gacagtcaaa aagaataacc tcagttttag atgggacccc   16020
agtgactcta tcgttaggtt aagggtgaaa caactgaact gtctacacac tcccatatcc   16080
atgtgattgc agggaaggtt gaatggagca ggaggaggaa aaggaaatta agaaaaataa   16140 accctttcaag ttgtgaccac agttttagcc ttcacagtga tttgccttga gggtttgctc   16200
tgtctgggtg gtccagggac cctccatgat aaatgaccct ccagccattt atcatggtta   16260
ctggtttcag actagtatta cttccatggc ctggcagatg gaaaggcaaa tcacgtgtgg   16320
agaaaggcct ttcattctag ggaattgctt ccagtaattt ttcaaggaca atgaacagta   16380
cattgtcaca agtaatcaaa catagtaaaa ataaaaaaat tagcaagcaa aattacctga   16440
gagatatata atatgtaata tatatgtaga attctttcag caatgtaatt aaaatttgtg   16500
tgggtttctt tatgtatata tacctaaaat tacgttttta cagaggaaaa ataataacca   16560
```

```
agcatgcatc caattggcac tgtgaataag aagagagcag aaacagatct ataaaatctt   16620
caaatgttgc aaatatcaga tggatttaaa acaatcactg ttaaatttaa agaattggag   16680
acaaacttga agaacaaaag actcttataa agtgacttag ggccaggcac ggtggctcac   16740
gcctgtaatc ccagcacttt gggaggccaa ggcaggcgga tcacctgagg tcaggagttc   16800
aagaccagcc tggccaacat ggtgaaactt tgtctctact aaaaatacaa agattagcca   16860
cgtgtggtga ggtgcacctg taatcccagc tgctcaggag gctgaggtgg gagaatcact   16920
tgaacctggg aggtggagat tgtagtgagc cgagatggca ccactgcact ccagcctggc   16980
ctataagagt gaaactgtgt ctcaaaaaaa aaaaaagtt actttggttc atgcctgtaa   17040
tcccaatact ttgggagact gaggtgggag ggtcacttga ggccaggaat ttgggacccg   17100
cttgagccca ggagtttgag gctgcagtga tgtatgattg tgccacactg cactccagcc   17160
taggcaacag aatgagaaac tgtctcaaat aaaggaaaaa aaatggctgg gcacggtggc   17220
ttatgcctgt aatcccagca ctttgggagg ctgaggccga cagatcacga ggtcaggaga   17280
ttgagaccat cctggctaac acagtgaaac cccacctcta ctaaaagtac aaaaaattag   17340
ctgggcatgg tggcaggcac ctgtagtccc agctattcgg gaggctgagg caggagaatg   17400
gcgtgaaact gggaggtgga gcttgcagtg agctgagatc gcaccactgc actccagcct   17460
gggtggcagt gcaagactct gtctcaaaaa agaaaggggg gggaaaaacc caacttaata   17520
gatttgcaaa aaaccaaata gaaattccag aagtgaacac tttaccaaat atacctaaga   17580
gattatgcct agctgaagaa agagttcatt gcctgggaga caaggcagaa gaaactgttt   17640
agagtgtagc acagaataaa aaagaaaata ttgaagagag gtaaagagac atggaagaca   17700
gaataagatc taatttcttt aatcagagct ctggaaagag aggagaaaga atggtacaga   17760
agtaatattt caaagatat ttctggctga aaattttata gatccaatga gaaaccagtt   17820
gattgattta agaaggttaa tgaatttcta gcaatataaa tagaaatcta cacccagaca   17880
aatcatagga aaactgcata aacccagata caaggagaaa agtcttgaaa gtagccagag   17940
agaaaaaaag atgttttca aagaagcaac tatggactga tggttgactt tcaatagaa   18000 aattacatat attctcaaaa taactgccaa tctagaattc tgtaattagc aaagaattat   18060
ccctctacaa tgagggtaaa atacttagtt gaacaaactc catcagctct ttctaaagga   18120
aattatgaag tatacattaa tacttaaggc agaaagattc tagataaaag tctgaggtgc   18180
aaaatggaat aaagagcaaa gagagtggca aatatgtgga tgtattaaaa gaaacgttga   18240
ctgtataaag tactagtaag accttaatta aaatatgtga caagaagctg ggcatggtac   18300
tttgagaggc tgaggcgggc agattgcctg agcccaggaa tttgagacca gcctgggcaa   18360
catagtgaaa tcccgtctct acaaataata taaaaattag ctgggtgtgg tggtgcatgc   18420
ccatagcccc agctactcag gtggctgagg tgagaggatc gcttgagccc aggaggttga   18480
ggctgcagtg atccttggtc gtgccactgc acaccagcct gggcaacaga ctgagaccct   18540
gtctcaaaaa aaatatatga caggcgaagg ccgggttcta agacctttgt attgtcagag   18600
agaaaggtag aaagtattaa ttgacttgac cttgataaat tatatgtttt aatttctttt   18660
tttttttttt ttttttgag acggagtctc gctctgttgc ccaggctgga gtgcagtggc   18720
gggatctcgg ctcactgcaa gctccgcctc ccgggttcac gccattctcc tgcctcagcc   18780
tcccaagtag ctgggactac aggcgcccgc cactacgccc ggctaatttt ttgtattttt   18840
agtagagacg gggtttcacc gttttagccg ggatggtctc gatctcctga cctcgtgatc   18900
cgcccgcctc ggcctcccaa agtgctggga ttacaggcgt gagccaccgc gcccggccta   18960
```

```
tgttttaatt tctaagttat cttctaaaaa tgtagaaacc agacttttaa cttctcaacc   19020
aacagaagat aacaaatgat taataaaaat taatcctgaa gaagtgaaga aaagaaagaa   19080
ccagtaggac aagtagcaca aagatgggta gatttaaatc taaacatatc accagctaca   19140
ttaaatacaa aatggattaa attattcagt taaaagccaa agattgttac actgaatttc   19200
caaaaaaatt cagttatatg gggtttataa ggaacatatc tgaaacctaa gaataaagaa   19260
gatcaaaagt aatcatcaca ataagacata ccatgcatat tctagcagac agtatggtac   19320
agttaatatc aaaggtggac agtaaggcag aaagcattat tggcagaaga gtcacctcaa   19380
atgataaaat gaccaattca ctgtgaagat ttaatagcct tagtaatata gtataacctg   19440
aaatatagct ttagaatatt tatagcaaaa gttaaacaaa actacaagaa atagacagat   19500
ttctcagtct taatggggta ttttttaaaca gctctttaag taactggtat aagaagcaga   19560
caggttagtt aggatataaa atatttgtat aacacaatga acaagtttaa cccagtgggt   19620
gtatagaacc cattctaccc aacagtggca ggctacacat tcttttcaag catgtaggat   19680
tttgggggga aaattgactg agtaataatg ttgtaaaaca agtttcaaca aatttcaaag   19740
gattgaaacc aaaaaagcat tttttttctgt ccatttttcat taaagatctc tatcaatagg   19800
gtaattttta aagcttcatg ttagaaattg agcaactatt aatacttgga aataatctgg   19860
tcaggcgcag tggctcacac ctgtaatccc agcactttgg gaggccgagg caggcggatc   19920
acgagggctg gagttcgaga ccagcctggc caacatggtg aaaccccgtc tctactaaaa   19980
atataaaaat tagctgggcg tggtggtgca tgcctgtagt cccagctact gggaggctg    20040 agacagaaga attgcttgaa cccaggaggc agaggttgca gtgagccgag atcgtgccat   20100
tgcactccag tctgagagag cgagactccc tctaaaaaaa ataataatcc atgcatcaaa   20160
gaagaaatca caatggaagt tagaaaatac cttgaactag atgattaaaa attttttgatt   20220 gatcaaattc cacaacttga tatatcttag accattgaaa gtgagagaat caaatgttat   20280
gtctttagat acgaagtttc ttgacacccc tccctgcctc ccccaaaaaa gaaatacccta  20340 ccacctatga aagattcttg attggaaaaa aaaaaaataa ctgagctgga gtttcattaa   20400
acttctagat ctactgggaa attcacagtc atttgatctt tcaatgagtc ataattgttt   20460
tgctgtggat ggtcttgcct cgatgttgat ggctgctggt tcatccctgg tggttactga   20520
aggataggat ggctatgcca gtttcttaag acaacagtga ggtttgcgac atcagttgac   20580
ttcttttcac aaaagatttc tctgtaccag gcgatgcttt ctggtagcat ttgaaccaca   20640
gtagaactgc ttttaaaatt agagtcagtc ctctcagatc tgccagtgct tcatcaacta   20700
attctatgta atattctaaa tcctttgctg tcatttttaac agtgtttgct cacagcatct   20760
tcagcaagag tagagttcat gtcaagaaac cacttttttt actcatccat aagaagtaac   20820
ttcccatttg ttcaaattc atcatgatat tgtagcaatt cagtcacatc tttaggttcc    20880
actcctaaat gtagttcttc tgctgcttct actacaccta cagttccttc ctccattgaa   20940
gttttgaact caaagtcatc catgagggtt agaatcaact tcttccaaac tcctgttaat   21000
gttgccagtt ttacctcctc ccatgaatta caaatgttct ttatggcatc gagaaaggtg   21060
aattctttgc agaaggcttt caattaatgt tgcccagatc catcagagta ataacgatat   21120
ctatggcggc tatagcccaa tgaaaggtac ttcttaaata aggaatgttg aaagtcacaa   21180
ttacttcttg atccatgggt tgcaagattt atgtgttagc aggtgagaaa acgttcatct   21240
tcttgtagct ctccatcaga gctcttgggt gaccaggcac attgtcaatg agtagtaatg   21300
```

```
tgttagaagg aatctttttt tctgagcggt gggtctcaac agtgggctta aaatattcag    21360
caaactatgt tgtaaaagaa tatgctgtca tccaggcttc attgttccat ttacagagca    21420
cagacagtaa attttgcaga attccaaagg ccctaggatt tttggaatga taaatgagca    21480
ttggcttcaa cttaaagtca ccagctgcat tagcctctaa taagagtcat cgtgtcctag    21540
gccaggcgtg gtggctcatg cctgtaatcc cagcactttg ggaggccgag gtgggcggat    21600
cacctgaggc cgggagttca agaccagcct ggccaacatg gagaaaccct gtctctacta    21660
aaaaaataca aaattagcca ggcatggtgg cacatgcctg taatcccagg tactcaggag    21720
gctgaggcag gagaatcgct tgaacccggg aggcagaggt tgcggtgagc cgagatcatg    21780
ccattgtact ccagcctagg caaaaagagc gaaactccat ctcaaaaaaa aaaaaaaaa     21840 aaaagtcatc ctgtcctttg aagctttgaa gccaaccatt gacttaggga aatgttgtgg    21900
ctggtttgat cttctatcca gatcactaaa actttcttta tatcagcaac taggttgttt    21960
tgcttgcttg cttttcttaa actatttttc ttttaattct tagagggtct cactgtgttg    22020
gctaggctgg tctcaaactc ctggcctcaa gcaatcctcc caccttggcc tctgaaaatg    22080
ctgggattat aggcatgagc cgtagtgccc ggcctgtttt gctttcttat cattcatgta    22140
ttcactggag tagtgcttgt agtttccttc aaaaactctg cctttgcatt tacaatctgg    22200
ctgtttggta caagaggcct gccttcaac atgccttctt cactaagctt aatcatttct     22260
agcttttgat ttcaagagag agacatgtga ctcttggttt cacttgaaca cttagaagtc    22320
attgtagggt ttttaattgg cctaatttca atattgaaat ctcagggaat aggaggccca    22380
agaaggggtt agggcagtag ctggtcagtg gagcagtgag aacacacaca acatttactg    22440
aagaagttca ctgccttata tgggtgtggt tcgtggcacc ccaaaagaat tacaatagta    22500
acatcgaaga tcatagaaca ctaaaataga cagcataata atgcagaagt ttgaaatact    22560
atgagaatta ctgaaatgtg acagagacat gaagtgagca tatgctgttg gaaaaatggt    22620
gccaacagat ttgctcgatg ctgggttgcc accaaccttc agtttgtaaa aaacaaacaa    22680
aaaccattat ccgctaagag cagtaaagca aagcacaata tgatgaagca tgcctgtaca    22740
gtttatactt cacagtcatt ggttaaattt actcattcct ttaagcataa aaaataaata    22800
tttagcacct ttgtgctgag ttgtatgcta ggcactggga tatagaaatg aatgatagtt    22860
tgtcttcaag gagcttacag ttaagtggta gaagtagata aataaagaat taaggacagt    22920
gtactgtgat gaaagtgtgc cccagatgca gaagaatcac agaaaaggag cacaattcaa    22980
tatgctttta ggggatggaa gacagatttc ctaggaaagg agatacttaa actgaatttt    23040
aaatacttca gatatacaaa atctttataa agaagagtaa ttaaaccttt tttagagaca    23100
gaccacctaa ataaatggta cataccctgt actgagtgtg gattggaaga ctgagtatgt    23160
taaaaatgtt agtatttctc aaattgatag tggatttatt gaaatccaaa tgcaaattcc    23220
tgtaggtttt tctatggaac ctaacaacct gattcaacaa tttctgtgga agctttaaag    23280
aggcaagaat agccaaaata tactttaaaa acaataaggt aggaagactt ctttaattcc    23340
tttttccact cggcaaattt ttaatgctct atggtaggca ctgctcatcc tggttattac    23400
ctttgtgaat gtgagatctg gctcccaccc aaagctcaca ttcagatcca cttgtagtgg    23460
tatctagggt tttgaataga acacttcctg aaatacaggt taagtactgg gactaccaac    23520
aaacaaactt acaacactaa ttttattatc tcatatttgt atttacaatt tttcttgatc    23580 atatttttc atacaaactt taattagttt ctattaattt cttttaacat aggaagctta    23640
gaaatagaca cactttgctt ataatagatc tttaatatta tgtcagttgg actatggctt    23700
```

```
tgttagaaaa ggagaggaga atctactgct gagtgctgtc caaagagcag ttacccaact   23760
gagcagagag ggaggatgac cttgagggtc tcacaggcat gggttttag gcccagcctg    23820 tggagcgtct gagggactta taaaaggaaa agggacccag gtgcagtggc tcatggctgt    23880
aatctcagca ctttgggagg ccaaggcggt tggatcactt gaggccagga gttcgagacc    23940
agcctggcca acatggtgaa accccgtctc tactaaaaat accaaaatta gctggctgtg    24000
atggtgcacg cctgtaatcc caggtactcg ggaggttgag gcccaagaat cacttgaatc    24060
cgggaggtga aggttgtggt gagctgagat tgtgccattg cattctagcc tgggcaacag    24120
agcaagactc agtcttaaaa acaaacaaac aagcaaacag aaaacaacag aaagaggaga    24180
tgaataacaa aatggcaggt aatactaaat aatatggatg aattttatat tcttacatat    24240
gggtaggtgg agggacacct gctcttgtgg cagattagtt gggaaaggat acacttgctg    24300
gaacaatgcc taccatatta ataaatgaa gctagacttc cccatctgtt atgcataaaa     24360
atcaatttct tgtaggttaa agattcaata caaaagggga aaccctgaaa gcttttagaa    24420
aaataaaggg acattattta aggcagagaa gaatttctta agactcaaaa aactagccat    24480
aaaaaatgga caaatttgac tacattgaaa atagaaactt ttttcattaa gccccattaa    24540
gacactcaaa aggcaaggca aggaatagaa gatacttata acacacacta ttagttatct    24600
attgttgtgt aattaccgaa gacttagcag tttgaaataa catttctctc acagttctgt    24660
gggtcaggaa actgagagtg gcttaattgg atgtttctgg cttagggcct tgaggctgta    24720
atcagtcaat ggctgcagtc atttgaaggc ttgactgctt tgtgctccct catgtggatg    24780
tagcaggcct cagagctggc tttctagaag ggagtaagag aaaacaccca agatggaaac    24840
cacagtattt tagtcttgga agtggcaccc catcacttct gccatattct ttttgttaga    24900
agcaaggcaa taactccagc ttacattcaa ggggagtttg tacaaggcac caccaggagg    24960
gtgaggatca ttgggagcca gtttagaggc tacctactac aacatgtaaa gaatgaactg    25020
gtatgaaaaa tatacataaa aaattcctat agatttctaa gacaaagaca gaacaccaaa    25080
ttggaaaaag ggcaaaaaat cctgagcagg catttgaatt aaaaaaaaat ttaaatgatt    25140
aataaacata tgaaatgacc cttaatctag ttaacaatta gggaaataga aattaaaacc    25200
acaatgagag accatttcat atagattggc agaaatgaaa aaatctgaca atattaaatg    25260
ttggtgaggc tatgaagcag tctgaactgt cttccactga tggatgggaa tgtaaattgg    25320
ggggaaaaat cctttggaaa ataataggat atcctataac cagcaatacc actcactctt    25380
aggcgtttgc cctagactaa tggttcttga gtatgcatca aagtcatctg gagggcttgt    25440
taaacccagc tgttggggct acccttagag tttctgatta agtaggaatt gggtggagcc    25500
tgatagtttg ctttgcattt ttaacaagtt cctgccggga gtgggctgag gggtgggggg    25560
gtgggatgtt ggtgctgctt gtccaggaat catactttga gagtcagcca ttgctttaga    25620
catagagaaa tgtgtgaata tatgaagtag gaagcatata tataagattg ctcataacag    25680
tattattcat attaaccca agatagaaaa aaagttcaag tatcctcagt agtgcagtag     25740
atatcattgt gtgtttactt atggaacaaa aaactagttc aaatagctaa ggaaaaaaac    25800
cacactacaa acagctcctg cctgcatcaa tatgtatgaa tctcacaaat acattagtca    25860
taccttagaa ccaagtcaca aaagattaag tgcaacatga ttctattcgt aaacagttta    25920
aaaacaaatg cagttaactg tattgtttag gaatacaaat ataggtacta gaattataag    25980
tagagatact agaattataa gaaaaatcaa gggaataatg atgataaaag tgagtgatag    26040
```

```
tgactacctc agggaggaga gaaagtggat gtgattaagg acaaatggga gacttttaag   26100
ataattggca atgctatttc ttaccttggg ttgtggggtt tgctttacag ttatgcttta   26160
atggaacgat gttttgcaaa cttctctaca tagctttata ataaagggaa aatttatctc   26220
atttaatttt catctctgat tactagtgag gttgagtatg ttttcatatg ttagcctttg   26280
ggttttttct taaattgttt atagacatgc catttgtaga ttatgctatt tgttttttaga  26340 acttatttt aggtattctg ttatggatag tcttctttat ccatcatatg tcaaatattt    26400
ccttctagtc cttttttatt tgtatttta tttattttta tttcttttt aagaggcagg     26460 cctcccactc tattgaggcc taggctatgg atagtcttct ttatccatca tgtcaaatat   26520
ttccttctag tccttttta tttgtatttt tatttattta ttttttaag aggcaagcct     26580 cccactcttt tgagacccag gctggagtgc agtagtgtga tcatagctca ctgcagcctc   26640
ctgggctcaa gcagtcttct agcctcagcc taagtaactg gacaaatgc acaccactgt    26700 gcccaactaa tttgaaaaag aaaaaatttg tagagatgga gtcttgctgt gttgcccagg   26760
ctggtctcga ctcctggctt caagtgattc tcccaccttg gcctcccaaa gtgctgggat   26820
tacagacgtg agacactgtt cctgccctag cctttcctta taaagacata tgttgttgtt   26880
actgtttatg tggtcagatt tagcagtctt ttcatttatt tatttatttt gattttgatt   26940
ttgatttttt taagaaatct ttcctggctg ggcgcggtgg ctcacacctg tcatcccagc   27000
actttgggag gccaaggtga gcagatcatg aggtcaagag attgagacca tcctggcatg   27060
gatgaaacat ggtgaaaccc catctctact aaaaatacaa aaattagctg gacgtggtgg   27120
tgtgtgcctg tagtcccaga tactcgatag cctgaggcag gagaattgct tgaacccggg   27180
aggcagaggt tgcatgagct gagattgtgc cactgcactc cagcctggcg acagagcaag   27240
actctgtctc aaaaaaaaaa aaaaaaaaa agaaaaaaga aatctttcct atccagagtt    27300
aaaagcatat tctctatatt gtcttctgat aaattgaaaa ttttaaaaat tttgtttagg   27360
tatttaagca gtctagtatt tgttatatga agatgtcttg ggggatgtta ttttcccaac   27420
accatttgta catatgtgca cagtcttttt ctcacttatt tgtaaagcaa cctctcattt   27480
ctaccagatt cccatggacc gatttctggg ctacttctta acctgtttgt ctataacctg   27540
tttgtccaca ttactacttt atatctttgg ttttggtaat gccagtctct tctctttgtt   27600
tatttgcggc aaacatatgc tcattcactc ttccacgtga ccattagaag aattagattg   27660
tcaatgtcct ctaagtctag gtatttggtt aaaaaaaaaa aaaagaatt aggttgtcaa    27720 attctgtaaa aagtactatt gggattttca ttgtgattgc attaagttta tatgttaatg   27780
tagggacata tatattagag atttattatg atactgagtt ttccaattca tgaacatggt   27840
ttttatcttc atttgtttat aggtctcttc cccccccacc cctttttttt tttttttttt   27900
tgagatggag tctcgctctg tcacccaggc tggagcacag tggcacaatc ttggcttatt   27960
gcagtctctg cctcccatgt tcaagcagtt ctcctctcag ccttccgagt agctgggact   28020
ataggtgcac accaccatgc ccggcttatt tttgtatttt cagtagagac ggagtttcac   28080
catattggtc aggctggtct cgaactcctg acctcaggtg atccacctgc ctcggcctcc   28140
caaagtgctg ggattacaga cgtgagccac cgcgcctggg ccatgtgttt ctattttag    28200 tagagacagg atttcaccat gttggccagg ctggtctcaa actcttgacc tcaggtgatc   28260
cacccgcctc agcctcccaa cgtgttggga ttacaggtgt gagccactac tcccagctct   28320
gttttttttt ccttaaaagg tttatagttt tctacataat gttttcatcc ttttggatgt   28380
ggaggattgg tattatttgc gagaatcttt ttgtgctgtt gtgaatgaga tgtttagaaa   28440
```

```
aaaatatatt tttttactgg atattcatat acagaagaat gaaactagac ccccacctct   28500
caccctatac aaaaatcaac tcaaaatgga tcaaagacct acctgtaaga cccaaaacta   28560
caaggtgaaa ccacagtgtg gtatcatctg gccccaggta ggatggctgc tataaaactg   28620
tagaagactt gggaaatgca aatcaaaacc acagtgaggg attgtctcat cccagttagg   28680
gtggctgtta taaaaagac aaaaaattaa aaatgctggt gaagatacag aggaaagaga    28740
actcttggac gctcttggtg ggaatgtaaa ctagtacaga cactgtatca gtatggaggt   28800
tcctgtgatc tagcaatccc actactggcc gtttacccaa aggaagggaa gtcagtacgt   28860
cgaagagaca tttgcatccc catgtttact gcagcacact attcacagta gccaagatat   28920
ggaatcagtt caacaacaga agattgggta aagacaatgt ggttgtatag catccgatgg   28980
aatgctattc agccgtaaaa aggaaaaatc ctgtcatttg cagcaacatg attggaactg   29040
gaggacatca cgttaagtga aataagccag caaaagaaag ttaaaccctg catgttctca   29100
ctcttatgtg gaagctaaaa agagttgatt tcatagaagt aaaaagtata acagaggata   29160
ctcgggctgg gaatagtagg ggtagagtgg aagctctggg gagatttatt catggataca   29220
aaattacagc tagataggag gaataagttc tagtgttctg tagtagtata gggtgactat   29280
agttaataat atatagtttc atatagctag gaggaggata ttgaatattc ccaacacaaa   29340
gaaatgacga atgtttctcc tgtctttagt gagaatgctt ctgttatgct tggtgactta   29400 cagactttt atagataccc tatatgaagt ttaagaatgt ttcttccatt tctagtttgc    29460
tgacagttgg gcattttta aaatcctaaa tggttgttga atttgttag atttttcg      29520 tacatttatt gaggtgatca tgttttttc ctacattgat ctatttaggt aagtaattgt   29580
attggtagac ttcctagttt tgagtaagca actcttgtgt cactggatac attttattgt  29640
atattctttt aattgattgt tgaattaggt ttgcctaatt caggttttta tttagggatt   29700
ttacgactgt gtttacaagt gagctcagtc tatacctctc tgagctgttc catggttttg  29760
gtatcaagag ctgattcgtt ttctagagtt ttctgtgatt ttggccagtt tttatatcag  29820
accaaagaaa atgtttctcg aaagtaagtt cattaggctt taagtaacca ctgggcccat   29880
tctttgactt tcaacttttc tgagtgagtt ttagatgtgg atgttatata cagcatttgt   29940
tcagggcttt ggtttgtgag ctgagtttct tttttattt ttttaataga tgagcttatc    30000
tcatttatat tttgttgata aggcagttct tccacattat taattatatt tttctttggg  30060
ggctttgtct cttatgggta tgtgtgtgtt tcccatctaa tagtttttga tgatttttta  30120
taaatcttat tctcttacta ccttcataga tttaatatct gtaagcctcc atttcttgat  30180
ttgtgaaaat aatcaggact atttaactc cttgctaata aggtaagaa atcagtaca     30240 cttataccct cctttcccca gctaccatta aaaaatttt tttccatctc ttcatatgag   30300
atataaacct tgtcattgaa aaaaatgcat ttatttttta ctttatcctt aagtctcaga  30360
gttacatgtt tgaatgggat taatattcac ctttaattct ttaaaaccat gacttcttga  30420
tttctaattc tgttttattt atcttttcat cagcttgatt ttcctatcaa gtagttctgt  30480
tttttctgcc aagaatggct tccttttttc ttcttcagcc atttcttcct gtttccaccg  30540
tggccttcat ttctgaagtg gtcttttat taccttccat ttctttcttg aaccctgcta   30600
actcactttt catttcctat ttcttttttt tgagacaggg tctgggtctc tcactcaggc   30660
tggagtgcag tgttgtgatc ttggctcact gcaacctctg cctcctgggc tcaagccatc   30720
ctcccatctc ggcctctcaa ttagctggga ctacagacat gtgctaccac acctggctaa   30780
```

```
tttttttgcat ttttttgtag aggcagggtt tcatcatgtt gaccaggctg gtctcaaatt    30840
cgccttggcc tcccaaagtg ctgggattac aggagtgagc cactgcctcc tgcctcatct    30900
cccatttcat ctgttcttca attttgtttt ttcagtcatt ttttccccct aaaatgcatt    30960
tgatagtgat agatggggat atatcagaga cttcttttgt ttccttgact aacttctggt    31020
gtttatctgt ctttgcctat tatgtttctt ctctcatccc ccactccctg ttttattggt    31080
ggtgtggcgg gtggggttgt taacgtttct cctcatagac cctttgctgg attgtttctt    31140
tttattactc atccttgttg tctttgagta gagtacttct atttgagcct gctctttgct    31200
taagaatgtt atgggggggct gggcacagtg gctcacacct gtaatcacag cactttggga    31260
ggccgaggtg ggcagatcac gaggtcaaga gatcgagacc atcctggcta acatggtgaa    31320
accccgtctc cactgaaaat acaaaaaatt agccaggcat ggtggcgggc gcctgtagcc    31380
ctagctactc aggaggctga ggcaggagaa tggtgtgaac cctgggggca gagcttgcag    31440
tgagctgaga tcgcgccact gcactccagc ctgggtgaca gagcaagact ctgtctcaaa    31500
aaaaaaaaaa aagaatgtta tggggaacag cagggagaat aagcctaagc aggcataact    31560
tttttctcag acatcttgtc tcagaaagct cgttcaccaa atctgttgtg ttctctaccc    31620
tgggaataca tcactcctcc attttttaatg tcttttttttcc ccttcctgcc attttgggcc    31680
aagccaatca ttcagtcagg atgaagactc catccaggca ggagatgggt gaggctgata    31740
gtgaagttgg acatcaaata gattcctgtt cgatgatttg atttttaatt tgttctgctc    31800
agctgccttt agcttttaac cttttatatc ttatgttcaa tagttattct cacaaaggaa    31860
ctggttccca acataaattt aaaattaaaa gtgatcagtt ctctcctcta gcaaactgta    31920
actgctttta ttttatgtga cttgatctga tgtattgttt tgttccctgg atcatttagg    31980
ggtggggaag taaagacagg gaggtctgtg tttcacttta aaaacaaaat ctaaaccaga    32040
taaaaactcg taaaatgtca tatttcaggt cctctgtgat cttgccctt cctacctctc      32100 tacccctgcc cacgtctatc agccatcctt gctgtgtact aaatgctcta gcacagtatt    32160
tcctaaagtt tatattgtgg atactgaata ttcaaagtgt ctcccaaag ataggttcca     32220 tagtttacaa ttttgggaaa ctttaaatgt tcctccttgt ctaacctgtt gagttttctaa    32280 gctcaaatga ggggggatac tgtgttatct aaatcttatt tgatttctgt attttacata    32340
ttaagggatt catctaaaaa gtatctgaat tgatttggca agcaggtgat accctgtact    32400
atattatata gctcccсtttt tgggatttca taattggata ttagcatagt aatggttgag    32460
aagaactgta gtaaagaagc ttaccttttgt tgatttattt ttttttttg acacagattc    32520 tcgctctctc acccaggctg gagtgcagtg gcacaatctc ggctcactgc aacctccacc    32580
tcctgggctc aagcaattct gttacccttc caagtagttg ggactacagg tgtgtgccac    32640
cacacctggc taattgtttt taaatatttt tagtagagat ggggtttcac catgttggcc    32700
aggctggtct tgaactcctg acctcaaatg atccacctgc ctcggcctcc gaaagtgctg    32760
ggattacagc attagccact gcacctggcc ttacctttgt ctaaattaga attgtataaa    32820
cttccttgac tatggaacat tgcttgtgtg tagtatatgc taatattctt tgaaacattt    32880
tagggaaatg ctgtttaata ccaatcaaat ccttgcattt tttcagggtt gtttcctgtt    32940
gtttctggcc ctttgtccta gaatgctctc ttccttcatt ttctccatac cacccaattt    33000 ttttttttcaa tggtttctga ggtgatactt accctgctgg gaggcatttg gaaatatttt    33060
gattgtcatg cctggaggat gctatttggg atttaatgcc ctcaaatcga ggaacacaat    33120
gcactaaaag tcctacacag caaagaattg ccccacccaa aatgccactt ctacagtggc    33180
```

```
cctccatatc tgcaagttct gcatcctagg attcacccaa ctgcagatca aaagtattag    33240
gaaaacagta aaaagtaata caataataca aatacaagat aatacagtat aacaactatt    33300
tatataacat ttacattata ttagtcatta taagtaatct aaagatgatt taaagtatat    33360
ggaaagtaag ttatatgcaa ataccctccc tttttatata agagacttcc gcatccaagg    33420
atcatggtgt tgtagggtag agtcctggaa ccaatccctt gtggatatgg aggaatgact    33480
gtatactcct ttggagaaca ctgaactcag caacttttac tcatccttta gaatttagtt    33540
ctggttatct tttccaaaag ctttctctaa gtactttgt tttcccctct accccacacc     33600
ctctcatttt ctctgcgtgg tactctcaga gtattttagg cacatcttga ttatttgaag    33660
taaccacttt gtagtatagg agcctataac tgtatacctc tactgtactg tgagttcaaa    33720
tctttgaggg caaagacatt ttgtatcctt ggtatatgat atataattag tcttttaaaa    33780
agtgcatgtt acatgaatac attaataaat aagttgtact tttactttaa atcagaattg    33840
tggtatgact cttaaactgt tgcttagact gcattaataa tcttgtgcaa ttgtggaaaa    33900
taatctcatt ttactctcat aatagaaaat taaaatatgc ttccttttgc tcagatatgg    33960
gtgacagctg ttagagtagt gttttatttg ggttttgacc ttgcctgtac atcagaagca    34020
cctggagaac ttcagaaggt acagatgcct ggggccctgc accagaggtt ctggtttttg    34080
agggtgaggc cttggtatct ggattttaa aagcttccaa ggtgattttt aatctgaagt      34140
taagattgaa aagtcattta gtgagacact gatatgtagc attttgggaa gtcagtaaac    34200
ttaagagtga gaagttacta aatcattgaa gaacagtgaa aggagtaggg agttttagct    34260
tagaaaaaaa aaatctagat ggagtatgtg agttctctga gggctatagg aatttgtccg    34320
tcttgctcac cactgtatcc tcaactccta gcatgagcct gagcacatac agggatttgg    34380
tagatattta ttggctgaca agaatatg tatcattagg tgtttaaaag atagtcattg       34440
tagaaccaca gagattatcc ccaaaaaagt tttatagtaa taatgtgcca cttaattta     34500 tgattaaaaa taatgaactg gatatttaat tcatttatca tttcagttta ttatttactt    34560
tgtgccagtc actgaggatt ccatttgatt ctctggtcaa atctatgaag tttgtatcat    34620
tcaaataata gggctgtgtc aagaaactga cacttggggg ttaagtaatt tgcctaaggt    34680
tacaaagcta agtgacaaga gctggaattc ttaaagtctg tactcttaac tgctatgcct    34740
taccataagt cttcaccaca accctaagag ttagatatgg tttagaaagg ttatgcagct    34800
tgcctaaggg cacattgctt gagtggaaga tttgggactt ggacccagac attgtgacac    34860
tagagtccat gctgttaact gccatgctat tggaaccccc aaccccctcg cttcctattg    34920
tataatgtac aaccatctgt tttcatgaga ttattaacca cagtggacag cttgtgttgc    34980
tctccttata ccttttggca tcctcactga cttttgactg atgggttgaa tttggattat    35040
tgtcttgaat ctccttagta ccctgggctg tggtagtcct agaaaataaa acatttcttt    35100
actaggttct ttttcttcat ttctttttcc ttttagttag gatttaaat tagaatttta     35160 ataaacttgc ttgcattaat acactgatat ctgttagctt ctgttatttt aagtcggtag    35220
tctccagact taaaaatttt gttctctatc ataaaaaaaa tttgagcaca ttacccctag    35280
tagatatctg ttttatttat gctatatgtg tactactgaa gaaaatggta atattttaaa    35340
aaatatgaac ttgttagcat gaattttttt aaagctaagc taaaaatgaa gtgagtttaa    35400
aattatgaag ggttttgct gatgtttcaa gtttagctaa tgtttcaagt tacaacatac      35460
cattaggcca aggttcgtta ttataatagt gtgtacaaat tcatatttta agtagcctgg    35520
```

```
ataatttttt taaaatagct agtttcttgt cagaaattaa gtaacctgga taattttta    35580
aaagccagtt tcttgtcaga gattattaga ttagggtttc tcaacattgg cgctgttgat   35640
gttttgaaat ggatgtaatt cttgcttgta gggttatgat ctgcagttga gtgaatccta   35700
cgatgtagaa cttgcagata tggagggcca ctgtaaaagt ggcattttgg gtggggcaat   35760
aatactatgt attgtaggat gtttagcagc ttccgtggcc tctgctcaca agatgccagt   35820
agtaccccca agtagaaaca tcaaaaatgc cgggagacat ttccaaatgt cttgaggggc   35880
aaaattgctt ctggttaagg accactagat tagaattttt tttttttta agacggagtt    35940
ttgcttttgt tgcccaggct atagtgcaat ggcgcaatct cggcccactg caacctccac   36000
ctcccagatt caagcgattc tcttgccaca gcctcctgag tagctaggat tacaggtgcc   36060
cgccaccgca cccttctaat tttgtacttt tagtagagac agggtttctc cacgttggtc   36120
aggctggtct cgaactccca acctcaggtg atctcccgc ctcagcttcc agagtgctgg    36180
tattacaggt gtgagccact gcacccgcgc tagatcattg tttttatcct gtattatgga   36240
tgacaagcag cttgtagtag agtagggaaa gtgttaactt tgattttttc ccctctagca   36300
gcaataatgt tttcttcagt atgaagtttg agatctgttt gtaggaatta attttaagtc   36360
acttgtccat tctataaggt ttagttaaaa cttggtaaca taatccatac gtttacttaa   36420
atcaatatat gtgagtcata gtatgtcaca atgagataaa tgcaagagga gagccactgt   36480
caagtgttct gcagtatgga atgcccagcc ttcagcagac ctcttgacta tatgtgtcac   36540
atctctgata ctaaccctaa gttagggtgc ctgtgtaaat attaaatgct gaggccaggc   36600
acagtggctt acgcctgtga tcccagcact ttggaaggcc gaggtagacg gatcacaagg   36660
tcaggagatc aagaccatcc tgactaaaca cagtgaaacc ccgtctctat taaaaacgca   36720
aaaaattagc caggcatggt ggcatgtgcc tgtagtccca gctacttggg aggctgaggc   36780
aggagaatca cttgaaccca ggaggttgca gtgagctgaa atcatgccac tgcactctag   36840
cctggatgac aaagcgagac tctgtctcaa aaaaaaaaa aaaattaaac gagcatggtg    36900
gcatgcatct gtagtcccag ctacttgggt ggccaaggtg ggaggattgc ttgaacccaa   36960
aagtttgagc ctgcggtgag ctgtgatcac actactgcac tccagcctgg cacagagtg    37020
aaaccctaca tctcaaaaaa taaatattaa atgctgactt tttctaagtt tctagatgaa   37080
cacattaact aaataatgta gcctaccat atccccaaaa aagagtcttc ctatgggccc     37140
tcaggtgtat gtgcatacct atttgtaaa ccacttgttt gaccatcaca ttgtaactta    37200
ttgttcaatt tgtgtcactg cagccatatt acccaaaagg gaaagtaat tttagctctc    37260
tgaactgacc tccacctaac caactcatca ggttaactga tgttctccat ttcaaaaaat   37320
atttgcggtc agattaggtg tgaatcatat ttaaaggaag attgttggtc ctatatcaaa   37380
gattagagaa tgaatgttca ttttacagtt ttaagttaaa atgtttaagg acagtgttta   37440
ccattgcaca tgattccctg atttaactga ccttttcagt taactagcca ctagacataa   37500
ttacattgac tataggggct tcttttgtgc cacaccagtg ttggaattgt gttgatttac   37560
ttgtggagtt ggaactacag tttctctcag cagcctgctt atctggttgt ttaaacttgt   37620
agctgaatta ttatacaaag ttttcaaact ttctgttttg gaatggtcag ttactcaaaa   37680
ctgtggcttc ctccttgcta ccttacaggg tagttgtgag agtattcctc aacaatagtt   37740
cagactctca ttacttcttg tctataattg tagcatgctt ttaatgggat tccctgcctc   37800
cagtacctct ctggcttgtt ggttaacata acattattg ccagattaaa catcctaaag    37860
tataatgtgt aatcagatca aaagccattt ataacaataa aaactacatt aaaaaattac   37920
```

```
ttatgtcctg ggcttagatg tggtctctgc aatcagatgt tcattaaaca aattatttaa    37980
aaaatacata catacacaca cacgcaaatt ctgaattgtg atatgtgcca aaagaaaaaa    38040 tgggggtga tgtgagagct cagtgaggat caaatataga ttgggaagaa gggtgatgag     38100
gaaagacttc tttgagaaag tgagatttaa actatctgaa gaagctgtgc ttagtttaga    38160
aaagtgctag gcaaagagtg ttccaggaag aaggaatagc atgtgtgaag gctctgctct    38220
gctgctgaaa ttgtggttca gtttattgag tatggcatag aatgaatagt gcctgatgag    38280
gcaggaggta ggctgggatg agatcttttc agatcttgca ctctgtacta ggaagtttag    38340
gttgtattct gagttactgg ggagccatta aagggtttaa ggaaggggag tgttgtgaat    38400
cagttatgtg ttttgcagat tctactctga ctacagaatg gatgagagca gaatgggagt    38460
tagagcaaaa gaaatgagga aaccagttag aatgcctttg taagtagtag gtcagagaga    38520
aaggatgata attttgacta gagtcatgac agtaaacaag gtaacacatg aagtgattat    38580
gtcataaact attaccatta ccctgtgaag gaagtatgag cagaataaga tttagaataa    38640
acttattcca agcccatcta ataaagggtg gtgtgaggaa ctgaaacaat gggtgtttca    38700
ggacattcgg tccttgtctc taaaataaaa tccaaactct gttgaagatt tttcagccta    38760
ctcttattat ctttgtcttc tcctaaactc ttactcacct atgctataat cataccaaac    38820
tattacagtg agtatcatga acatttcctg taccttgatg ccactgatga ttgtttacta    38880
tggctggaat actcttactc ccacatacac ttaacaaaac cctactcatt gtttaggatc    38940
cagatcaaat atgaatgaag ccttccaaat ttgcctccag attgatattg cccatttatc    39000 ttctttttaac catagtagtt catattacta tcacattata gtatattatt caacagatgt    39060
ctatgtaatt gattatgtgc caggtactat gtgtagacat tatggatata tccacataca    39120
aaaatagaca cagttgccgc atttgtggaa actacattgt aacacagacc ttgaacaaaa    39180
tctgggcaca aatatgtaac taaatgttaa taagaggtat gaaggaatac ctgcaggttt    39240 ctgaaacccct aataaggccc ttgaggtcaa aattatttc ataatcctac taagatacta    39300
tttgcctttt cattctcgtt cttgtgagta tgtagtagtt ataggatgta tgatattcca    39360
acaaattgaa tacagaaggt gggagaatcc agatatcttt tgttaaggca gacattaaag    39420
aaattggcaa aaaaaaaatt tttttttta aagccacttt ggggccaggt gcggtggctc    39480
acacctgtaa tcccagcact ctgggagtct gaggtgggca gatcacttga ggtcaggagt    39540
tcaagaccag cctggccaac atgatgaaac ctcgtctta ccaaaaatat ggtagctggg    39600
tgtggtagca catgcctgta atccgtccct gtaatcggaa ggctgagagg cgggagaatc    39660
gcttgaacct gggaggccaa ggttgaagtg agctgagatc gtgccattgc actccagcct    39720
gggcgacaag agcaagactg tgtctcaaaa taaatgaata aataaacaaa caaataaata    39780
aataaataaa aatgaataag acactttgcc ctctcattgt ttttgttgt tttggaaaat     39840 gtggttattt ttttcattaa aaaatagatc acttttgtta attagttttt ttgtcatttt    39900
aaaatgaatt ttaaacattt cttggttata atttttaatg tggtaaatac tgatagcgat    39960
aaactacata gataaaagct ttctagggtc ctccataatt tttaagagta taaaggggcc    40020
aagtgtggtg gctaacacct gtaatcccaa cactttggga ggccaatgca ggaagatcca    40080
acatagcaag accctatctc tacaaaaaaa tttaaaaatt agccagacgt gatggtgtgt    40140
gcctgtagtc ctagttactt gggaggctga ggtgagagga tcacttgagc ccagagtttg    40200
agattgtggg gagctgtggt catgcactac attcctgcct gggctacaga gtgagaccct    40260
```

```
atctcaaaaa aaaaaattat atttttatac acacacacac acacacacac acacacacac   40320
acacacacac acacatatct tatatatata taagagatcc tgaaaccaaa atcagagtcc   40380
ctgtaatggg gagctgattt aaattggggg cttctggaga agtaaaagat atcttatgtc   40440
tctgttaaac acttatgttc ttctagaaat taggagtgtg gttttctccg tatttccaaa   40500
aactgcaagt cttttatat aacgagtgtg ttggttgaat ctaattttaa aaaaattt   40560 tttaatttaa aaattttta attttaaaa atatggagtg cttcatgaat ttgcatgcca   40620
ttcttaggca agggccatgc ctatcttctc tgtattattc caattttagt atatgtgctg   40680
ctgaagcaag caccaaattt tgttatcaaa gtctactgta gatggccgtt cttctttga   40740 tttgtggttt ggttgaaacc tttgttggaa ataccatctt atttcttatt actgtaggaa   40800
atagatctgg attcaaattc ctcttggtat gaagctggga agattactta acctgctaaa   40860
ccttaccatt atttatctgt aacatggaat acatattatc ttactgtggt gtaatgattt   40920
aatgaactaa tgtatgtgac ctgattcata agtgaccaga acagagacaa tccataaaat   40980
ggtaattctt tttattttat atacacagca catacatact ggggttagtt tcagttagtg   41040
agcagagagg tctgtggata aatcaggata taacaatcat cattcaagga tatattcacc   41100
attcaaacag tttatcagaa ggcagaaagc cagaatgatc tattgtgtat ggttattcat   41160
ctttagaaaa aggaacagaa agtgtgggct tagaatattt taaataagta gctctatgtt   41220
acaatgtaga tgatttaggg atggggtaga gttttatgtg tctggcacta cagcagtgcc   41280
tcacatttac taaatgtttg aataatatta attaactaga gattcttgaa aacacatttt   41340
tagaagcctt gaaaagtta tatacgacag attaaaggcc aagcctgaga aagcttacat   41400
ggctaactgg aaaaataaat aaaggtacca tagaggaaaa acaaaattgc cctgtgggga   41460
gaacatgtgg tgtcatatgg tgtgactaaa taggatccag taagataaga caaggtagag   41520
catcttggga gtgattccat gtttcaaggt taaaatgtta actacattaa aggtagtaaa   41580
ccagtgaaag aatcctcaag atcccagtgc agaatgtttg ccaagagata agaagatcaa   41640
ctgttttggt attcatagca gaaagccata ggaaaattat cttttgata ttctttttg   41700 aagaagatag gtcctttatt tatttattta tttatttatt tatttattta ctttatttta   41760
ttttattttt tgagatggag tttcgctctt gttcccagc tggagtgcag tggtgcaatc   41820
ttggctcact gcagcctccg cctcccaggt tcaagcaatt cttctgcctc agcctcctga   41880
gtagctggga ttgcaggcat gcaccaccat gcccagttaa ttttatttt tagtagagac   41940 ggggtttctt ctccatgttg gtcaggttgg tctccaactc ctgacctcag gtgatccacc   42000
cgcctcggcc tcccaaagtg ctggcattac aagcgtgagt caccgcgccc agccaaagat   42060
aggtcctttt ttaagacaga tacttagggc tgggtgctgt ggctcatgcc tgtaatccca   42120
gcactttggg aggccgaggc aggtagatca cctaaggtct ggtgttcaag accagcctga   42180
ccaatatggt gaaaccccaat ctctactaaa aatacaaaaa ttagctgggt gtggtggcgt   42240
gcgcctgtag tcccagctac ttgggtggca attcaaggag aattgcttga accccgggga   42300
ggcagaggtt gcagtgagcc gagatcgtgc ctctgccctc caacctgggt gacagagcaa   42360
gactccatct cacaaaaaaa aaaaaaaaa aaagatactt tgataaagaa ataatagtta   42420
tttctcattt tatttctcat ttgagatgaa ctcaaagttg gctaaagtga cacacagttt   42480
tggacctata acttgcttac attttaaata ttaggttggt gcaaaagtaa ttgtggtttt   42540 tgccaccccaa tagaaaggat tgtagacatt ttttatttg acaactgtaa agcattgcag   42600
gaattatatg tggaattata ggcttacttt gttttattgt gtttcatttt attgtactac   42660
```

```
acagataatg tggttttttt tacaaattga aggttggtgg cagccttaca tcaagcaagt   42720
ctgttagcgc cattttttcca acagcacatg ctcactttgt gtctctgtgt cacattttag   42780
taattcttgc aatatttcaa actttgtctg ttttggtgtt ctgtgatctt gcatgttact   42840
attgtaattg ttttggggtg ccacaaacca cacccataat aaggcagtga acttaatcag   42900
taaatattgt gtgtgatcta actgctccac tgactggctg ttcccccaac tcttctccag   42960
cctccgcatg ccctgagaca caacaatatt gaagttaggc caattaataa ctctacaatg   43020
gcctctaagt attcaagtga aaccaagagt cacatgtctc ttgaaatcaa aagctagaaa   43080
tgattaagct tagtgaagaa ggcatgtcaa aaagctatgc cttttgtgcc agacagctag   43140
gttgtgaatg taaaggcaaa attttggaag gaaactacaa gtgctactcc agtgaataca   43200
cgaatgataa gaaagcaaaa caggctcatg cctgtaatcc cagcactttt aagaggccaa   43260
ggtgggagga tcacttgagg ctaggagttc gagaccagcc tggccatcat agtgagacgt   43320
cgtctccatt cattttaaaa aagcaggcaa gcaaaacagc ctaattgctg agatggagaa   43380
agttttagtg atctggatag aatatcaaac cagccacaac atttccttaa gtcaatgaca   43440
ggctttaaag cttcaaagga caggctgact cttactagag gctaatgcag ctggtgactt   43500
taagttgaag tcagtgctca tttatcattc caaaaatcct agggcccttt ggaattctgc   43560
aaaatttact ctgtctgtgc tctgtaaatg gaacaatgaa gcctggatga cagcacattc   43620
ttttacagca tggtttactg aatattttaa gcccactgtt gagaccccct gctcagaaga   43680 aaaaagatc ccttccaaca tattactaat cgttgataat atacctgatc acccaagagc   43740
tctgatgatg tacaaggaag attaatgttc tcttctgttt tctatgtgtg tgtgcttttt   43800
ttgttttgag acagggtctc attcttgccc aggctggtgt gatcatagct ctctgcagcc   43860
ttgaacccct gagctcaagc aatcctcctg cctcagctgc ctgagtaggt gggactacag   43920
gcatgcacca ccatgcccag ctaatttttt ttttttttt aatagagaca gggtctatgt   43980
ttcccaggct agtctcacaa actcctggtc tcaagtgatc ctcttgcctc agtaatgttt   44040
ttcttaacca ctaacgcagc attcattctg cagcccatgg atcaaggagt aattttgact   44100
ttcaattctt cttatttaag aagtatcttt tattaggcta tagctgccat agatattcct   44160
atgatggatc tgggcaacat taattgaaaa ccttctgcaa attattcacc tttctagatg   44220
ccattaagaa tgtttgtgat tcatgagagg aggtcaaaat agcaccatta acaggagttt   44280
ggaagaagtt cattctaatg cttgtggatg actttgaggg gtcaaaactt caatggagga   44340
aggaattgcg ggtgtggtag aaatagcaaa ataactagaa ttagaagtgg atcctgaaga   44400
tgtgaccgaa ttgctacaat gtcatggtaa aacttgaaga aatgagaagt tgcttcttat   44460
agatgagcaa agaaagtgat ttttgagat ggggtttact cctgctgaag atgctgtgaa   44520
cactgataaa atgacagcaa aagatttaga attttacata aaattagttg atgaagcact   44580
ggcagatttg agaggactga ctccaagttt gaaagtagtt ctactgtggt tcagatgcta   44640
tcagaccata ttgcctggtt cagagaaatc ttttgtgaaa aaaagtcagt cggcacagca   44700
gacttcattg ttgtcttgtt ttaagaaatt gccggccggg cacggtagct tacacctgta   44760
atctcagcac tttgggagac caaggcaggc agatcacctg aggtcaggag atcaagacca   44820
gcctggacaa catggtgaaa ccccatctct actaaaaata caaaacttag caagtcgtgg   44880
tggcacgcac ctgtaatccc agctacttgg gaggctgagg caggagaatt gcttgaaccc   44940
aggaggcaga ggttgcagtg agccaaaatc acgccactgt actcccaccc tgggcgacag   45000
```

```
agcaagactc catcttaaaa aaaaaaaaaa gaaagaaatt gccacagtca ccctaacctt    45060
tagcaaccac tgacttgatc cggcagcagc catcaacact gaggcaagac ccaccaacac    45120
aaaaatgatg actccttgaa ggcccaggta attgttagtg gttttttaaca ctattttaaa    45180 attaagatat gtgcttttt tttttttttt ttttagaata atgctattgg acattactag    45240
actacattat agctacactt ttttgttgtt aatttaaaaa ttgtgggccg ggctcagtgg    45300
ctcacgtctg taatcccagc actttgggag gctgaggcag gcagatcaca aggtcaagag    45360
atcgaaacca tcctggccaa catggtgaaa ccccatctct actaagaata caaaaattag    45420
ctgggcgtgg tggtgcacgc ctgtagtctc agctactcgg gaggctgagg caggagactc    45480
ttttgaaccc gggaggcaga ggttgcagtg agcagagatc ccgccattgt actccagcct    45540
ggcaacagag caaacccta tctcaaaaat aaaataaaat aaattatggc caggcgtggt    45600
ggctcatgct tgtaatcctg gctctttggg aggccaaggc aggtggatca cttgaagtca    45660
ggagttcgag actagcctga ccaacatggt gaaaccacgt ctctactaaa aatacaaaaa    45720
aaattagctg gcatggtgg tgcatgcctg taatcccaac tgcttgggag gctaaggcag    45780
gagaatcgct taaacctggg aggtggaggt tgcagtgagc tgagatttgc gccactgcac    45840
tccagcctgg gtgacagagc aagactccgt ctcaaaggaa aaaaaatgg atacataatg    45900 attatatata tttctggggt acgtgtgata ttttgatata ggtatacagt gcgcaatgct    45960
gaagtcaagg tgattgggat acccatcacc ttaaacattt atctttgtgc tggaaacatt    46020
acagttctct tctagctatt ttgaaatata tgataaattg ttaactgtaa tttccctact    46080
atactgtgaa atactagaac ttactgtttc tgtccagttg tatgtttgta tccattaacc    46140
aacttcccct tatcccttcc tccctcctt tcttcccaga ctctgataac cactactcta    46200
ctgtctacct ccatgagatc ctttatgtat tctggatata gatcctaatt aaattcatga    46260
cttgcagcta ttttcttgca ttctgtaggt ttttttcact ttcttgagaa tattcattgc    46320
acaaaaggtt ttaattttgt tgaagaatga tttgtcagtt ttttttttgtt gctcgtactt    46380 ttggtgtcat atctaagaat ccattgctaa atccaaggtc attaagattt accccctatgt   46440 tttcttctga gagtttttatt attttagctc ctatatcatt tattcatttt gagggttttt    46500
aaaatatggt gtgaggtagg ggtggacatt tattgctata aattgtcctt tgagcattgc    46560
ttttgctgta tgccatcagt tttggtatgt gtgtttttt tgttttcatt tgtctaaaag    46620
tattttctaa ttttttcttgt gatttctttt tttgaccttg tatctatatt caagagggat    46680
attggtgtat aattttcttt tttgtacagt cttttgtatt agtgtaaagg tgatgctgga    46740
atcataaagt gagttggaaa ttacttactc cttttctgtt tcatggaagg tattttgtag    46800
aggtggtctt atgtcttctt taaataccctg atagaatttg ctactagaga tttattttta    46860
gaaaggtttt taactatgag tttaatttcc ttaatagtta caagagtgtt cagattatct    46920
gttttatctt gtgaatataa aagatatctt cagatatctt ttatcctgtg agagtttgt    46980 ttttctttgg tttttgagga attggttcat ttttttctaa cattttgaat ttatgtagag    47040
tttttcatag tattcttatt aacctttaaa tgtctgtgtg taggggagtc tgtagttcat    47100
tgttttttta ttactgatat tgttaatttg tgtcttccct ttttgtcagt cttgctagag    47160
atttgtaaat tgtattggtc ttttcaacaa acaagctttt gttttcaaca ttttttttctg   47220 ttttcaatct catggatttc tgcttttat tattttgtg ttgctttctt taggtttatt    47280
tagttcttca agtttcttaa gatagatttg caactgtttt tctttgctga tataaatagta    47340 tcagtttaag agcagggctt ggtggcacat gcctgtaatt ccagctattt gggaggctga    47400
```

```
ggtggtagca tcacttgagc ctaggagttt gaaactagat tgcgcaacat gcaagaccca   47460
cccccccccc catctcttaa aaaaactaaa aaaaaaataa tggcacaagc ttaatgatat   47520
taattcactg tagcactact gtatttgcat cccacagatt tagtatgctg tattttcatt   47580
cagttgaata ttgaactagc cttgtggtcc tgggattaac cttattgtca tgtttattat   47640 gcctttaca attgctggat tctgtatgct aatattttac taatgattat gaggaatatt   47700
agtatgtaat ttgggcttc catttgactc aaagattatt tagaaatgtg ctgtttaatt   47760
tccaggtgtt tggagatttt cctattaact ttctatttct agtttaattc tattatggtc   47820
agagaacaaa cgtttgtggt tttttttttaa gcttgtgaaa gtttgtctta tgactcagaa   47880
tatggtctgt tttggtgagt gttccatgtg catttgacaa gaacatgtat tcagctgtta   47940
agtagaatgt tatataaata tcaatcagat caggtggatt gatgatgttc atttcttcca   48000
tattcttact gattttctgt ctactagttc tattactgaa aggagtgctg aagtcatcaa   48060
atataattaa gaatttgttt tcctatttgt aatgttctgt aagttttac ttcatgttct   48120 ttgaagctcc attattaggt gcatatatat tagttatgct ttctattatg aaaattatat   48180
ttgaagtgaa ttactcgtag actacatata gttgggtcat tttaaaaatt cattctaaca   48240
atcttgtctt ttaatttgta tctatagact attcacattt aatgtaattt tggcatgttt   48300
agatttaggt ttaccagttt agtaatttgt tttctgttag ctgcttctgt tttccattac   48360
tctgtctttc ctgcattctt ttagattgtt tgaacaactt ttagccattc tgttttaatt   48420
tacctgttgt ggcttaaaaa ttcttaactc tccatatagt tttagtgatc actccagaga   48480
ttacattata aaaacttaac attttcacca cctgctttaa aataaattca tttctttaaa   48540
tggattatgg tccacttaaa gaaatgttaa aactacgtag gtctctttat cttctctcca   48600 cctttctct tattgttggc tgtatgttac gtttctatta attgaaagct tcattgggca   48660
atgctattgt ttttacttc aaccattaaa catatttaag gaaactaaga ggagagggtt   48720
aatgtatttt tgtctgcatg tttaccattt tgcttactcc tcaacctact cttccaggtt   48780
tccttccggt attatttccc ttctgtgtga ggaattctt ttagcaattc ttttagaaca   48840
ggtctgctgg tagcaaattc tcttagttcc catttatctg aaaatatctt tgttttatga   48900
ttgctctgaa agatacttta actggatata gaattctacc tttgatagtt tttttctctt   48960
tcagcacttt aaaatgtgta acttccttct ggccttcatg gttctgctg agaaacctgt   49020 tgtcatttga agtggtgttc ccctatattt tatggattgt ttttctctgt tttcaagata   49080 attttaggc tgggcgcagt ggctcccacc tgtaatccca gcactttgga aggccgaggc   49140
gggtggatca ccggaggtcg ggagttcgag accagcctgg ccaacatagt gaaaccctgt   49200
ctgtactaaa agtacaaaaa acttagccag gcgtgttcgc gggcacctat aatcccagct   49260
tctaggaagg ctgaggcagg aaaatcgctt gagcccggga ggcggaggtt gcattgagct   49320
gagatcacgc cattgtactc cagcctgggc gacagagcaa gatgctatct caaaaaataa   49380
tagtaatttt ttgtgtttca ttttcaacac tttatgatgt gtgagagtgt ggaattctac   49440
gtatttatcc attttggat tcaccgacct ttttgaatct gtagttttat gtcatttgtc   49500
agatttggga aggcttttga cattatttct tcagatattt ttaatcatcc tattctttgc   49560
ttttagaagt tcactgacac agatgttaga tcttttttgtt actgtcccat agatccctga   49620
tgtattactc tattcttgaa ttgctataaa gaaatgcctg agactaggta atttataaag   49680
aacagagatt cagttggctc atggttctgc ggactgtacg ggaaacatag cagattctgc   49740
```

```
ttctggggag gcctcaggaa acttaaaatc atggtgaaag gtgtaaaggg gaagcaggca    49800
tatctctcat ggctggagca gaagcaagag atggggaggg tgccacatac ttttaaatga    49860
ccagatctca taaaaactca ctatcacaat gacagcacta aggggggatgg tgttaagcca    49920 tgggaaaccg cttccatgat ccaattttct cccatcaggc cccacctcca acattgggga    49980
ttacatttga acatgagatt tgggtgggga catagattca aaccatatca cctggattct    50040
gttcatttta ttttaatccc cacagctaca tcaattggag acctggttct ctccctgctc    50100
tcagaatgtt ggctcttttg aagatcctat tgttgccgct gccaccatgg ggttacgtga    50160
gaaaagtgag gggaaaaaac tgagacacta tctttgaatg ttatttcttt gccttttttt    50220
tttttttttt ttactttttt tcttttaaaa agtaaacttt tttaggcca gtcgcggtgg    50280 ctcacgcctg taatcccagc actttgggag gccaaggcgg gcagatcaca aggtcaggag    50340
atcgaggcca tcctggccaa cgtgatgaaa ccccgtctct actgaaaata caaaaattag    50400
ctggacatgg tggcgcgtgc ctgtaatccc agctacccgg gaggctgagg caggagaatt    50460
gcttgaatca gggagttgga ggttgcagtg agttgaggtc gcgccactgc actccagtct    50520
ggcgacagtg agactccatt tcaaaaaaaa aaaaaaaaaa gtatgtaaaa tgtaaactca    50580
ctgatggttt catgatgatt cagatccttg tcctctatcc caatcgtcta ctgctattta    50640
cttccagtgt tgtcgattag ctgctctatg tgttctgtcc aagttttata gttggactaa    50700
atctttgaag tgtgttccca ccacccccgt aatgtgtgac tactaatatt tctgctcaat    50760
ttgttctttt tcccctcctt gttttttattt ttattcttgg cttcctaggg gttgctcctg    50820
tctttccata gcttaatgtc aagctaaaga tttgtcagag gttttgttca aatatttcaa    50880
ggccagtaag gtttctattc tttctttgtg tgtctatctg tgtatcaggg agtatattca    50940
aacttcaggc caccatgttg cctgacctgg cttttgcttt cctccgggct cctctgtgtc    51000
tcctgtgtgc atgaacatgc agaggctcag tcagtcaagg atgtgtggag gtgtgggccc    51060
tgtccagacc ctgtagcacg tgcttgcagt gtccgttcaa ctagtggagt gtggaaagtg    51120
tattaagccc ccaacttgca gtggaggtta tcacttaaat tcacagcact ccaaatcaat    51180
tgtcaacacc ctcacacaca cacagtctct agctgaacac atgccaacag agggagagat    51240
tggtcagtca tctgaagaag ggatggcagc agcctcaagc aaaaatgcca cagatggctg    51300
ggcatggtgg ctcacgcctc ttatttcagc actttgggag gccgaggcag atggatcacc    51360
tgaggtctgg agttcaagac cagcctggcc aacatggtga aaccctgtct gtactaaaga    51420
tacaaaaata gctaggcatg gtggtgcatg cctgtaattc cagctacctg gaaggctagg    51480
acaggagaat cgcttgaatc tgggaggcag aggttgcagt gagccgagat cgtgccattg    51540
cactccagcc tgggcgacga gcagaactct gtctcaaaaa aaaaaaaaa aaaaaaagc    51600 cacagactgt gatgttctta ctcaggttca gcctttagct gaagtccaga gcactgaaat    51660
ggttgttttg acggttttgt ccagctttat agttgctttt gggggagagg atttatcaat    51720
gtactcattt catcatgcca gaagtagtag tattgatatg atttttttata tatatcttag    51780 aattttgaag atactgtttt cttattttct agcatacaac aatctgattc ttgttttttta    51840 ttccttagaa ttttattggt actttcttat ttccttttga gttaactta gcaggatttg    51900 tttaattttg tatccctcca agcacccagg ctggagtgca gtggtacaat catggctcac    51960
cacagcctcc acctcatggg ctcaagtgat tcttcctctt tggcctcctg aatagctgga    52020
actacagaca catgccacca tacctggcta attttttattt ttttttattt ttggtagaga    52080
tgaggtctcg ctatgttgcc caggttggtc tcaagctcct gagctcaagc agtcctccca    52140
```

| | | | | |
|---|---|---|---|---|
| cctcaacctc | ccaaagtgct | gggcttacag | gcataagcca | ccatgcccag ctcttattct | 52200 |
| ttctttgtta | aaaaaggaac | tttggttctg | aagactctta | tttgccttttt ggctcaagga | 52260 |
| gaaattctta | aattttcttt | gttatttctt | cttcttattt | taattctcat aaaatttctc | 52320 |
| ttagatgtat | gtaggataat | ttaatctgta | ttctgggata | ttaactttac tctcataatt | 52380 |
| taagctttca | ttttacttca | tattttttt | ttaactttt | gttaaagtac catggacttt | 52440 |
| agctttgtcc | attttgctag | ttaactcctt | ttttaggttt | atttcaacag acattttaaa | 52500 |
| tttcaagctt | gttctgtgca | atttatttat | ttatttattt | atttattttg agatggagtt | 52560 |
| tcactcttgt | tgcccaggct | ggagtgcaat | ggtgcgatct | cggctcactg cagcctccac | 52620 |
| cttccagatt | caaatgattc | tcctgcttca | gcctcccaag | tagctgggac tgcaggcatg | 52680 |
| tgacaccaca | accggctaat | tttgtacttt | tagtggaaac | ggggttcacc atgttggtca | 52740 |
| ggctagtctc | gaactcctga | cttcaagtga | tccacctgcc | gcggcctccc aaagtgctag | 52800 |
| gattacaggc | atgagccacc | gtgtctggcc | tctgtgcaat | ttagtatttt tgttttcttt | 52860 |
| agtgagtgca | gctcctccat | aatagcacta | tatacaatat | aattttctgt gctatgcagt | 52920 |
| atattagcca | gtagctgcag | tggctgggaa | tgtggcctgt | gagagtgaga aactaaattt | 52980 |
| tatattttat | ttaatgttag | tttatataaa | attaaatagc | catacatgtc taatgattac | 53040 |
| tagattggac | agcacagctc | tacaatttaa | gaatccttat | acttttggc ttcaaaataa | 53100 |
| ttctgatgcc | ttagttcatc | tcctcattca | attgcatgtc | tgttttttat gctcttggtt | 53160 |
| tttttaggt | gtctaaaggt | taataaaggt | taaaaatatt | ggaagttaga gtaggtttcc | 53220 |
| tcaacactta | agtgagtttc | ttctggagaa | agtgaatatt | gaatataaaa atccattaat | 53280 |
| ttctagttct | actaagtgag | ctaggcagtc | cttgctttag | agaatatggg tacttcttct | 53340 |
| caatatgtgt | atgtgtgtag | cctctgtccc | tgtggtggcc | agaatttact ataattctgt | 53400 |
| ctctggccat | agtgtccaga | cagaaatccc | tgtaagctga | ttacccttttt ccaccaggtt | 53460 |
| tagatcagat | acaaatatat | gggggcaaag | actgagttac | tctttttttt ttttttttt | 53520 |
| ttttgagac | ggagtcttgc | tctgtccccc | aggctggagt | agtggcgcga tctcggctca | 53580 |
| ctgcaagctc | cgcctcccgg | attcacgcca | ttctcccgcg | tcaccctccc gagtacctgg | 53640 |
| tactacaggc | acgtgtcacc | atgcccagcc | aatttttttt | tgtatttttt tttgtatttt | 53700 |
| tagtagagac | agggcttcac | cgtgttagcc | aggatggtct | cgatctcctg accttgtggt | 53760 |
| ctgcccgcct | cagcctccca | aagtgctggg | attacgggcg | tgagccaccg cgcccagcca | 53820 |
| gactgagtta | ctcttgaaca | tgtgatttgc | atctaaacca | aatttgttaa aagtcttttt | 53880 |
| tttttttttt | tttaagtaag | aaaaggcagt | gattttgatt | tgtaatgtct tttgttagga | 53940 |
| gaagtaaaag | aaaaaaaatt | cttgaagaaa | agtgagccag | aattactgcc tagggagtga | 54000 |
| tagtcatgta | ggttcacaat | gaagtttaga | agtgctcttc | gtggttccgt ttcctctttt | 54060 |
| gctttagtgt | tcaggaaact | aaaaactgac | agtagactag | ttggaagata gactaggttt | 54120 |
| tttttttttt | tttctagtta | acctaagtca | gaagggtgat | atcactagag acttggaagt | 54180 |
| aaaaagagct | acctgcaaag | acttgaagta | ctaagattac | ctagaatctg aatgccctgt | 54240 |
| gttactctgc | agatagggca | ttttactgtt | atgaagagat | aagatctatt gtaaatagtc | 54300 |
| taaactaata | ataacgagta | agtatggaat | tggcgttttt | cctttaaagt tttagcatat | 54360 |
| aattttgaaa | tgtttaagaa | atattttga | aatgttctcta | tttttttaatt tctcttttag | 54420 |
| aagtcttatc | taaaataagc | atgtatatct | tacatgtaag | gaattattaa cttcattttt | 54480 |

| | |
|---|---|
| tcataaaaat aatcagagta agactttcaa cagatgtcag gatagctgaa gttctccatc | 54540 |
| actgtcatac gtttcactta tgacaggttt gtaatttctg ttagggaatg tcatctaagt | 54600 |
| gctctgcatc tggtattttc tcctgcaccc tcatgacaag aaaaaagcct ttgattattt | 54660 |
| ctcttttctc tctatttaca tgttcaccac tgccttccat gttcagatgt gatctacatg | 54720 |
| caatgatgat tactctttcc ttcctttccc ccttgccctc ttttatcgtc tttctttctt | 54780 |
| cctttttttg gttgaccctg tttaaatggg atctatcaaa tataccaagt ttcagtgaaa | 54840 |
| gttacttcct tgtgttaaaa gtcatgactt tctcttttat ttatacactt aataacttga | 54900 |
| ttatatatac ttgaattttg ttttagtgca gaataatttt ataatctttc tgaaggtatt | 54960 |
| ttaaagtggc agttaattcc aacatttgta ataccaacaa tgcagataac tgagttgaat | 55020 |
| gacaacagca tgaatagcct tgattaagtt gtacatgtgc agatagctac tgtgtatatc | 55080 |
| atgcctgcca tctggacaac agtgattttt ttttcttttt tttttttgt ttgagacaga | 55140 |
| gtctcagtct gctgcccaga ctggagtgca gtggcgtgat ttcggctcac cgcaacctct | 55200 |
| gtctcccagg ttcaagtgat tctcatgcct cagcctcctg agtagctgga attacgggtg | 55260 |
| tccgccacca tgcctggcta ttttttgtat ttttagtaga cggggtttt cgccatgttg | 55320 |
| gccaggtagg tctcgaattc ctgacctcaa gtgatctgcc taccttggcc tcccaaagtg | 55380 |
| ctgggattgc agacatgagt cactgtgcct ggtcagaaaa cagtgatttt taagatgtca | 55440 |
| tcaattgtat ggtagaatct gaattcaaag atgttaagaa ggggatgggg gaaaggtgtc | 55500 |
| tcttagaaca tgtaaaagaa catgttattt ctgtcaactt ccaaactttt atctccagcc | 55560 |
| acatctctta cttgatttca gatttgtata cccagctcct gttttacatc tccactctgg | 55620 |
| ttaatgtgcc tcccgggata ttttaaatat aatttttaat tctgcatcct atgccttgtc | 55680 |
| ctcccaacct cagtgttcct tcttcattct ttttgatttt tggctcttac atcctttgac | 55740 |
| ttaggttata aactgtagag tcgaggatga ctccctttta tcatacctca catccaattt | 55800 |
| accagcaaat cctattgact gtaccttat aatatattta gcatctgaca catcttatca | 55860 |
| tctcttccac tatcagtctg ataaaagcca ccatcatctt tcacttggcc atcatttccc | 55920 |
| atctggtttc ttggcattta cactatagtt catttccagt atagcagcca gagtaatact | 55980 |
| ttaaaaatat aattgatcat attgtttcct tttttttcaaa agtaacttca ttgagttcac | 56040 |
| ctaccataca aatcactcat ttaaagtgta cagtgcggag gttttagtgt attcagtgtg | 56100 |
| cacaacaacc atcaccaaat ttaattttag aatgttttca ttagccctaa aagaaacccc | 56160 |
| acacccttag ccattctccc ccaatcctta tattcccccc atttctaggc aatctaattt | 56220 |
| ctgtctctgt ggattttct attctggacc attttatata cgtggaatca tacactgtgt | 56280 |
| ggttttttgt gactgcttct tttacttagt gtaatgtttc caaggtttgg tcatgttata | 56340 |
| gaatgtatca gcattttgtt tctttttatt accaagtaaa attccactga atggatatgc | 56400 |
| gacattttat ttattcatca gctgatgaat gtttggactg ttttaacttt ttggctattg | 56460 |
| tgaataatgc tgttatgaat attcacaagt ttttgtgtct cctcctgctg tggactactg | 56520 |
| tttccctaac agaacgtatt aattttcttt tgtacaaaag ccactccaaa gcatagtgct | 56580 |
| taaaacaacc actgctgggg tcaatgagca cactatattc tgcactgcac taactttggc | 56640 |
| tgtgctcatt catgtctgtg accagtggtg gttttaggta gatggctagt ctaggatggt | 56700 |
| cttgagtgga caacttggtt ctagtaaact agtccaggca tgttctcata gaaaggcaca | 56760 |
| ggtgagagag tgagcaagtt caattgtaca agaggacaag acttgcatat ttgcatttta | 56820 |
| agcttctctt tgggtcatgt ttgctaatac tacattacaa ggtatcacaa gagcaaggag | 56880 |

```
aagcccaggg tcagaatgga aaggggattg cagagttacg ggtaaaagat gtgcctacag    56940
agaagccatt aattgggggt cattaatgct atgtctgttg cacataccaa ttttgcttct    57000
accttaatgc ttttttgcatt tgtttccctt ctgtttgaac tagttttctc ttacatacct   57060
gcatgctgaa cttgtttcac ttccttccta tctctgttca tgtatcatct taccaatgag    57120
accttcaagt tttaccatac tacaaaatga atagccaccc accccgatcc tgctcacagt    57180
ctctgttttt ctctataact ttttatgacc atctgacatt gtctgttttt tttttttagcg    57240 tttatcttcc cttaactaga atgtatgctc tatgaggtca gggactttag tttaattaca    57300
ctgtcttcat tgcctagaac cctggcactc attaaatatt tgttgaatga aaaattaatc    57360
tacattgatc cattttttacc taaattggaa ttatcttaaa gttctaaccct gccttcatgc   57420 tatggcatgt ataaagtgtc agtcttttga ttagaatacc taatgatgga atatttcttc    57480
tacttcttat agagacatag accatgcaat atatgagtaa ttctaccatt tacttagctg    57540
tctgacttgg gccaagtttt ttttaacctc cctgtttcct catctgtaaa ataggggtaa    57600
taatagtccc agcctcatgg agcctggcac aaggtaggca ctgtataagg ttggtgcaat    57660
gtgtattgca taatatttttt tatcacctac ttgttattgg agtatatggc acagggaaaa   57720
tggaattgaa agctggagca atcttatatt atggagaagt tgcaaaatct ttgaaaacta    57780
ttttttcaaa gggacaaagc acataaagca aatgaaatag gtgatttttt ttcattgaa     57840 tgcatcataa cattatatcc ttaaaacact gtcttacaaa gtgctctctg aaaaatactg    57900
ttctttattt cagggtttac gaaaaagtac ataaaactag tgagcataca tcttaactct    57960
ctgagagtct tataagtacc atcctagatg catggagaga agataattca ttacttacac    58020
taggtcatgc cttaggtcgt taagacttaa gtatctcatg gaaccccagt tgagaaagaa    58080
caaaaatata acatcttgac taaggtggct agtgcttctc tgatcttaac tattatttct   58140
ctagcctcag gtgagccttc ttgaatgtga tttcatcagt ctcctctaag cttacccaga    58200
atatagaatt tttaatattt tatatagcca gcacttataa actacctgct tcatgctagg    58260
tagtatactt aggtgctagg agtaaaaactg atcaagtggg gtaagttcca aattcacaga   58320
gcgcacagtc ctaacaggct gtcatgcctc agttgtttat ttgtgacagt gtttcccaca    58380
gacttttaat tttggaatga taggatgtgg tgctctggaa tggtgtccca gggttttgga    58440
gaactgagag taacctggga aagcaggtta cagtgagaga aagttatgac caggagttgt    58500
accaaaacgc aggaaacatg atatgtatat tgttatggtg cataaaaata cttacaatta    58560
aaagtcctga acctacacta catctattgt ttcacatatt ttccttcaat ttaaatcctg    58620
ctccaaatac agctcctttc cgaaaattca gttttatgtg acagaaattt gatctgtttc    58680
actgaaaacc catttgaata gtaattgtga gcaattgttg aatttgtaaa tgttacgtaa    58740
atttagtgga tgactttgtg gacagtttga cgttatggac agttattctt gatactgttt    58800
cccctccttt cccctgccat ccctgaaact ttagggctta atctgctttt aattagccag    58860
aaaaaaatgt ttgatcctct tattcagttt tagattattt tagatgattt ctaagttaaa    58920
ctctaagtta gaatagtttc tgcttattga tttcatgaat atcacttctc tatttctact    58980
tctcaccttc tgccaggcca aaggaattgt ggaactatga tcatcaaact cctaaatcat    59040
cagccttttc cttaaaagac ttaaaagggt tctatctatg tagacacttg tctggctcct    59100
gattacagtt ttaccattct caagtgatac tatttgtttc atcacagtcc acataattca    59160
gggtcaagat actattatga aatgactgta aaaattacta ataccctttgg ctctctaatt   59220
```

| | | | | |
|---|---|---|---|---|
| tttctctctt | ttcatcatat | gggcctgaca | aaatgcccgc | tacctgcctg | cacttaggca | 59280 |
| attgaatgta | gtgcttttaaa | tgtataccaa | aaccctcaac | agggcatcaa | caatgtctgg | 59340 |
| cagtgcagct | gcttcttcac | tttcccaatt | aaaaatgcgt | ttgctggctg | ggcgcagtgg | 59400 |
| ctcatgtgtg | taatcccagc | actttgggag | gccgaggcag | gtggatcact | tgaggccagg | 59460 |
| agttcaagac | caggctggcc | aacatggtga | aacccgtttt | ctactaaaaa | tacaaaaatt | 59520 |
| agctgggtgt | ggtggcgtgt | gcctgtaatc | tcagctactt | gggaggctga | ggcaggagaa | 59580 |
| tcgtttgagc | ccaggacgcg | gagtctgcgg | tgaaccaaca | tcgcactact | gctctctggc | 59640 |
| ctgggcaaca | gaatgagact | ctgtctcaga | aaaaaaaaaa | aaaattcatt | tcctccactc | 59700 |
| attgcaaacc | tctcacagct | cccactccta | tctgtggaat | tcacttcaaa | ctttactgag | 59760 |
| aaattaaatg | cagctcttgt | catcttttca | ccaccaattc | tacaaacttg | tctgcattgg | 59820 |
| tcctcttgtt | ctgtcttcct | ttcatttgtt | atcgaagacc | attcccgaca | gtctgatttc | 59880 |
| tctacttgtg | actcagattt | catctttcct | gcatctctgt | cttccatatc | attcttctcc | 59940 |
| cctcgattaa | attcccttta | gccacaaaca | tgctctatta | tctcccagcc | ccaatacatc | 60000 |
| tgcaaatgta | tgtaaatagg | aatgaccaaa | tatgtacaga | tatacaattc | ctacctttcc | 60060 |
| taatgtcttc | tagccactat | tatgtgttcc | tattcttatc | taataaattt | tcttaactga | 60120 |
| atattttttc | cttctacctc | agtgtctgtt | tctttctttt | cagccatttt | tggtttctct | 60180 |
| tgtaaatgtt | tatgatcccc | agggctgagc | cttcttggcc | tatactctct | tgtaggtctg | 60240 |
| cctcccagta | tgctagtgac | acccaaatat | gtcttcagcc | tcatctctcc | tccagggttc | 60300 |
| taaacttgca | taaccagctg | ccttcttgat | catttagtaa | gcctctcctg | ttggtgacat | 60360 |
| aatgcttgat | ttctctccct | catggcatca | ctgtccaccc | gttgcacaca | tcagaatttc | 60420 |
| agaatcagcc | ttaattctta | gttttttctc | actcttcctc | catgtctaat | ccagtagccc | 60480 |
| tatctccact | gttttcacct | tggtccaagc | aatcatctct | tgcttaacac | aaccatagtt | 60540 |
| tcaactagtc | ttcctccctg | cattcactct | tggcccaagc | aatcatctct | tgcttaacta | 60600 |
| tggttgctta | acacaatcat | agtttcaact | agtcttcctc | cctgcattca | ttcttggcgc | 60660 |
| accgtaatcc | attcttcact | agagtgataa | ttagaggtac | tataatatat | actgctctag | 60720 |
| agttatattg | tctagaattt | actagctgag | tggccttgag | caatatactt | aacacttatg | 60780 |
| ccacaatgtg | ctcgtctata | aaatgggatg | gtatatttat | ctgttctctg | attgctataa | 60840 |
| aggaatacct | gagactgggt | agtttataaa | gaaaagaggt | ttaattggct | cacggttctg | 60900 |
| caggctctac | agaaagcatg | atactggcat | ctgctcacct | tctggggagg | cctcaggaaa | 60960 |
| cttacagtca | tggcagaagg | caaagcagga | gcaggtgcgt | cttacatggc | aggagcaagg | 61020 |
| ggtaggggga | ggtgctacac | acttgtaaac | aatcagatct | tttgagaact | cactcatcaa | 61080 |
| aaggacagca | tcaagaggat | ggtgctaaac | cattcatgaa | agatccaccc | ccatgatcta | 61140 |
| gtcacctcca | accaggcccc | acctccaaca | ttggggatta | caatttgaca | tgagattggg | 61200 |
| tggggacaca | gattcaaacc | atatcagaag | taaattgtta | gtaaaatata | aatcagatta | 61260 |
| tgtcacacat | acctgttttt | gaaactttag | attctcattg | ctcttagaat | aaaattaaaa | 61320 |
| ctctacttac | cgtggctttc | aggatccttc | ataacctggc | atattgccta | attttttctga | 61380 |
| tacccatctt | gtttctactc | tccccttgct | taccatatag | ccacagtcac | tatctttaac | 61440 |
| tttctagttg | gaaacatggc | tttttgtggg | gtgtatttcc | ttttactttc | tattgttttg | 61500 |
| ggaccaactt | atttacgtca | gttttgtgtt | tgttttgtta | tatgtaaaaa | tagtgcctta | 61560 |
| aaaaatcagt | ttttttttttt | aacctggtga | atcatttgtt | ttatctttat | aaatgctggg | 61620 |

```
acgagaggcc tactcctttt ttccaatttt gtgagagatt ggtaaaattc ttagaagtgg    61680
aattgctagg tcaaaagata gaaatgtttt cagatggatg attcctattg aagtaaattt    61740
tttgagaact taacatgtcc aaaaaggttt tcatttgccc tcatgcttga ctggtagttt    61800
gcctggatgt aaaattccag attcacagtc atttttgccc agacagtgaa aacattattc    61860
tactatcttt taaaaaataa cagttttatt gaggcataat tcatatacca tactatgtgc    61920
aatttagtgg ttttttaatat attcatagag ttgtatagcc atcaccgcag tacattgtag    61980 aatatttta tcactcaaaa atgaaacccc tggatttatt agcagtcatt ctctgttccc    62040
accaatttgc ccaccccca gccttaagtc aacaagtaat ctactttccg tcttcattgt    62100
cttttaatgt tgctgatgaa aagtctgatg ccaaattaat tctagttata ggaagctttt    62160
agagttttcc gttttgaatt tctggaattt aattatgtaa actaggattt atgtagatat    62220
gagtctttta attcatccgc cttagcctca ctgagcccct ttactcagac cattggtgtt    62280
tttaactcca aatattttta gcataatctt tatttattct attttcttca tttagaactc    62340
ttactaaatg tattttgaac ttcccaaaca tattctttat atctcttcaa cttttttactt    62400 gtatcaccca tttctttctt tcttgctctc tcttttttaa cctctctacc ttctgggaca    62460
tttctttgtg ttacatatca ctactatgat ctttatcaat actacttctg ttatttaccc    62520
cttctcctca agtgttttct tagtaataat atttcagttt tctccttgcc catttattct    62580
gtttgttcat tgtgatcttt ttcttttcctc ccattggata ttcatagtgt cttgtgattc    62640
ttgtttattg aataaggact aaattgcaaa aaactttgca gttacatagg tctaggattc    62700
ttttctaaat gggaaatgac tacaagtgtc atgtattcat tgactggctt tcctccaggg    62760
tgcagggatt ttaagaggca ggcttaaggc caccccagtt accaaagtaa ggacagcttt    62820
actatgttta ttcctggaag gagctagctt acttacttag tatcctcctc cttcagtatc    62880
ttccctcttt ccctctcgcc ctcccacttt tcctttctac ttcaagtata tagtaaagtg    62940
tagggaataa tataataact atgtacctat tactcagttt tgttgaattg tcttatatat    63000
gcttcagatt tttataaaca aaaaaattat agacacagat atagcacctt acagtcttac    63060
tttgatactt ttctctgccc tttctgcctt ttcagaagta accattatcc tgaatttact    63120
gtttatcatg cccatgcaca tttcagatac ttttgctgtg ggtgtagatc cacaaacaat    63180
ctagaacgtt gattgcatgt ttttgtgaac cctgaaagaa ccaacccttt aaggcagatt    63240
ctgagtggct aacagtccaa attcaaaata gacccacgcg atcctttgca gacatgtaga    63300
gatcatatgt gtactccgca ttcctggaaa acctatacac ccagtaactt taggactttc    63360
atagctgtct gttcctattt atgccacctg aattaacagc taccagaaaa taccatttgg    63420
ccttttgtac ctaacaaaca ctctgtgacc tgcctcagcc aatcagaact gaacaagttt    63480
gcacccctca tttgtatagt ggaccagagt gggaacctga ctgtgaactt tctctgtaaa    63540
tgacaacccc ttttctttgt tctctcagaa ggcgccttta ttttctacca aggtacatct    63600
ccacggtttg caaactgttt gctggaataa agcctgtttc ttttttaaga aagaaaatct    63660
ttttctgtag attgttgaca ttttaaaagt tgtatatatc ctgaaacttg ctttttcatc    63720
aatattatgt ttttgagatg tattcatgtt gataaatata gcgctagctt tttgttttga    63780
cttaatatgt ggtattttgt tatacagatg taccagtttg ccatttttc tctcttaggg    63840 aacatttgag ttggttctag tttttttgcta ttataaacat tgctgcagtg aaaatgtctt    63900
gtacatatgt gaatataagt agctacatga taggatatgc tcatccttag ctttactcta    63960
```

```
gatattgcca gtttactttc aaatatttat attataccac atgtagaata tgatagtgtt    64020
tgttgctaca tgtacatgat taccaactct tgtattatta ggcccaattt ttttgcagtc    64080
tcactgattt ttcatatgta tgtatgtatt ttttgagaca aggtcttgct ctgttgccca    64140
ggtgggagtg caataatgca ttcctgtctt attgtagcct caaacttctg ggctcaggca    64200
atcctcccac ctcagcctct cagcctctgt tagctgggag tacaagtatg tggtaccgca    64260
tccaactaat tttctttttt ttctttttt tttttttttc tagagatggg gtcttgctat    64320
gttgcacagg tgctgggatt acagggatga gccattgtac caggcctggt ttttcattgc    64380
atttctttga ttactaatga ggtcatttat tttatgtgtt tattagatat tcgaattccc    64440
tatagtgaac tacctattca taagtctttt gcccattttc ttttggatta gttgacettt    64500 tccaaaagga tggccactta ccctggaaat atttattata tagtccgttc tgttccccac    64560
taaattataa tgccaatgtg aaccatatgc tgtgtaaata aatacctgtg cctctgtttc    64620
tgagccctct attctgtctc tttgggcttt ctgtctctat gctagtatca tttctctgta    64680
agtcttgttt tcctggtaac accagtctta ccctccttat tattcaaaat agccaaaggc    64740
tactattata cagtgcttcc ataaaaattt tagaatcagg ctgggcgcag tggcttacgc    64800
ctgtaatccc agcactttgg gaggctgaag cggacggatc acgaggtcaa gagatcaaga    64860
ccatcctggc caatatggtg aaatcctgtc tctactaaaa atacagaaaa ttagctgggc    64920
atggtggtgt gcacctgtag tcccagctac ttggaggct gaggcaggag aatcacttga    64980
acccaggagg cggaggttgc agtgagccga gatcatgcta ctgcactcga gcctggtgac    65040
aaagtgagac tccatctcaa aaaaaaaaa aaaaaaaat ttacaatcag tttttcaagt    65100
tccatggggg aaaaattatt tttggaattt tgtttattgc actacactga atttatttgt    65160
ggaaaattga catcattata atattgaatc ttcccataaa aggatattta tgtaggtctt    65220
tgtcaagtga aggggaacac atctgcatgc acacatacat gtcatttggt gtaatgtgaa    65280
ataaggttta gtggagaaaa ataaagaagt attaaggcac acacaattcc ctaaggtctg    65340
ttatccccat atagatgtgt gcactggcca gacacatcta gaactatgta ctgtggaaag    65400
ggctcctgtg taataattgg agctttgagg ttggtgaaat ggtcttacta gggaaagcca    65460
tcagtactct gtggctgatc agccttttct tgcatgaaac aaactcagac tcctgagcc    65520 aacttttga taagctacca aaacaggggt ggaaacctct agagtcatct gactctgtct    65580
ctcttcttag tagccttttg tgcacctgca cattatttg ttgtttccgt cacaaaagtt    65640
ttgggaatct tttgttagac ttttcttcta gattctttat aatgttacta tcatgagaag    65700
catctttttt taattggctc tggctaatgt gttagaacac catgtaattt tatgtccttg    65760 atttatatc caacaaacct tgctaaactc ttctgttagt ttttatagtt aataggtatt    65820
agccctgatg gtttgtagat tctcttgggt ttttctgtag atagcatgtt tcctacaaat    65880
aagttttttg tctctataat tctaattctt atgcctcttt atataaatat atatttatat    65940
aaacacttat ataaacacta cctatactac caagattcaa tgattgttaa catttttactg    66000 tgtgtatatc tcctaagaaa aaggaaatta tttcatttaa ccaaatatc atatgtagga    66060 aggttaaaat tctatcatct tacatctgat atgtgttcag atttccatgg ttgtcccaag    66120
aatgtctctt gcagctatct tccatcccta aactaagatc cactctgcat gcactgaatt    66180
atttgttgac ttttagtagt agttatcttt tagtcttaaa ctgaccacct actgttttgt    66240
tctcccatga aatgatttat taagaatcc aggacagttg tcttagaatg tcccacattt    66300
tggattagtc caattgccaa ggctttgact ttcaaagaga agaaaaatgt cttagagaat    66360
```

```
gttccacaat ctatatttga ttatttcagt gtagcagtct tagcgtattt ctctattccc    66420
tgtgtttctt ctaaaccaga agttaagtat gaaggcttga ttagattcag tttaaatgtt    66480
ttgcatgtat acttcatggg tgatgtctca tgttgtatca catcaagagg catatgttgg    66540
gttgttccac tattaatgat tctaagccac ttgaaggtat gttttcccct tcatctttaa    66600
tctgtggcga aatactttgg cactatgtaa gtatcctgtt ctccatcagc ttttctccta    66660 atgatttta gcatcatttg atccttcct gaaccaatta ttttatatta gctggcattc      66720
ttttgtaaag aagcatttcc ccatatcaag tgggaataac taattttcc taaaaaggcg     66780 ggatacatgc ataattttt tcatttaaag ttcagttttc taagggtgta ataatcccct     66840
acagtgtgag caactgctct cccacccttt aatttttat ggaatttga aggttttttg      66900 tttatttgtt tgtttttgca taccatctgt tatagtcaat tacagtactt attcttttg     66960 ctgaaaatct ccaaatttgg tcagtaggag tcccttcaag ctggcctctg atgttgttct    67020
gatatctggc acaagatgtt cctagatctc tcttcttgaa taataataga taggtttgaa   67080
atgctgtaat gctggccctt tcccccatta atgtagtcat tgtgttgttg ttactttgtg    67140
taatctaata atgcttattt tgttaagacc taatatgctt attaataaac tcattagtaa    67200
aacctaaatg cttatttagg tttactttca tgtatattag tctctagatt ctccatctgt   67260
gttcattttc tatggctgca ataataaata acaacaaact tggtcactta caacaccaca   67320
aatgtggtgt actctcttac atttctggag gtcggaaatc cagaatgagt ttgttttact    67380
gggcaaaaat caaggtatca gcaagacttt gctctctcta gagacaataa ggaaaaatct    67440
gatttcttgc cttttccagc tcctagagct gcactgcttg tatttcttgg ctcatggcca    67500
cctcctccat cttcaaggtc agcagtgtag catcttcaga tctttctctg ctgagttttt   67560
atatcaccta atcatctata gtaaaattcc ctttattc cctcttataa gtatgcttgt     67620
cgattacatt tagggcttac ccagatatcc agaataatct ccctgtttca caatacttaa   67680
tcacatctgc aaagttcctt tgccacata ggataacatt tacaggttct tctgggtctt    67740
ggtatatgtt tagttatctt ggtgggggc cactattcag ccctctcatg ccactctttc    67800
tttgatatta cttcttgatt cagtttcctt tttctaggtt gtcagttatt ttcttcttgc   67860
accttaacgt cagttcatta tcttcttgct tcttttactg atgttgagaa gtatgccatc   67920
agtctgactt gtctttactt tctggttgac tttaagaact gaactttttt attttcacct   67980
gttttggaaa atttatggcc agcttctgtt caaatatctc cccattccct gtttacctcc    68040
cagattaact cattttgtgc ttcgtgtctt tcatattttc cattcattta tctctgcctt   68100
ttggctaatt ttctcagaat caccttctag tcctttaatt ctctcttcag cagtaatctg    68160
ttttacgtta cctgaggttt taatttgatg actgtatgat tcaaaactca tgtctttata   68220
gtttcctcat gcttcttctt tatatgtgtt gtctttaggc ttgctgttct tccagagtta    68280
tctcagtaga aatttacttt tgtgttttgg tctgcaattt attagctttg atttcttgt    68340 caaactgatt atattcgttt tctgtttttc aggaatgttc tgaatttttc caactaagtg    68400
gttgatggtc ctggcctcct tgctttcagt actgtgattc tttcaaccat tttcttgaaa    68460
ttttaagacc acttctgtct ctcccttccc tccctctgtt cctcccccaa ccccaccttt    68520
cgtaacaatt atttgtttct tggaatctct taggctagtc ctgtagtttt cccctttgac    68580
ctattaagta ttatgttact ggattcctaa ttaatgatta ttcttgcttt taatatatat   68640
atttatatat actattatat atgtttatat atcatatata ttaatttaag agtttgatgc   68700
```

```
ctttcttcac agtttggatt attttatgtt ttgtttgttt gtttgtttag agatagtctt    68760
gctctgttgc ccaagctgga gtatagtggc gtgatctcag ctcactgcac cctccatctc    68820
ccaagttcaa gagattctcc tgcctcagcc tcccaagtag ctgggactac aggcacgcac    68880
ccacacctag ctaattttg tactttagt agagaaaggg ttttgccttg ttggccaggc    68940
tggtctcaaa ctcctggcct caggttatcc acctgcctca gcctcccaaa gtgctgggat    69000
tacaggaatg agccattgta cgtggcctat ttttttttat gttatctttg ttgagttttg    69060
acatctaggt tttgctagct tcttaaagta atttagaaga tatataagta tatatatgaa    69120
tatatatata aaatcacctg ttactaattg atattttaat tacatttttct ttaagggatg    69180 aggggagcca atggctgtag ttttttttt gtgccatagc tcccccttcat gtccttccat    69240 agcagtttgt ctgcatttat attttaacat gggcatcttc taggattttt taaaaaaat    69300 tctcagtctt ttttttggag aaggagtttt gccatttgta aagtcactaa aaatgatcag    69360
ttatttacta agcttgcttg gctgtaatag ctgtggtcta ctgaagagat taaaacagga    69420
gaggagatct tttagtaact ttcttgaagt ttttagtttt gttttaatt ttttcatctc    69480 ccttttagga ttgtggtaac aggtttttct ttttttcca agaagatgtt ttaactatgt    69540
acctaccgtt agcttttcag tatcttattc tacttttaa tatatctcta ttttataaga    69600
gtcatcaaag ttcttctct gactcttctg gagattctga aagactttct ctcccaaaca    69660
cattctttaa aattccaaca agggtcattg tgactttttt ttattcttcg gatataaaat    69720
tactcttctt tggggagata aaaaacctga cttccagaca cttatggtct ggccccacta    69780
tacctagcca atattatcat tttcttttac ttttttttg agacgaagtc ttgctcttgt    69840
cacccaggct ggagtgcagt ggcgcagtct cggctcactg caacctccgc ctcctgggtt    69900
ccagtgattc tcctgcctca gcctcctggg tagctgggat tacaggcaca cgccaccacg    69960
cccggctaat ttttgtattt ttagtagaga cggggtttca ccgtgttggc cagctggtct    70020
cgaactcctg acctcaagtg atccacccgc ctcatcctcc caaagtgctg ggattacagg    70080
tgtgagccac cactcccagc ccaatcttaa ccgttttta taccccagca agaaaatttt    70140
attctaatca gctcattctc ttcatttctc atctctgatt attttccccc actttctctc    70200
tcccatcctt tgagagaaat agttctttat gctaactgca tatgagtttt tatggaacat    70260 tgaaaaaaa aagggagtgt gggtaatatt gtcctgaatt tactgaccct aagaaagaat    70320
cactgaacta ggatgacctg ttttctttcc taccctattc tgaaaccagc ttaaatcttc    70380
agctttaatt gcatacctat tatgactaag acaccaaaat aaatcatgag gggacaaaaa    70440
aagaaaatgt ttctgatctt aaagtagcta atagacatgg aaaacataat caactttatg    70500
ttatcaaatt atgacttaga aaacagtttt gccgagttga tcagtgaaca catcatagag    70560
ggatgctcta aggaaagatc catcctggac aatgtggcaa acccccatct ctactaaaaa    70620
tacaaaaatt agccaggtgt gctgctgcgt gcctgtagtc ccaactactt gggagtctgg    70680
ggtgggagga ttgatgccag ggaggctgaa gctgcagtaa accaagattg tgccactgca    70740
ctccagcctg ggagacggag accctgtttt aaaaataaat aaagtattca ttttttttta    70800
aacaaatata tgtttgctta ttgtatgcta ggcactgttc taggctctgg ggataaatca    70860
gaaaaaataa gacaaaaacc tatgccctcc tggacttcat tctgttgggg agtgggaaga    70920
cacacaccaa taacaaaatg aacacgtaaa atatatatag taaggtggtc acatatgcta    70980
cggaacaaat aaaattaaca aagggcatag aagctgattc tgtgccttta aggaatggga    71040
gggatagagc ctttctaaat gagaaggtaa gagaatgctt cattgataag gtgacattgg    71100
```

```
gataaagaga tgaatgaact tggtaagaca gcaaacttta tagaaatctt aggggaagag    71160
cattccaggc agaaggaata gtaaattcac aagtcctgca ctgggagtat acttggcacg    71220
ttcagttagg ccaaatgtga ttggaatggg atgagtgacg ggagaacaat aagaaatgaa    71280
gctagacaaa tagcagaggg ccaggtcatg gctttggtga ttttagtgg ggaagccagt    71340 ggagggtttt gagcaagaga atgacatgtg atctgcagtt atagttttgt ttttgagatg    71400
gggttcactc tgttgcctag gttggggtgg cgcgatcaca gctcattgca gcctcaactt    71460
cccaggctca agcaatcctc ccacctcagc ctctgggacc acaggcacac accaccacgt    71520
ctggctattt ttttttttc ttttttttt gtagatacag gtcctacta tgttgcgatc    71580 ctcccgtctc agcctcccaa agtgctgaga ttacaggcgt gagccaccat gcatggcctg    71640
cagttacagt ttttgaagaa tagctactgt gccattctag gcatgaaata ggagaggcca    71700
tttcagaaac tcttgttaat aaactaacag agaaatgaag gtggcttaga ccagggtggt    71760
aaagttagag aaggtgacta atatctacat atattttgat ttggagatgg attgaaatgg    71820
attgtcagat gtgagaaaag agtcaaggat gatgctgaag ttttggttt actcaaagaa    71880 gggagcttat ttcctgaggt aaagagacta ggaaaaacaa gttttgtggg ggtgatgggg    71940
gagatcagaa gttagtcttt gaacatgtta agtttgaaat gcctattagg tatactagta    72000
gacatattca gcaggcagtt aggaatctgg tgttgagagg aaaaggtaga gttggatttt    72060
aaatttgggc cttcatcagt tcatagttgg catataaaga tacaagattg gatgagatca    72120
cctagggagt aagtgtagct tgacaaaaga agccatctga cacttttttgg agatatgaaa    72180 aattagcaaa ggcatcatga aagaaaacat tgaaatacct gactggaaaa acaatttgga    72240
acctctatca ctgcttctca gactttaata tgcatatgaa tcattttgtt aaagttcagt    72300
agatctgaga tggagcttga gcttctgctg tgtgttttgt ttgtttgttt ggttttggt    72360 tttttttttt ttttggcagg ttgtggggtg gcggtagaaa ctgagtctca ctatgttgcc    72420
caggccggag tgtagtggtg cactcatggc tcaccgcagc ctcaacctcc tgggctcagg    72480
taatcctccc acatcagcct tctgagtacc tgggactaca ggcatgcacc accatgcccg    72540 gctaatttt gtatttttta tggagatggg gttttgctat gttgcccagg ctggttgtga    72600
actcctgggc tcaagcaatc cacctgcctc ggcctcccag agtgttggga ttacagatgt    72660
gagccactat gctaggccag cttctgctgt tctcacagtc tttcagaaga tgctgctgct    72720
tctggtctgt ggacccacac tttgagtagc aagactttat atgacaagag tcatgaaaaa    72780
caattgaaag accttaacat tgtagaaga ataaagatta tatccagaa taaagactat    72840 ctataaatga atatggaaaa aacaaacaac tcaatagaat aaaagggagt gcagtatagg    72900
gaattttcca aaatctcaaa tggccagtaa gcataaaaag tgctcaactt tgtaagaaat    72960
acaaattaaa acatgattgc cttttcccctt tcagactggc aaaagtttag aagtgtgatt    73020
gtgctgggtg ttggtgagat tgtggggaag agtggactta taccctgcag atagggactt    73080
gacttgatac atttcttctt ttggaagacc atttggcata tttattaaat tttaaaatag    73140
gtatatcctt caatcctgga atcctatacc tagataccaa aaaataaaac ttgcactttt    73200
actctgaaaa gcagttcaga actatttgtt ggagtattgt ttgatgttga ggaaatggaa    73260
taatctaaat gtcctttagt aaggaaatta ttaaatcaag agatttggaa ctctttttt    73320 tcatttattt cccagtacat ttaaaaattg atatctgaca ttttttcatt ataactttga    73380
atagtttaaa aggccataat ttctactgtg tgttatattt atgttaaata catttttgg    73440
```

```
acaagcctta aagctgcaga tttagatcat tcaacttaga aacagaatct tccgtataac    73500
ctaatagcca gttctcacta tcaaaccaga caaattggac tgttttcctt ttttattaag    73560
aaaaaaaacc tgattactta tttatcttaa aacagatata ctaatatatg cctttttaata   73620 accactaaac ttctggattc tagtctggct ggctggtgat gggtaaggct tggagccttg    73680
ccacaaattt gtttcattga taaaatatgg tcctgctctt aattttttccc cctttctcct   73740 caaggaattt ccctatttaa ttgtctattt gttaggtact ttggaattta tacgtctcag    73800
aatggtgcat cttagtagta tttgaggtgg aaaagaactt tgcctttctt ttataaagtg    73860
gaaaataatt attttaaaag aggaagtaga caaggagaac cagttcttaa gcagatcaat    73920
cagggagcat acagataaaa cttgaggatc tggaaattct cttaaaattg tctatgccca    73980
cctaacccct ggataccact gaagtttaga gactgttgaa ataagcagtg caatgctatg    74040
aaatgaatgc tatataacca ttagggagta aaatatatgc atattgacgt ggagagactt    74100
ctgagacatt actccatgaa aaaagcaagt gttaaaagta ttttatatat agtatttaat    74160
tatatgtgta catttcatat atgtatgtct taatgttttt tccatgagta aaagggagac    74220
atggaaggct gctcaccaaa ccataaacag aacttaacct ttttgaaagg gggcctggga    74280
atgtgaggaa gatgaagaga gatttcatgg tttattctga atattcatgt attctttgaa    74340
tcttttatag ttgagaatac gttgtattac tagtgtagaa aaaaatttaa agatgtttca    74400
taataaaaga gaaaaaccac tgtactaaat gatctctaag ctcaaaattt gaggaacact    74460
ggcagttact gtgatgtagt tgtctatgtt aaaatatttc taattcatat actaagtgat    74520 tttatttaa attcttttga aatattttt aggtgtggaa tatcaaacaa atgattaagt     74580
tgacacagga acatatagag gccctattgg acaaatttgg tggggagcat aatccaccat    74640
caatatatct ggaggtaagc ttttgagtat catatctagt aattttgaaa agaaaaaaaa    74700
tgaacttata aaaacatttg tactgataat cttgattatt ttaggaggtg ggattaggaa    74760
tagatttggg aagagagaat tagctttgcc tgtattatac ttcttaatct tgttttgtgt    74820
cacttgttaa aataaacatg tattttataa tttagaaaac atcagaacta aggggggaagt    74880 gatataaatt tcaaggtatt actctgaatt aaattttttat ttttattttt attttatta    74940 tttattttt tttgagacgg agtctcgctc tgtcgcccag gctggagtgc agtgacacaa     75000
tctcagctca ctacaacctc cgcctcccag cttcagacga ttgtcctgcc tcagcctcct    75060
gagcagctgg gactacaggc gcacattacc acgtccacct aatttttttct attttttagta   75120 gagatggggt ttcaccatat tggccaggct ggtctcgaac tgacttttgtg atccacccac    75180 ttggcctccc aaagtgctag gattacaggt gtgagccact gtgcctagcc aattttttt     75240 ttttttttt aaagagaaag cacacagttt tggagctcag caaaccagtt accatattgg     75300
aaaatggggt aattttttaa aatatttttt ccagaatgag tttccccaaa attggtttct    75360
gcttccttat aggtaaaatt tgtaattttt aaatagctca acattgttta gcttactgt     75420 ttaataatgc cttgaggttt gtgtcaagcc ttgagcataa ttgtaaattt atattcatta    75480
atcctatgag ttagtaggtg ctgttataat cacagatgag ctttcttagc attagttttc    75540
ttaagtagtc agtcagactc cacagccaac aaggtgttac agaatctagg tggtaaggct    75600
ctacagccca cactgctcac tactacccta cacacccttt ctttataaaa gctggctcag    75660
ctgtcatcac tagtgaggca aggagatgga gaactctaaa ttagaaatga tcaggttgcc    75720
atttggctcc aaataccaga gatttttaag cacagattga aagacttctg aactaaattt    75780
gtaacttagt aatttaatta cttttttgaag ggccagttaa gtcttaagga ttttatgaga    75840
```

```
aagttaagtt tatatttctg aagtaaactt ggaagtttgg aaataacagc taatatgctg    75900
ttttctttct cctcttcttc atgtggctca tcccagatca cactcctagt taatatcaaa    75960
gctaggacta gaattcttat ttctcattac tagttagtgt acttcctaat agcctgtgct    76020
atcttctata catatattat taggaggctg atcaaaggtg tcataaggaa gcaagtactg    76080
ctaatgagaa tggcaatttt ttattaatca gaattagaca atataaccag cagttttttct   76140
tccaaccatt tctatgtctt ggagactttg aacccatgct gagatgtaat tcatttgcat    76200
caatagctat gtccccacta tagcagtgat tcactgcccc ctcctcacat aactcttcag    76260
gcttttttact atttgaagac tgatcactaa caacaaacct tagagcttct tattctgtgc   76320
ccagtactgt gttaaatgta ttttattgct taactcattt cttatagtta ctttgagcaa    76380
gatactaggt actggatatt tttgttattc ccatttttaca agtgaaaaaa cagagaggtt   76440
aagtaactta actaaggtga cactgctagt taggaaagaa ggcagatatc taagtcagaa    76500
atctgtgttc ttgatctcta tcttattcta cctttatcat gacattgtct cgctctttcc    76560
ccaccctcac cccccagaca gcttttctta tttgggctaa atatttctat tcccttcagc    76620
cattcttagt aacataattt atggaccttt tattagatac agtcttttttg gttggttctt   76680
ttagaattag acacacaaaa ttgaactact tattaaaatt aaatctgagt aggacagcat    76740
acatcagacc ataactcaca ggttatatta ttagcttgtg gtaaaacaga ttcttatctt    76800
ggggacttgt ggtatacaat gtgtgtgtat tatgtgtatg tagtatgcaa aggtatgcat    76860
atacacatgt acatacacac acactgaagg cagcagtata atataataat tacgatgagc    76920
catggagtca tacagactcc atgtttgaat cccaactctg gcttagtttc tgtactcaag    76980
atatccagcc ttcttatacc ccacctcatt agtaaagtgg aaataatatc acatcttggg    77040
taagttaagg attaattgag tttataatta tgaaataaca tagttcctga ttcaaatatt    77100
aagaattcta taaatagttg atttatcttg tactgctcta ggccttgggg aatagcaatt    77160
gtctgtcttt tttttttttcc tcctgagatg gaatcttgct gtctcccggg ctggagtgca   77220
gtggcacgat cttggctcac tgcaacctcc acctcccagg ttcaagcaat tttcctacct    77280
cagcctccca agtagctggg attacaggca tgcaccacca tacccagcta attttttgtgt   77340
ttttagtaga cacagggttt cagcatgttg gccagtctgg tctcaaactc ctgacctcag    77400
gtgatctgcc cccttggcc tctcacagtg ctgggattac aggcgtgagc caccgtgcct    77460
ggccgggaat agcaatttt taaaaaatgg ccaacaatct ccgccttttt aagcttatat    77520
tttaatgagg ggatggatat atagacaatg aacatataaa tgagttttag aacattgcac    77580
ttatcaccat tttattttt tatttttttgt tgagatggag tctcgctctg ttgcccagtc    77640
tggcatgcag tagcacgatc tcagctcact gcagcctcct ctcctgggtt caagtgattc    77700
tcctgcgtca gcctctcaag tagctgggat tacaggtgtg cgttatgact cccgactaat    77760
ttttgtatttt ttagtggaga caggtttcac catgttggcc aggcttgtct caaactcctg   77820
acctgaagtc atccacctgc ctcggcctcc ctaagtgcta ggattatagg cgtgagccac    77880
cgtgcctggc catcaccatt ttatatacta tgaatggact ctaaccagcc caagagaaaa    77940
gacctgtaca tactgtgatatt taaaggccca tcagtgaaga gctagatcta ctgattactc   78000
actgagaccc accgttctgc aggtttctca tctgccattt aagattcctt tacactttttt   78060
tttttttattg gggtaaaata tgcctaacaa aatttaccat tttaaccatt tttaagtata   78120
tggttctgtg gcattaagtc cattcatgtt tttgtgtatc cttcaccacc atccatttct    78180
```

```
agaaatttta tcatccaaaa ctgaaactct ctagccttta aacactaaat ctctatttcc   78240
ttctttctct agttcgtagc aaccaccatt ctactttcta tctctatgat ctatgaattg   78300
gactactcta ggaacttcat gttaatggaa tcatataata tttgtccttt tgtgactggc   78360
ttatttcatt tagcttaatg tctttgaggt ttatccatgt tgcaacaagg ataatgcata   78420
tatcaaaatt ttttccttt ttaaggctga ataataatcc attcattgta tgtatttacc   78480
atattttgat tatccattca tccatcagtg gacacttggg ttgcttctac gttttggcta   78540
ttatcaataa tgctgtgaac atgggtgtac gagtatctga gttccttta cttctttggg   78600 gtatatacca ggagtagaat tgcaggatca catggtgatt ttatgattat tttttctgga   78660
gttgccacac cttttctgt agcacctgcc ctgttttata ttcctactgg catcgcatgg   78720
ggttctaatt ttttacatcc ttaccaacac ttattatttt cggttgatta aaaaaaccat   78780
agcctaggct gagcgcggtg gctcacacct gtaatgccag cactttggga ggctaaggtg   78840
ggcggatcac gaggtcagga gtttgagacc agcctgacta acatgatgaa atcctgtctc   78900
tactaaaaaa tacaaaaatt tcaggtgtgt gtagtggtgc gcacctgtaa tcccagcaat   78960
tcaggaggct gaggcaggag aatcgcttga atccaggaga agaggttgca gtgagccgag   79020
atcatgccac tgcactccaa cctggggac agaataagac tccgtctcaa acaaaacaaa   79080
acaaggcaaa acaaaaaaaa catagcctca tgtgcgtgaa gtgatacctt attatggtgc   79140
tgatttgcat tttcctgatg actaacaatg ttgagccttt tattatgtgc ttattggcca   79200
tttgtatatc tttttgaga aatgtctgat ttaagttctt ggtccattt ttaattggat   79260 tgtttgtttt gttcttgtta ttgagcgtag ttctttatat agtctagata tcagttctta   79320
ttggatattt aatttgcaaa tattttccc attgtgtggg ttcccttttt actctgctta   79380 tagttttta gtccaaatta tctatttttc ttttgttgc tcttgccttt gatatcatat   79440
ccaagaaatc atcaccaaat ccaatgccat gacattcttc tcccaaatgc tcttgcattt   79500
gggtctttga tccatttga gttaattttt atatgatgta aggtaagggt ccaacttcgt   79560
tcttttgcat atggataccc agttttctca gcatcatttg tggaaaagac tgaatggcct   79620 tggcacccctt gtcgaaaacc atttgactat atatgcaaga gtttatttct gggctttcta   79680
ttccattggt ctatatgtct gtctttatgc tgtcatcata ctgttttgat tacactagct   79740
ttgtgtagta agttttgaaa tcaggaaatg tgagttctcc aactttgttc ttttcaaaa   79800 ttgttttggc tattcaggat cccttgagat tcctttttt tttttgagat ggagtctcac   79860
tttgtcaccc aggctggagt gcagtggtgt gatcttggct cactgcagcc cacctcccag   79920
gttcaagtga ttctcgtgcc tcagcctcct gagtagctgg gattacaggc acctgccacc   79980
atgcctacct tttgtatttt tagtggagac ggagtttcac catgttgacc aggccaatct   80040
cgaactcctg acctcaagtg atccacctgc cttggcttcc caaagtggtg ggattacagg   80100
tgcaagccac tgtgctcagc ctccatgtga atttttataaa ggatgtttct ctttctacaa   80160
gtaggtcatc aggattttga tagggattgg attgaatctg tagattgctt tggttaatac   80220
tgatatctta agaattctta actctgaaat atgagtggac agttaagaat aaccagatat   80280
ttaaagaaag ctgtcaacag gaaagacagc agcagaaatg gtcaacagaa actcagaaac   80340
agtgcagaaa acagaataaa acttaaaaat aactataatt agcatcagag ataagatcta   80400
ttagtcctgt cttgctttgt agcaatacta aagaagcaaa agtaacagag aacaagaaag   80460
acctcttgga aattaaaaat acaatagcca gaaatttatt tttatttta ttttttttta   80520 attttctttt taattctcag caaggcaagt tacgtctata gaagggtgcg cccttacaga   80580
```

```
tggagcaatg gtgagcgcac acttggacaa gggaggggaa ggggttctta tcccatatgc   80640
atgtggctct tgctgctgtg tcattcccct gttggctagg gttagactgc acaggctaaa   80700
ctaattccga ttaataacta gaattttta  attttatta  ttatttttct ttttttgaga   80760
tggagtcttg ctctgtcacc caggcgggag tgcagtggtg cgatctcggc tcacttcaag   80820
ctccacctcc cgggttcacg ccattctcct gcctcagcct cccgagtagc tgggactaca   80880
ggcgcccgcc accacgccca tctaattttg tttttgtatt tttagtagag actgggtttc   80940
accgtgttag ccaagatggt ctcgatctcc tgacctcgtg atccgcccgc ctcagcctcc   81000
caaagtgctg ggattatagg catgagccac tgtgcccagc ccagaaattt ttaaaaatat   81060
atgtatatac agacatatag gtatgtacat gtgtatatat gtatgtgttg tatatatata   81120
aataaatgtt gaaaataaaa tattggaaga taaatgttct agaaagcaga gtaaaagcag   81180
agagatggga aattttagag gaaacatgag aaaaattaag gaataaatcc caatccataa   81240
aaattataaa tgcgtttaac tgcaagaaac agaaccctt caagaataagt ttctggaaca   81300 aatagggatt ttcatttcct ttcacatagc aagaagcgta gaggtaaatt attgtaagac   81360
tagttctaca caggtcagtt gtcagatact tggttgaatc gctatagtcc ctttagcttt   81420
tctgtcaaga ccacagcaga ttttttaagat ctttccctca tacaactcct caaagcagaa   81480
agcagagaac agagaagttc tcttgtatac taagctcttg ctaggaagaa aatctttctc   81540
aaaaatcctc tataactctt cctttatat ctcattgact agaatgaggt cacatatcac   81600
ccctatacta gtgactatgc ttacatttcc tgaagtaaga gtctaataag tcaaaaattt   81660
ccagtgttca gttttcttc agattagttt gtatgctgtc aagtagaagt tgtgctatga   81720
ttattttatt ctataacatt tcaacagaaa ccccttttaa gtttctatag gaagataaat   81780
cttcaactac ttattcttgc ttcttctctt cattgtagca aaacagagaa attggttaca   81840
ccaccatcag aaatcctctt gattttcttt ttcccacgta ctaatttatt taaaagccat   81900
cttttcagtt ctagatgttc tcctactggc agataacagt taacattcta ttgattccct   81960
tgatgataac tacagtgaaa tatgagatac agtactctaa agaatttcaa atttgtcttc   82020
tcagttgatc tttggttccc ttttttctac catcatccaa aggaagaaaa gataaattta   82080
ctctgaaaag ttgttcccca gagtttcttc atttcctctc agtgtttcca tattcattta   82140
tccaacaaat tattggaatg ccttctatgt gtaagatata atgctagatg cttttctagt   82200
agtagattct tctttctgta cttgattat tggagcccag agatgaaggg atactgtctc   82260
tgtaatcacc ctacagctga gtcctaacta cttcagaatt tatggttgaa tcctacagtc   82320
ccctgtagac tgatgaagac agtaacagct cctgacattt actgagtatt tactatgtat   82380
caggtactaa tcatatatta gttcatttaa tcttcagcct accctttgag ttacacttaa   82440
ctattctcat tttcatttta taaatgaagc aattcaggca cagagggatt taataatatg   82500
gccaaggtta cacaacttgt aattggtagc caaggtttga atcccagaca ttctgaattt   82560
acagcccatg cgtttaatca ccgtatcatt cttacacttg gcagcctttc tgattttag    82620 tctatataga acctagaata atacagaggc attgtgtcaa accttcaat gaaattaata   82680 ctggaagctg gatgcttcct gtggaatgca gaacagtcca ttatatatca tttatgggca   82740
gtttgtaaga tttcattgta tcttgtgaga gtaagaataa ttagactaaa tttaattaac   82800
taaatgataa aaaataaaat ttttatttcg ctgcttttc  tcattacatt gaattaaat    82860 agatccttag atttttttcc cttctgtttt aattgagaaa taattcacat actatacgat   82920
```

| | |
|---|---|
| taacttttta aaactgtgta attcagtggt ttttactata ttcaccacta tcttattcca | 82980 |
| aaacatttt atcactcccc aaaagaaacc ctttatgcat tagtagtcat tccctgcagc | 83040 |
| ccctgacaac cactgatcta cttttgcct ttatggattt gctggttgaa atatttcata | 83100 |
| taaatagaat tatattatgt ggccttttgt gactggctgc ttttacttaa tgtaatgttt | 83160 |
| ccaaagtttg tttatgtagt agtatgtatc agtacttcat ttcttgttat ggctgaatat | 83220 |
| ttcatcatac acatatatca tgttttgttt atccattcat caactgatga acatttgggc | 83280 |
| tacttatatg ttttgccat tatgaataat gccaccatga acattcacgt gcaagttttt | 83340 |
| gtgtagatat attttcattt ttcctggctg tatgcctagg aatagaattg ctgggtcttg | 83400 |
| tggtaactct gttttacact ttgaggaact aactgccaga cagttttca aagttgctgc | 83460 |
| actattttgt attcctaaca gcaatgtatg agggttacag tttctctcca tcctcatcaa | 83520 |
| cccttgttat tatctatttg ttttttaat taaagccatc ttagtaggtg tgaattgta | 83580 |
| tttcatttgg ttttgatttg cagtttccta atgactaata atatagaaca tcttttcatg | 83640 |
| ttcttgttag ccatttgtat atcttctttg gagaaatgtc tattcaaatc ctttgcccac | 83700 |
| ttaaaaaaac tgggtttgtc cttttattac tgagttgtaa gagttcttta ggccaggcat | 83760 |
| ggtggctcac acctgtaatc ccagcacttt gggaggctga ggtggatgga tcacttgagt | 83820 |
| ccaggagttc gagatcagcc taggcaacat ggcgaaaccc cgtctctaca aaaatacaa | 83880 |
| aaattatcca ggcgtggtgg tgcatgcctg tagtcccacc tgcccgggag ctgagatgg | 83940 |
| gaggatcgct tgagcctggg aggcggaagt tgcagtgagc caagatggca gagtcaccca | 84000 |
| ggctggaatg caggggcacc atctcgactg actgcaacct ctacctccta ggctcaagcc | 84060 |
| atcctcccac ctcagcctcc cggcagctg ggactacagg catgcgtcac tgtgcctgga | 84120 |
| taattttgt atttttgta gagatgggga tttgccatgt tgcccaggct ggtctcgaac | 84180 |
| acctggactc aagcaatcct cccgccttgg cctcccaaag tgctgggatt acaggtatga | 84240 |
| gccaccgcac ctggccagga gttctttata tattctagat agtagatcca tgacttgcaa | 84300 |
| atattttctc ccattctgtg gtattttttc ccactctttc aattttgtct tttgaagtac | 84360 |
| aaaagtttaa atgtggatgg aattccaatt tatctatttt aaagtttaaa tgtggatgga | 84420 |
| attccaattt atctattttc tgtggttgct gtgcttttgg tgtatcatac atgagagacc | 84480 |
| attgcctaat caaaggtcag gatgatttac tcctgtgttt ttttcctaag agttttatag | 84540 |
| tattagttat atagccaaaa caggtttagt tgcttgctgc ctgcagagtc caattagtaa | 84600 |
| gagcaaagtc tagtataaag tgactttttt attccaaagt tagcttaaag gaagaagacg | 84660 |
| tacaggcttc ctgccttaag ggtactgctt ccctgttgga gcagaaagtg ggtgctttta | 84720 |
| aagaaggtgc ctacacgggg gcagaaatga gcggtggaa gatctgcata ttcccttcgg | 84780 |
| tgccttcttt ctcaggcagt caagttggtg gcttcatggg caaaaatacc tcagaggtgg | 84840 |
| ctgaaaactc tagcagtctt acttttggtt gtagatcaac tattacctct tgaggcaact | 84900 |
| tcctgacggg tgagagttcc actcaggatt gtctaagcac ataattagat caacttgcct | 84960 |
| tgtagggaat gtctggtgaa aaggagataa aaggccataa ttgcatttct tttattcttt | 85020 |
| tatcttttc ttttttgaaac agaatctcat tctgtcactc aggttggagt gtagtggcat | 85080 |
| gatctcggct cattgcagcc tctacctcct gggctcaggc gatcctcccg cttcagcctc | 85140 |
| ctgggttgct gggactatat gtgcatgcca ccatgcccag ccaagtttca tattttttt | 85200 |
| agagatgggg tttcaccatg tttcccaggc tagcctcaaa ctcctgggct caagtgatct | 85260 |
| gcctgccttg gcctcccaaa gtactgggat tactggtgtg agccaccacc cctggcatat | 85320 |

```
aattgcattt ctaaagagct aagtaggaag tggggaggag gaggaaagaa aaaaataatt   85380 aaacttttc ttagaaaaat gagggtgctc aattatataa tagatatgtg acccattttg    85440
ttttgttttt aattttttgta aagatggagt ctatgttgcc cagtcaggtc ttgaactcct  85500
ggcctcgagt gatcctccag cgttgacctc ccaaagagct gggattgcag gcgtgagcca   85560
acatgcctgg cctatttcga gttagttttt ggatatgttg tgaggtagta gcccaacttc   85620
attcttctgt gtgtggatat tcagttgtac cagcgccagt tgttgaagag accattcttc   85680
ctgcattgaa ttgtcttgct ggctttgtaa aaaaaaaaa tcaattgact gtaaatgtaa    85740
ggttttattt cttgttctat tgagaaataa ttcacatact atattattca cttttttaaa   85800
gtgtgtaatt cagtggttct tagtgtattt acacaatgga caactgtcac cactatctga   85860
ttctaaaata tttttatcat tcccacaaag aaacccttca tgcattggaa gtcattccct   85920
ccagcccctg acaaccactg atctactttt tgcctttatg gatttactag ttgtaccttg    85980
ttctattctg ttctatatgt gtgttcttat tccaaaatta ttgcgctgtc ttgattacta    86040
tagttttata gttaagtttt ggaatcagga agtataagtc ctccaacttc tttttctttc   86100
tataagattg ttttgataat ttcaagtccg ttgtatttcc atatgaattt taagatcagc   86160
ttgtcagttt ctacaaaaaa aaattgagat tttgagaagg attgcattga atctgtagat   86220
caacttggga agcgttgtca ttttaatgat attaagtctt cttagattct ttttctttt    86280 ttgagatgga gtcttgctct cgttgccagg ctggagtgca gtggcgtgat ctcaactcac    86340
tgcaacctcc gcctcccagg ttatcaatta ttactaatac aaatatttat tggattttg    86400 ctatgtggta gtctctacaa taatttgttt tacttgtgtt atctcattta atcctcacaa    86460
aattattttg aagttgagaa aaatttgcca tataaagaag agtatgataa aatattctaa   86520
aggagataaa gagaaaggat acctcttctg gattttgaca aagagagctt agaattagac   86580 ttttgaaaa atatttagag ttttgatgag aaggaatagg gttttgaac aactgtctcc     86640 tgaagaagtg gtatctggta tctgcagcat cttgaataac caaaagaaat ggtggtggtg   86700
gttgtggttg aggtttgcac atatgttgga gtggcttgct catattagta gagtgagaaa    86760
acagaggaaa agggaaagt agatgatatg agagaaaact gagggaatgg tagactaagg    86820
ccctaaacac ccaatattag cactgaagtg agagtagaag aagaatgggg aaagatgtgg    86880
agaattttgt agataaagaa gtagagtaaa cttttcattt tgatgacttg atcttccgag    86940
tggatttgaa ggtaatgtta ttttcagagt gaattaaaag ttgaaggatg aagttaagat    87000
ccagagaaga attaggaaga ttggaataac tgttttgact gtaatatgat gttaaaaaca    87060
agcatgattt tcaggcagta gtgtgaagga ccaggcaaat ctaagttcca taaattgatc    87120
atagaactaa ttagaccagt tttattattt tctccaacag tgtgtggtaa cctgacagga    87180
aaaaatagaa caattgaatg gtcagactta cccaaaattt gtatctggca agctagttga   87240
taaaataaca agaattagcc tgaaaatctt aagatatcac caatggcatt gttgtagttg    87300
tgagccgcaa agtatgtgaa ggaagacaac aatggccaaa tcttagcaac tgtttgagag    87360
attaatgttg accttgaaca gattaatgta atgagataga catttaagaa gttgggataa    87420
gtatgtgtgc cccaggggtg cgtgaggttc taaatcgaga tcatttcatc atttttattg    87480
cttttgtaaa gactgtgatg cttctccggg tcttaaaggt agaatggaaa taaatgcttt    87540
tagaggtgag aggtttagag aaatctatgg cagtgttaaa agagtaattg aagttcatat    87600
tgaatgcagc aagggcagta ggtaaaatga gccagggcc ttggtagatt gcagctttga     87660
```

```
ggatagggac agatggaata agtagatgtt ttgtacttaa caaaaggaaa agctattgat   87720
agatgtggtg aagtgatagt ttataatctg tcatggaggg atcagtatac tttcaaaaat   87780
taaagctaac attttggtaa ggaaatatgt ttggaaaatt gttcttttca ttacttttcc   87840
taaggtttat tttgtctagt aactgtactt gctcaggtga cagtaaataa gaatatttta   87900
tccatgcagg aggaaccttt gtgttccaga ctgcatttat gtgatcttca aagagtagga   87960
attgtgtttg tcttatgtgt ggttgtagtc tgagccctaa cagtgccaag cacatgtatc   88020
agtatatatt tactgagtga ttgaaggctc aataaataaa ttttattgag agaagtatgc   88080
ttaagtaatt aggccttggt actgaaagct aaaccaaatt gtagctcaga aaatttggaa   88140
tctatctgtt tataatgccc tcatctacta tgaaacaggg tctgggtagg gcaactagca   88200
ggctgtaaac aaagaagacc ttttgatgaa gtttaaatct cttcctcagt agctcttgtt   88260
actattcccc gcccccctta tttgttcgaa agtatgtggt aagatgcagc atagcagggt   88320
cctgtggccc ttattgaaat gaaatttctc tttcattctc ctctacattt tataattctc   88380
ccttcctccc ttacattcag acttgatagc atggcgtata tactctctac aatctattcc   88440
ctttcacctt ttcagcccta ttgtttcttt acctattttt catttaaatt tctttctttc   88500 cttttttaaga aaacagggat gctgctaaag cttcatttaa atttcacaaa catatattga   88560
tcttttgcta tgtcccaggt attgtatgac attgagctat acctatctat agttttcat   88620 gtgtcttaaa ctttctcgcc tttgttacag aaaaaacaaa ctcttttgtta cagaatttt   88680 cccatataga ggattccttc ctccctactt tcttcatcca tctaaatgcc aacctttcaa   88740
ggctgtcctc cttcctcatt attactttgt gtcaagaata ttgtttattt ctcatgtaca   88800
tcagttacac aaataaaaat acacccatcc tactccactg cccaacagta aactccttga   88860
gagacgggaa aggccatttt aaaatatttg cttctctctt tcataaatgt ttgtagtatt   88920
gcatctattt gagatggtag gtagaaatag tagagcatgg tgtgagtgag gggattacca   88980
atgccaaaaa gaactatgga cttgtatatt ccaattcgtt caatgtcatt ctgttctttt   89040
aaaatttgat atcttgtatg gttgcttgac tttatagcct tcatcaaatg aaacttctag   89100
gaagatactc tgatggatag tagccccata atttcttggc tgtagggtat aagccacatt   89160
ttcaaataca attctgtttt ttttttttct ttttttcacaa ggcttacagc tttgcatact   89220
agttccaatc tctaagcagc attaggtggg gaaagaagtc atcaaacagc catactgaga   89280
agagtaaagt attttaactg ataactattc cagaaagaat gtggcagtta cacatcttct   89340
aaaccctatt aaggaggttt tggtactaac agtgagatct ggtactgtgt cctaaatttt   89400
ggggtttttt tggacaaatc cttaatacct catgtccttt tcaacttctt tttctgttga   89460
gagagagaga gaacgaatgg aattcatatg cctacaactt ttccgggaca aaataattct   89520
tttaatggga ggaacacttt tccttgatac agtgttttat cttacgttag acatgatttg   89580
gaaggtaaat ataagtggac cagaaaattg gaaatactgt gctttttat tattcatgga   89640 ccatctagat atcacatatg tataggtcaa atttatcagg gtaatatag tgtagtgtct   89700 aataacaaag aatttatcaa tttaaaggtg aaagtattca tttatagtat ttctggcact   89760
tattttgtaa tttgaaactt aaaaccctat caactggtga aaagattata atcaaaggct   89820 aaaatttat attctctttt gttaatgtca ggacaaagtc cggattgaat ataagtctgc   89880 tttatttat aggcctatga agaatacacc agcaagctag atgcactcca acaaagagaa   89940
caacagttat tggaatctct ggggaacgga actgattttt ctgttctag ctctgcatca   90000 atggataccg ttacatcttc ttcctcttct agcctttcag tgctaccttc atctctttca   90060
```

```
gtttttcaaa atcccacaga tgtggcacgg agcaacccca agtcaccaca aaaacctatc    90120
gttagagtct tcctgcccaa caaacagagg acagtggtga gtcagtttta atatcaccat    90180
tttgctgttt ctttgtattt ttcagacaga tcagttgttg aaaattaata tattattact    90240
tcatactcag aggtcatgca aatagaggca tccatgtcat acaggaatga aaaatatgta    90300
attatttggt ggcaaagtct atattcctta actgaaataa atggtattgt ctctagtgtt    90360
ggatttgaca tttaaacctg tctgccaaac ttgaaccaca gtcatgtcta agcactagtt    90420
taaaataaat caggatttta agacttgagc ttgttcatta tctaatgtgt gtcaggtaag    90480
actcattctt caccccttgag aaatctcctt tctgagttat attatcagat gttgaacgtt    90540
cagtgtgatt gatatgtttc ccctcatcta cttcatttt ggttgttgaa tattagtatt    90600
aaccattgga acagcgtacc ctgtaagtaa catttgaagc atttaaagag aaatctgtgg    90660
aattattgtg ggtggtctat aatccttaag tgcaacgaat attgttagta gacttaataa    90720
gtaacccatc tgtatacatc actacttttt aaatgtctgt ggttacttt gacaataaaa    90780 attccaaata caactgaagt caaaattttt cattttttt ctctgacaac agaaatcaaa    90840
agtgcaattg gtcattgttt aatgttccaa aaattccttt ctgacttgaa aaaaaaatgt    90900
tattatagag gcattttact ttcagaagtt aagaattcct gcatatgagt ttagaaaact    90960
aatggagtta cgagttacca gcctgtaagt ttttatctta ggaaatatgg ctttctaaag    91020
gcatcattta ttgtcaggga ataaaaagta ataaaataaa aagtcatact tttctgccc     91080 tttttccatg tacagacaaa agttggttgt aaaaaataga ctctaattt tcattgtaca     91140 gaattacaaa tcaatttgta aaacaaatcc agttctaccc tttctctta ttctgttggg    91200 tagaataaaa ttaaaattat ttttcccaca ttaagatggg gaattactaa gcatatcttt    91260
ccagggatgc cccacttaaa aggggaatat caacatatga attatctgta aatagataat    91320
cttcgaagca gcctaacaaa actggcaaac atcccatccc cagtagatct taaattaatt    91380
ctttattgtc tgtattcatg agcagaaagt aggaaatgtg ttcttcagtc ccaggcgttt    91440
cccttctctt catcacggta ttgttccttc caggttccac tcaacttagt aattttgtga    91500
gtttctgtat acaaatgtaa aattggggtt gttggagcct ttcaaatttc tcaacctaat    91560
gattaagttt aactagcctc cggccgggca cagtggctcg tgcctgtaat cccagcactt    91620
tggaaggctg aggcgggcag atcacgaggt caggaggtca ggagatcgag acagtcctgg    91680
ctaacacacg gtgaaacctt ggctctacta aaaatacaaa aagattagcg gggcgtggtg    91740
gtgggtgcct gtagtcccag ctaatttgga ggctgaggca ggatagtgct gtgaacccgg    91800
gaggcggagc ttgcagtgag ccgagatcgc gccactgcac tccagcctgg gcaacagagc    91860
gagactccat ctcaaaaaaa aaaaaaaaag gtttaactag cctcctcata tttatgagag    91920
aggccaagag aaatttacag gtatcactaa agcttataat ttccctttta aaagaaata    91980 aaaacaactg agactcttca aagatgtaaa atgataaatg aataactatt aggcaattga    92040
ctaggcttac cttaattatc ctggctaggc ttagattaaa taagtaactt gttcttgtcc    92100
gtcatactcc cagtttaaca attcgtattc aatactcaga aaaactgtat atcgtgaact    92160
taaaaggcct tatgaatcat cagtaaatgg gtttgtggta ttaaactctt tcaagaacgt    92220
tattttgcca ttctctcttt tatctgaatc tgttaaccct tttcttaact acctctttc    92280 ctctccttttt cttctctcaa ttcttattaa cattaacagt tactatttga gcatttgcca    92340
tgctgtgttc caagttctgt gctaaggact ttacatacat cttctcagcc aggataattc    92400
```

```
acattctaag taaaattgtt tgtggtagtg aatgacagtt cctctatcaa aatacatgtt   92460
tctgtttgtc ctgaacactc aggaacaaag ggcagtagaa cctactagca gcaaatgaaa   92520
tcaagtacca agaatgagat tatgtttttt aaagtggact tagatttgta gtccaagata   92580
gcacgctaaa cacttgcctt tatatctttg ttcctttcca gaaatttcat tgaaatgata   92640
gtaaagatat gtaaaagaa taataaaaca ggataggatt ctgtcagaga actagaaatt    92700
tttaagaatt cctggaagat ggaaaatata tgaatggtta cgtaaataag ccaaaataga   92760
aaaccaaaca aaatactagg agctagattc ttacatgaag ggagccattc ttagcaaaat   92820
cctgatgaag cagatagcat agtcagcaga ttacaaagaa gtggatttgc ctcttgggta   92880
gtcgtcagag taattagtcg aaggtcttgc tctggcagga agacaaagtc atgtgtcttc   92940
ataaatcgag ctggtgatat aaatatgaat attttgaagg tgtgtgttag ttgtgagtcc   93000
tgtggagaac caaacaaac ctcaactaaa aacattgaaa ttctgaattc aaaaaaaatt    93060
ttttaaaggt catggcctga tattttaga catctgataa tggttgctg agtcctgagt     93120 ccccagtata gccttacatt gcacatgtcc atagagatgt gaatgttgcc tcctggagtt   93180
gtacaacaag gggatcctgt tagttcctct tctgtatata tggaacaaat aatttgtagc   93240
atttattcca tgaaaaagct ctaaaagtcg ttttctaaac aaaatttctg cctggagagt   93300
tctatgtgac tgctgtgtgt gtttaaatgg tggaactgaa catcagatgt ccctgaacct   93360
cagagaaatc cagtggggta aaagtaaac gttaatctac cgaggagtaa aataatactc    93420
tgcttccatc tggaatatac cagacttctt ctcacgtctg tacccattag taatctgttt   93480
ggaaaacaaa ctgcttcccc ctactatact gtcaacacaa caattttg tgactagatg     93540 tgtggggtg ttttcccca ccaagcaatc tccagttctc tgtagataat caactgggtt     93600
ctccacccaa ttgtctgcaa ttgttgttaa gttgccttca atttaactca attctgacac   93660
tatctaccca ggtatagcat agaccccaca ggttaagagc tcagtcccac aagactgtcc   93720
ccctcttgag atgctagtcc caagttccag gttgtgactt acacttctga ccagctggct   93780
ataaatcaag gattcccaca tcttctaatc tttgatcatt tgctagaata gctcacagaa   93840
cttcaagaaa cacttaacat ttactggttt gctataaagg atgttacaag aggtaaaaga   93900
cgaacagcca gatggaagaa atgcataggg aaaggtatgt gggaagggat gcagagcttc   93960
tgtgctctct ttaggagcat caccttccac tacctccaaa tgttcagcac cctgaaagct   94020
ctaggaacat tgcatttcag tgattttat ggaagcttca tcatataggt gtgatattta    94080
ctaggtcaat ctccacgacc tccccacttc tcagaggttg gtggatgggg ctgaaagttc   94140
acattatggc ttggtctttc ttttgaccac cttccattca ggaacccacc aaaactcacc   94200
ttgttggaac aaaagatgct cctaccacct aggaaattcc aagggaatca gagctctgtg   94260
tcaggaacca aggtcaaaga caaatatgag aacaaaagat gcacctggca ccctgatcac   94320
tcaggaaatt acaagagttt taggagctct gtgcctagaa ctggggttgg aggccaaagg   94380
gttgaagacc aaaatatata ttattataaa ccacaatatc agagtttgtc aacataataa   94440
accacttgcc atttgttgga cctatacaac tgtacaggag taagtccaca ccaaatcaac   94500
ctaattttta tttataaata tgactagaac accaacagca acagagaaaa ctcaagaaaa   94560
gaaagcaact agaagatgta aaaatattat agctcaggat gtacttcatt cttgaagcca   94620
aatcagtttg atataaaaat tgagtcattc agaggaccac agagtttgtg caaattgaaa   94680
gtatgattgt tgactttgt taaacagaaa ggccaaacat taggatagct agagttaata   94740
agtattttgg aaagtaaagc taaagacata cctttaaga tatgagataa agtgggcaaa    94800
```

-continued

```
tatgagaaaa aagataagag acatggagag agcaaaagtt ccaacttctg tttaataaag    94860
aagcaaacaa aaatagaggg aagatgtatt cacagacata atacaggaaa attttcctgt    94920
gttaaacaaa aaccagcctt cagatagata ggggcaactg actgtcaaca ggaaaacaaa    94980
aacagagatt gacctggata cttgctgtat aattcgaaag ttgaaagaga accttttcag    95040
aaagataaac tggtaatctg cgggagaatg aaaactggat cgttttctca ttggcaaact    95100
gagggctaga aggcagtgga tcagggccat taaagatctg atggaagtta atagccaagc    95160
taatattaaa agtaagacac tttgggtatc tagggactga aaattatttc agtggaatat    95220
aataggtatc tagaaataga tcccagaatt tcagaaaatg taatatgaaa aaaatggttc    95280
aatcagtaag aagaaggtga attatttaat ttttggtgct ggcatatgta aagaaaata    95340 aaattgggcc cacatcttag actgcttaca aaagtaaatt ctatcagaat caagagatta    95400
aataccaaaa aaaaaaaaaa atgtaaatct ttcaagaaaa atctagtagg ctgcatgtaa    95460
aatctaggag ttgaggtcac tatcttaatc aaaacttaat tagctcaaaa gctgtaggag    95520
acagatggat taaatacaat tttgaaatta tgtatgcccc cccccacaaa aaaaaaacct    95580
taacagagtc aatagtctgt ataaatttgg aaacagcatt ggtgcccaga taccaagaag    95640
taaatagtct tctgaatata caaagaacac ttcaaaattg gcaagaaaaa gacaaaaccc    95700
agcagaaaaa tagggaaaag atataaatag gcagttcgta taagatgaaa tccaaatgaa    95760
cagtaaagca tgtgaacact gttcagatgc agtcagtcag ttgtgagtgt acaaattaaa    95820
actatgagat catttcatct gtctggcaaa atataaatta ttattggcag gggtgtagtg    95880
agaaaactgc tcccttagtt aaggatagaa atgtgaagta tcacagctta ttggaaagca    95940
ctttgataat atctgtcaaa atttacaaga actgtatctt ccaagccagt actccatcta    96000
ttgggaattt agcacataaa agcaccaata tttatacaag gatatttgtt aaatcatcgt    96060
aataagaaaa aaatatagaa tgtcatcagt agagaaatgg ttgtataaat catggtacag    96120
ccacaccatg tagtacaatg cagcctgtga aaagacttgt acttgaaggt ttttctgaga    96180
ggtattataa ttgagaaaag gaaagctgtt ggaaactctg atattactta cttattcttt    96240
atgtatatca cattgcaata ttctagtagg tctagaaata tctctctcaa ctagaaatgc    96300
tgaataaaat atgtttattt aaatgtatag ctgagctcaa tagaaaaacc tatagagggt    96360
gaaaacaaag acggagttga aaaaaccaga aaagcatagg agctgatatg ttaaggtatc    96420
gctgaactat aaccctcaac aaatctaacc caccatctat ttttgtatgg cctgcgaact    96480
aagaatggat tttacatttt taaatgcttg aaaaaagtta aaggaataat agtatttcat    96540
aatctatgaa aatcacacga aatacaaatt ttggccaggt acggtagctc atgcctgtaa    96600
tctcagcatg ggaggctgag gggagtggat cacctgaggt caggagttct agaccagcct    96660
ggccaacatg gtgaaaccca catctctact ataaatacaa aattggccgg gtgtggtgcc    96720
gcatgcctgt aacccagcta tttgggaggc tgaggcagga aatcgcttg aacctgggag    96780 gtggaggttg cggtgagccg agattgcgcc gttgcactcc agccggggca acaagagcaa    96840
aactccatct caaaaaaaaa taaataaata aaatttcagt gtccatcagt aaaatgttat    96900
tggaacacaa caatgctaat ctgtttatat gttgtctgtg ctggtttca tgctttagca    96960 gtggtgttga gcagttgtac atcacagtgt aatctacaga acctctggtt ctttatggaa    97020
gaagtttgct gacctctgcg gtcgtggcct caggtgggcc agtttgtcac tctgaacaa    97080 aggatgtgaa tatcaatgtg tgggaataca acactgggcc ttcagcctgt gtcacaaagg    97140
```

```
tagttggaac ccagattctc acataaagct gacccttga aggacattac cttcagtgaa    97200
aggctgaaat ctattaccag aatacataaa gataacaata aacttgactg tctttgacag    97260
tactctaaat aaagtttccc ctgtgatttt ttaactatgg acctattctc atcattgtgt    97320
gggattcaaa tttatactgc ctgcattgtc caggaaccct caagccatga agtggacata    97380
acgactggtc ttggagtggt aatagcactc aggcactgca cagaagcaat ggaaaccctc    97440
cctcagcccg tctaggtctc atagaattca cagaaataat gctttactga ctatctcaag    97500
atctcaagtt gtaagacatg caaggaaaca gtctacaatc agtgagttag cagacttaaa    97560
acagcagggt tagactccta agaaagaacc aagtagaact tttaggtagt cttgatttaa    97620
acctcatcat ctatgaagta ttcttgcttg gatgggacc ttctatttta taagaaacac    97680
aggggataga ggaaaaaggt aagcaccatg aggaaacaat tagacaattc agaatgttga    97740
cttcctgtaa gacaatagcc ctagactcct tgataagtta atgtcttgga caataaaaag    97800 gttgggat ttccacact gtacaagacc aagtgcacat aacaaccaaa tgcagtgtgt    97860
aatcctgagg ggggaagaat cattcttggg acttgggaaa ttttaacat tgattgaata    97920 ctacatattg ttatggaatt aacgttctta aatgtgagga tggtaacgta attatatagg    97980
agaatgtcct tgttcttagg aattacatgt ataagtattt aggagtaaag tgttaggatg    98040
actgcaactt cccccgcaaa cccacgcttt tttgagatgg aacttataca cagtagaggg    98100
tacaaatctg aagtatatcg ctcagagttt ttacatgtgt aactaccatg tagattaaga    98160
tgtaggacat ttcctgatgc tttagagggt tctcctgtgc ccctcccaat tcactaaaaa    98220
taaccactat ttcatttcta tctctgtcag ttacttggaa acttaacttc aaatggtgtg    98280
atggaaatca acatgcagag aaagagaaaa gcaaatacga aagataatc ttagaatcta    98340 agaaaatttc gatgttaatt gtaccatttg ttcagatttt ctgtctgaaa ttttttgtaa    98400
tagagttgga aaaattgaaa acatagaaaa aagaaatgt agaaagttca aagaaacag    98460 ttatctctag gaaaaaagag tgaacatact gatactcatt tgaggatgta gcaagataac    98520
actttaagta aaatttcagt atgtcaagtt agttacagca aattacatag gaaatgttta    98580
aatgtcacat agaaattcaa atatttattt aaaaaactca gtgaataagg taaagctaga    98640
ttaaacccag ccaaagaatg aattagtgaa ctctggaaag tgaagaaaga gagttataga    98700
aaatataaaa gagaggttaa gcagtatgaa aaatggaatg agcattatat gcctcaaaga    98760
gttccaaaag gtaagaatag aaataaatga gtagagaaaa attcaaataa attagggcta    98820
acatttacaa atgacataaa tctaacgatt tgggaagcac aatctctgag ttggacaaac    98880
aatttgaatc caggatagac ataataaaac caaagaatat tgttttaaaa gcactcaggg    98940
aaaaaattat atagaaaata attaaaatta gactaggaaa atttgttatg gcagttgtag    99000
aaatcagaaa acaatagaat aatatactca gagtactgag aggtacctgt aaatctctca    99060
gctaagttaa gctataaatt tgattaggtt gacttgggca aatgcaccat aaagtccttt    99120
ccagagaagg agttcacttt tcataggttc tacttgaagg aattgtccaa gaaggtttac    99180
tgtataaagg aaattgaaca cagaaggaat gaaaagtaaa aattaaacct aaaatttgca    99240
gaagaaaaca ctacagaaaa ttttgtgac ctgggggttg gcaaagattt cttaaatatg    99300
acaccagaag cacagtctat aatgaacgta ttagtttatt gggttaatca aaatgtaaaa    99360
cttctgctct tcaaaagaca gtattaagag aataaaaaga gaaaccacag attgataatc    99420
tttgtaagcc atgtatctga tcaaggacat gtagaatata taaagaactc tgaaagctca    99480
atagtaagaa aacaaatggc tgggtgcgga ggctcatgcc tgtaatccca gcactttggg    99540
```

-continued

```
aggctgaggc aggtggatca tgaggtcggg agttcaagac cagcctggcc aagatggtga   99600
aaccccatct ttactaaaaa tgcaaaaatt agctgggcgt ggtggcaggc gcctgtaacc   99660
ccagctgctc gggaggctga ggcagaaaat tgcttgagct cgggaggcag aggttgcagt   99720
gagccgagat tgcgccactg cactccagcc tgggcaacag agtgagactc catctcaaaa   99780
aaaaaaaaaa agaaaaaaca acccaattaa aaacggacaa aggatttgaa cagtttcatc   99840
aaagatatat ggatggtaat aaacgcatga gaagacgctc aacattagtc attaggaaaa   99900
tgcaaattaa ataggcacgc gatacccttta catgcctcct agaatggctg aaattagagt   99960
gaccatacca agtattagtg gggatgtgaa agaactagaa tttccgtaca ctgctgatag  100020
gagtgtttaa ttggtacaac cactttggaa taaaatttgg cagtttattt aatgaaacct  100080
tttcaaaatc ccaacgggct tttttttttt ttcctcagaa atagaaagtc cgtcctaaaa  100140
ttcataccgt atctcaagga atcccgtata gccaaagcag tcaaaaaaag tacagagttg  100200
ggggcatcat gcttcctgat ctcaaaactt actacaaagt tagagtaatc aaaactaagt  100260
ggtactggca tgcagacaga tgagagtcct gaactaaatc ttcacattta tggtcaaatg  100320
atctttgaca agggtaccag gaccactcca tgaagtaaag agaatctgtt cagcaaatga  100380
tgctggcaac tgaatatcca catgcaaaag aatgaagtgg tacccttccc ttataccatg  100440 tacaagaat aacccaaaat ggatcaaaga cttgaacata acagttaaag ccataaaact  100500
tttactacaa gaaaacatag gagaaaagca tcataacttt ggatttgtca atgatttctt  100560
ggccgtgatg ccaaaagccc agggaacaca agaaaaaatg gaaaaattgt actattatca  100620
gaatttaaaa cttctgatca tcaaaggata taatcaacag agtgaaaagc caacctggaa  100680
tgggaaaaat atttgcaaat cttgtatctg ataaggggtt aatatccaga atataaagaa  100740
ctcctgtaat agcatacaac cttgttaaaa aatgggcaga ggacttgaac agacatttct  100800
ttaatgaaga tatccagatg gccacgagca tatgaaaaga tgcccaacat tgctaattat  100860
taggaacatg caaatcaaaa ccacaaggag ataccacctc acacccatta ggatgtcggc  100920
tatcagacaa aaaagaagat aacaagagtt ggcaagggtg tggagaaatt ggacccctgt  100980
tgcactgttg gtggaaatgt aaaatggagc aactgctatg gaaaacagta tagaggttcc  101040
tcaaaaaact aaaaatagaa ttaccatata atccatcaat tctccttctg tgtatatacc  101100
caaaataatt gaaagcagga tctcaaagag atatttgtac actcatgttc atagcagcat  101160
tattcactat agtagccaaa ggcagaagca acccagattt ctgttgatag aggagtggat  101220
gaacaaaata tggtatgtat atacattgga atattattca gccttaggac attctaacac  101280
atactacaac atgagtaaat ctcaaggaca ttatgttaag tgaaatgagc cagtcataaa  101340
acgacaaata ctgtatgatt ccacttattg aagtacctag agtgttcaga ctcacagaga  101400
cacagagtag aatggtgctt gccaggggct gggggaaggg gtgctgggga gttgtttaat  101460
ggttatagag ttttagtttt gcaggatgaa aagagttcag gagattggtt gcacaacatt  101520
gtgaatgtac ttaacactac tgaattgtac acttaaaaat ggttgaaatg ttaagcttta  101580
tgttagatat attttaccat aatttttgtga aataatagta tggtagttat gtaaaacgtt  101640
aggctggaca cggtggctca cacctgtaat ctcagtgctt gggaagtca aggcgagaga  101700 atcacttgag accaggagtt ccataccagc cagggcaaca tagtgagacc ccatgtctac  101760
aaaaaaaatt tttaattagc caggagtggt ggtgtcatc tgtagtccta gctacctgag  101820
aggctgaagc aggaggatca cttgtgccca ggagttaaaa gctacattgt gctatgtgca  101880
```

```
ccattgcact ccagcctggg tgaaagagca agaccctgtc cacccccaca aaaagtcaga   101940
tgtacactta gcatatcaca cagcccttct actcctcggt atttacccaa gagaaaaggg   102000
agcatatgtt cgtagaaaga tttgtatacg aatgttctta gttgctttgt catagcccca   102060
aactggaaat aacccaaatg tccataaaca ggtgaatggt tggattgtgg tgtatctata   102120
aaagggaata ctactcagta gaaaggaatg aactgctaat gcacacaaca tagatgaatc   102180
tcaaagtaat tatgctgagt gaaagaagtc agacaaaaaa tgattacacg ttttaaaatt   102240
cagtttacat aaaattctag aaaatgcaaa ctcttctata gtgacaacag atttgtattt   102300
gcctgggcac aggactatgg caggatggaa gatttacata ggagcacaag gaacctttca   102360
gaaagtgatg ggtatgttca ttatcttgaa tgtgatgatg gttgcatggg tatatacgta   102420
atctcaaaat gtatcaaatt gtgtactcta aatcattgca gtttattgta tgtcagttgt   102480
acctagataa atctgtttgt ttgttttttta atagcctttta agaaagctga tagtactgtg   102540
gaaatattat atgaaataga ctttgggaga aagaattatt attaaaattt ttttttcaac   102600
ttttatttta gattcaggag gtacatgcac agctttgtta tctgggtata ttgcatgatg   102660
ctgaggtttg atgtacaaat gatcccatca tccaagtact gagcatagta gccaatagtt   102720
tttcaacctt tgccctcccc gctctagtag cctccggttt ctgttattgc tgtctttatg   102780
tccatgagta cccaaagttt agctcctact tagaaatgag aacatttgat atttggtttt   102840
ctcttcctgt gttaatttgc ttaggataat ggcttccagc tgcatccagg ttgctgcaaa   102900
ggacatgatt tcattcattt ttgtggctgc atagtattcc atggtgcata tgcctttgct   102960
attgtgaata gtgctgtgtt aaatatgtgg ttttttcgta gaatgattca ttttcttttg   103020
gatgtatata taccgagcaa tgagactgct gggtcgaatg gtagttctat tttaagttct   103080
ttgagaaatt tccaaactgc tttccacagt gcctaaccaa tttacattcc caccaacagt   103140
gtacaagcct tccctttttct ctgcagcttt gccagcatct gttgtttttt gccagcactt   103200
tgggaggttg aggcgggagg atcacttgag gtcaggagtt cgagaccagc ctggccaaca   103260
tggtgaaacc tcatctctac taaaaataca aaaaaaaaa ttagccagcc atggtggtgc   103320
acacctgtaa tcccagttac ttggagctga ggcaggagaa ttgcttgacc ctgggaggca   103380
caggttgcaa tgagctgaga tcccaccact gcactccagc ctgggtgaca gagcgagact   103440
ctgtctcaaa aaaaaaaaaa aaaaaaaaaa tgtaattcag acgctgggtg tagtggcttg   103500
cgcctgtaat cccaacactt tgggaggcca aggcagaagg attgcttgag cccaggagtt   103560
caagaccagc ctgggcaatg taaccagacc ctgtctctac aaaaaattag ccaggtgtgc   103620
tagcatgagt ttgtagcccc agctacttgg gagactgagg cgggataatc caggattttg   103680
aggcttcagt aaggtatgat tgtgctgctg cactccagcc tgagcaactg agtgagtccc   103740
tgtcttaaaa aaagactttc tagatcctgg agtatgtgca ataactaaaa agaataagca   103800
tatatgttcc ttgagatttt tatttttaat tttatttttt gagagtgagt cttgcccaga   103860
atggagtgca gtggtataat cacagctaac tgcagccttg acttctcagg ctcaggtgat   103920
cctcccatct caccctccaa gtagctgaga ccacaggcgt gtgccatgcc taatttttaa   103980 attttttttgt agaggtaggg ccttgctatg ttgcccaggc tggtctcaaa ctcttgggct   104040
caagcaatcc tccctctgtg gcctcccata gtgctgggat tataggcatg aaccactgca   104100
cctggccctg agatatattt gaataattgt aaaaatctgt taattggggt tattggaggg   104160
atggggatat tccctgggac aagaaaaagg gactgacctt ttacttttat acttgatacc   104220
cttatttcac ataatgccaa ggtgtctgtt ttttatgatt gttcagggtg attatatatt   104280
```

```
tattcatgta ttgtttagag tagttgtatc tcatttagct atttctttct tgatggataa   104340
ttaggtaatg ttgcagtata tatttaagta catatatcct gaaacactgt gggaatactt   104400
ttattgggga agataaatac cttgaaataa ttattgggtc atagaatata cacactgaaa   104460
actttgcgat aacttaatat cagaaaagat tttgattctc aacaagtgta tgaaacttcc   104520
ttttcccaca agatcctggc caacatggaa tgttaacaga ttttttaaaag tattaccaat   104580 ctaataaaat ttaaagtata tttgacttga atcctgtgtg tattgtttgt ctgtatgaca   104640
gttgtttgta ttatatgaca aaaaattaac caaaaaatat tagactcacc tgattacccc   104700
aaaagatggc ttgtgttcta agcctgttta ggcttataag tcaaaagaaa atttctttaa   104760
aaaaatttta tttgatggtt tattgagata taattcaaaa gccatacaat ttacccattt   104820
aaagtataaa atgattttg tatattcaca aagttctgtg gccgtgataa ttcatttaaa   104880
aatatttttt catcccaaaa ataaacactg tacccgttag cagtcacttc ccattcctcc   104940 catcccctatg taaccaccca tttgctccct atctctatag atttgcctat tctctggcat   105000
ttcatataaa tgaaatcata caatatgtgt tgtgactga cttctttac ttagcataat   105060 gttttcaaag tccatccaca ttgtaccctg tgtcagtcct tcatgccttc ttatggctca   105120
gtaatattcc attggctgta tataccacat tttgtttaca catttatcag ctgatggaca   105180
tctgtgtcgt ttctactttt tagctgttat gagcaatgct gctgtgaaca ttcgtattca   105240
aggttttgtg tggacatatg atttcatttg tgcctctagt aacctttaa gagactggca   105300 gaatgttttt caaaatggct acaccatttt actttccctt gagcatgagg gttctgtttt   105360
tttcacatca ctgccaaact tgtttattat ttgtctttt tattatagcc atcctaatgg   105420
gtatgaaatg gtatctcatt ttgggtttta tttgcatttc ccttatgact agtaatgtga   105480
agcatctttt tgtgtgattg ttggcttta tatatctttg tggagaaagg atttgctttt   105540
atatagatag ttttacatgc aattcataga taaataccaa tgacctgaga cgagaagaat   105600
tacaaaggtt tttgaacaat gctctaataa tagaaatcgg acagaaaaga gaaagtagcc   105660
aagattattt cctctagaga tgggaaaatg tacaagttct ccaaggatct atgcacaaac   105720
aagagaaaga agtggagata acaagaataa aactgaatgc tctagagaca caaagggaa   105780 atactgaaga taggtaagct ctcttcagta tcttctttgt ttttaagttt attcctaggt   105840
aagctatctt cagtgtaagg tagactacgt aagataggta agctgtcttc agtataaggt   105900
agactagata agctatcttc aaaataaggt agactaagtc aaaggattgt aatatcaaga   105960
aatgtgatag accctggatg tggtctttta catcactaaa tgaaaccat acttaataag   106020 ttgtatatag tattgtaaag ataattgcct gttttaggta tttcaaaatt ggtgactttg   106080
gtttagcatt tagaaaatat tgttcataag gttttttaac tttttattta gaaaatttaa   106140
aacacttggc cggtgctggc gtgttggctc atgcctgtaa tcctagcact tgggaggcc   106200 aaggcgggcg gatcacctga ggtcaggagt tcgagaccag cctggccaac atgatgaaat   106260
cctgtttcta ttaaaagtat aaaaattagc caggcattgt ggcgcacacc tgtaatccca   106320
gctactcggg aggctgaggc gggagaattg cttgaacctg ggaggcagag gttgcagtga   106380
gccaatatcg tgccactgca ctccaggctg ggcaacagag caagactcca tctcaaaaaa   106440
aaaaaaaaaa ttaaaatact tgtatggaaa aatataaagg acaatatatt aaacagctgt   106500
ttagtcacct acaatgaaca aatactaatt ttttgttata tttgcttcat attatacata   106560
gaagtacaaa tttaggttcc actaccagtc ccattcctct gctggacacc catcgtccca   106620
```

```
tcttgtcccc aaaaagacag tcactatgat aaatgtgagg taccttcaat catattttg  106680 tattttatta tatatatgtg tagccataag ccaatgtttt tgttttttt ttaatttgta  106740 aggtgatacg atactatatg tatgtaatgg tcagcatctt gtccttttta ttcaaaatta  106800
tgatttcaag gtgtatgtat ttatatgtta acacatacag atctatttca ttcaatgcta  106860
ttatcaagta ttctagcttc ttaatatacc acagtttatc ttttttctcca ttgatgagca  106920 tttaggttat atttggattt ttttgttatg acaaacagtg ctgtaataag aacattcttg  106980
tgcttgtctc cttgtacaca tataacaagg tgtcacaaac ctgaaagtgg aattcctggg  107040
acagggagta tcatttgaag agactgtcct ttccccagtg tatgttcttg gcacctttgt  107100
caaaaatgag ttcactgtag atgtatggaa ttatttcatt gttctctatt ctgttccatt  107160
ggtctatatg tctgttttta tgccagtacc atgctgtttt ggttactata gctttgtagt  107220
ataatttgaa gtgaggtaat gtgattcttc cagttttgtt cttttttgctt tggctattct  107280 gggcctttgg tagttccata taaattttag gattattttt ctatttctgt gaagaatgtc  107340
tttggtgttt tcatagggat tacattgaat ctgtagatta ctttggggtag tatggacact  107400 ttagcaatat tgattcttcc agtccatgaa catggccggt cttccatttt tttcatgtgt  107460
tctctccagt ttcttgcatc agtgttttat agttttcatt gtagaaatct ttcacttctt  107520 tgttttaag tttattccta ggtatttat ttgtagctat tgtaaatgga gttactttct  107580 tgattttgt ttcggattgt ttgctgttgg catgtagaaa tgctgctgac ttttgtatgt  107640
taattttgta tcctgcaact ttactgaatt tgtcagttat aattgttttt tggtggagt  107700 ctttaggttt ttccaaatat aagatcatat tatccacaaa caaggataat ttgacttatt  107760
ctttccaatt tggatacct tttttttttc tcttatccaa ttgctctagc taggacttcc  107820
aatagtgtgt cgaataacag tggtgaaagt gggcatcctt gtcttgttcc aggtcttaga  107880
agaatacttt caggtttttt tcattaatta tgattctagc tgtgggtctg ttgtctgatg  107940
aaaagtctga aacggtacct aaaactacta aattaatttt aacatctttg agttgttttt  108000
agttctgtga gaagagcata tctattttgg tttactcagt gagtagagta gtgtctaata  108060
ctgagtaaat gtactgtaag tattttttgaa agaatgagtc tttgggttta catacctgg  108120 ggtttgtaaa caaatatctg ttgattggca ttaatcctga tggtatccaa ggtacaggaa  108180
tggcaaaggg aaaagatagg gcaatactga ctgatgcttc aaaatcatgc cctagttatg  108240
ctataatcaa gcaggaaatg tttatggaat ggaaagatta aggaaaaggt atgttcttat  108300
tttagcaata aaacgaatac cagaagcttt aacattcacc agtacaaata aatagtttca  108360
atggaatagg tcgaaagtaa agggacatca ctagagtaaa tgctagacct tccctctcct  108420 tttatttta gcaacagcaa agcagaaact aagatctaca agtgatcaaa gagggtgatc  108480
cattcagttt ctgtgtagac aggaataata ataataccctt tacatattg gtacagtttg  108540 taaaaacact ttcacttact catttaatct tcatagcaac ttgatgaggt agaatactat  108600
aggaagcagt attagctcag gttggtacgt aaattactgt gtttaaattt caataaaaca  108660
gctatggaat ccaagacatt cttggcgcct aataaactgt attctttgcc aacagtgaaa  108720
gtgcttctct gttgcttggt aagttttttc cccttagaat actaataaag taattgatta  108780 acttctttc ttattttgat ttgattggga cagcaattta gcagtaaaaa atgtcacctt  108840
tataaatcct gtggtttctg gttcttggcc agttaaattc aacctgacca ggaggcacgc  108900
ttaattctaa aattgctttt accttctgaa gttttgtgg tatagacatc ctccttttc  108960 tactttaatg aaagcatgtt ataagcagat cataacaatt ttttttcctt taaaacaata  109020
```

```
ttgtaattag gccagttgca gtggctcaca cctgtaatcc cagcactttg ggaggctgag   109080
gcaggcgggt cacttgaggt aaggagttcg agaccagcct gaggaacata ctaaaacccc   109140
gtctttacta acaatacaaa aaaattagcc gggcttgctg gcacatgcct gtaatcccag   109200
ctgctctgga agctgaggca tgagaatccc ttgaacctgt gaagtggagt ttgcagtgat   109260
tctaggtcgc accattgcac aagcctgggt ggcagagcaa gaccctgtct caaaaaaaaa   109320 aaaaaaaaa aatggctcac acctgtaatc ctagcacttt gggaggctga ggcgggcgaa   109380
tcatgaggtc aggagatcga gaccatcttg gctaacaagg agaaacccg tctctactaa   109440 aaatacaaaa aaaacaaaa ttagccaggc gtggtggcag acacctgtag tcccagctac   109500
tcaggaggct gaggcaggag aatggcgtga gcccgggagg tggagcttgc agtgagctga   109560
gatcacgcca ctgcactgca gcctgggcga cagagcgaga ctctgtctca aaaaaaaaa   109620 aaaaatgtaa ttgatgtaat agtcccaaaa aagaacttgg cattaagtta aattataaaa   109680
tcagaaagct atgtaattta aatttgtatt caaaatctgt atattggcat gtatattctg   109740
tgccagttta tttaagatgt tactgtatca tgaagcttac ttaaggcata taatcgtctg   109800
cactgtaaaa caaactacca aattaatgta ctatctcaaa gaattaaaca tataacaatt   109860
ttgatgacca cctaaatttt agaacaactg ttttttttaaa aaacttttta ctatggaaac   109920
ttttatatat ataatatata taaattatat atgttatata taatatatat atgttatata   109980
taatatatat gttatatata atatatatgt tatatattgt ataaattta tgttatatat   110040 aaattatata cattatatat aaagtataaa ttatatgaat tttatatata tatatttttt   110100
gagatggagt ctcactctgt cacccaggct ggagtgcagt ggcacagtct tggctcacta   110160
caacctccgc ctcctaagtt caagtgattc tcctgcctca gcctccctag tagccaggat   110220
gacaggagcc tgccaccatg cctggctaat ttttgtgttt ttaatagaga tggggtttca   110280
ccatgttggc caggctggtc ttgaactcca gacctcaggt gatctgcctg ccttggcctc   110340
ccaaaatgct gggattacag gcatgagcca ccatgtctgg ccaactatgg aaaattttaa   110400
acatacataa aagtagagta gtatatgaat cattgtgagc tcattaacaa agataatttt   110460
cagttcactt taaaaattga cgtgtgaaag tttggactca tacattttgt tttggtctaa   110520
agtttccttg gcaaatattc acatggttcc attgactctg ctccttttt aagataggat   110580 gctttttat ttttttaaga gaaaaattat tgctctgaca agctaatcaa agatatttaa   110640
ttttggaatt tggaggaaag gcataaacct agtttattac aaaaatacct cttttagtt   110700 ttcctagcct taaagtagga gacaacctcc ctccctttac acaggttata ctttcatatg   110760
gtatttgcat aaagaaatct tgttttcacc ctggcctaaa tatacatcca atttctctg   110820 caccttttag gtaactcttt tttaaggagg gtgtgtgtgt gtgtgtgt gtgtgtatgt   110880 atgcgtccgc atgcatgtgc atgtgtgtac acgcatgtat ggattttcat ggttttaaa   110940 atatagacat aagtacaaat acatttattt ccccactctt catacataag atacataata   111000
ctgtatatat cattctgtat tttgttttta acgtttatgt aggccattct ggaaattttg   111060
tttcatacat aatttttat atatatacaa ctacagttcc attgtataga tgtactatag   111120
tgtatttaac cagtgatgtg tgtatggtca ttcaggttct ttctagactt ttgatataca   111180
gtcagtactg tagtgaataa tgttgcacat acattattct tatgtattgc aggcatatct   111240
gtgagataga ttcccagaag tatgcttgac taggtcaaag agaaatttgc atttgtgact   111300
ttgatagata caaatttcgc ttcatggatc ttgcttaatt atgagatgtc tgtttatagc   111360
```

```
ttcataccag tagaatatgt tatcaattt  tttttggatt  tttgccaatc  tgataaatga  111420
aaaataactt  cactagtttg  ggtttgcttt  cctctgagtg  agactgaaca  tgttttcata  111480
tgtgtgaagg  ccatttctac  ttctgtttct  gggacctgtc  tctcatatat  ttttcccttt  111540
ttctcttggg  ttattggtct  tcatctcaat  ttttcaggag  ctctttgtgt  atcaggaagc  111600
taacacatct  gctaaatgag  ttgcaaatat  attttcacc   atttgtactg  tcttttact   111660
tcacttttaa  tgtgtttgtt  ttgccatcca  aaagttttt   tttagcttta  tgtaggtgaa  111720
tataatattt  ttttccttta  tgacttgtag  attttgcatc  agagttataa  aagccttttt  111780
catttgaaga  tttgaaggtg  ccatgctttc  ttctagttct  tttatggttt  gtttcactct  111840
ccttcccttt  cttccttcca  gcatttaaat  atttgatcca  tttgtagttt  attctggtat  111900
acaatatgaa  gtatggatga  accttttttt  ctagattagt  tccagttgtc  ccagcatcag  111960
ttatttaaaa  gttcatcttt  accccatttc  agatgttgcc  tttatcttat  tcgcactttc  112020
tttatgtgtt  agggtctatt  ttggtctttc  tgttttgttc  cattgatttc  ttcatctgtt  112080
gtacaggtac  tatcatgaaa  gaacaaatag  tataaaatt   cagcctacaa  aagtggaatt  112140
aagaaggact  gatagatggc  ttgccttggt  aatagagcag  aaaccaaat   ttttgcctgt  112200
tgatgaaata  tatatgcaac  ttaggatcag  catatgtaga  gaagcatgag  ggagcatagc  112260
catatttgaa  gtgcattact  ggagtgccta  agggaaatta  ccaaagaggc  tgaaggatag  112320
atagctccaa  gtcattggtg  gccttttatg  acacattatg  gaattggaat  tttatcttac  112380
aaataatggg  aaaattttaa  gcaaactagt  gaaatttaag  attatatatt  agaatgggtt  112440
aaatgctgag  ttcagtgaac  tcagcgtggg  cttcagattc  cacaaaccct  atgaaatttt  112500
gtttcagaga  gcacatttga  ggctttcatt  agattctcag  aagtctttct  ctctctcccc  112560
ctcccaccct  cacacacaca  cacacacaca  cacacacaca  cacaggtgtg  catgcacatg  112620
catgcccaaa  agttaagaat  accttcttaa  aagtaaaaaa  ttaaaaacaa  agataaaaaa  112680
gaaaaaaga   atgccttctt  tagaaagatt  tctatggtaa  cataggatag  gatacattgg  112740
atgtggttta  aaactaaaga  tcggtcacca  gtcaggaaat  tttggcatta  gtataggcgg  112800
aagacgaatg  gcacagggaa  aagtgagctt  tcacttaagt  ttattattc   tgaaaggtta  112860
caaccagttc  tcattgttcg  tagtagttat  ggtctataaa  ttcactacaa  acaattagtg  112920
aacactgaac  cttgctccta  ggggaagtac  aaggattatt  attattaaaa  tgagccaaaa  112980
aaccctctg   tatattggcc  tctaggttgt  ttcttccatt  acaacaggtt  gagacctatt  113040
ggcttaaaag  tgtgcttgca  ccaaactaaa  tttttgtac   atctaattgt  tttaaatata  113100
atcctgataa  gcagatttt   agccactgag  agcctgccta  ctttgcagtc  cccacaaaac  113160
tgctttgtac  tcaacatcta  ttaggtataa  ataagatcaa  atcccaaggc  tataaagatt  113220
ccaagctgct  gttgcccttt  ggagctcttt  gatacataga  ctccctgctg  ggttgtctaa  113280
cattgtcagc  tagacatata  agctccctct  cctactcccc  tctcccctga  gagtcccta   113340
gccctcctct  tctgggtgat  agccactcca  cctcagcttc  tggccagtcc  tgtttgggta  113400
gtggccactc  tgccttagcc  tctggacagt  atgctttaag  gacatcctct  gcctgcagat  113460
ctgtcaatgt  cacccaataa  agctatgcat  gctactgcca  cctcgtggtc  atatcttttt  113520
ccttgatcag  accccagatc  cttcacattt  aaaatacagt  taggttccta  ccagcctcta  113580
gtcacatttt  catcagtcag  tcgatacgta  accttgtttt  gtgtgtgttt  ctgtttaaag  113640
acatattgtt  gattcattaa  cattgaactc  acggctgaca  ttactataac  tcatgcctga  113700
aggaagctgg  cctaacacat  gtacttactc  tgccagggac  attatagcct  tcttatgctt  113760
```

```
accagccota aacagcacgt gagcactatg cttagggatt attttaaaca gaagaatcat  113820
caacaagaag cacaaaagtg agaaaaaagt ggcaccaaat aggctctgcc caggatactt  113880
gtttatagta tgaaaattga aacaagaagg caagagaaag cttcactgtt caacctcagt  113940
tggagaggtg catgcattag gcgactcaaa tatctcattg ctctgcgcat gtctatgaaa  114000
gcactaagag tattgacttt agagttacaa ataaatttta gcaagtagag agatttcaag  114060
tatggactcc acaagtaatg aggatcaact gtaccatcca gtctctttaa tacttccagt  114120
gatgagccca gtctctcatg acaaactttt accttgctgg gtaggtaaaa gttcagggtt  114180
tttctttgtt tgtttgtgac agtatctcgc tctgtcaccc aggctggaat gcagtggtac  114240
gattttggct tgccgcaacc tctgccttct gggttcaagt gattatcgtg cctcagccac  114300
ctgagtagct gggattatag gcgcccgccg ctctgcccgg ctactttttg tgtttttag   114360
tagagatggg gtttcaccat gttggctaag ctggtctcga actcctgacc tcaaatgatc  114420
cacccacctt ggcctcccaa agtgttggga ttacaggtgt tagccactgc acccaacctg  114480
gatagtttta atggttatat tgcactaccc tctgcgtcct gttatttctg gtcatagatc  114540
ctaattaggc tttctggact ctttccccct tcaatatatt atttgaattc agctgtctta  114600
tatttacctt taccccottt ttttccccto tagcataaat attcccaatt tctttggaaa  114660
cttttggttt gctaagcacc tcaatttaaa tgaatggaac ttattgttac aaactaaact  114720
ttcccottct tcttacacct cccaataaaa actgtgtcct ctgtattcac actgcctcac  114780
tgtagtctac accttcagtt ccaagtaact cagatttgcc tgtgggggat gaggcaagga  114840
aaaggctaaa gatagataac tttaaatata cagagagatt acttttttt tccctttccc   114900
tttccctcct tctctgtctc tctcttccca tgtcatcttt gctgcttcgt atgttagctt  114960
cattctataa cagattttct cagtgtggtg gagaatatgg ccattgaggg ctccagattt  115020
gtatcttctg caaatctaca gaactacagt agaaacaagg acttttctct gtcagtgtcc  115080
atgtgtcaat ttagggaaga actcaggtac tgtttgggtc atatatatag ccctggacca  115140
gttgctcttg ccgggggtat gggaaactga ttagccagct tctgtcatct gtagtgacat  115200
aaaagtagtg acccttgata gcttttctag taccatgtgg atttctagag aagggaatat  115260
tcccagagga aacaggggca ccaaacaaca aatatcaagt atacatgtta agacaggttt  115320
ttttcttccc gctatgttta gggccagtaa gaggtctctt aaggacagtc agtgtgattg  115380
aagggttata cagttttcag ctttgaacag tattggatca aaattgattt tgcttttaat  115440
attgacatct attattgctc agtgatggat atactgcgtt ggtgggtata ttgtagcaga  115500
tactgttact tcttcttttt atatgtttaa agtatttcat aattttaata aaatagaaaa  115560
ttaactttgc tttgatttaa gttggtgaat aataacaaat atttgggtta taatttccct  115620
ttagtattaa gttagctgta gaaatggtgt tgtatctgac ctagtaaccc atttgacttt  115680
ttaaagatga attactaaat tttttttaatg atatgaaaaa atgtaatttg ctcccttac   115740
ctcttatcaa tatatttatg ataccatagg tacctgcaag gtgtggagtt acagtccgag  115800
acagtctaaa gaaagcactg atgatgagag gtctaatccc agagtgctgt gctgtttaca  115860
gaattcagga tgggtatggt ttgtatgtga cgtgaaattt tgtttaaaaa gaaaatcaca  115920
cattaaactt tgaagttttc ttaggatctt taccaaaacc tagggaattg aaagtgtact  115980
ttaggaaaaa gtattaaaat aatactaagt tagcctgaag aaatactgta ggccatatga  116040
ggagttaaat aattgtatat gactgtaggg tttgttactt tgatcaaatg attttatttg  116100
```

```
gaatttgaga ttcttacaat tttgaacca ttcagagtgt gatttatttg gataatagac  116160
tcttaccccc ctcccatttt taatacaaac tcatagtttc acaaaaggta tatcaaaatt  116220
aacattttat attgacctac ttttctttca gaaagtgtct aacattgttc caagaccctc  116280
acattttgaa tcctctttaa aaaaaaaaaa attatttgg gggcatgttg tccctgtccc  116340
ttgagtactc ttttccttg aatggataga taagtccgta cctgtgattt ttttttttt  116400
tttttttttt tttggacccc aggaacaatc cattttctgc tgttgtaggt cttttctgga  116460
gctgacttga agaaaagagt acatctcttt accctgctgt tgtccaaga gtgatacatt  116520
tatttggggt aaacttaaaa ttaatttatt gccatttaaa tttctaacga tggaatatta  116580
gggagccaaa cctccctcac tgttactagc ccctcgataa ccaattttca tatcttcagc  116640
atgaggtata tgaatatttt taggtgtaat aaccaagaaa ggcttgtgtc tacatttttc  116700
agagagaaga aaccaattgg ttgggacact gatatttcct ggcttactgg agaagaattg  116760
catgtggaag tgttggagaa tgttccactt acaacacaca actttgtatg tatctttaca  116820
tttttttttg aaatgtcaaa aatgtttaga ttttaatgaa tgaattttta tttagggaat  116880
gtgaaatatg gatgagtaat tttggaactg acatttacc tgagttgaaa tcagttgttt  116940
tctttaaaaa cttgtattta aacaagagtt taatttaat ctttatactt tcttttaat  117000
ttaaaaagt aaaatgtatg cattgttaaa agataatttt gaatagtgca gaagtatgtc  117060
aagtaaaaaa agtgaaaata ccctcctaga ggccaacatt tgtttagatt aacagattat  117120
tgttctgtct tccaaacttt tttctgtgta cacaaacgtg tgcttgtacc tgtaagccta  117180
aagtttttc ctttctttt ttctctcttt ccttcattac tttctttct tttccctttc  117240
ttaaatcaaa gtagagccat gctatgtgat attctttgcc ttattttttt ttaattcaac  117300
aggatgtcac ggacatcttt tcatgtcagt ataccttggct ttattttagt atgactatgt  117360
aataattcgt aagaatagga attcattata tttaaccatt tctctattga tagacattta  117420
agttttgta ttataaaaaa tctgttacat acagggctaa acaaggtctt tctgcatata  117480
tcttgacaca cttgtacaca cccttgtgtt tctgaaggat aggttaatgg aaatagaatg  117540
gctggatatt aaactctcca tgaggctttt ttctttgtct ggttttgca tttgctagaa  117600
cctagcataa gcctaagggt caccagcata aggcccggaa tgtgggacct ttccacctta  117660
gagatgagga tctacataga acttgagaac ttatcccta aaatggcagg cagaagccaa  117720
aagttgtctc tgaatcagga atacatttct tacttttctc tatgtatgga attttggcca  117780
gagtttttc taggtggata attactgcta ccctttaggc gtcaagtgtt tcccatgtg  117840
tcttggtgat taatccagct gggctcttaa agcagatgat tgattagatt atttcctttg  117900
gggtttatgc tttcaagcct ccattagtag tgaataatga aatcatgttt gtgtttctgt  117960
aaggcatttt ttgggagaag tgtaagatac acctaatgtc aatcaaattt tactgtgcag  118020
caaataattt tttaacatgt tgaattttaa gtggataaat cttaacattt ttatttaagt  118080
tcttaagaat acaaatacag ttgagcatac atttcatagt gattactact ctgtttctta  118140
ataattcttc ttagctagaa attgaatatg aggagataaa agaaagacct aagttgctaa  118200
gtgtgagaaa atagtattaa aatgatgcct caggaaggtc cttgccacag aaggattgtg  118260
aaagcaaact gcagattgat tccagagtat ggaaattgtc accactcagt tggataccctg  118320
ccagtaaatt tttattgaga actttccatt tgccaatacc atatcttacc tagggatatg  118380
acaaatgaat aagacagtgt cactgccata gagtagagag aagatttaat aaattttcat  118440
aaacattcat aattactata tatgtataaa gttctataga tgcacagaga ttcctaacct  118500
```

```
ggcttttgag gagttaggaa ggtttctcag agacagaaat atctaagctt aggcctgatg  118560
gatgaggaag taagtatcaa gtaaagagta ccctaaacag agggaagagc aagaaagcat  118620
gttacctttc aaagttttga aagaagttca gaatggatga tacaaggttg aagagtaggt  118680
tgttaacagt attgtgggta gaataagagt tgtgggtaga ataagcagag tccagctcat  118740
gaaaatcctt gttagccata ttaaagattt ggattttct gtaaaataat tagaaatgta  118800
atagttgtaa gcttggggag aaatgtgatt agatttgtgt gttagaatga ttgctctgag  118860
tgccatatag aggcaagatc aaaaacctat gttctgctta gaaggaaaa gtgttcttgg  118920
ctgtcttggg ttttgcttgg ctattcaagg agggctgctt atgcctcatg gtttcatatt  118980
ataaaagcaa tcccttcagt atttctctat atcccaagag tccttgggaa ctgggaagtg  119040
ggaaaacaag atttgaaact tttatatcca aaccttctcc tttttctgca gacactcagt  119100
gtcttccttc acacagcccc acaccttaca aattaatgca tgcaaattac cttgactgtg  119160
cctctcacta atttgccata catatttatg tatactcaga tactagatta agtgtaagct  119220
gtgacccaaa agaaagatat atcttcctgt gctcatcttt attgacaaag gtatacttac  119280
agatacaggc atatattgct taaaatttat gatcaaatgc atatccacat gttttcttc  119340
cttcagctgt tttggtcacc tacctacttg gtttggtgaa taatggccac ataaaaatt  119400
ttaaagattt taaatttct tgtatatcca gagacaaatg gaaaagaac acaattagaa  119460
atagacattt acctgtttta tatcccctag aaagtgatac ataggaaaaa aggtgaagaa  119520
aataagagtc acttttaaaa ctaaatgtcc tcaaaaagcc agaatgtatt atatatcagg  119580
atgtaatttt cttgaaatat tttcaataac tttctattct taatggaaca gaatgtgtaa  119640
ataaatgtgt attgaaaatg gacttttggc tgggcacagt ggctcatgcc tctaatccct  119700
tgagaggccg aggcaggcag atcacttgag cccaagagtt caagaccagc ctgggtaaca  119760
tgacaaaacc tcatctctcc aaaaaaatac aaaaagtagg tgggcatggt ggtgtgcacc  119820
aatagccttg gctattcagc ctgaggtggg aggataactt gagcctggga ggcagacttt  119880
gcagtgagtc atgattgtgc caccatactc cagcctgggc aacagagcaa gaccctatca  119940
aaaaaaaag aaagaaaaa gaaagtaga cttttgatgt tgaaatctat ttaatgtatc  120000
ataaaaaat ttacatgtag cagaatagat taggaagttc taattcatgt tgtatatagt  120060
cagggtaagt agtgttgtat gaatacagtt atatatggag tcataatgta aaatatcatt  120120
atttgtgatt aaaactctga aaactgggc acagtggctc acgcctgtaa tcccagcact  120180
ttgggaggct aaggtgggca gctcacgagg tcaggagttc aagaccagcc tggccagcct  120240
ggtaaaatcc tgtctcattt gaaaatcttg tgagttgtaa ctggttttat acaaatatt  120300
gaagagtgga aattgtataa ttacaatcat gtaattaaaa gtattaacca ccccccccaa  120360
aaaaaaaacc tgtctctact aaaaatacaa aaattagcca ggtgtgatgg tgtgcgccta  120420
tagtcctagc tgctcgggag gctgaggcag gaaaatcgct tgaatccagg aggtggaggt  120480
tgtagtgagc cgagatcgtg ccactgcact ccggcctggg tgacagtgag actctgtctc  120540
aaaaaaaaaa tctctgaaaa actgaaatga attaagaata tagaggccga gtgtggtggc  120600
tcatgtctgt aacactctgg gaagacgagg caggcggatc acttgaggtc aggagtttga  120660
gaccagcctg gccaacatgg tgaaactcca tctccaccaa aaaatacaaa cgttagctag  120720
gcatggtggt gcatgcctgt agtccccagc tactgggag gctgaggcag gagaatcact  120780
tgaaaccagg aggcagaggt tgcagtgggc cgagatcctg ccactgtact ccaacctggg  120840
```

```
cgacagagcg agactccatc tcaagaatac agagcaaaga acaaataatg aaatagaagt   120900
cacccatgct ctcgccactc tgaagtagcc actcacattt tgatatttat tcttatattt   120960
tcttattatt atatacacta aataaatata ttttaagcaa tttctggctt tagtgggata   121020
gattcttcct agtgcagttc tgttacgtga ctcatgttct acatcatttg cctttgacat   121080
ggaattctta acatgttgcc ttctaagttt cacctagaga agtgttcaca ataagtttta   121140
tgtggcccaa acattctaat cctctaagaa attgatcatt tgttagaaaa aatagatctt   121200
attgtctttt aggtgatttt tctgtttctt atttttttta gtaagattag aagagctgt   121260
ttcaatttc atatgattac ttactagttt tataaataat tgtttttaca tttttatcca   121320
aagttaacca ttatgttttt ggaccataga tcaggggttc tgattctgtc agctattttg   121380
tttttgtttt tgtttttagct attatgtaga ttgtatttat agtctctctc cctcccaccc   121440
ccaattccac tctggaggaa ttcactgtta atttttaatg gtttctgttt taagctcttt   121500
tggtgattat tttcatctta ctaaatacag ttacacattg cctgatgact gggatatgtt   121560
ctgagaaatg catcaatggt gattttgtta tgtgcttaca caagcctaca tggtatagcc   121620
taactataca actaggctat atggtagagc ctattgcttc taagctaata acctgcacgg   121680
aatgttactg aactgaatgc tgtaggtaac cttaacacag tggcaagttt gtgtatctaa   121740
acgtagaaaa ggtacagtaa aaatacagta taaaagatca aaaatggtct acctgtgtag   121800
gatacctaat atgaacagag cttttaggac tggaaattgc tctggtgagt gagtggtgag   121860
tgaatgtgaa ggcgtaggac attactattt gttactgtag acttttatga taaacattgt   121920
acacttaggc tacagtacag ttttaaaatt tttcttttta aaaagtttat aaagtaaaaa   121980
atttacatta aactaaggtt taatttttt taacttttg actcttgaaa taacagtttc   122040
aaaagtttaa aaacattata tagctataca aaaatatttt atgtgcttat tctataaact   122100
tctattttaa aaatttttaa tttttcttt ttacttttta aacttttctg ttaaaaatga   122160
agacacaagc tgcacacggt ggctcatgtt tgtaatccca gcacttgagg aggcctaggc   122220
agacgcatca cctgaggtca ggagttcaag accagcctgg tcaacatggt gaaacccttc   122280
ctctaataaa aaataggaaa attagccagg cctagtggca tgtgcctgtg gtcccagctg   122340
ctcgggaggc tgaagcagga gaatcacttg aaccaggagg tggaggttgc agtgagccga   122400
gatcgtgcca cagcactcca gcctgggcga cagagccaga ctctgtctca aaaaaaaaa   122460
aaaaaaaaa aagacacaaa catacacatt agcctaggtc tacacaaggt caggatcttc   122520
aaggtatcac taggcaatag gaattattca actcctttat aatcttatgg gaccactgtg   122580
gtatgaagtc catgattaac tgaagtgtca ttatgtgaca catgactgca attatctttt   122640
agccacaatt tcttgcttta ttaactttag atatcatata ctgattactg attgtataag   122700
gaattagctc atttatagtt cttcctctcc ctcctctccc ccaatatttt tattagtagt   122760
tttttggttc ttctattggg tgcctttgta actttaatat atgcctttct tgttccgtca   122820
acaccagtcg gcatttctta acctcccttc tttgtatgat aattaaagta taggcttctt   122880
cctttcacct ctgtttcctc ctcctttttca tgtctacttt tactttatg ttgtcaagct   122940
tgaaatcagt tgccagcctt ttactcattt ctcattttt aacttctggg ttttaagtt   123000
agatagtggg gtgggaaata aatatgtgta gtccatctat tatcttgaac ccccggtttt   123060
cattttataa tagtacttta gtatgtgagt ttcatgatat aaatatatta caactttgtt   123120
attttaaaca agagagtaga tacgtcagtt tctagaaagt tttcttgtga gtttttgaaa   123180
tctctgtgat tttttactttt gcaggtacga aaaacgtttt tcaccttagc attttgtgac   123240
```

```
ttttgtcgaa agctgctttt ccagggtttc cgctgtcaaa catgtggtta taaatttcac   123300
cagcgttgta gtacagaagt tccactgatg tgtgttaatt atgaccaact tgagtaagta   123360
atccaaaaat atctcttttc tacctaccat tttacactta aattttctta atgtgaagct   123420
acgatgtcta aaagtctgtg agggttttc ttccatacga ttgttataga gaattttttt   123480
taagtgtagt tagagaataa tatgtggaat ggacagtatt tctctcccaa attgtaatgc   123540
tggttcagct atacagttaa tttatatttt atattatcgt ttaattaatc aagacccta   123600 acccatagaa accattttg gatagtttct aggaggagag ggagagttgt tcaattaaa   123660 ttaagcatta tgattttgta ccacagatca ggtagtctga ttctgttagc tattttgtaa   123720
attacgttta tattcttcct ctctctcctt catccccatt cagctccctt ccccaattt   123780 atttgagtaa gatgtaaaat ttttgtatcc agtatatatc tctttctaaa atttctcttt   123840
gctgtatgcc agttttcta atagattaga ctgagtctat tatctctttt tgtgtcattg   123900
gtgctgctgc tgttaaagtc ttacttttct tgatcacctg agcaaataaa acttaactct   123960
gtactttaag taaattataa tgtcacctaa tttacagtag atactttta ttctcattct   124020 ttaaccataa agcatgattt tcatcttgta gtatgtagaa atttgctgaa ctgaatgatt   124080
agttttaagt tataagcatg cctttgaaag tgcaatacaa ttttttttaa aataagcctt   124140
tagacaaaaa tacaactaat tgaattttaa cagttgtttc tgagaatgga atttgatctc   124200 agttttttg gttaactatg tattttggta tatgaagctt ctgggttttg cacaagttag   124260
gtttgttttg ttttgcctca cagtttgctg tttgtctcca agttctttga acaccccca   124320 ataccacagg aagaggcgtc cttagcagag actgccctaa catctggatc atcccttcc   124380 gcacccgcct cggactctat tgggtatggt ttgacttctg ctcttgggcg acatgctact   124440
tgaaccgctt tcttttggat ctcctggtta attagaaacc tttccaatgt ttaaattgtt   124500
aaattaagga ctttttcccc aaataactta tcataccact cagatattta catgcatttg   124560
atacaaataa atgggattaa agctgacata gactatttca gaatcagtcc tgaaaaaatc   124620
aatattgggt atgatttgac ttctgctctt cagtgacatg cttcttgaac tgctttcttt   124680
tggatctcct ggttaattag aaacatttcc aacatttaaa tgcttaaatt aaggatcttt   124740
tccccaaata acttatttta tcacaccagt cagatattta cttgcatttg gtacaaataa   124800
gtgggattaa agctgacata gactatttca gaaccagtcc tgaaaaaatc atgcaacaga   124860 tcatttgag tctacacctt gagttcatct tttattaggt atagaagtat atgacttcca   124920
cttatgaaga agcattgata tgtgagacaa tggcaaacaa tgtaaaaata gtatataatt   124980
ataatctaca atttatgatg gagtatattg aagtatgtga tgaggacata aatgtattca   125040
tgtttacaga aggaagaata gtgaggaaaa agagagtgct caggaaaact taatgaagaa   125100
ggtggtattt gaactagact ttaaagaatt actacaatct gaacgggcct agggaataga   125160
agcatggtga aagggaatg gagaaacaac agatataaag ggaataaaca gatataaagg   125220
gaatgaagat gttaggttta gaagctagtg aagaaaggtt tatctaactt aagaactacc   125280
atgtgtaaaa ccagattatg gagagtcttg gaattgaggc cagaatttag acttaaaggt   125340
ctttaagcag attactaact tgatgaaaat ggctttaaag aaaaaatcaa ttagcagtga   125400
aatacagatg gattgacaga aaatttaggg tgaagaaggc caacctagga tgttgttggt   125460
agtgaaaact gagagaggca gtgaagacaa gttcaagtgc tagaagtatg gaaagggat   125520 agatattcat aaagcgtaaa agaaaaaaat gaacagtatt attaatcagt tgaggataaa   125580
```

```
gctgagaagt gactttaaaa ataatgcaaa ggcagccggg tgcggtggtt cacgcatgta    125640
atcccagcac tttgggaggc tgaggcgggc agatcacgag gtcaggagtt cgagaccagc    125700
ctggccaaca tggtgaaacc ctgtctctac taaagataca aaaaaaaaaa aattagctgg    125760
gcatgatggc acacacctgt aatcccagct actcaggagg ctgaggcagg agaatcactt    125820
gaacctggga ggtggaggtt gcagtgagct gagatcgcac cattgcactc cagcctgggt    125880
gacaggtgag attctgtctc aaaaaaataa aaataatgca aaggcgtcat ttaagcttca    125940
tagtaggaaa taaaaaggaa gacacaataa agatgagtta agtgggtatc agtttacttt    126000
ggaacatttc tcgaactcct ggcctcaggt gatcttcctg cctcagcctc ccaaactgct    126060
agaattacag gcgtgagaca ctgcacctaa ttagctttgg aacatttctg acacaggtct    126120
gtgtactctt tcacattgaa tttggggcag cgttatttag gctgcgtctg gaagcacatg    126180 cttaaaaaa aaaaaaaaa aaaaaggccg ggcgcggtgg ctcactcctg taatcccagc    126240
actttgggag gccgaggcag gcggatcacg aggtcgggag atcatgacca tcctggctaa    126300
cacagtgaaa ccccgtctct actaaaaata caaaaacaaa attagccggg cgtggtggcg    126360
ggtgcctgta gtcccagcta ctcaggagtc aggaggatgg cgtgaaccca ggaggtggag    126420
cttgtagcgg gccgagatca cgtcactgca ttccagcctg ggtgacagag caagactccg    126480
tctcaaaaaa aagaaaaaaa aagtccccat acagcattct gtcctagaat attcctgaga    126540
tgttaagatt agaaatattt attgtcagtt ttaaccctac ttcctcccac tcttcacagt    126600
gtaatgccat ttcttcagat ttctacctag agaaatcttt tcaaaatcag ttgacatttt    126660
cagtacaact ttgtaatttt tacaaagcca acctttctgg tgatctcatg ggttagaaaa    126720
ttttgcaaaa gaattttgtc ttaagcagtg agtatactta cctatttgga acactggaaa    126780
atgcagccgt tgtgttctct tgtcaggttg tagcagttat ctcttctagt ggagtcattt    126840
tattcccgtt ggctctatca ctacttgtgt gcagctgtgt ttttttaga tggtcaaatc    126900 aaaatgttat tatttggttg gttttttaatt aatcttttgg ttataatatt ttctcctgac    126960
agattctgta gaccatgatg cctttctaat ggcaggtccc agttctgtga gcagttataa    127020
aacaccctaa tgaaattagc ttggcctctc tgaaggttta taatggtaat gatccaggac    127080
atttgccttc cagtgaagga atgctatctt aaaattaaga aaccatttgc ctgtgccatg    127140 aatatttat tggtaactga actgaaatat attctgatct tgagcaaatg ataagatgtt    127200
caaacttgtc tgtaagtcat tttcctgatg ttttttatgac ataactccat atggttgtct    127260
ctgtaaagat agaagccaat cttgttcagt atcaaaactc ttttgcagtt tgttactagt    127320
cctgataaca ataataatgg tcatgaaaca agtgtaataa tggatgtaat caagaaatat    127380
tggagaagca atacattgcc cagttttgaa tacaaagtga gagataccctc cttttctact    127440 ttttaaaaat gctgtagaat gtataaattt gtgagaggtc aacatttaaa atgtacgtat    127500
caccagacca aagttttcaa aacttttaaa tattctagat taagaatgag atctaaacta    127560
actggtaatt tgctgaaggg tattataatt aaaattcctt ttgtctttaa tttggtactg    127620
ctttaaagag gtttactgca agataggtac aggtatcatt gggagaaagc cagtttgccg    127680
actgccaaga tacttcatag ggtataagtt accttggtta gtggaaaaat ttcccagtat    127740
ggtaatgtaa ttttatcgat tcccagaaat gatgagattg ggagttatac tggtttgtat    127800
taactgaaat cagaaaaaaa attgaatcag gataccaggt aatatttttc agtgaaaaat    127860
atacctgtta tgtaaattag acttcttgtg ttgtgtgcgc caccactcac tcttcttttg    127920
taagagattt atgggaaatc aaattataat cagaagactg ttttcgttaa gcatagaatt    127980
```

```
aggacatggc tgagatattc aatgacatca gattatgatc acttcaagtg ttcccttgta    128040
cttgccctga aagctagaga agttgacttg gtggaccaag acacaactat tagataccaa    128100
ctaccaaatt gagtttctct gattttgtat aatacgcaga tatcatcatt ttctaatata    128160
tacattcttt agatatgata gtgaagtgtc ttagattaaa tctggttttt gttttcttc     128220 tggaccaatg tcttttgcat acttaactct gatttgttat ctactacatg tttctgtcat    128280
attcctaact tggtgagttt cagaagtgac ttactgccat ctctgcctat cccagatcaa    128340
ttattacagt agactatctt atgcaattct agttattcat acttttttcca attttaagcc   128400 tttttttttt tttttttaaga tggagtctca ctttgtcacc caggcgagtg cagagacgtg    128460
atcttggctc actgcagtct ctgcctccct ggttcaagtg attctcctgc ctcagccccc    128520
tgagtagctg ggattacagg cccttaacac cacacccagc taattttttgt attttttagta  128580 gagacagggt tttactatgt tggccaggct ggtcttgaac tcctgacctc aggtgatcca    128640
cctgctttgg cctccaaaag tgctgggatt acaggcatga gccactgcac ctggcctgcc    128700
ttgagacttt aaatcagcct gtaaatggtt gtcagtcagt cagtgccctt tctaaaactt    128760
tattgactaa tgtcatttttt gcattctttt tcctgctcct aaaattttct agctatagac    128820
atatatttgg ctacctaaag caaaaataaa gacagctctg tcagaaacca aaagtttctc    128880
aataatcaga aaaaataaaa aggacctaga tggaacatgc taatttttcct aaaggcttgt    128940 ttcttaccta taattctcat tgagccgata ccaatttttt tttagtacat aatattttat    129000
tatttgcata tcaattctaa gtggattcat ttcattaata taaacacatg aagtcaaaac    129060
ttctttcctt atctttaata atatgcttca aagaagtaaa attgtgaact ggtgtggttc    129120
agattctgac atgtttttatt cagagactga ctttcactgt taggcttcct tggctcttca    129180
aacctttatt cattcctttc ctactatatt tttttcccat tcctcacgtc tcacaaaagt    129240
gtctttttat tccctcaaca ttgtcttttct agctgtgtct tagtaaccac taataattag    129300
tttgcataaa atagggtgga atgataacca atatgtgaag agagcttatt ggcacttagc    129360
cattcattgg tcctgatgga gttaagtgag acagcttacc tcatctatca agtgacactc    129420
atttccccac tcctaggata cccttttctga ggggctacat ccttccaagt gtttacaatc    129480
tagtctcaaa actttagtgt tctctgtgag tgccaggttc attttagggt gagatatcat    129540
agactatgtt atttagctac ataccgaaaa taggtatgta acatattttg gtgatttttcc   129600 aaatagcata caaatgtaac attttggtgg ttttccaaat agcagttttc aaaaatattt    129660
gctttagtgg ttaatatatg attctcttgt gtctctgtta tcaataatgg gcatgataaa    129720
aaatccagaa tatgagagat attggcactc tgaggatcat cttctgaatt tgaaaggat     129780 ttttcaatat tgttctggat tttcattcaa ctcctgtaaa ggaacaagta catcattcag    129840
gtcctgaaat atgcatttgt attctcaaaa tatttataat ttcttaatat gtaaaatttt    129900
cattttagta aattcagatg tcaagacaat gttagaaaaa aatggcaaat tatattcagt    129960
cattctcaga gcattttttat ataacttcaa aggttgaact tcttcagttg atggccacag    130020
gtaatttcta gccataagta aatttcccta gtgttttcca ggtaagaatc agtggtctta    130080
tcattgatag ttcctggagg gcctacttga gcaaagcagc tttggcagta ttggattttt    130140
aaattaatac ttttaaaagt cattactgct aggttttttaa tgctttaatg attttgagaa    130200
tataaaaaca agaaaatcct tttatcttcc tttttaaata ttattccctt tatatcgtta    130260
ctctgaatct tatcttccaa tgacttcatt tttccaggcc ccaaattctc accagtccgt    130320
```

```
ctccttcaaa atccattcca attccacagc ccttccgacc agcagatgaa gatcatcgaa    130380
atcaatttgg gcaacgagac cgatcctcat cagctcccaa tgtgcatata aacacaatag    130440
aacctgtcaa tattgatgta agtatccagc attgctagaa ctaaaaaaaa accaagtatg    130500
tatctttatt tttctgctat aattataact tagatcagaa ataagtgcca tttttcattt    130560
atcacagtta ttttaagtga taagcttctt gtgaatcaca aatcagaaaa gcttctggtt    130620
tctctctgat gacattaaat atttcactga ctccaggtta tacagtcact ctgattttt    130680 tcccttatga taccatctct ataaaagtca tcttcaaatg aaaatggttt aaatatcaaa    130740
ggactgatag aagcccttga cagaattaag ttctttaaaa cttttataaa aatgattatg    130800
attgtgctat aagaggtgga tatgaaatta agaatttcag gccaggcata gtggctcatg    130860
cctgtaatcc caacactttg ggaggccaag atgggtggaa cgcttgaccc agaagttaga    130920
gaccagccta ggcaacatag tgagaccccca tctctaccaa aagtaaaaca aattagccat    130980
gcatggtgag gcatgcctgt agtcccagct actctggagg gtgaggtggg aggattgctt    131040
gagcccagga ggtcaaggct gcagtgagct atgtttgcac cactgcactc cagcctgagc    131100
aacagagtga gaccctgtct caaaagaaaa gaatttcaat ttgtgctatc ataagcttgg    131160
cattatgacc aacaaaaact tgattttttc tgtgtttatt ttaaaattag catataattg    131220
aaactataaa ttttattaaa tattaatata aagaaaaac ttataaattt taattttgta    131280
attttaggta aatttgcaaa tcagactttc ttcccacttt ttactaagaa attttctcta    131340
tttttattgg gttcatttta agtgacttt ttctagtact agttttcctt aactagcaag    131400
gttcacctct atctagcaag acctaaaaac aaaggaagaa aggggaaaag gagaatgtga    131460
tataagaaat caaaccatat gtccaggtta gggttgttct cagtctgtcc aaaattgcaa    131520
ccttcatctt tactttgaaa actatcatcc ttttagacta ttccctttt ctctgattgt    131580 taccactgtt ccctggtatg ttgggcttca tttagagtgt catctttgta tcttgccttt    131640
tcatcctctc tcgtaaccag tcacagggta tcaccttttc atgtgcatct caaactggtt    131700
tttacttatt accgctgcca tttgggccca tatttttca cttgaattat atactacatt    131760
aatctcctaa atagattttc tgccattgat ttctctctat ctatttccat tccttctgca    131820
actgtcagaa ttttttttaca cttctagcat catctgttct cttgttccaa aacttttagt    131880
gacttactgt tgattacaag gtaaagtgca aactctttag cattttatt catgttcaag    131940 cacttatgat tccattaaaa agatttacta ataactgtgg gctatgcatt gtgttaggca    132000
attgggaatt atttatgaat tagcacatgg cctttgccct caaggaagtc acagtctaat    132060
aggtgaatca aacatttaaa tagataatta caaaatatat aatggtagtt tagagaaggg    132120
ggtaataaac tccatctggt tggatctagg aacattgagc agagaaggga caacctttaa    132180
gccagattat ggtgaataag taggagtaca ctacataagg gggttaggaa agtcatttgt    132240
taaggaaatg aaaggcatag aagtgccttt acatggaatg taattaatag ttgatattga    132300
agtttagggt ccaggagaag gcttggggaa tggtggaagg tgaaactagg caggtaatat    132360
ctacagtgaa aggctttgtg tattactctg aaatctaaag cagtgctagg gaatctgaag    132420
aattttgatt gggagaggaa gtcatcagct ctatatttta gaaaaatctt tgatggtaga    132480
gtggaggata gatgaaatgg gaaacacata gaggcaggac tgtcaataat gtggttttta    132540
cagtatttca gacaagaaat gatatttaaa ctcaagtaat agcattggtg ctgagaaaga    132600
gtgtgttttg ggggagggaga ctatgaatta gtgaattagt ggtaagagtc ttaggaatca    132660
tgttgaaaat gactactatt tatgaatact tattacatac aggtactatg ctaagtgctt    132720
```

```
tacgtagact ttcttatttc atcctcataa aaactcatag gttatgtact atgattatct   132780
ttattttact gttaagaaaa ttagatttac agaggttaag aaacatacac agattacact   132840
gctgataaat tactgaagtg ggttcaaacc tggcctttct ctcttacact taaccactat   132900
actgttttgt agtagaggag aggagtgaaa aatatgagaa gtagaggata atgccaggtt   132960
tctggcttat agatacttag cttatagacc gagtttctgg taaatagcac agtttgttaa   133020
ataccaaagg aaaacaaggt ttgcagaagc agcaatttta gcttttgggg ggcatatatt   133080
gactttaaga tgcctgtggg actttcaggt ttagaaatcc agtagcagtt ggatataagg   133140
accttgagta gagatacaga tttaggagta attagcatat ttatgtcagt aaagccatg    133200 gatgtaaatt gctcaaagag catatgtaaa ttgaaaaggg gagaaaatgt aaccctgata   133260
aacattaaca ttggaggtgc aggcagagac tctctgtctc ctttatgggc tggctcttcc   133320
taagtctagc cccagataac taagaacaag tgttgcagaa gccaaaggaa gaaaagggt    133380 ttcaagaata ccaaagtagt tggtgtcagt tgccattacg attcaaatga gataaagact   133440
gaaaggacta tcaattttgg caattgaaat gtcatcttta cttcattgag agctgtttta   133500
gagggccagt aagaggagaa ggcagcaggt gaggaagtag gattaagtgt taattttgag   133560
aagcttggct gtgaaggaat gacaaaagag gatagcttga ttcagggttg agggacaatt   133620 tttttttggtt tttcgggttt tgttttttgtt ttgttttgtt ttttgagatg gagtcttgct   133680
ctgtcaccca ggctggagtg cagtggtgtg atcgctgctc actgcagcct ccacctcccg   133740
ggttcaagca attctcctgc ctcagcctct cgagtagctg cgattacagg ctcccgccat   133800
catgcccagc taattttttgt atttttagta gggttttgcc atgttggcca agctggtcct   133860
gaactcctga cctcaagtga tccgcccacc tccgcctccc agagtgttgg gattacaggc   133920
gtgagccact gcacccagcc aagggacaat tgttttttaat gtaagagaca ttagtatatt   133980
tgtaactgga gaggaagaag gcagtgaaga gaaattgaag ataacaagag aggaaatgat   134040
tgatgtagta aaattccttg agcttggaaa ttatgtctct cagagactgt gaagaattaa   134100
agatggacat agccagctct gtaactcttt acagactgtg tgatgttggg caaattattt   134160
aatcctgggg ctagtagtgt ttgccttcca tagtggtttg aattgcttat tatgcctggt   134220
acataataag aattcagaaa ttatagctaa tattaatatg caaatagtta tagatattag   134280
agcagaaaag ttgtttgatg gcttttgttt tctctattat gatgaaggga agggatgtaa   134340
gtaagagaag gaactacaaa agagtgggaa aaaagttgaa atatccagtt ttcaaatgct   134400
agaagaacct ttgtaaccta gaatgagtag aaaagattgt caaggagctt taagaacaca   134460
ttcggaattt aaaaatctaa gtttatgttg ttactagcag taacttgtaa gagtggagaa   134520
agcaaaattt ggttaatcca tagttgtgga gagtttcaga gctgatgcaa cagaaaagaa   134580
agggatatgg cctttgtctt gtagttcctt ccacctgaaa gactctttgc ttttctacat   134640
gcctatctct gaaaccccaa ctcagagtaa ttccttgact gctttatcag tgaccaagtc   134700
ctatagttat catacacagc actaaaaatc ttatcggctg ggtgcagtgg ctcacacctg   134760
taatcccagc actttgggag gccaaggcag gcggatcgcc tgaggtcagg agttcaagac   134820
cagcctggcc aacatgatga aaccccatct ctaccaaaaa taaaaaatta gccgggcatg   134880
gtggcaggcg cctgtaatcc tagctactcg ggaggccgag gcaggagaat cgcttggaacc   134940 caggaggcga aggttgcagt gagctaagat cgtgccattg cactccagcc tgggtgacaa   135000
gagcaagact tcatctcaaa atcttatcac ctgtatcact tagttggcaa tcaattgagc   135060
```

```
agcaaacttt ggcatctctt ttattatatt cttatgcaat tattcttaaa ttatttgatt   135120
ttcacttact tccaatgtgt gcatcttact tcccatgaga ttgtaagctc tcaagaatgg   135180
aaagttaatg acatcactag gattttata tttgttagta gccatataac tcctgtcacc   135240
ttcttttcag gtacgtattt gattttctg tagaaaatgt tgaagacttt atatgataca   135300
ttaaacatga tagaaataca tcttaaaga atttactttg ttttagcctg taaacaaaaa   135360
gttgtctatt tgcagagact attcagagat atttggggcc attcaatccc tcatatttaa   135420
gttaaactaa ataaacagac taatgcaagt tctacccatc aaggcccaaa ttgcattacc   135480
agtagcgact gtccccacta ccatcgttgt tataaagagc taaatatata tatagttttt   135540
tttttgtttt ttttctgtga tggagtctca ctctgtcacc caggctggag tgcagtggtg   135600
caatctcagc tcactgcaac ctccgcctca caggttcaag caattctcct gcctcagcct   135660
cctgagtatc taggattaca gtcgcgtgcc accatgcctg tctaattttt gtatttttag   135720
tagagatggt gtttcaccat gttgaccagg ctggtctcaa actcctaacc tcgtgatcca   135780
ccagcctcag cctcccaaag tgctggtatt acaggcttga gccaccgcac ccggcgcata   135840
aagagctata ttttaataat aaagacaaat tttagtggcc ggttgcggcg gcttatgcat   135900
gtaatcccag cactttggga ggctgaggtg gacggatcac ctgaggtcag gagttcaaga   135960
ccagcctggc caacatggtg aaaccccgtc tctactaaaa atacaaaaat tagccaggca   136020
tggtggtgcg tgcttgtagt cccaggtatt caggaggctg aggcaggagg atcacttgaa   136080
cccaagaggc agaggttgca ataagccaag atcacgccac tgcactccag cctgggcgac   136140
agagcaactg agtctcaaaa aaaaggacaa atttttaacaa aacctttcta tgagccactt   136200
tgtttctttc ctcttctagt gtgcccttat ccatccatat ttttatgatt gtaaccagtg   136260
tacttttaat tttatatttt taaattatac tataaacatg tttcatgatt caagcttcat   136320
aattattttg gtagctgcat aatacttcat taaattgata caccataatt ttcttaacca   136380
aaatatgtca aaatgcctat aatagagaaa taattattta taacttttta gtatgatgga   136440
taatgttgca ctaaacatct ttgtgcatat cacttttct tctgaattat ttccttaaga   136500
aaagttccca gaagtagaat tacagaatca aaggatatga acattttat ctctcttaat   136560 gtgcaccagt ataattttt ttaaggattg atgaagccat ttttaaaaa tttatttatt   136620 tccaaagttc aggggtacat gtgcaggatg tgcagggttg ttacgtaggt caacatgtgc   136680
cacagcggtt tgccacacag attatcccat tacctcggta tgaagcacag catccattag   136740
ttattctttc tgttgctctt cctccttta ccatccaccc tccaacaggc ccagtatgt   136800 gttgtttccc ccatgtgtcc acttgttctt atcattcagc tcccacttat aagtgagaaa   136860
acacagtatt tggttttctg ctcctgcatt agattgttga ggataatgga agccattggt   136920
tttgaatggc ctgaaatgga catcaacatt tgattaggac taataattgt ttcattatag   136980
gtttacattg gcaagtgctt caaaatttag attgtattat gttcactaga taattccaaa   137040
ttgttttgtg taatagttat aagatgtatt gttttaatta ataaaataat tcttttaacg   137100
ttagtggaaa attcagtgtt atcgctactc tctgattata tgcttgcttg gaataaatat   137160
acattactat ttatttgtag gacttgatta gagaccaagg atttcgtggt gatggaggta   137220
agtagtgatt tcaggttttt taaaaactc aaggaaactg caattgcttt gctgcttatt   137280
tcctttatac ttgcctcttt caagtaacag acacagagaa aaatgtgtag agaaacccaa   137340
aatttttttg tttttctgta gtgtttgtca tttacctcta ataaaatgtt aactagttta   137400
taacatgagt agaaaagatg actggacata aaaggaagtc ttttttttt tttttttttt   137460
```

```
ttttgagacg gagtctcgct ctgtcgccca ggttggagtg cagtggcgcg atctcggctc   137520
actgcaagct ccgcctcccg ggttcacgcc attctcctgc ctcagcctcc cgagtagctg   137580
ggactacagg cgcctgctac cacgcccggc taatttttg tattttagt agagacgggg     137640 tttcaccgtg ttagccagga tggtctcgat ctcctgacct cgtgatccgc ccgcctcggc   137700
ctcccaaagt gctgggatta caggcgtgag ccaccgcgcc cggccaaaag gaagtcttaa   137760
aatgtattat ctacagtttt aaaatttctt ccaggatcag acaagatcgg acacgttcag   137820
gatggtatgg ccgtagacta cagttttaaa atatcttacc aaggaaagat ccttaatttt   137880
tatacccgct ttattaattt ctaaccatct tgaaagctat tgttgataaa tttcctttgt   137940
ggggctccac tgatacttaa agattgacct tagaatcaga taaaacttaa ctttgctaaa   138000
tcattctgaa gagggggttt gtcagacatt atcaaccact tccttcaact ttctggaagt   138060
gttttaaatg tacattttat agaacagacc cataatggca aagcccattt gtcctcttct   138120
taggtcagta aatacacaaa tgagaaactg aattgagatt tccaactgaa ttttcatcta   138180
gtattcactc tagcacataa gacaacattg cttaagaaaa tacttttgt aagcattacc    138240 ctatataatg ttttataaga ggtgatattt gagactgtct tgaagtgttc ttccaggagg   138300
tcctttacac ttaccttccc tgttgtcttc tgcctagtaa ggaagacctg taataactgc   138360
ttatcatgct tagagttgac ctcttcactg tgaccttctt tatcttcaaa atatctaagc   138420
ccagactcaa caatatttta cattgagtaa acattgttat aaaccttctt ttgttatgtt   138480
tctgtatacc catgaagcaa ccaaaataat aataagcctg cattctatac tctggacttg   138540
gtattgatgt tagcacatag ttacacaagc ttttttttc ctgtttgtta tttcatgaac     138600
ctgccaatta atgttgctgc cagtttgact ttcgtatgtc ttaatagctg tggcttttga   138660
taattttgcc taatacatcc agcatttaaa tgttgccatc atgttagcat cacaaaatta   138720
acttagtcat aaacacagcc tgcttagtac ctaaaagcaa gtggcatttc ttgtccttt    138780 catgagtcac ttttaaaaa atcattggga ttttatgaaa ataagcagat ttttggtcca    138840
gaattatttt atgaaacagg cttcaattca tcttgtttat tccccatgac ttctttcatt   138900
tcttctgtgt gtctgtcttc ctgtgtttgc ctgccctct ctttctcttc taacagcccc    138960
tttgaaccag ctgatgcgct gtcttcggaa ataccaatcc cggactccca gtcccctcct   139020
acattctgtc cccagtgaaa tagtgtttga ttttgagcct ggcccagtgt tcagaggtag   139080
ttgggctctt ctttcttgtt ttcacccaaa gcaaactaaa tataaaacta cagatgctgt   139140
ttgtgcctca ccctcacagc gtgtgttgt aagtgtgaaa gttttcagta ctaaatttct    139200
gtttggcctg gctggaatgc tttgaatgta cgtctcacac gtactcactg ccacaagctt   139260
tctgtatgct gtctgtcata aattttaaa agcaagaaaa tcctgacctg agatttccat    139320
cttgtttttt cgttatttta ttacttcttg gtcttgataa tttcttaaac ttagtgggtg   139380
ggaataaata aggtgggtgg ggaagagctt actggattcc tttgattta atgcatttaa    139440 gtgattattc ttgatgactt aatatttgtt aattttgtgg tttttaagaa aattaaagtg   139500
tcaatggaaa cttctattat gagatttat taggcttttg gcctttttc agattctgta     139560 atactagcag tgttttttgg gttttctttt cccccaatat gggatgtgta tatttttgtc    139620
aaaggtaggg agctgttaaa aaagacaaaa aaaagattta taacatattt tagatatttc   139680
agtgtacttc agaaatttga gaatttatcc ttttaattat gtcctaatag aagaaagttt   139740
acagtataat ttcattctcc catttcatct tgccatgttt tatttagtag ttaaactgat   139800
```

```
ttgtaaaaac ttaagtcggg ccaggcgcgg tggctcacgc ctgtaatccc agcactttgg    139860
gaggccgagg tggatggatc acctgaggtc aggagtttga gaccagcctg gtcaatgtgg    139920
tgaaaccccg tctctacaaa aatacaaaaa aaattagcta ggcatgatgg cggatgcctg    139980
taatcccagc tacttgggag gctgaggctg gagaatcgct tgaacccagg aggcggaggt    140040
tgcagtgagc cgagatcaca ccattgtact ccagcctggg tgacagagca agactccatc    140100
tcaaaaaaaa aaaagtaaaa attgggacag atgtctttct ctaaatatttt ttaaagattt    140160 atatttactg actcttgcta gttagtatct gttatatatt ctgaatgtag taatggtgct    140220
ttagattttt gctctctcag ccctgctgtt tctcagaaaa tccatagaat gggatggaag    140280
tcatacagta gtgagtaata caactaaatt aagtgataca ataaaactac ttagtagatc    140340
ataaccgtga agcctggtca agcagtcgag gctttataat gttgaaaatt atcaatggaa    140400
ggtagaaaat ggattgtgct ctacttaata gacattgtgg ataccatttt attttagaaa    140460
attgcatatg agataatgaa aattctacat ggtgatataa tatgatgtaa taatggtaaa    140520
cattttctac agattaaaca tttaaatgtg gttattggta tccttgttat ctgaaagata    140580
gtggctcttt ttttccttaa gagtagcagt catttttttaa aaagaatcta ttttcttgag    140640
gtcattttgt tgttctgtat atagaactat tgcctggaca tctgagttct actcagctgt    140700
attcaggccc cagtaagatt cactgccctg aactcttctg aaccaggtgc tactgtacct    140760
taactcagga tgtttgccat gagaaaggta tgcaaccctg ccaacagaga tcacttccaa    140820
agagtatact cctcaggctc acttgaccta tagaatattt gtatttatag taacttggct    140880
gagaggccat agcgcttact taacaaagct ctcacttaca aaggcagaga ttttttcagaa    140940 agtcttgaga aatatgcccg gctttattta cattaacttt gttttgtagg taacaaataa    141000
tctttgttta ataatgtaag cctccaggaa ccaatgatac tgaccaatat ctcttaaata    141060
gtagagcatg tagtttagga ttatatttga gtttagtgat taatatgaat aagtcagata    141120
ttttcaacat tatggccatt attagaaaat gtttccatct ggggatttcc ttttttttaa    141180
tattgattgg ctgttgaggt aatattaaat aattaattaa aaatgtatttt gttatatagg    141240 cttttacatt tattttgctt tttgattttt ttcatcaaag aaacagaaac ttgggagtat    141300
ttttagtatt tctgtcttgt tttagagaga ttgttttttct cctagatttt gcaccagtaa    141360
ataaagtatg tgtctatgtc tatcatcaga tatcttaaag gtcattaaat tggccagaaa    141420
actaaaagaa attatagttg taatcaccaa atgaggcccc ttttttggccc atcctttcca    141480 aaaggtctat atttaaacat gcactacatt ttaaaattaa gtctaaatat cccccaacct    141540
tctacccctg ataaattaac atacttgctc ctccttaatg tatacatttt tcttttcact    141600
aatttaggat caaccacagg tttgtctgct acccccccctg cctcattacc tggctcacta    141660
actaacgtga aagccttaca gaaatctcca ggacctcagc gagaaaggaa gtcatcttca    141720
tcctcagaag acaggaatcg aatggtaaga gtatatgata tcttttttttc tctgaattct    141780 ttcttcttag aagtcacagc caaatgtaat attatccttt agatatatta tgtccatatg    141840
tgacacagaa ttcccataat taaataaatt taagaactga tagttttttg cttaaagcat    141900
atttctacgg cactgctttt tgctgtcatc tataatataa tttagtaaaa ggcagttttg    141960
gaagagtaac agtattctgt tctaaagtaa ggaaaaagag agaaagctaa tattagaagg    142020
cacgaaaagg ctggtccaga attcagatat ttcagatatc tactgaagga cattcttccc    142080
tatttaaaaa atcaactttc ttctgcaaaa tgaatccacc atggcacatg tatacgtatg    142140
taacaaacct gcacattctg cacatgtatc ccagaactta aagtaaaatt taaaaataaa    142200
```

```
aaacgaatac tgtttagccg tagtattgct actaattgtt gaataagagg atcttttacc 142260
ctaccaaagt aattttatat gttgattttt tttttttttt tggaaagacc gaattagata 142320
agatacatga agaaatttag cactgattga aaaagactac ctagatgaat tgtcagtagt 142380
taccacaggt taacttaaaa ttttttgtga tttagagcca aaactattca caaatatagc 142440
agcacttatc ttgctcctta aagtcttcca gatgataaaa acattttact tatttcagta 142500
atatacattc ctgctcatac cccataaata atttatattt tttaataaat tgtttccatc 142560
ctaaccatcc ttctgagcaa agtatcacaa ggacagaaaa ccaaacacca catgttctca 142620
ctcataggtg ggaattgaac agtgagaaca cttggcacaca gggcagggaa catcacacac 142680
tgggacctgt catggggtag ggggagggga gagggacagc attaagagaa atacctaatg 142740
taaatgacaa gttaatgggt gcagcacacc aacatggcac atgtatacat aagtaacaaa 142800
cctgcaagtt gtgcacatgt accctagaac ttaaagtata ataaaataaa aataaaaat 142860 aaattttttc catcctaata ttgacttcag tcttaaattt aagttttgta ttttaagagt 142920
catactttta actactattc ttccagagaa tttttcttaa ggggatctct tcctgtatcc 142980
ctctcaggca taaggtaatg tacttagggt gaaacataag gttttctttt tctgtttggc 143040
ttgacttgac tttttttactg tttttatcaa gaaaacactt ggtagacggg actcgagtga 143100
tgattgggag attcctgatg ggcagattac agtgggacaa agaattggat ctggatcatt 143160
tggaacagtc tacaagggaa agtggcatgg taagtatgta atgtggtgac attgtgacaa 143220
gtcataatag gatatgttta acaactttta ttttgtaaaa aatatcatca aaggaaatat 143280
tcactgttcg catcaataaa ctattttgat tagtttcagg actcctccaa aagtttctaa 143340
caaaaattat gggaaataaa aactgttcac agcagtcggg actcctacca ttttattaca 143400
gtaataattt ttaaagggga attcctccag gttaactagt cctcaaaagg attttatttt 143460
cttttagagt ctttcagctg ataattttat ttgtattata agtcacaagt aaacatatta 143520
aaaatgtact taatggctgg gcgcagtggc ttatgcctgt aatcccagca ctttgggaag 143580
ctgaggctgg ctgatcacga ggtcaggaga tcaagaccat actggccaac atggtgaaac 143640
cccatctcta ctaaaaatac aaaaattagc tgggtgtgga agcacgtgcc tgtagtccca 143700
gctacttggg aggctgaggc aggagaatca ctggaaccca ggaggcggag gttgcagtga 143760
gctgagatta cgccactgca ctccaccctg gtgacagtga gactccgtct caaaaaaaaa 143820
aaattaacaa agaaatataa gtggccagta aacatataca aaatgttcag ccttactagt 143880
tatcaaagaa ttgcaaattc aaaaaataga catcattatt tgcctcttag ttggacaaaa 143940 tcttttttaaa ttggattata ttaagagtag tggatgtatt ttcatcaaag gtttaatatc 144000
aatgaaaagt gaaagtgaac atgtatccaa ctaatagaga attggataaa tttataccat 144060
catatgtgat tatataggag ttaaaatggc atggtagagg tacatttatt gatgtagaaa 144120
ggtgtctttg gtatatgaaa ttttttcaaag cagtatgtgt aagataccat attatggagc 144180
tcatagaaat atataacata attttttata tgacagtatt ttaggccagg cacagtggct 144240
cacgcctgta atcccagcac tttgggaggc cgaggcaggt ggatcaccca aggtcaggag 144300
ttcgagacca gcttggccaa catagtgaaa cctcatctct actaaaaata caaaaaatta 144360
gccaggcttg gtggtgggcg cctgtaatct cagctactca ggaggctgag gcaggagaat 144420
tgcttgaacc taggaggtgg aggttgcagt gagccgagat cccgccattg cactccaacc 144480
tggataacag cgagactgtc ttaaaaaaaa aaaaaaaaaa gactgtgttt tagtttttat 144540
```

```
ctccttaatc tatcttttca caggtgttca taaatattca cactaaattc atgtaaaagc  144600
ctaataacat ataatgtcac ttttgagtga cataattaag ggatttttt tataccttca  144660 aaatgtcttt aaacttttct taagtgctgt acagtatttt atgatacaaa cagtagaata  144720
agcactgtat tactttgata attgaggaaa atcaatgttg atttaactta ttaaaatata  144780
catacaggtt gagtatcttt atttatttat ttttgtttgt tttgttttgt tttgagacaa  144840
ggtctcgctc tgtcgcccag gctggagtgc agtggcacaa tctcaactca ctacaacctc  144900
tgcctcccag attcaagcag ttctcctacc tcagcctcct gagtagctag gattataggc  144960
gcgtaccacc acccctggct aattttttgta ttttgagtag agacgagttt tgccatgttg  145020
gccaggctgt tctcaaactc ctgacctcag gtgagccacc caccttggcc ttccaaagtg  145080
ctgggattac aggtgtgagg cagcacacct ggccaggttg ggtatcttta atccaaaatc  145140
ccaaacccga aatgctccaa aatccaaaac tttctgagtg ctgacatgat gctcaaagga  145200
aatgcttatt ggaggatttc atatgtttgg attagggatg ttaaactggt aagtataatc  145260
aaaatattcc aaaatcagaa aaaatttgaa atttgagaca cttctggtcc caggcatttt  145320
ggataaggga tactcagcct gtgtataaaa gtgcacataa attagccagg catggtggca  145380
tgtgcctgta ctcccagcta ttgaggaggc tgaggtggga gaatggcttg agcccaggag  145440
ttcaaggctg cagtgagcca tgatcacacc actgcactcc atccagccta ggtgacagag  145500
caagactctg tctctaaaaa aattaaataa acagaacatt actagcactc tagaaacacc  145560
ctcccatgtc ctcttctagc caatcacctc tctcccaagg gtaaccacca ctgtgattac  145620
aacaggaagt gcatagtgtg tactcttttg tgtcggccct tttcactcaa cattgtttat  145680
aagattcatc tatattgttg tgtgaagttg gaggtcattc attctctta cagtatttca  145740 ttgtgtgact ataacatgat ttcttctttc atctgttgca attggatcgt ttccagtttg  145800
gggctttgat tgatgctggt gctgtaaaca ttttagtgt atgtcttttg gtgaacatgt  145860
aaccattgat gggtatatat acctaggaca gaattgtgag accacagggt atgcatatgt  145920
ccagttttag taatgctgcc aacaatgtta caaagtagtt gtaccaattt aaacacctac  145980
tggcagtgtt gacgttacag ctgtttcaca taaagttttt ttttttttgat gattttaata  146040 aaatatcatt ttcttttttt attattatta tactttaag ttttagggta catgtgcaaa  146100
gtgtgcaggt tagttacata tatatacatg tgccatgctg gtgtgctgca cccattaact  146160
cacatgaagt ttttttttaaa ttttagtgac agttttagtc atttttcctaa ttgaaagtat  146220 cataagtaat ccataaattt gaaaaaaatg ttaactactc tgataaaaaa gttttatagt  146280
ttcctacttt taagcaaaat tccatagggc ctggtaattg tagtttcaac attacttgca  146340
gtttcagtta gtaaataaat attaagccta gtaagtataa tttaatattg tcaaataatt  146400
tggaaaatac catgggtact taattgattt taccaaattt ccatggaaca aacaaggttg  146460 gctattttt ggattgatat tttgaaatac tagtacagga atatcattgt tagttgaatt  146520
tttagcctta gaaacaaat ggagtttaga tagctaaagt ataatttatt tgtgatttaa  146580
taatggtatg gagttagggc tatgataatt agtgaaaaca cccaagaatg tttatactt  146640 ttaaattta aaaattgaaa tgacacttgg agtaacaatt gccttttagg tgatgtggca  146700
gtgaaaatgt tgaatgtgac agcacctaca cctcagcagt tacaagcctt caaaaatgaa  146760
gtaggagtac tcaggtgagc ttgtgtgaat tactcttttc cagagaaaga agttattttt  146820
attagctcct ggttcccagt ggtagcaact attagcttta cagatttact caaaatgaat  146880
aaatttgtag aaacagagta tgtctgagta tattttttgtc tttaaccaca ttcttttaag  146940
```

```
tagtatgcaa tgttatatgg tatggctgat agaatactta gtcctagact gaattaatgg 147000
aagtatagta ttctgataat ataaagtaat agttctactt atgaaaagaa tactctccag 147060
ttttaagctt atcagaatac atttagaggt ggtatttagt cctgggctct ggaattttag 147120
aaacattgac aaactaggat atgcctagtg aggaccacct aaatagggaa gattctagag 147180
gtgtaacggg ggaaaataat caacagaact gaggatattt agttcacaga aggctgttat 147240
gttcaagaga gtgcacagtt attccagagt gcggaaaaaa aagttattcc agagagcaga 147300
ccagggaagc aagccagagg tgaaagttgt aagaaaatga ttttgtctca acacttggaa 147360
actttataat accagaacca cttaaataaa gatatgagag tcagctacaa ctgagtgatg 147420
aacttcccat agttgaaggt atttaagcaa cctctagttg cctgtcagat atatttaaaa 147480
agatatctct gcataaagta ggaggttaga cttggcaatt gccagtctct tctaaatgta 147540 tcctttgtt gcctttttta aaaaaaaaa agcttttct gacaacattt taccgacaga 147600
ctactttggt tctcttttgt aagaattgct aaagtttgtc gacatttaat gtttactgtc 147660
acatttcttt gtacaggaaa acacgacatg tgaatatcct actcttcatg ggctattcca 147720
caaagccaca actggctatt gttacccagt ggtgtgaggg ctccagcttg tatcaccatc 147780
tccatatcat tgagaccaaa tttgagatga tcaaacttat agatattgca cgacagactg 147840
cacagggcat ggagtaagtt ccattcgtta aatgtcttgt aaattatttt tgaagaccat 147900
tgaggatgtt ttaaaggttt tggctgctat tcttttggat tgcattttaa attactgtcc 147960
aggaacataa ggatgctaac taatggctgg taaataatat gatactaaaa aataaatgtc 148020
tctgtctagt gcagccttca gaacatatat caagtatttg ataataaata catgactgca 148080
aacttaggct tagcactcag tgattgagct aagcaagaga ggttcagaag atagaaacag 148140
caaaaacctg ctaaaaagtt gttagcagtt gtgcaagtaa acagaatggt tgttagttac 148200
tttttcaaat cagtttctct gagtgcccgt attttttggtt gcaaaatggt cagttaataa 148260
agttaaagtg aaaaatctgc attctgaccc tttttgagga tttcagagtg agttcctatc 148320
tgttgaattt tgctatgcaa tttaaggagt tattttataa agtttaccat aagctaatat 148380
ggggaactga ctttgaagga taaattttaa attttgcaac tcttaagtgc aaatgaatag 148440
gtaaattaaa aggtaaaatt aaacaaattt tgaaagcact taggtgaaaa ttataaactc 148500
agtaaaatat gaattttgaaa gctctgtgag aagtttaaaa atagatatga tctgaatttt 148560
gttttttaca aattgctttc acttacatag attattatgt catttaatct ttataatgtt 148620
atgaaggaga tctttttct ttttacagat aaggaaattg aggcttttaa gttccttgtc 148680
taagggcaca catttaataa gtggcaccaa aggtgtttaa ctcaggattt ctgactccca 148740
atccagtatt ctttccccat aaccactatg ctactttac attacaaaat tagaataaaa 148800
gagtaaaagg gtatatatgt actaacacct acaactctaa ctgagtattg ctcctagcaa 148860
gtaagtatag agccaagact ctaaaccaga tctggctctt agatcttcca actataccac 148920
cttctctttc tcaaaactag gcaatatatc tataatttag attgtttaca agcctatatt 148980
cggccaaaat acttattaca gcaaattatt accttattca gtaacacccc cacttacccc 149040
tagacttgaa acaatctcaa cgtttcagat aagttagaat ctctgaatct gttcgaatct 149100
aaaggctttt aaagaattaa atcttggcc aggcacagtg gctcacactt gtaatcccag 149160
aactatggga ggccgaggca ggcggatcac ctgaggtcgg gagttcaaga ctagcctgac 149220
caacatggag aaacccccgtc tctactaaaa atacaaaatg agccaggcac aagcctgtaa 149280
```

```
tcccagctac ttgggaggct aaggcagaag aatcacttga acccgggagg cagaggttgc   149340
agtgggccaa gatcacacca ttgcactcca gcctgggcaa caagagcaaa attccgtctc   149400
aaaaaaaaaa aaaagaatt  aaaatcttgt gaagagtaaa ccatggcaaa gattgtgaac   149460
attcagtgag aaacaaaggc ttattctctt cccacaccac tggtctcttt gcaatttctt   149520
cagcaggcca agcgtgttcc ttctttagga cctttatgtt tgttatattc tctttaggat   149580
acacatgcca caaatatcct tgtgtctcgg ttcatatgtc ccctttaat  agaaatcctt   149640 gctcacctta tataactaac atgtccccac gtcactctgt cactctctat acccataggc   149700
ttgattttct ttataacgca tagctccatc tgacttgttt cttgtctttt atccccacta   149760
gaatgcaggc tgtatgagag caggggcttt ttttcattat tttatgccta atgcctagaa   149820
tgggacctgg catactcagt acataactgt taaatgaaaa tgattacaca caactgcata   149880
ttattgatag atttacccttt cagaagaaag agatgccaaa tccttctcac atcacagctg   149940
agaaatgtgg ctgggcatgt tggctcacac ctgtaatccc agcactttgg aaggccaagg   150000
tgggaggatt gcttgagcct aagagttcaa gaccagccag gaaacatagg gagaccctcg   150060
tctctgtaaa aaataaaaaa tttagcaagg tgtggtggca cttgcctgta gtcctagcta   150120
ctcactaggc tgagttggga ggatcacttg agcccaggag tgtgaggatg caaggagtcg   150180
tgattgtgcc actgcatcca gcctgggtaa cagagcgaga ccctgtccca aaacaaacag   150240
gctgggtgta gtggctcatg cctgtaaacc caacacttta ggaggccgag gtgggtggat   150300
taagacaaga agtaacagta aagaagaaca ttatcaaatt ggaatagtgc tgcagtctga   150360
agaacagtca gtgaagaggt gatatatttt caaaatatca ctttacagtt tgggattatc   150420
agtgtaaact ttagtcatct actctgaaac actttggttg tgttttttaa tagatcttac   150480
catttaacat gatgcaatga gtgtacgata gtatgaacat agatcattcc attcagttta   150540
tcctagattt tagtaactga aaaagtatta attccaagtt ttaagccctc cagcagagta   150600
tactttttag taccagttta aaattaacca aggaggatat agtttctttt ctcttttgt    150660 tttgtcttgt aagatcataa catacaactg gttaaatgta ccgacacatc ttcagtttct   150720
gaaggatttg gcaggttgaa actcctctta ttaacagggc tatgagtttc agattaaggt   150780
gacagatttt tgctccttcc tggaactcca ctaaaactgt aataaaggaa ttttttttaa   150840
agcatggaca cataaggatg gggataacag agaggaatga acaatatca gcaacatttt    150900 gaaagctgga gagcaggtgg aaaagtgatc atagacttag accccaaaag gctaaatgat   150960
cagtcagcag tggggaaatg aaagccaacc tggtttatac cgtagaatcc tcaattctca   151020
ggaattggca atatcagcta tctcagggga tgaaagggtt aaaatgaaag gcctgtttga   151080
aaagctgtta tttctctaaa tctgttctct tactcaccag gtaactgctc catccctatc   151140
ctagcagtag actggaagtt tcttctctag agaggggaaa ataaatatct ctggactggg   151200
agaccctaat ctatgtctag gacatgtata tctttcccaa acatgggga  tttgatgact   151260 gtgtgcttac taaatgatga agggagattt ccccagccct ctcttttat  ttgattcctg   151320 acatgctagc agccaaaccc tactcttccg aaatgcagaa gattcgaaga gtcttgggtg   151380
aattttacca gctcaagagg aaagacccaa agaaagtgac atcagggatt ccacctagat   151440
tactgtatag ttcaaaaata gcaagcccat ctgtatgctt aaagcctcca ggcagcttgt   151500
aagtccctca cttagtctaa gtaagagtat cgctggataa ctagatattg gtggggaagt   151560
cttatgcaaa taagagagac tgtaaaacac atagagaaaa ataggcattg ggagaaacac   151620
atacaatgca agattatctc tcccctgcct cacccccacct ccaaaaaaacc tatcagtttt   151680
```

```
ctcagaggga gaaaagataa ctttatgtcc actaaacagg aacagaggtt ttctaaggaa   151740
cattcatgta acagcagcaa caaaatgcta aaatgttgat atttacagta cactggaaat   151800
tatgtccttt gcaattattt aaatgtaact tttaaatgtt aatttaaaag gagttaacgt   151860
agtttctcag aattctttta aggggtgttc agcaaaaaaa gttttaaaac tattatgtta   151920
aacactatat ggtttaatat taaattccta tattatgcaa cataattcgg aagggacact   151980
tagataaatt ttttacaaac caagttacat aaaatatgta taattaattg aacacataa    152040 ccagattgca tcagtgagtc ttgaagtgga tattcctgtt ttcttctcta gtgtcaatga   152100
ctaaagcaca ctattttcac tacttttttt aaattttgag acagagtctc actcctctgt   152160
cacccaggct ggacaggctg gagcgcagcg acactctctc agctcgctgc aacctctgcc   152220
tcaagtgatc ctcccacctc agtctcccta gtagctggga ctacaagggc gcaccatcac   152280
acctggctca tgttttgta ttttttgtag agacagagtt tcgccatgtc acccaggctg    152340
gtctcaaact cctgggctca agcgagccac tgcctccgcc tcccacagtg ctgggactac   152400
agatgtaagc caccaggccc ggcctatttt cagtacattt gattgaactt tgttgttgtt   152460
gttgttgttg ttgttgttgt tgttgttgtt gtagttaaac aatctgtttt aatcaggctg   152520
acagatgtta gaacaaacag gatggtccta ggggtcatga actggttctt caaatcctaa   152580
ctgttgctgc tgattttgta acagatttta acatatcttt tgacttctgg tcactcattt   152640
cagcctcatg tttggttctc tgttttaatt tcccctatc tattcccatg gatcaaatgg    152700
cacagatgga attccttaca tacctaattt ttcctcccta tttccaatac tgttcatctt   152760
gaatgccaac catagtttca tcttgagggc tttgttttgg aattatctcc agaagctatt   152820
cccagttaga agcctgcttg gataattaat attgcttctt agctccctcc agctctcttt   152880
ccttctgtcc cctggctcta ccctgagcac aaatgataat tctctgtgac catcacagcc   152940
accatcttac tgtgcctcct ttcaactctt catgtctata tcctcttccc tgaccagcat   153000
catctcacaa aggactgacc aagccagata tagtctatag ctagacaata aggctatagg   153060
gtatttaaat agcctcttaa tatgtacttt tgcaaagcct ttatttcaga atagcctgcc   153120
ctatgttgaa agtgatcttt tctgactgct caccaaaatt cattctaaag tctctggata   153180
taagcagaat aggaacaaac ggattcattt tataaagtgc taaggttgca gttaactcat   153240
aagataaaac ctttaataat tagaaaagtt agtctggaca cggtggctca cacctgtaat   153300
cccagcactt tgtgaggcca aggcaggagt attgcccgag ccaaggagtt caagaccagc   153360
ctgggcaacg gcaaaacccc gtctctacaa aaaatacaaa aattagctgg atgtgatggt   153420
gtgcacctgt gttctcacct acttgggagg ctgaggtggg aggatcactt gagcccagga   153480
agtcgaggct gcagtgagcc atgatcgtgc cactacactc cgccctggat gacagagcaa   153540
gaccctgtct caaaaataaa taagaataat tagaaaagtt gaatcattag gactttcaaa   153600
tgtgtcacct ttattggatt acagaatata agcaaaaaat ggataggtaa cattttttcct  153660 gtgtggttat atcttccatt tgtacctcag tgaaaaacta tttctgattc ctaggtttac   153720
ttgaaaagga gcagagctgt tctaatggta gataattata aactcactct gaggaatcag   153780
ggttggtaaa gtatgttta tcatcttctt tttttggtttt tttttttttt ttttgagatg   153840
gaatctcact gtcacccagg ctggagtaca gtggcacgac cttggctcac tgaaacctcc   153900
gcctctcagg ttcaagcgat tctcctgcct cagcctcctg agtaactggg attacaggca   153960
cccaccacca cacctggcta attttgtatt tttagtaaac gggttttcac catgatggcc   154020
```

```
aggctggtct tgaactcctg acctcaagtg atctgcccgc ctcggcctcc caaagtgctg   154080
ggattacagg cgtgagtcac tgcacctggc ctgttttatc atcttttcac ctgccagtca   154140
ttgattcatc ccaaggaccc agatatctta agaatactgt tactaaagaa attccaggaa   154200
tggtcagtac attgtgcctt tttttttttt ttttttttggc aggccttata atttcagtat   154260
aatatttatg gtatgatttt gaatttaact ttatcaaaaa attaaatcac agaggcacat   154320
agaaaaagtt acagcctatc gatatattta cagaagcatt atattctcaa ataagatga   154380 ttaaaaataa tttggagata aatccttaca atttactttg ttttaaacaa tgatgagcat   154440
gcctctttta ctcataagtg aacccagttg aagatagaag gactaattaa agctgaaaaa   154500
atggtgaaca tgtattagtg attgataata attctaagtg gccgaagaat atttaattat   154560
agtgaacata attttctggt cggtaaaaat aataataggg tgctgataat aataataatc   154620
agaaaatgca aggtaaaaca aaaggtacc actttccacc cactggaatt ggcaaaatgc   154680
ctgagttctg ataagatcaa atgttcatag gattagagga attgcttcct gggtcatttc   154740
tgatgcaacc agccaccta acagcattct ggaagtagct gttaaaatag gaaatgctt   154800 attctaaccc caagaaacat tagcttttgt tccaagtcgt gtatacagaa agagatgtat   154860
tataggaaac aatataatag tgaaaaattg gtctggatgc agtggctcat gcctctaatc   154920
ccagcacttt ggaagactag ggtaatagga tcacttgagg ccgggagttt gagaccagcc   154980
tggatgacac tgtgcgaccc tgactctatg taaaacttaa aacattaagg acatttttt   155040 aaaaaaagaa aaacttattg aaaaattgga aacatgttca tcaggagaag acttgataaa   155100
taacatattg gcacttacat acagtagaat cgtatatagt agttaaaagt ggattatata   155160
tgtatcaaca taaagcttta aaatattaat gttaagtgag aaaagcaagc tgcagcatga   155220
gaccacttaa aaatttttaa gcagaacatt ttttacattt gggctttaaa aagtggtgtg   155280
tatgtatata tgtaaaagta ctgaaataag gattagaaag caaagatcaa gtaacatagt   155340
gattatctcc aggaatcaag tacaaacttt gaaaaaagac tggaggtggc caagcacggt   155400
ggctcatgcc tgtaattcca gcaccttgga aggccaaggc aggtggatca cttgaggaca   155460
ggagttcgag actagcctgg ccaacatggt gaaacaccat atctactaaa aatcaaaaa   155520 atcagctggg catggtggcc ggtgcctgta atcccaatta cttgggaggc tgaggcaaca   155580
gaatcgcttg aacccaggag acggaggttg cagtgagcca agatggcacc actgcactcc   155640
agcctaggtg acagagcgag attctgtctc aaaaaaaaaa aagactggag gtgttttagt   155700
ccattttctt tactataaca gaatacctga ggctgggtaa tttgttgttt ctgcaaaaa   155760 gaaacttatt tctcatagtt ctagaggctg gaagtccaa gggcattggt gctaacatct   155820
gctgggcttc tggtgagggc tttcctactg catggtaaca tggtggagaa gcagaagagg   155880
gagtgggcac acacaaaagg ggcagaacac aagggacagc ctcactctat agcaaccccc   155940
tttcacagta actgtagaag tcactcctgg ccaggtgtgg tggctcatgc ctgtactact   156000
agcatattgg caggctgagg agggaggatt gcttgagccc aggagtttga ccagcctg   156060 gacaacatag taagacctca tctctacaaa aaattttttt ttaattagcc aagcatggta   156120
gcacactcct gtagcccag atactctgga ggctgaggca ggaggatcac ttgagcccag   156180
aagtttgagg ctacagtgag gcatgattga gtccactgca ctccagcctg ggtgacaaag   156240
tgagaccctg actcaaagaa aaaagaagt cagtgactcc tgctttcatg agggcattcc   156300
tcatgaccca gacccaaatg cctcttaaag gtcccaccaa ctctcaacac cattacactg   156360
gggccaagcc tccacatgag ttttgtgggg acaagccata ttcaaactgt agcaggaggc   156420
```

```
aaatgtataa aagttttaat gggtctgatt atggtaagaa tatgagtgac attatccttt 156480
gctactgcag ttttttaaa atttcaaaat catgttacga ggaaatatgt aatcattata 156540
ggaaattcag aaaatgtaaa cataaataaa aagcaccagt aatccaccat caagagataa 156600
ctgtcattaa tattttgatg tgtattgtgt atcctttcag aatgatgtgt tttaatacta 156660
tacacaatgg tttcttgctg ttgttttaaa tcatactggg ttttccttt tactcttaaa 156720 tatctctact ggtcaataaa tatctgatac cagctctgct acatactgtt aactcactgt 156780 ctccccttt tctttatgcc aactatgttc tgtggggttt cttaaaatat actgtaatgt 156840
atttagcaat gatatgcact tactatgtgt cagacattct gtgtacttta tatacattac 156900
ctcatttact cctcaacaac cctgtgaggt tgcagctttt attatatcct tgttttatgg 156960
atgaagaaac ctggttatgg aaggggcaag taacttgccc caggtacttc agctccaggg 157020
tgtattcctt taaccattaa agcatgttgc ttccccaact tattcagtcc cttcgaaaac 157080
ttcaagtaga cccttaatgt tagggcag ttacactttc agtttcctag ttcattcact 157140
gtcctctttt agacactgtc ataccgcctc aaaacctcat atccttaagc ctctaaaacc 157200
tcttcttcaa gaaatcagcg atgacattgc ttgccatctc tttaagacag ttggaagtaa 157260
ccattatgac atctacccac ctgcctgcat tcataccagg ttcttctgcc ttatcactag 157320
taaaagccaa tccctccatt tgtacactag attccatccc cttaccccta cccagagaca 157380
tcttttgagt aaatctccca tcttgtttat catcagtttt tcctttccta ctgaatttc 157440 tcctatttta aaacatcttt tggctgggca cggtggttca tgcctgtaat cccaacactt 157500
cgggaagctg aggcgggtgg attgcttgag ctcaggagtt caagatcaga ctgagcaaca 157560
tagtggaacc catctctacc aaaaaataca aaaattagcc aggcgtggtg gtctgtgcct 157620
gtggtcccag ctacttggga agctgagaca agtggatctc tagagcctgg gaagatgagg 157680
ctgcagagag tcaagatcgc gccactgcat tccagcctgg gtgacagagc aagactctgt 157740
ctcaaaaata agtaaataaa taaaacatct ttcactgagt gcagtggttc acacctgtaa 157800
tcccagccct ttgggaagct aacgtgggaa gatcacttga gctcaggagt tggagaccag 157860
cttgggtaac agagtgagtc cttgtctcag aaaactaaag taaaatttaa aagtagggca 157920
ggtgtggtgg ctcacacttg taatccaagc actttaggag gctgaggctg gtggatcact 157980
tgagcccagg agtttgagac caccctaggc aacatggcaa aacccgtctc tacaaaaaat 158040
acaaaaatta tccagatgtg gtggtgtatg tctgtggtcc cagctactcg ggaggctgag 158100
gttgcagtga gtggagattg caccactgca ctccagccag ggcgacagag tgaaaccctg 158160
tctcaaaaaa aaaattaaga agtaacagta ataatgaaac atctttctta tgcacatttg 158220
gcagaatgtt gacatttgtg gaatctatgt ggaaggtgtg tgggtattct ttccattttt 158280
ctgtatgttt attttctttt ttgttgttgt tttgttttt ttattattat actttcagtt 158340
ttagggtaca tgtgcacaat gtgcaggtta gtaacatatg tatacatgtg ccatgcttgt 158400
gtgctgcacc cattaactcg tcatttagca ttaggtatat cttctaatgc tatccctccc 158460
ccctgcccca cccacaaata gtccccagag tgtgatgttc cccttcctgt gtccatgtgt 158520
tctcattgtt caattcccat ctatgagtga gaacatgcgg tgtttggttt tttgtccttg 158580
cgatagttta ctgagaatga tgatttccaa tttcatccat gtccctacaa aggacatgaa 158640
ctcatcattt tttatggctg catggtgtat atgtgccaca tttcttaat ccagtctatc 158700 attgttggac atttgggttg gttccaagtc tttgctattg tgaatagtgc cgcaataaac 158760
```

```
atacgtgtgc atgtgtctttt atagcagcat gatttataat cctttgggtg tatacccagt  158820
aatgggatgg ctgggtcaaa tggtatttct agttctagat ccctgaggaa tcgccacact  158880
gacttccaca aaggttgaac tagtttacag tcccaccaac agtgtaaaag tgttcctatt  158940
tctccatatc ctctccagca cctgttgttt cctgactttt taatgattgc cattctaatt  159000
ggtgtgagat ggtatctcat tatggttttg atttgcattt ctctgatggc cagtgatgat  159060
gagcattttt tcatgtgtct tttggctgca taaatgtctt cttttgagaa gtgtctgttc  159120
atgtcctttg cccactttt gatagggttg tttgttttt tcttgtaaat ttgtttgagt  159180
tctttgtaga ttctggatat tagcccttg tcagatgagt aggttgcgaa aattttctcc  159240
cattttgtag gttgcctgtt cactctgatg gtagtttctt ttgctgtgca gaagctcttt  159300
agtttagtta gatcccattt gtccattttg gcttttgttg ccattgcttt tggtgtttta  159360
gacatgaagt ccttgcccat gcctatgtcc tgaatggtaa tgcctaggtt ttcttctagg  159420
gtttttatgg tttaggtct aacgtttaag tctttaatcc atcttgaatt aattttgta  159480
taaggtgtaa ggaagggatc cagtttcagc tttctacata tggctagcca gttttcccag  159540
caccgtttat taagtaggga atcctttccc cattgcttgt ttttctcagg tttgtcaaag  159600
atcagatagt tgtagatatg tggcgttatt tctgagggct ctgttctgtt ccattgatct  159660
atatctctgt tttggtacca gtaccatgct gttttggtta ctgtagcctt gtagtatagt  159720
ttgcagtcag gtagtgtgat gcctccagct ttgtgctttt ggcttaggat tgccttggtg  159780
atgcgggctc ttttttggtt ccatatgaac tttaaagtag ttttttccag ttctgtgaag  159840
aaagtcattg gtagcttgat ggggatggca ttgaatctgt aaattaccttt gggcaatatg  159900
gccattttca tgataactga ttcttctacc catgagcatg gaatgttctt ccatttgttt  159960
gtatcctctt ttattcatt gagcagtggt tgtagttct ccttgaagag gtccttcaca  160020
tcccttgtaa gttgggttcc taagtatttt attctctttg aagcaattgt gaatggaagt  160080
tcactcatga tttggctctc tgtttgtctg ttattggtgt ataagaatgc ttgtggtttt  160140
tgtacattga ttttgtatcc caagactttg ctgaagttgc ttatcagctt aaggagattt  160200
tgggctgaga cagtggggtt ttctagatat acaatcatgt cgtctgcaaa cagggacaat  160260
ttgacttcct ctttttcctaa ttgaataccc tttatttcct tctcctgcct gattgccctg  160320
gccagaactt ccaacactat gttgaatagg agtggtgaga gagggcatcc ctgtcttgtg  160380
ccagttttca aagggaatgc ttccagttttt tgcccattca gtatgatatt ggctgtgggt  160440
ttgtcataga tagctcttaa tattttgaga tacgtcccat caataccctaa tttattgaga  160500
gttttagca tgaagggttg ttgaattttg tcaaaggcct tttctgcatc tattgagata  160560
atcatgtggt ttttgtcttt ggttctgttt atatgctgga ttcatttat tgatttgcgt  160620
atgttgaacc agccttgcat cccagggatg aagcccactt gatcatggtg aataagcttt  160680
ttgatgtgct gctggattcg gtttgccagt actttattga ggattttgc atcaatgttc  160740
atcaaggata tcggtctaaa attctctttt tggttgtgt ctctgcctgg ctttggtatc  160800
aggatgattc tggcctcata aaatgagtta gggaggattc cctctttttc tattgattgg  160860
aatagtttca gaaggaatgg taccagtcc tccttgtatc tctggtagaa ttcagctttg  160920
aatccgtctg gtcctggact ctttttggtt ggtaagctat tgattactgc cacaatttga  160980
gatcctgtta ttggtctatt cagagattca acttcttcct ggtttagtct tgggagagtg  161040
tatgtgtcga ggaatttatc catttcttct agattttcta gtttatttgc atagaggtgt  161100
ttgtagtatt ctctgatggt agtttgtatt tctgtgggat tggtggtgat atccccttta  161160
```

```
tcatttttt  attgcatcta  tttgattctt  ctctctttc  ttctttatta  gtcttgctag  161220
tggtctatca  attttgttga  tcctttcaaa  aaaccagctc  ctgggccagc  cgccccgtcc  161280
gggaaggagg  tgggggggtc  agcccccgc   ccagccagct  gcctcgtccg  ggaggtgagg  161340
ggcgcctctg  cccggccgcc  cctactggga  agtgaggagc  ccctctgccc  agccagctgc  161400
cccgtccggg  agggaggtgg  ggggtcagc   cccctgcccg  gccagccgcc  ctgtccagga  161460
gggaggtggg  ggggtcagc   ccccgcccg   gccagccacc  ccgtccggga  gggaggttgg  161520 gggtcagcc   ccccgcccgg  ccagccgcct  cgtccgggag  gtgaggggcg  cctctccccg  161580
gccgccccta  ctgggaagtg  aggagcccct  ctgcccggcc  accacccgt   ctgggaggtg  161640 tacccaacag  ctcattgaga  acgggccatg  atgacaatgg  cggttttgtg  aatagaagg   161700 aggggaaaag  cggggaaaag  attgagaaat  cggatggttg  ccgtgtctgt  gtagaaagag  161760
gtagacatgg  gagacttttc  attttgttct  gtactaagaa  aaattcttct  gccttgtgat  161820
cctgttgatc  tgtgaccta   ccccaaccc   tgtgccctct  gaaacatgtg  ctgtgtccac  161880
tcagggttaa  atgattaag   ggcggtgcaa  gatgtgcttt  gttaaacaga  tgcttgaagg  161940
cagcatgctc  cttaagagtc  atcaccactc  cctaatctca  agtacccagg  aacacaaaca  162000
ctgcggaagg  ccgcagggtc  ctctgcctag  gaaaaccaga  gacctttgtt  cacttgttta  162060
tctgctgacc  ttccctccac  tattgtccta  tgacctgcc   aaatacccct  ctgcgagaaa  162120
cacccaagaa  tgatcaatta  aaaaaaaaaa  aaaaaaaaa   acagctcctg  gattcattaa  162180
ttttttgaag  ggttttttg   tctctatttc  cttcagttct  gctctgattt  cagttaattc  162240
ttgccttctg  ctagcttttg  aatgtgtttg  ctcttgcttt  tctagttctt  ttaattgtga  162300
tgttagggtg  gcaattttgg  atcttttcctg  cttctcttg   tgggcattta  gtgctataag  162360
tgtccctcta  cacactgctt  tgaatgtgtc  ccagagattc  tggtatgttg  tgtctttgtt  162420
ctcattggtt  tcaaagaaca  tctttatttc  tgccttcatt  tcgttatgta  cccagtagtc  162480
attcaggagc  agcttgttca  gtttccatgt  agttgagtgg  ttttgagtga  gtttcttaat  162540
cctgagttct  agttagattg  cactgtggtc  tgagacacag  tttgttataa  tttctgttct  162600
tttacatttg  ctgaggagag  cttacttcc   aagtatgtgg  tcagttttgg  aataggtgtg  162660
gtgtggtgct  gaaaaaaatg  tatattctgt  tgatttgggg  tggagagttc  tgtagatgtc  162720
tattaggtcc  ccttggtgca  gagctgagtt  caattcctgg  gtgtccttat  taactttctg  162780
tcgcgttgat  ctgtctaatg  ttgacagtgg  gatgttaaag  tctcccatta  ttattgtgtg  162840
ggagtctaag  tctctttgta  ggtcactaag  gacttgcttt  atgaatctgg  gtgctcctgt  162900
attgggtgca  tatatattta  ggatagttag  ctcttcttgt  tgaattggtc  cctttaccat  162960
tatgtaatgg  ccttcttggt  ctcttttgat  ctttgttggt  ttaaagtctg  ttttatcaga  163020
gactaggatt  gcaacccctg  cctttttttg  ttttccactt  gcttggtaga  tcttcctcca  163080
tccttttatt  ttgagcctat  gtgtgtctct  gcatgtgaga  tgggtttcct  gtatgcagca  163140
cactgatggg  tcttgactct  ttatccagtt  tgccagtctg  tgtcttttaa  ttggagcatt  163200
cagtccattt  acgtttaaag  ttaatattgt  tatgtgtgaa  tttgatcctg  tcattatgat  163260
attagctggt  tattttgctc  gttagttgat  gcagttctt   cctagtctcg  atggtcttta  163320
cattttggca  tgattttgca  gtggctggta  ccacttgttc  ctttccatgt  ttagtgcttc  163380
cttcaggagt  tcttttaggg  caggcctggg  ggtggcaaaa  tctctcagca  tttgcttgtc  163440
tgtaaagtat  tttatttctc  cttcacttat  gaagcttagt  ttggctggat  atgaaattct  163500
```

```
gggttgaaaa ttgttttctt taagaatgtt gaatattggc ccccactctc ttctggcttg   163560
tagagtttct gctgagagat ccgctgttag tctgatgggc ttcccttttgt gggtaacccg   163620 acctttctgt ctggctgccc ttaacatttt ttccttcttt caactttggt gaatctgaca   163680
gttatgtgtc ttggagttgc tcttctcaag gagtatcttt gtggcgttct ctgtatttcg   163740
tgaatctgaa cattggcctg ccttgctaga ttggggaagt tctcctggat aatatcctgc   163800
agagtgtttt ccaacttggt tccattctcc ccgtcacttt caggtacact aatcagacgt   163860
agatttggtc ttttcacata gtcccatatt tcttggaggc tttgttcgtt tcttttatt    163920 cttttttctc taaacttccc ttctcgcttc atttcattca tttcatcttc catcactgat   163980
accctttctt ccagttgatc gcatcggctc ctgaggcttc tgcattcttc acatagttct   164040
cgagccttgg ctttcagccc catcagctcc tttaagcact tctctacact ggttattcta   164100
gttatacatt cgtctaaatt ttttattatt ttcattaaaa aaactttttg gggtccctcc   164160
cttaatcctg cttctctctt cagttattac ctcattcctc ttcttccttc gacagtaaaa   164220
cttctcaaaa gacttgttgg tattcactgt ccagttgctc tccttccttt ttatcttgga   164280
ccccactcaa accaggcttt tgcccctgct gctccagaaa acatctttt tttttttttt    164340 tttctctctc tcaaggaaga gtctcactct gtccctcagg ctggagtaca atggcatgat   164400
ctcagctcac tacaacctct gtctccaggg ttcaagtgat tctcctgcct tagtctccca   164460
agtagctggg attacaggtg cacaccacca cacccagcta attttgtgtat gtttagtaga   164520 gacagggttt cactatgttg gccaggctgg tctggaactc ctgacctcaa gtggtctgcc   164580
catctcggca tcccaaagtg ctggaattac aggcatgatc cactgtgcct agccaggaaa   164640
cagcgtctta atatgatagt tactggtggc ctccatgttg ctagatccag cagtaaaatt   164700
ctcagtccac agtttatttg acctgtcaga aacatctgat acagttgatc acacacttct   164760
tcatgaaaca ggttcttaat cccttgttta attgtgttct tagtttcttg ctgctcagaa   164820
tgtggtctga gtagcatctg taccacctgg gagcctttta gaaatgctaa gtttagata    164880 ccacccagca cctgaatcaa agactgcatt ttaacaagat ccccaaatga ttcgtgtcca   164940
tattaaagtg tgagaaacac tgctttcagg catattctcc tgattaccct tctactcact   165000
gtctactcct cagctggttc ctcctctcct tctttggtgt ttcgtggttg gacaagtcat   165060
ttaaaatacc tgtaatcagg gccgggtgtg gtggctcacg cctctaatcc cagcagtttg   165120
ggaggccaag gcagatggat cacttgaggt cgggagttca agaccagctt gaccaaaatg   165180
gtgaaacccc atctctacta aaaatacaaa attagctgga cgtggtggta cttgcctgta   165240
atcccagcta cttgggaggc tgaggcggga gaatcacttg aacccgggag gcagaggttg   165300
cagtgagcca aaatcgtgcc attgcactcc agcctgggtg acaagggcaa aactccatct   165360
taaataaata aataacctat aatcagaacc agcaatacaa agtattatca aggataaaga   165420
acaactggaa ctctcataca ttgctggtaa agattttaaa tgatacagcc attttaggga   165480
tcaggttggc agtttctttt aaagttaaat ttaccatttg tgcaattcta atcctaccta   165540 attcccaaa ataaatgaaa ccatcagtca acaacaaaga cttgtatatg aatacagcat    165600
cttcttcata tttgccacaa actaggaaca acacagtgtc caataagtaa atagataagt   165660
tgtgatatac ccatacccg taacactgca tgcagccagt gcgtgaatct cacaattgtt    165720
ttgctgcgca aaagaagcca ggtgattctg tttatatgaa atttgagaaa aggcaaaatt   165780
aatctgtagt gacagaagtc attatcaatg gtttcccaag cctaaagggg gtgttactaa   165840
tcgcaaaaat gtatgaagaa actttctggg gtgacggata ttctttatat tgattgtgac   165900
```

```
tggtcattac acaagtgtat gtgtgtgttg aaacttttaa aactgtccat gtaaaatggg  165960
tgcatcttgt gtgtaaactg tacctcagta aatttcagtt tttaaaagtg aaaaatacct  166020
gatggcttac acctataatt ctagcacttc gggaggccga ggtgggagga tggcttgagc  166080
ccaggagttc aagaccagcc tgggcaacat agtgagaccc atctatacaa agcagttttt  166140
taattatcca ggcatggtgg cgcccacctg tagtcccagc tacacaagat gctgagttgg  166200
gtggatctct tgagcccagg aggttgaggc tgcagtgagc tgtgatcatg ccactgtact  166260
ccagcctggg caagagagca cacccctgtc tccaaaaaaa aaagtgaagg aaactaaaaa  166320
atcaaggcaa aaatagaatt taggccacta tggagcataa ctttaaaata tgtgaacttt  166380
acctattcga tattttaatt atttttaaag tgataaatga ttactgacta cagagaagta  166440
acagaatgcc attctcgtta atcttacttt ccagggttgt aataagggag cagagggcat  166500
caaagtataa ggaaggctgt aatttggcac tgtcaccact atcataccta ccagtccagg  166560
tggtcaccca aggagagact catcttgctg cctaaagtct gatgaacctt tgtaaaattg  166620
tgcagtatta ggtgaaagag ggctgacatg caaatgtcta agtaggtcag ttctgtgttt  166680
taccaagagt ttaaaatact tgaaaatggc agcagactta agtgagagat gctagtggct  166740
tttacaaata agctaagttg ataaattagc caaatggcat agcaatatta tcaataggca  166800
ttttaatgat aatctctcat tgtttttctta aggataagat caagtgatgt aacatgaatg  166860
acaggattta actgggttca tactggatga atgatcatac ctgaagacag caaactataa  166920
tgagattcct atcctcagtc ctctcttgaa tataattacg tatttagaag taacttatgt  166980
gaggaattat tagcatgccg atctttaaaa atctcctttt ttcagctctc acgtaagact  167040
cttgaaacaa gaaaataaaa ataacctatg ttttattaaa gaaaaatgaa gcaggcaaga  167100
aaaaaccgac ttttttagtg aaagctaaag ttttaatctg aaattataga ccatgtctac  167160
aaaatttaaa atcctaaggc tgggcgtggt ggctcacgcc tgtaatccca gcactttgga  167220
aggctgaggc aggcagatca cgaggtcaag agactgagcc catcctagcc aacatggtga  167280
aaccccatct ctactaaaaa cacaaaaatt agctgggcat ggtggcgcgc gcctgtagtc  167340
ccagctactc aggaggctga ggcaggagaa tcacttgaac ctaggaggtg gaggttgcag  167400
tgagccgata tcgcaccacc gcactccagg ctggtgacag agtgagactc tgtctcaaaa  167460
aaaaaatcct agtcaagtcc aaaaaagag aaatatacaa gtataagatg gggaaaatgt  167520
tttataggag caattcaaga ataattattc taggattgta attgaatata atccttttg  167580 tgccctttt taaaaattct atttattgtc ataaattttg acccagcagc aggaagcatg  167640
taattaaata taatttaat tggactcagt agcatgactt tggctgccat aacaatcaca  167700
ataatgtctg atttaatgtt gtatgccac catgtgggag atgaagatga ggatctcacc  167760
atagtttgtg ttggttagat ccgatctgaa gtattgcttt taatttgggg caccacatta  167820
tgctctgtaa gaatgtggaa aagctgaatc ttggataaga gcttgaagta gtgtgagaag  167880
aaattttacc agatgatttt gtagctctaa gattaaatgg ttctataggt ggacactttt  167940
tcttcaagga atgagactgt taagagaaac ctatcaagag aatgtgttgt tcctttggtt  168000
gatagcatat ttgttctttc ctagtacttc tgtaaaactg taatgctctc cttaacatct  168060
taccaaggaa agagggaggt ccaatctaat tatcctaatt aatggattga cttctgtgtc  168120
atatatggca aagtaaagtt gatatattct tgttcccttc cctactccca aacagttatg  168180
tgagttattt gttttctgtt attttttgttt gggttttttt tttggcattt tccattgtaa  168240
```

```
ctgggtggtg cttaggaaat tacgttttag tgtccccccta tatagaatta tttagggtag 168300
tgattactgt gaaacattat cttatgtagg gattcggttg tgtctcatcc catttctcta 168360
gctgggggat tagaccccct tttccttcca gcctttcatt ctacagacct ggacttctac 168420
tctttgctgc ttttgttaca gaaggattac agaaagagaa ttattcaatg agataaaaat 168480
taacaaagca gtttgtaagt aataaaggat tacacaggta taaagtgttg tttcaggttg 168540
tatttttatg caactcggcc tataacaaat ttatgctata taacttctat gctgggtata 168600
tcactggttc cccaattaca tttatatctt gttaattatc tagtgctttc ctggtcagaa 168660
aatttctctc cccactctcc ccagttacat ttctgtctac tctattcttg ctatattcct 168720
ctgcatcaaa tttgttgaaa ggattaacac catcccatgg agaacacctt tatcttcccc 168780
tcttttatct tcagcatgcc tctgtatttt gatatggttg aagcccattt gttttttgttt 168840 ttaagtcttg caggaaaaag aacctccttt caaagaccaa caccttggct gtatactaga 168900
tcccaggtct ctctgagtgc aggacctagc tccaccaacc aacaccatca tcatttatcc 168960 cccttttcttt ctaatggaga caagatctca ccatcttaaa gctttgattg gggcccattt 169020
atttccacca gttttaact ttgtatgtca ctgcagaact ttgtaagcag tgagacctat 169080
aaccgaaata acatttttctt tcagtgaaag agtgacaata tgatgtagaa cactgagcct 169140
aaagtcatga caagataatt ttcaattgta gtaaatgcta tgaagaacat aaactgtgat 169200
atgaatagta attggagaag ggattacttt agataaatag taatttgaaa tgaaaatttt 169260
atctagaaaa tacttaaaa tttttgatat tgggaagaat gaggacgttt aaatgaagat 169320
gagacagcat gaataatctt ggttatttgc aaatcttcca cttttaacag tgtttattgc 169380
atgattttga ttataccatt tggatttaa attctcattt taaggtaaaa ctgtctaatg 169440
atcattgtca gatttcagaa gtgtcatata gctattctct ccggtattca attaagaaaa 169500
ataaccttga ctagcacatt atatgcatct tattgtagtt gattcagtag acatgtattg 169560
aatacttacc acacatacca agcactgttc tcggcactgg gtatacaaag aaataaacaa 169620
gacacagccc ttttgagaca ggaggatctc ttgagcccag gaggtggagg ttgcagtgag 169680
ccaaggtcgt gccactacac tccagcctgg gtgatagagt aagactttgt ctccccaaaa 169740
acaacaacaa caatgctgcc ttttacttca atgaatgtag ctaaagcagt ttttaggggt 169800
aacatagatg atttaaagt tatcgttgac tttaaaatag acctactatg gccatttag 169860 agaaagtttt ctcctcacta gttttaagaa atatttaa gaatatatga caactaccttt 169920 taaaaatagt tttaattacc aaactgcatg ttctagtagt ttacattcca aatagaagtg 169980
aacataggca cgttgaaaaa acacatgaat caagccatta ttatgataat tactacataa 170040
gttgagcagt gaaagagcac tttcagttcg gttagtcatg ggaaagcttc actcaggagt 170100
tagaatttgt attcagtttt aaaggatgga tatgaatagg tggaaaatag aacgaaagct 170160
aacttggagg gttgggtgta ggaggggagc attgaacaca gtggtgggat taaatatcaa 170220
ggtatattta agggacatgg ataaatagc ttgactggag tgaaaggttt gtattggtaa 170280
ctagtaaaag ataaagcaaa gtcttttaat agaaacaag attttgactg taccattata 170340
gtgatatgtt cctataatct taaattcatt tacagtctat tttaatattc tgtgaagggt 170400
ttattacaat gtactatttt cagttgtatc atgattctaa ataagtcttt acacccccaa 170460
gtatgttctg tagatttcga ggccagagtc ctttagccct actcaggtta aaatgatgtt 170520 ttgttttttca gttacttaca cgccaagtca atcatccaca gagacctcaa gagtaatagt 170580
atccttcctg aaatttgtct gcgaagtttg aaaacatcct gactttttct tctgcatttt 170640
```

```
gtcttcacat tatgtaaaaa cagttttcat gctaagttcg atatactgta aagagaatta   170700
ataaaggatt gtgcatgcat gtataggaga gcaggatacc acagcctgct tttggtttct   170760
cgacaactga acattacaag aaaatctatc agaagtcttt acaatagtag gagtttttga   170820
ttgcttgctt acattttatc agcactataa aactgatagt tttgtagcta tctattagtc   170880
cctttcagac ctctgacctt gctcagtggt agttgagata taactgaaga ctctaaatta   170940
tataacaatg aggtgagaaa aacataatat ttctcttccc taagtgcaga ctaagatact   171000
atctgcagca tcttcattcc aatgaagagc ctttactgct cgcccaggag tgccaagaga   171060
atatctgggc ctacattgct aaaatctaat gggaaagttt taggttctcc tataaactta   171120
ggaaagcatc tcacctcatc ctaacacatt tcaagcccca aaaatcttaa aagcaggtta   171180
tataggctaa atagaactaa tcattgtttt agacatactt attgactcta agaggaaaga   171240
tgaagtacta tgttttaaag aatattatat tacagaatta tagaaattag atctcttacc   171300
taaactcttc ataatgcttg ctctgatagg aaaatgagat ctactgtttt cctttactta   171360
ctacacctca gatatatttc ttcatgaaga cctcacagta aaaataggtg attttggtct   171420
agctacagta aaatctcgat ggagtgggtc ccatcagttt gaacagttgt ctggatccat   171480
tttgtggatg gtaagaattg aggctatttt tccactgatt aaattttttgg ccctgagatg   171540 ctgctgagtt actagaaagt cattgaaggt ctcaactata gtattttcat agttcccagt   171600
attcacaaaa atcagtgttc ttattttta tgtaaataga tttttaact tttttcttta   171660 cccttaaaac gaatattttg aaaccagttt cagtgtattt caaacaaaaa tatatgtctt   171720
ataaacagtg tttcatattt tattcttaaa taaatatgaa cccttaaaac gaatattttg   171780
aaaccagttt cagtgtattt caaacaaaaa tatatgtctt ataaacagtg tttcatattt   171840
tattctaaat tgtttaaagt attttgtgtt caaaatgttc tgtgtaccct gttgaaaaaa   171900
aaaacaggta tgcaatttaa ggcaggtgtg atccacagcc attattatgg ttttgctaag   171960
agaactactc cttttaacag agaagctgtt tcgcaatctt atttaagcct aaattggaaa   172020
gttacttcct ttagactaga aagtatctca taattatggg gcagctggaa gaggaaagac   172080
aaaaaaaaat gagaggtaga ttaacagcct tgtgctgtct tgcatagctc tttctttctt   172140
cttgtttttt gctttgtgga aaagaagaaa gagaagttct aaaagaaggg aacaaaaact   172200
tgtgtgcatt gcagcaagct gtggaaagct cagtcatatg aatcattccc taaaacagca   172260
ttcttaaaag ggtccctcac accgttttag agggtccaca agatcttccc tttgtgagac   172320
aagattttct ttatatcctt caaccaaaac aacacattgc aacagactga gtgcaaaagc   172380
aaatatgaga atccagctgg ctgctgttaa gccagacatt gaggagaatc acaggccact   172440
catggtggct ggagtccata gttccagcta cctgggaggc tagggcagga ggatcacttg   172500
atcccaggag ttgactggcc tgctcaacat agtgagaccc catctctaaa ccataaaagg   172560
aggataattg tagtactatt cttcttacta aactttttt tgataatagt tatttttcat   172620
taaaaatgaa tgatctgtgt aacatctac ttgttattat tttagtagtt aaatgaatta   172680
ctagtttaat ttctccatta aattttaatg gtaaacatcc acagatataa tctacctaaa   172740
caaaagttct ttatcatcct caataatttt taagagtgaa aaagagtcct gagaccaaaa   172800
agtttgaaaa acacagctct aagctgaata cagccttttcc aaaagtctta gtgcaattct   172860
aagctttaaa taacttaatc tgcactaaga ctttcgggca ccctgctgga aacagaaaag   172920
ttgtaagggc tttcaaagcc acaaacttta tgtagcagtc tccagaaagg gaagtccaag   172980
```

```
ataggactcc caagtttgtc aaaataaacc tagagttaaa ttgagctgtg atttcttatg    173040
acagtaagtg gaattagggc aggtggcaag gtggaagagg ggacattgga cttagaagat    173100
ctgtattctg gtaccctatt tggccattaa cctgcaagtt tcttaacctc ctctaagtct    173160
acatctgaaa tgttgagttg gactagtaga tttccaatgc ccctttttc taagattcgg     173220 tgactggagt tagctagatt ttttccatta tttaacatat gtttaacttt taattaataa    173280
ttataagtga tagaaaaatt aataactata atctgatgtc aggcacctt attaaggcat     173340 acacaccttg tgaaaagat ggcagtgtat cctaaaaaga tgagggaaaa cagatttaa      173400 gtgctgaaat tgcaaaacct aaaattataa acaattgtca cgtgctttta aagtatgtta    173460 attttgact atgtgggaga gttaggctca atcaagtctc cagttttgtc cttactttt     173520 caaaaacctt agtttataca gtttgtagat tattatacat aaagttttat attttcttac    173580 aattaattt ttgttgatac ctgtgtaaat gggtttctcc tttattcttt catgctgagt    173640
tttaagacga gagaataata gccaacagta cccttattg ttaaaccaat cctgggttga     173700
tactgccctc agaaacaaat atggaacatc cgtatcatag gagagaagag tttggtcata    173760
actaaggctg tgtggtcctt tgaattatat acaatgttct tctcaacttt gttttatttg    173820
tatcttagga gagaaagaaa cctttgtgag agttttaca aattaaatca ctaaattgaa     173880
gattcgtcat gcatttctta aaataggtga catgcaactt ttcatcaaac tgtctaccaa    173940
caacagtgtg agataaaact aaattaaaaa aaaaagttc atctgatttc tactccatct     174000
ctcacaaaaa ttggtcaggc tttgaacatt ataccttgc cataccagcc tctcagtatt     174060
ctggcttgct tattacatca cagttatatg tggtttattt tgtactgtat tactaaaagc    174120
aactatgaac aaaatgtatg acaaagcgaa gtagatacaa ccttctcctt cacttccatc    174180
ctctcacgct cttcaggaca tcccacagat cttccatcag tggttctcaa ctttggttgg    174240
acactagaat catctgtgga gctttaaaga ctaattaatg tttgggtccc accccagac     174300 tctgttacgt tgtgtgattg gactggagtg tagtctggac gttgagggt ttaaggctcc     174360 gcgggtcatt ctcatttaca gctgttgctc agtgccatta ttgcctctcc ttgtgagatg    174420
cctgccttac ccagagcaat aaccaggaat cttgtcccag gtctttcagt catttttgca    174480
gagttagtac cacttttgct gtcaaattga cattgtcaca aacttttcat taatatactg    174540
ccatttcgat tccttccaaa tgaaacaata cagaagacgc aaggtgaaag aataactctt    174600
ttaagctaat aattaaccaa ctgtttattg tatttcatgt aaataagaaa cctaattgtg    174660
caatacaatg actgaaatgt gtaaaaatgt agcaaatatg attgtttcat tgcccaagaa    174720
gcagcagcca gaagattctt tataccatct tttactaaat ctacctgctg tcttgctttt    174780
gttaataaag catccatggc atgtttatac catatgctta ttccatagtt tgaaagggga    174840
tttgagttta tcagtcctga aattctacca ttattttcta aggtgtcctc agatgagaaa    174900
agttgtttgt accaatggga aaacttaaat tgtaagacag ttactacagt agttgtgctg    174960
ctcctaagca tcttataacc acaagtctag tatttctttg ctgaatcagg aatgggaagt    175020
gggaactgat tctaataggg taagtcatgg gaagaattca tctggcaatg atggtatttt    175080
ctgcagaaag attgcctaaa taattactaa attataaaat cttagtaata caatacaaaa    175140
tctctgctaa tactgtctct ttctgagtat gtagaggttt tttcttcag cttaatcagt     175200 tttatttctt tgactattaa gagaattgat tacatattag acaggtgttt taatggtaaa    175260
agcattgctc taggaattat agtaggttgt ttttcagtct ttattcaatt gaagtgaaga    175320
atatttttct ttgtatgttc taacaggcac cagaagtcat cagaatgcaa gataaaaatc    175380
```

```
catacagctt tcagtcagat gtatatgcat ttggaattgt tctgtatgaa ttgatgactg   175440
gacagttacc ttattcaaac atcaacaaca gggaccaggt aaatatttac cacgtcttgg   175500
tgtttatttt accgtctata tacaaggctc cagttgtaga aaataagtgt taactcctgg   175560
gtaagcgtga aggatagatt tcttgatttt ttgttaccag ttttagaaat cgtttgtata   175620
cttttggcag taatagcaac acgttaagtc ctttcctcag aatatcagtc atgaatgtta   175680
caatggaata aaattcctga ttttctgact agaaactaca gttacaagaa tggatatttc   175740
ttgaccatcg cacaattaga agaatgagct ctgctactat agcatctggg cattatactt   175800
ttcactgtat cacagattgt gctgtcagaa caggtactca gctatgagat ctttatatta   175860
aattctttta aaattactaa ggtttcttga aatctttaat ttttaaaact aggtaaatgg   175920
aagaaatcat gctttgattt ttctataatg agaatgctag taggagggta attttttact   175980
tcttttcctt cctaagcaac tattccctgt cccttacctt ccaaaaggta ctaacatagc   176040
ctcatggagc tcttagcctt ttctatctct gcctcagtag gctcgcttag acttttaaaa   176100
ttggccaaga aaagtgaatt atctttacta aaattacctt ggataactac attttaaaag   176160
atttgtgatt gtgtgtgtag agagattaca acagttacac tgttaatata ttagaaaaca   176220
ctagttgacc acataaactc tgattaaaga atatttcgac tttatgctgt gatttgcctc   176280
agaatcacct ggaaattttg cttaaaaatg gagaaactgg agcagattgt aattaaatgg   176340
ggagggtcca atcacctgca ttttttttctg tttcccaggt gattctaata cagaccaaag   176400
ttgagaatca ccaatctaaa gatttttttt aaaaacagtg caggcttttt aggtatttca   176460
taacttccca acctaatgaa atggtagttt ttgtatataa atgttactgc ttcatttaag   176520
tgatttgtct gttttgtcaa gagctcagct ctatctttt ggtgctagct ctgagtagct   176580
ttctcacttc acctattgtg atatcggaga aataatctct taagttacca tgtactttgt   176640
gtgtgtactt actgaatcac catatgcccc ttacacaaca gtggtcttga ctgtgtttga   176700 tggttttttaa aaatggctac atttctaccc agttcattat aaaactaaat tttagttggt   176760
gttggccttt ctaactactt catagctta gaatgttgag tcttagcttt gagtgtgtaa   176820
caacatgact ttggatctga tgttttaagc ctgcaggaaa cttagattca ggatggactg   176880
aaatttcagc taaagaacat aattgaaaca ttgtacttac tgtacttgtg atagatctag   176940
atcactgaaa tgattgattt gacaatggca gttggggtag caaaatggtc tctaatttac   177000
aagcttcatg tcctctgtct tttacagtct tatttattca atcatacagc ataacagcct   177060
gtaccatgtt cacttttcct gtatataata ttttctgga ggaattatgg attttttagtt   177120 tagtttcagt tgatttatca tatagactac aaattaataa aaatttatga acctaagatc   177180
tggatgaaat tcatttgtca gtgaatacgt ttatcttagt acaataataa aattataata   177240
tagaaacaag tattatctcc aaaatacaga taaaagcatc ccagagttct tctctcatcc   177300
acttcttggc attttaggtg ctttgtcctc catgggagta taataaatga tgtggcaagg   177360
gcttactctc catgagagga atgtgtgacc aacagaaggg taaggccttt actagttaat   177420
tctttctaat agtatagtta gaaccttctg gaatttgcta gtctgaaacc aagttaagta   177480
tttaatggag aagaaggagg taaagaatg atgtcctctt acaactaccc ccattctgct   177540
tcattacccc ctagtctact tacgtcaaat agtactttct atgaaactcc acattttgaa   177600
gggttaactc tggccatcct cagtgaagct gccccaggta ttgctccatt catcctttga   177660
tttttctttt gctatctata atacttggat ctccatagct ctcagattag acttctgttt   177720
```

```
aagaatccag gaatattctt tactatgcaa tgtgaatacc attccctag  actctcatac   177780 ccatagtctg aggtggcaga ttttgcctgt aaattcagag cacagctggt aaagcagtgt   177840
gatgtaatgg caggccttgg actcaggtag gtagactagg tctacctacc tctctgggta   177900 tcttttttt  ttctttttc  tttttttttt tttccaagac ggagtcttgc tgtgtcgccc   177960
aggctggaat gcagtggcct gatctcagct cactgcaacc tctgcctccc atgttagcga   178020
ttcttctgcc tcagcctccc gagtagctgg gattacaggc acgcagcact acacccagct   178080
aatttttttg tattttggt  agagacaggg gtttcaccat gttggtcagg ctgggctcaa   178140
actcctaacc tgatgatctg cccgcctcag cctgccaaag tgctgggatt acaggcgtga   178200
accactgcac ctggcctttt ttcttttttc aattacctgc aaaataaggg aattcggcta   178260
agaatttctt ccagcttcaa aaatcagatt cttttctaaa atagttctct tagctctttg   178320
caaagtagtg tgccttttta cctttattca ccctagcact aaagtctggg aaatcacttt   178380
gtcatccccc cactctcttt atcattctaa cattttctc  tctaatcacc ctgttcttcc   178440
ctccttcagt gcattttctc ttgtaaattg ggattaataa tgtgctcact taagtatatt   178500
gactatacct ttatggcttt cgttccttgg agtagaagtg ccgtgtcttc tttgaagaat   178560
agatagcata tatctgttat ttcaagtgta ttattccagt tataattgct gcataacaaa   178620
ccacccagaa tgtagtagct taaaatatga atctgtaggt tgggcttttc tctgtgagga   178680
agattcttac ctgtttcaca ccgtattgac tagagtagat ttacggggtg ttaaaaggat   178740
ctactcagaa gtggctcatt catgtacctg gcaagttggt gctagctaga agctagaagc   178800
tcagttattc tccacatgag cttttccttg tggacctctt cgcaggtctt caaggacctc   178860
ttcattggtc tttctcacag cgtggttgct aggttctaag cacaagatct gaagaaacag   178920
gaagtaagta ctagtctctt atcagtaggc aaattatttt aatagaaaat gttttcaata   178980
ccaactatat gcaaagcact atggaatata gaaggattca aaatgaataa aacaaaaccc   179040
aggctctgct ctcaatggca tgtgcagttc tgttgaggcc gtgctggggg tgatactgaa   179100
aatgagcaga catgagctcc agtaatacca tggagtgaat tgacagggtc gagacaccag   179160
gagtactgag tgtgtattga aagtatgaaa aatcagtccc agaatttgaa gctggggtat   179220
tggtttcgtt gtgtatgtgc cacatgaatc ttctgtccat gaataacatc caggaaaaac   179280 ttccctttt  tcttctttct gtttcttcat cagtcagcct ctgcaccca  ccccagcaga   179340 tactgaaagt ttcctgcttt ctgctctgca ctaactaaat tctgtgggat gtataaaaac   179400
atgagagttg tctttgattt ttttttctcac attcctcctg aaagactctt gaaaaactat   179460
gtatctcctt gtatatttt  taagttggca tctaaaagtt tttatcttaa gtttaaataa   179520
ttgcaaagaa tgtaatttcc agtatattct attaacattt taaaataaga ctactatatt   179580
agatacatat atatccctct ttttgaaata tatacatcaa aatctaaaaa ccataccgat   179640
tttatgccta ttaaaaaata ctgaagctct tcattaattt ctggaagttt tacatggttc   179700 ctttttctc  ttcaaactat ttgtattgtt tctgtcacag aacttcatcc taatgtaaca   179760
tatttgtatg ttttaaagcc ttttattgat tacctaagtt acatctctgc aataaaagta   179820
tgtatataaa tttaaattta gaattttaca aaattgtgac ttcaagctct gattattaat   179880
tttttaattc tgaattatgt ttttgttgca agtaatatat aactgatgaa agtagcatat   179940 aagtttttgat atatggaaac atagaatgta aaattatatt ggaaatatgt atcttaatga   180000
atgacatggg gcttttcttt tcccttcaat taatgtatgt atctgtggat aaatacaact   180060
tttttgttag gacactagat actaagactt agtattgatt cttccatat  ttcattttta   180120
```

```
aagaggtaaa tactgagaaa ttttatctaa attataagaa gatgacaaag gcaggagttt    180180
tgttataatc acatgcagag tttagtagtc cccaagacca gcttcaggtt tgttaaaagg    180240
acttgctgaa aactcactga aagctgctca agactcactg acaactgtta cattcacagt    180300
tacagtttat tacaatgaaa gaatacagat caaaattaac aagggaagag actcatagga    180360
cagaattcag aagcgttctt gttggagctt cctgtcaccc tctcccaatg gagttgtgga    180420
cagagcttcc agtagcaatg tgtgacaaca cacatggatt attgccaacc agggaagctc    180480
acctgagcct tggagtctag agttttattt ggggttcagt catatgatta accacctgcg    180540
gggctgacct tagtttccag ctcctgcaga ggtcaagctg atgccacatg acccagagcc    180600
ctctataaat cacattgtta gcacagtctg tctggcatgg cccatggccc ccagataaac    180660
agacactctg atcaggcagg acatttcaag gacttagtga ttacctccca ggagccaaga    180720
gcaaaggcta gctctctctt tgggcaaggt taattctttta ccacatacta tatatcactc    180780
aatcatctga gctcattcct ataatgtacc aaaatttaca tagtaacttg tcattaaaaa    180840
tgttttaaaa gctcagctga catttcaatt aatattttg aaagtaaaga attggaaacc    180900
aacagactcg ttacccattc gttggagccc agtttgacac cagtatttag aaatgtctct    180960
ttgttgcccc agaggttttt acaccctggg acaatgtata ctatagttag gttacatatg    181020
ggtaaaaggt gtgccttttt ttttttaatt aaagttttag ggtacatgta cacaatgtgc    181080
aggttagtta catatgtata catgtgccat gctggtgtgc tgcacccatt aactcatcat    181140
ttagcattag gtatatctcc taatgctatc cctccccact ccaccacccc cacaacagtc    181200
cccagagtgt gatgttcccc ttcctgtgtc cacgtgttct cattgttcaa ttcccaccta    181260
tgagtgagaa tatgcggtgt ttggtttttt gttcttgaga tagtttacca agaatgatga    181320
tttccagttt catccatgtc cctacaaagg acatgaactc atcatttttt atggctgcat    181380
agtattccat ggtgtatatg tgccacattt tcttaatcca gtctatcatt gatggacatt    181440
tgggttggtt ccaagtcttt gctattgtga atagtgccgc tataaacata cgtgtgcatg    181500
tgtctttata gcagcatgat ttatagtcct ttgggtatat acccagtaat gggatggctg    181560
ggtcaaatgg tatttctagt tctagatccc tgaggaatcg ccacactgac ttccacaaag    181620
gttgaactag tttacagtcc caccaacagt gtaaaagtgt tcctatttct ccacatcctc    181680
tccagcacct gttgtttcct gacttttttaa tgattgtgat tctaactggt gtgagatgat    181740
atgtcgttat ggttttgatt tgcatttctc tgatggccag tgatggtgag cattttttca    181800 tgtgttttt ggctgcataa atgtcttctt ttgagaagtg tctgttcatg tcctttgccc    181860
actttttgat ggggttgttt gttttttttct tgtaaatttg tttgagttca ttgtagattc    181920
tggatattag ccctttgtca gatgagtagg ttgcaaaaat tttctcccat tttgtaggtt    181980
gcctgttcac tctgatggta gtttctttttg ctatgcagaa gctctttagt ttagttagat    182040
cccatttgtc aattttggct tttgttgcca ttgcttttgg tgttttagac atgaagtcct    182100
aaaggtgtgc cttttgtaaa gtggtagaag ggcagttata acagggaaaa tgggaaagca    182160
agataagtgt tacacttcca cttgagtggt tctctggcaa atcagttttt tcaaggggga    182220
taccagtaag ttgatagttg tagaaattaa ttcccttaaa accaccatgt tggctgggcg    182280
tggtggttca cacctgtaac cccagcactt tgggaggctg aggcgggtgg atcacttgag    182340
gtctggagtt cgagaccagc ctggccaaca tggtgaaacc ccatctctac taaaaaaatg    182400
gaaacattag ccaggcatgg tggtgtgcac ctgtaatccc agctacttgg gaggctgagg    182460
```

```
cagtagaatc tcttgaaccc aggaagggga ggttgcagtg agccgagatc acaccactac  182520
actctagcct gggcaacaga gcaagactgt ctcaaattaa aaaacaaaaa caaaaaaaac  182580
cccaccatgt ctatacacct ctggcaaagt cttcctgtaa ccccagggat acttgactct  182640
aatttaaaga ctatagacct atgacatggc tgatcaacta gcaaaaagtt atcactcacc  182700
ttaatgaaca gttaacttaa acattgaaaa cctcttgtgt ccacaaggtt atgttaaata  182760
ctggaggtag tggtgttata gatattttt aagaattttt tttttttga gacagtctcg  182820 ctctgttggc cagtctggag tatagtgtgg catgatcttg gctcactgca acctctgcct  182880
cctgggttca atcaattcct tgcctcagcc tcccacgtag ctgggactac aggcacatac  182940
cgccacaccc agctaatttt tatattttta gtagagacgg ggtttcatca tcttggccag  183000
gctggtcttg aactcctaga cctcatgatc caccctcctc agcctcccaa agtgctggga  183060
ttacaggcgt gagtcaccac gcctggcttc tttaagaatt tttttaaaat atgtatgtat  183120
gagtcacaat ctctctgcct gagcacccat agtctcattg gagaacttag ataagataca  183180
tatcacaaaa agattaataa ccatacaagg cagtaaatga tcatcacagc tagtggtggg  183240
aagaaggacc attattactt ctaggtgtgt aaagaaaggt atgataagca tggttacctt  183300
tcagttaggc ctgatcatct gggttcagg tagctagaga agggtgaggg agggcattat  183360
aagcagagta ggagcagcgg caataaaaaa gttaaaagta gctttgtatt gggatagtct  183420
tctctacaaa tcctgttact tacttaactg tattatctcg ggcaagttac ttaatttatt  183480
tgagcattgg attccttatc tgtaaaacag agtcaacacc aaccttgtag aattcttttt  183540
tgagtattag atgatatcta gaatccaagt gtcccaacgt tttttggcct ttcagggcca  183600
ccttttccac tgatagccaa gtaagaatac ctgaattgct gtccataata tatgactata  183660
ggaactccag atcctttctc tcaactttga agacccctgt ttgaagtgct ttacattctc  183720
ctggctgttg cttgtcactt gttgctccaa catattattc caggttgctc ccaaaattct  183780
aagactgctg tcttccatta aaatgatgat gttatgatgg tgtagcttca gtaggggca  183840 ttgtgaaaga aaactgtaat cccctcaatt cagtaactct ttccaaggtt catccttta  183900 cctctactac atagaggcca cattgcaatc aaagctttac taatgcctgg cagttaaaca  183960
agggtcatta cagcaccaaa caggaaataa cacaatgtat caagcttggc ggtttctaaa  184020
attcatcagc tctgccctgt agcagggatc ttttatgggc tttctccact ttagcctcta  184080
ctctccccct gttgcaccta ttccctctaa gaccaaaagc ccttctctca ggctgtcctc  184140
cctgagtccc aagactccta acatctatcc ctgcctgccc tcaaaagagg caaaatatta  184200
ggaaattaag aaattagaaa aaattataaa tctctgaatc cagggaagac aagcctttt  184260 atttcgttaa acagattta gctcctaatg gcttcccctt ctctcctctg gcggaggctc  184320
tggtttgtat aaccaagtgg cccattagcg tttccacaat aaaagggctt aagatgcaga  184380
tgccaaaacg actgctaaaa tgttaacctt tttggttttc cctacacata tatagaggac  184440
ttaacacaac gtccaacaac aagaagtgct gaataaattt ttttttttt taaagtaaag  184500 aagaggcact gtcagatctg ttttagatgg ttaccctgtg agtgggaaaa tggactggat  184560
aaagagagac caaagcagg ggagcaatta gagaaccttt gccacagtcc aaggatcatg  184620
aagatttgag cttgcactcc ttttgtgggt ttcccaccat ctatgatgtg gcattggttt  184680
tttaaaactt tttattgagg tgtaaatacat acatcgtaag ctgtaaatgt acagcttatt  184740
gtgttttcaa tgagtgtgaa gtatattttt caacttatct acaaggttga attatttccc  184800 tttttttct ctctccagat aattttatg gtgggacgag gatacctgtc tccagatctc  184860
```

```
agtaaggtac ggagtaactg tccaaaagcc atgaagagat taatggcaga gtgcctcaaa    184920
aagaaaagag atgagagacc actctttccc caagtaagta aaagcttcat gctatccaaa    184980
agaacagact aacattcata gacagatttc tgagcacttt tttgggcaca cagtgtgtat    185040
ttcatgagtt tggattctat gtgcagactc cagacaagaa aacacattaa gatggcttca    185100
tgagggttga gcagtggcac acctagaaat tttgggtcct aatacaaaat attcagaaag    185160
actttgcatt tgtccatcag ttctcagact tctcagtctt tgaactcttt tacacattta    185220
aaaattatcg aagaccccccc cccccacaaa gagcttttgt ttatataagt tttaattcct    185280
tattagaaat taaaactatt ttttaaaata ttaatgaatt aaacatagta aaccaatatg    185340
ttaaataata tttagaaaaa aacagttcta ttatctaaga gaaaaaaatt agtgaggagt    185400
tgtattgttt tactttttttt gcaaatccct ttgcaaaaag aagacagctg gattctccgc    185460
ttttgcactc acattgcaat atctcacatc atgtcacccc taaaaactct acttaacgct    185520
tgtaaaataa tgacagtaaa aaaggcaaat gatatcttat tgttattaca aaaatagttt    185580
tgacctcgtg gatcccctgg tggtccacgg accacatttt gtgaaccact gctttatttc    185640
ttcttggtgg taaacagatt caagcttttcc tttaatactg ggtctttttg agggcatttt    185700
ctgcctgatg cagaaaaagg aaaaggcagt aaggcatttg tcagctcagc ctgcctttac    185760
ctaattcttg ataactcact gcttttttttt ttttttttcc atattggaag gataaagcct    185820
taagttaaca aatttcaaaa agaactgtaa ctaaggccag gtgtcgtggc ttacaaatct    185880
caacactttg ggaggccaag gcaggcagat cagttgaggt caggagttcg agaccagcct    185940
ggccaacatg gtgaaaaccg tctctactaa aaatacaaaa attagctggg catagtggca    186000
ggagcctgta atcccagcca ctcaggaggc tgagacatga gaatcgcttg aacccaggag    186060
gtggagattg taatgagctg agatgacacc actgcattcc agccagggca acagaatgag    186120
actctgttta aaacaaaaca aaacaaaaat atctaaatac ctcaactagc ttacagagtt    186180
tagctgtagt agatattata atataaatgc aatgttttct gatacttagg gagctcctga    186240
tagcactgga taaatatgcc ttgatgaatc agtacagttt caagtgggaa gtgctatttc    186300
ccatagtaac cctgctacca taattactgg agtgttcatg tatgaactct taggcctttg    186360
aatgcccagt cctagctgag taactcagac agaagtcaat gttacaggaa ttagattcac    186420
tcatccttta ttttttaaatc taaaaaatgt tattcttctc taaagaatga aagaagataa    186480
aattgatggt tttaacaagt ctgtcagggt gttgcctaag aaaagaaagg gaaagctaag    186540
tggttggctg ggtagatata agtttcattt atcaggtttc aaagttactg ttcctttgag    186600
gaagagtttt tatttttttct ttttatttttt ttatttgttt ctctaagtca ggaaacctct    186660
gggttgagac tgtcctggtg agagacaagt gctgctgagc agcttcagca tgaccctgtc    186720
ccatgttctc ttttcacgtc atggtgctcg ggttcttact tagaatgttt attgacatta    186780
ataatgcaaa gtcatccctt aggcccactt tttaaatgat attaaagggg gcaaaatgct    186840
tagctccata cttctaaata taacatttca ttaattacat ggtttcaaaa actgaagtgc    186900
atatgtgaac tttccagatt attggaggct atcccttaa agtgttattt tgaaattttt    186960
gttacaggat atcttttcac accatactgt tatatgccac ataaatttta gatggctgaa    187020
gatctatatg ttttataaaa tatgaaatca ttttttatagt tttgaggtag gaaaggcttt    187080
cttaatagac aaaattcaga aggaaaaaat tagcagatgt gagtacatta aaaatttta    187140 aacttctata tagaaaaata acattgaaag ataaaaagaa taattgtagc atatataaca    187200
```

```
aaaagtaaat gtttataata tacaaaggac tcctccaaat caataagtaa caaacaatag  187260
aaaatgggca aagggaatat gaacaggtga ttcacataat aaatacaaat ggtgaatgaa  187320
cttaggaaaa ggtgtaaata tttccatggc agtcagtaaa atgcaaagac acaacagtga  187380
aatatatttt aatttcgcct ctcaggttgg taatatccag cactgggaac aatgttggga  187440
agtgaggagg agcattctat gtaaaatttt aaaggtttgg tggaaggcag cattttggaa  187500
gaccttggta gaatccataa attcaaaata cttctaaaaa tctgtgctat gtaacctatt  187560
tcataagtat tcagatatat ataagaatgt ttactataat aagaaaaaga cattaagatt  187620
aagttagttt tgtattgatg acatggatat tggtgagaga aaaagaaaac aagacagaaa  187680
acaaaatgta gtatgatacc tcattttttt tttttatagg ctgggcctgt tctgttgccc  187740
aggctggagt gcagtaatat gatcatagcc cactgcagcc tcaaactcct gggctcaagc  187800
gatcctctca cctcagcctc ctaagtagct gggattgcag gtgcctatca ccacacccag  187860
ctaatttctt gtggtggtgg tggtggtggt tgtagagata gattctcact atgttgccct  187920
ggctggtctt gaactcctgg cctcaagcga tcctctcgcc tcagcctccc aaagtgctgg  187980
gattacaggc gtgagcccca gtgcccagcc tgataaccac tttaaaaggt taaacagagg  188040
ccaggcacgg tggctcacgc ctgtaatccc agcactttgg gaggccgagg caggcggatc  188100
acctgaggtt gggagttcga aaccagcctg accaacatgg agaaactctg actctactaa  188160
gaatacaaaa ttagccaggc gtggtggcac atgcctgtaa tcccagctac tcgggaggct  188220
gaggcaggaa aatcatttga acccaggagg cggaggttgc ggtgagccga atcgcacca  188280 ttgcactcca gcctgggcaa caagagtgaa attccatctc aaaaaaaaa aagtggtgtt  188340 caggtgggcc ttgttttcat gtatgtattt ttatacataa aaaaaggtac tgaagaggcc  188400
aggcgcagtg actcacacct gtaatcccag cactttggga ggccaaggtg ggtggatcag  188460
ttgaggttag gagttcgaga ccagcctggg caaaatggtg atacccgtct ctactaaaaa  188520
tacaaaatta tccgggcgtg gtggcacacg cctgtgatcc cagctactcg ggaggctgag  188580
gcaggagaat cgcttgaacc tgggaggcgg aggttgcagt gagctgagat cgcgccactg  188640
cactccagcc tggacaatag agtgagactc catctcaaaa aaaaaaaaa aaggtacaga  188700 agaaagtata gactctaaca gtggttatcc ctggagagca ggatttgaga gccttatact  188760
ctttatacat ttctatagta ttttaatttt tatttgcatg ttatacttgg aatttacaat  188820
tttttgcaac tgcttacttc tttgtcttat actaatcatc ataaagatta cttttaaaa  188880 aaaatttaac ttttaaaaac aattttcagc caggcatggt ggctcatgtc tgtaatccca  188940
gccctttggg aggccgaggc aggcagatca cctgaggtca ggagtttgag accagcctgg  189000
ccaacgtggt gaaaccctgt ctctgctaaa aatacaaaaa tttagctggg catggtggtg  189060
cgctcctgta atcccagcta ctcaggaggc tgaggcagga aatcgcttg aacccaggag  189120 ggggaggttg cagtgagctg agattgtgcc actgcactcc agcctggttg acaacagcga  189180
gactccgttt caaaaaaaaa aaaaaattgg tatctcagga caataacaaa agtaataata  189240
atagctgcta aggttttatt gagtgcttat tataggccag gcattatgcc aagccctta  189300 aacatgtttc atgattatga acatgcatta tcatgctgta tgccttcaag gattataacc  189360
tgtttctttg tgccttaaaa ttgtgaattt ctgcatttta tatattgggg tctatttgtc  189420
gagttctcct atctttgctc ttgggttgtc ccctgtcact tctcatgtgc tactagcact  189480
ctgggtctgt gaggttctgc tttcaattag gtgtatgtaa aacatttccc atggctaggt  189540
ttctttaaag ggcaagtagc tgtgataatt ctgtttagag atagtcataa agtgctttac  189600
```

```
ttatttatac tccatcttct tcccaaaaga gacttgtggt ctataacaaa aaggtataaa 189660
attggtttta aatttctatt atttactgtt tcaagactaa caaatgatct aaaatataaa 189720
taaaagctga ctaagaatta ctctccccat ttaatttaca gagagagttt cttcttaaga 189780
aaaaatacca attatttaca aatattttcc caagcattta tgacaatgct gaaaacaatg 189840
taagatttca ggtgcttact tgtaaagtgt gatgggactc ttaaagattt ataccaccca 189900
gattttcatt cttctttctg tttttccttt ttctttcttt ctttttcttt cttttttctt 189960
ttttttcctt ttttttttct tttttttttt gtagattctc gcctctattg agctgctggc 190020
ccgctcattg ccaaaaattc accgcagtgc atcagaaccc tccttgaatc gggctggttt 190080
ccaaacagag gattttagtc tatatgcttg tgcttctcca aaaacaccca tccaggcagg 190140
gggatatggt gcgtttcctg tccactgaaa caaatgagtg agagagttca ggagagtagc 190200
aacaaaagga aaataaatga acatatgttt gcttatatgt taaattgaat aaaatactct 190260
cttttttttt aaggtgaacc aaagaacact tgtgtggtta aagactagat ataattttc 190320 cccaaactaa aatttatact taacattgga ttttaacat ccaagggtta aaatacatag 190380
acattgctaa aaattggcag agcctcttct agaggcttta ctttctgttc cgggtttgta 190440
tcattcactt ggttatttta agtagtaaac ttcagtttct catgcaactt ttgttgccag 190500
ctatcacatg tccactaggg actccagaag aagaccctac ctatgcctgt gtttgcaggt 190560
gagaagttgg cagtcggtta gcctgggtta gataaggcaa actgaacaga tctaatttag 190620
gaagtcagta gaatttaata attctattat tattcttaat aatttttcta taactatttc 190680
tttttataac aatttggaaa atgtggatgt ctttttattc cttgaagcaa taaactaagt 190740 ttcttttttat aaattttgag tgcaggtgac caaaaatatt gctgaggagt ggcacgtttg 190800
acatgagtaa aatgtcttaa cttcggattt ttagcgggaa aatgttataa attggagttt 190860
cttttaaata gctttttttta aaatacatta aggatgtctc gctcatgtag aagtcaaatt 190920
ttgttgcaaa cgcattgctc ccttcacacc caatctctcc cctgcaaaaa atcttcacag 190980
aattctgtga gaactttag gtgtgttttt ctttgagata cctctggttg ccaaacacca 191040
ggtaatagat ttttaaagt tgttattaga ttattcttac ctctcatgat gcatatttta 191100
gcaatcacct tatcattgtg tctcatgttc tgtcctcctt atattctttg cccagcaaga 191160
ttctacttat gatgaatgaa tgctcttctc ctttttttcat tcaatggtat gaagtatttg 191220
ttagggttct ttagtactta cactttgttg tgtagaaaat gactgtaatg tggtggtcag 191280
tgtattctta ctgtgattca gagggaatca aaagtagaaa gcaacagcac gtggtcctat 191340
caaagatttg gccatctctg cttcactgtc agcctcttaa ctatatcttc acttactcaa 191400
tttggttttg tcatgatttt taaatgtagc caatagatca aggttcttcc agtaaacaca 191460
tatctgcata aatgcctcct tgaagtcaat aaagaaggaa attgagaaga ctttaaatta 191520
atgataattt agttttaag tacccacaaa taaattttg aaacattttc tttatttgaa 191580
tacttagatg tcatccagga aaatcactca ataataatta cggcaaatct ttaacccctc 191640
atttgggtag cttaagataa gtaatgccat tatgaatcag aattgattca tgactttagt 191700
taagaaaatg aaaaggaaca tttcacgtat ttttaaaaat gatactaagg aataagaag 191760 tacaactatt ggaaaatatc taagtatatg atttttaaat cctccagtgg cattaaatat 191820
atgattatta gtaattgtta gatagggttt tattcattca caaatagaag actagcaagc 191880
atgtaactaa caaagttttt acaaaattga ctttgtggaa tgctccaaat gtttggccat 191940
```

```
tttgaggcac aaggtcaggg gtctctttat tgatagagct ccttctataa tttcccagca   192000
tacctgcctc acagttatct tcctttcatt gttcactctc ttttcttct caatgccatc    192060 ctgcctaggc tcccatcatc tgcatctgac acctttcctt tctttcttta ctagtctcct   192120
ttgcgatggg tgtggctaag ctctgtagag ccactcagaa actcattgtt ccattctgta   192180
gccagtaaaa catgcctcca aagtgtcaca gagtaattct actctctctt ttaaattagg   192240
tccaccggaa atgttagtga aaggacatta aaaatgtgac aggtgacatg tttagctaac   192300
atggatctgg agaaatagga agcagtagaa ttaaatgttt cccttcagg tttaattgta    192360 tttgttcttg ggttttgttt tatactgagt tttaaatata ttctccaaat aaaaacatta   192420
ttttttctaa ccatatgtag agttaatctc tttgactaag taattgaaac aaaagaacat   192480
ttgttctttt gtgactgctt ttttcctaaa acctgagccc tcttttttt ttttgaaatt    192540 aaagttgatt tccttttttt tttttttttt tttttttttt tttttttttt ttttgagaca   192600
gagtctcgct ctgtcgccca ggctggagtg cagtggcggg atctcggctc actgcaagct   192660
ccgcctcccg ggttcacgcc attctcctgc ctcagcctcc caagtagctg ggactacagg   192720
cgcccgccac tacgcccggc taattttttg tattttagt agagacgggg tttcaccgtt     192780
ttagccggga tggtctcgat ctcctgacct cgtgatccgc cgcctcggc ctcccaaagt    192840 gctgggatta caggcgtgag ccaccgcgcc cggccttaaa agttgatttc cttcttcagt   192900
aaggaaacct ttttataaat ttgttttgca ttttaaaagt tttactaatc aatgatgagg   192960
aaaaagattt gtcttcttga tttaaatag tttcaggatc acaggatgta atcagatgct    193020 tccagttat ttattttcag gtattacact agccatttaa tctttttat ttatttattt     193080 tcttcctgcc cctcggatgg catataccag ccatttagat actaaactct aatagttaaa   193140
ccaatagtta aaattgtcct ctctaaaaca ttggctattt aatataccag cttaaatggc   193200
ctttctctca agtgagtcac tcttagttta agaaaattat gtgcctttt aaaaaatatt    193260 atgaaatggt acttcatgac agaaacattt tatcagttat agtcttattt gattgaaaat   193320
tgttgagcat ttctgtaaaa ctttttactt tactaaatat ttcatctttc ctgtgactgt   193380
tttctcaaag aatttaaaag actcgatgtg tctatgccag aatgtttctc atcctttga    193440 aactgcctgg gccaggcgta gtggctcacg ctgtaatccc agcacttttg gaggccaagg   193500
tgggcagatc gcgtgagccc aggagtttga ccagcctg acaacatgg cgaaacggtg      193560 tctctacaga aaaatttaaa aattagccaa gcatagtggt gcacaactgt agccccagcc   193620
actcgggagg ctgacgtggg aggatcccttt gaacctgggg gcggaggctg ctgtgagcct  193680
tcatcatgcc actgcactcc agcctgggca acaaagcaaa accctgtctc aaaaaaagaa   193740
aagaaaaaaa gaaactgctt gaaagtcatg acgaagaatg tcaggagggg acttattctg   193800
gctgcagttg actttctcct taaatgtcaa gtagtgattg atttggataa gaagtaaact   193860
gttacttttc ataacatact ttaaggaatt tatcaaattc tatgtataat gcccattaaa   193920
atatactcca ttctggagta aagggtaaga gtaatatttt taaactagtt aataaagtct   193980
ttagctttca cataaaccat gatatttgag gtgtctaaaa tcacagggtc tttttttttt   194040
ttttcagtct tccagttgt tctctgctct attcctaaat aaagttaact tgaaaatgca    194100
tggccggttg tggtggctca cacctgtaat cccagcactt tgggaggctg aggcgggtgg   194160
attacttgag gccagttcga gaccagcctg gccaacatgg caaaaccctg tctctactaa   194220
aaatacaaaa attagctggg catggtggtg tgcacctgta gtccagctac ttgggaggct   194280
gaggcacaag aattgcttga acccgggagg cagaggttgc agtgagccaa gactgcacca   194340
```

```
ctgcactcca gcctgggtag tagagcaaga ctctttcaaa aaaagaaaca gaagatgcag   194400
cttaaattat cctcaacctg aaagaagggg aaagaaaata tttcaatttg gcctcaaatt   194460 gattttttt  tattaattaa tataccaaga ttttttttaa gacatagagt atctaggtat   194520
ttcacttcaa ataacttcac acaagcagag ttggctcttc aaatagaaga cgggtaggaa   194580
gtagaatagt agagatttcc agatgggcaa gaaggaatca ttaagaaaag atactttttg   194640
tgaaagcaga ttcatcacct gttactccca tgttttcctt aaattctcca tgttttaggg   194700 acatttaag  agtcttattt tattgattcc tgaactatgg attcttttat ttttttcccc   194760
tcaacaccaa gtatgactat aaaaaggact gcattctgtt agaagcacta gacttttgat   194820
agagtgatag tgtttgcttt gtatttgatt tggagtttgt tggtaaaaat ttgttctttg   194880
tgcggttgtt tggttttaaa ttttttttgga gacagagtct tgctctgtca ttcagtctgg  194940
aatgcagtgg tgcagtacca ccacaccctg gtaattttt  tgttttgag  acagagtctc   195000 attctgttgc ccaggctgga gtgcagtggt gtgagctcag ctaactgcag cctctgcctc   195060
ccgggttcaa gtgattctcc tgcctcagcc tcctgagtag ctggaattac aggtatgtgg   195120
caccacacgt aatttttttt ttttcccagt agaaacagtt tcaccatgtt ggccaggctg   195180
gtctcgaact gctgagctca ggtgatctgc tcacctcagc ctcccaaagt gctgggatta   195240
caggcttgag ccactgcacc tggccctaat ttttgtattt ttagtagaga gagagtttcg   195300
ccatgttggc caggctggtc ttgaactcct ggcctcagat gatccaccct cctccgcctc   195360
ccaaagtgct gggattacag gcatgagcca cctcgccggc ctggtttttta tttttaagac   195420 taatatttaa gtttgtggag tatgacactt caacaaaatg aaatttctaa tcattataat   195480
gaacaggaaa catctgaagt tgtgtgcgtg tgtgtgtgta ttttgttttg ttttcgagac   195540
agggtttcgt tactcaggct ggagtgcagt ggtacaatcc tggctcactg cagcctcaac   195600
ctgctggtct caagtgatcc tcccacttca gcctcctcta ggtagctagg actacatgca   195660
tgtgccacca catccaactg atttttttt  tttttttttt ttggagagac agcgtctcac   195720
tatgttgccc tacctggtct caaactcctg ggctcaagca gtcctcctgc ctcggcctcc   195780
tgaagtgctg ggattatagg cgtgaaccac tgtgcccaac cttagctgaa gatttttta   195840 agtattttt  aatgtagtat attaacattt ggcttagata ttagcatttt ctgatttttt   195900
tatttaatag attaattcta ggcattttca taaagatttc ttttctataa atcttatttt   195960
tacattgact tccttttaatg agatttgatt tggctagata catgattact cataagaatg   196020
ttgcaagtca ttttaaagaa acattaaaac actaaaaata gcaaccttaa aattataagt   196080
actcaaactg taagcaacaa tagtaagaat gtttgtatat ttctggagtg tgttaccata   196140
atagcctcct atgattatac tccaaatgtt ttactctaag gtcttagtaa tttaatttag   196200
cctttttttt tttttaaatc agtgctagat tccccaatcc tcttaacttt aaatatgagg   196260
caataattct tttaccctttt cttgatcttt ggactcacaa tacctagtt  aattgcttgt   196320 taaaaggaat tcatgcatag aaagagataa tagactatct gcagttcatt agtagttgta   196380
ttcagattgg gaaaacaaag tgttaattgt tgaaagttgt ttagggactg ctgggtcttg   196440
gagtcagcac ctgggtttgc attccttctc tgcaattttc tgtatatgat ctcaggcaag   196500
ttacttgacc actctaaacc ctggcttcct catctatata atatagatga tagcatctgc   196560
ctcatagggt tatcatgaga attggatgca gatgtgtaca aactgttccg tgaggcatca   196620
ggcactcagt cagtcactaa tactatcagc ttacaaagct gaggattcaa tcatccagtc   196680
```

-continued

```
attagcaatc tgttgttggg atgtgccagt gttatctagc aaccagttgg aatctgatag   196740
caatcagaaa ttagataggt tattcctgga ttaaacagta tattcatata agtgattgct   196800
tggatcctca tcagaagctg ctattgaaaa atagtgatat ggctggccgg gcatggtggc   196860
tcatgcgtgt aatcccagca ctttgggagg ccaaggcggg cggatcatga ggtcaggaga   196920
tagagaccat cctaactaac acagtgaaac cctgtctcta ctaaaaatac aaaaaaatta   196980
gccgggcgtg gcttcatgtg cctgtagtcc cagctgctgg ggaggatgag gcaggagaat   197040
ggcatgagcc caggaggcag ggcttgcagt gagccgagat cgcaccactg cactccagcc   197100
tgggtaacag agcaagactc cgtctcaaaa aaaaagaaa aatagtggta tggctgacta    197160
aattttgtta attgtcagtt attaactaat ccccagaaat taactatggt gtgtataaca   197220
ggaattggcc tttagttaca agtagaaact atggacaaaa tggtagatga aaaataatgg   197280
cggccgggtg cagtggctca cacctgtaat cccagcactt gggaggccg aggcaggcag     197340
attacctgag gtcaggagtt tgagaccagt ctggccaaca tggtgaaacc ccatctctac   197400
taaaaataca aaaattagcc aggcctggtg gcggatgcct gtaatcccag ctacttggga   197460
ggctgaggca ggagaatcac ttgaacccag gaggtagagg ttgcagtgaa ccgagattgc   197520
accattgcac tccagcctgg gcaacaaaag caaaattcca tctcaaaaaa aaaaaaaag    197580
aaaaaaataa tggcatgaag cccccaaatt cattaagcta aaggagcatg atatcacaaa   197640
ggtactttgt ggtttaaaga attctttatg ctgataatta tgttcagtga tgtgcctata   197700
tttaattttt tgttagattg aaggtgaaat taactagaaa ataggcagtc tggattttct   197760
ttctctgtca aacgtgtggt gtgaacaaat cagttgacct cttaattgta tctttagcaa   197820
aatgaggata actactgcct ctctcttcct aatagtggca ttataataat atgataggtg   197880
aaaatgagtt gataattcag aggtggaagt attctacaaa ttgacattac tactttacat   197940
tcagtttctg agaaattttg ttcattggaa ctgttttcag cttgatcaga accatgatac   198000
ataaaaccca actggaaaat tctgcagact tgctatttaa ttgatagagc tgaaccatat   198060
tctgtatact atatatgttg tgttcttcca tgggtttcag ccgttttgc ttttaaatta     198120
gcaatgctgt tgctagactt gaaatatata actagttact tttcagtgaa gctcaaatga   198180
ggcttttctg tgtctctagg ttatttgaga tgactttttt aaaattagct cttgtcctcc   198240
ctctacagga gaatttgcag ccttcaagta gccaccatca tggcagcatc tgctcttatt   198300
tcttaagtct tgtgttcgta caatttgtta acatcaaaac acagttctgt tcctcaaatc   198360
tttttttaaa gatacaaaat ttccaatgca taagctgatg tggaacagaa tggaatttcc   198420
catccaacaa agaggaaag aatgttttag gaaccagaat tctctgctgc cagtgtttct     198480
tcaacaaaaa taccacgagc atacaagtct gcccagtccc aggaagaaag aggagagacc   198540
ctgaattctg accttttgat ggtcaggcat gatggaaaga aactgctgct acagcttggg   198600
agatttgcta tggaaagtct gccagtcaac tttgcccttc taaccaccag atcaatttgt   198660
ggctgatcat ctgatggggc agtttcaatc accaagcatc gttctctttc ctgttctgga   198720
attttgtttt ggagctcttt cccctagtga ccaccagtta gtttctgagg atggaacaa    198780
aaatgcagct tgccctttct atgtggtgcg tgttcaggcc ttgacagatt ttatcaaaag   198840
gaaactattt tatttaaatg gaggctgagt ggtgagtaga tgtgtcttgg tatggaggaa   198900
aagggcatgc tgcatcttct tcctgacctc cggggtctct ggccttttgt ttccttgctc   198960
actgaggggt ctgtctaacc aagcaggcta gatagtgctg gcacacattg ccttctttct   199020
cattgggtcc agcaatgaag ataagtgttt gggttttttt ttttcctcc acaatgtagc    199080
```

```
aaattctcag gaaatacagt ttatatcttc ctcctatgct cttccagtca ccaactactt    199140
atgcggctac tttgtccagg gcacaaaatg ccgtggcagt atctaactaa accccccacaa   199200 aactgcttaa taacagtttt gaatgtgaga aatttagata atttaaatat aaggtacagg    199260 ttttaattc tgagtttctt cttttctatt tttattaaaa agaaaataat tttcagattt     199320
aattgaattg gaaaaaaaca atacttccca ccagaattat atatcctgaa aattgtattt    199380
ttgttatata aacaactttt aagaaagatc attatccttt tctctaccta aatatgagga    199440
gtcttagcat aatgacaaat atttataatt tttcaattaa tggtacttgc tggatccaca    199500
ctaacatctt tgctaataat ctcattgttt cttccaactg attcctaaca ctatatccca    199560
catcttcttt ctagtctttt atctagaata tgcaacctaa aataaaaatg gtggcgtctc    199620
cattcattct ccttcttcct tttttcccaa gcctggtctt caaaaggttg ggcaatttgg    199680
cagctgaatt cccagacaga aatagagca attttaggga tattaggact gagggagggt     199740
gtgggaaagc tgtcatcagt tgtttttata gaaagaactg gcattcatta agaacctaaa    199800 tcttatctt gcacaaatgg aaaatataac ctagttatag cttcctttgg cctttattaa     199860
agggtaatat caatcacagt catagcaaag aaagcggatg tattaatggc aaattaatgg    199920
aaaacctccc ttatcaggaa tctagactca gaatttagga acacaaatca aatcagacca    199980
accaagctat agccaaggac ttgaaagaaa ttaaacaaga cccagaataa atcaaggaat    200040
tagaaattgt tatttaaaaa tttcagattg taactccagg ccctgctgtc tatattgcag    200100
ccactaaaag ctcactacca ttagattttt gctaacatac atgtattcag aagaaagcct    200160
attgaaattt tcattgtctt gtaaaaggtt gtcctagtaa aatggaaaag atccttaagt    200220
tattaatcag tttgaaaagc aaatttgttt ttaagtttta catcagcagg gcagtgtctt    200280
acaaaattca gaaattgcaa aggtggaaat aattcacgct gatttgaaga acatcttctg    200340
tgcaataata ctgcctctct tgaaaagcat tggctgtttt ttcttttaa atatatctct      200400 agatgctttt aaatgtggct gtgttccctt taccaagatt ggcttcaagt ttccgcaggt    200460
agagagacct gggcttgaac aagaggatgt gtttcatgtc ctgctgagga ggtagaacat    200520
gtgcagcctg ggtccgggac tgcctccgtg gggcagggc aggggcggta ccattaggga     200580
ggaagcttag catttcagtt tcttaaacaa tattcagggt gatacactt ttcttccctt     200640 gcatttaga ataggctggt atctcatttg aacgggggag cagacttgat ctcaaatgaa     200700
gctgtgccca ggagccaggc ttagcatatt gagatttta tagataccctt aaaaaataaa    200760 atatttaaac ctctcttttc ttccttttc tatgaaatag gttttttctc tagtttacaa     200820
atgacatgaa aataggtttt atttgtgttt tatctgcttt attttttgat gcttagacaa    200880
cagttagact tactgagctc ctaaaaaaac gaggaagaag tccttatttg tgaaaagcac    200940
tttatgagta attgtataga cagtatgtgg ctgcgtcact gatcatcttg taagggtgta    201000
acagtcttgt ctgtaaagtg gctgcagtgc cttctgtagt gtgtttttat tttggtaggg    201060
agaggtgaag ccttctgaaa aatttgagag caactacaga ggattgtttg taactgtgta    201120
gtattcctga tggactttt tcatcgttag agtcaaggac ctagacttt gccactgaaa      201180 taatattgac caaaaaaata gttttataaa gggatttgtg aatagaaaat tcagtgtgat    201240
catttgttgt taatgtgcac cttaaaagaa gattctgtct agctgtcaaa ttctggttcc    201300
cgaatatctc accctgatt gtatttgaga tctagtaggg catactgggg cattttagaa     201360
gataaaatcc catacaaatg atatatgcta tatttatgtt ggtgttggag aagaaagagc    201420
```

```
agtatataaa gaaataattc aagactgcag cactgtcaac ctgaaacttt gtaaatattt    201480
cctagcttct ggtttggtgc ggtgacagca ctttcatcac aggatgttac cttgtattca    201540
ccaggcggag tgcgagctgc tgcacatcct cctcagatct cacctgtccc cactgtacat    201600
ccacccgcca gctgcttgca aacctcatct ctagctttag ttcgaaacca cattgcaggg    201660
ttcaggtgac ctctacaaaa aactacctct tcagaatgag gtaatgaata gttatttatt    201720
ttaaaatatg aaaagtcagg agctctagaa catgacgatg atttaagatt ttaacttttt    201780
tgtgtacttg tatttgagca ctctcatttt gtcctaaagg gcattataca tttaagcagt    201840
aatactgtaa aaaaatgtgt tgctcggaat atctgaatgt tgttgaaagt ggtgccagaa    201900
ccggtttagg ggtacgtttc agaatcttaa ccttgagtca attgcatgaa attaaatagc    201960
tgtggtatca cttcactaac agtgatgtaa ttttaattt  cagtaggctt ggcatgacag    202020
tacatcctca taatgagttt gctgcagctt tgtcacatgc acaggcattc atagaaagac    202080
cacccagcta agagggtaga atgattactc tttttgcaag attctcttct ttgtccaagt    202140
tggcattgtt agtgctagga ataccagcac cttgagacga gcagattcca accattaggc    202200
tataaacacc atagccagag atggaaggtt tactgtgagt atgaacagca aatagcttac    202260
aggtcatgag ttgaaatggt gtaggtgagg ctctagaaaa ataccttgac aatttgccaa    202320
atgatcttac tgtgccttca tgatgcaata aaaaagctaa cattttagca gaaatcagtg    202380
atttgtgaag agagcagcca ctctggttta actcagctgt gttaataatt tttagagtgc    202440
aatttagact gcataggtaa atgcactaaa gagtttatag ccaaaatcac atttaacaat    202500
gagaaaacac acaggtaaat tttcagtgaa caaaattatt ttttttaaagc acataatccc    202560
tagtatagtc agatatattt atcacataga gcaactaggt tgcaaatata gttcagtgac    202620
atttctagag aaaacttttttc tactcccata ggctcttcaa agcatggaac ttttatacaa    202680
cagaaatgtt gacagaaatt gctgtagttt agggttgaag tactgtatga tgggcagcaa    202740
tcatgtatta acttagaagg ggaaattgaa atataggacc gaatttggtt ttatcagttt    202800
ccagagtact gctgccaacc tagacactga ttttttcagag tttgaaatgt aaatttcttc    202860
ccgggacttg attgcacatg aagctggact gcgttagtca tcctgtccca aagcgctgtg    202920
ggggccaggg tggaggtctc aaggcatcct ttatgacctg gccattggat gtaaaagaaa    202980
acatattcca tgctgtggtt cttgtatctt gtttcattcc tcaccattga aagagaaagt    203040
ccatgtattg tctccagcac atccttgaaa tgttatactg ggatggatta ctgatgccca    203100
tcggtagttg agccccagaa gagggtagta gcatctctgc ctcaggtgat gatttgtagc    203160
ttggccagag gagagcggag tcaccagtat atctgtggtc catgttgcta gctctggtaa    203220
aattaaaaat actggtaaga tgtttgtttt attagtacac tagacagtaa gctctgtttt    203280
gttgttttca aataacctat tttcactttt gtttgggcaa agacatttaa attgaaattc    203340
aattctaatt tttgttaatt gtggaaaggg taattaacag ttcctatcag gtattttttaa    203400
tgtggaaaag gacagaaacc caactcctaa aatcttaaat taaggtaaca gtgctttaaa    203460
aaaaaaaaat gcatggggca attagtcggc aactcaatga gtgactaaag tacttttatt    203520
taacatccac aacttcaact gttaagtttt attaattact aaatcagctt tattaaaatg    203580
ttgacattta tttagctatt ttgaataatt atagtgactt gacgagtgtg tatgaggaca    203640
cagccaatgt aagccagtgt atccattttt tagaggtgca ttttttttta aagaattctg    203700
tagatagaag tgctctgaaa acaactaaaa tatgttattt catggtagta tcaaaaaatg    203760
tttgtacaaa ccatctgctt ctcccggcca gccgagttca ttctccagca ccgtgaccgc    203820
```

```
tggttctcat gtacagcaca tatgcgggag agttggcaga aaatttgtga agagatgccg   203880
caaaggaagg gtctgttgac gggtgggatt gggggttttg atgaagttgc ttagtcctgg   203940
ttttgttttg aaaattactg cgttgcattt ttgtgttaag ttttttgaacc cacgtgtgtt   204000 ttggtggagt atgagttgga agtcactgca aactagcata aacaacaaag ctcacagagt   204060
aggcacagat gtagagaaca gagaccaaaa tggggtgagg tggcagtaaa tctaggatag   204120
ggaaaaatta atgtgagggt gggaaataaa ctgtaattac ctgaaatcaa atgtaagagt   204180
gcaataagta tgcttttat tctaagctgt gaacggtttt tttaagaatc attccttcct     204240
aatacatttg tgtatgttcc atagctgatt aaaaccagct atatcaacat ataatgcctt   204300
tttattcatg ttaatgacca acgtaagtgg ctagccttta tgtcttattt atcttcatgt   204360
tatgttagtt tacatacagg ggtgtatgtc tctgtgctgt cccttctcc tgccttcatt     204420 ttaaaatgca tccatgggtc ctccgtgttt cctttggcca tgccacatat atagactcag   204480
tttggccttc atgatatcgc ctgattttg aggactgtat cacagtgata tgtatttgtg    204540
gtaatctcat ttgttggttg tacatctgat cctttcctca acatggcaat tgctgccttt   204600
cctaagatag gatcatacaa ctgatcaggg gattgaattt gatcattcat caacatgtgt   204660
ctctgaattt tattcagtag ttgtcattgc tctttggttt agaccaagaa aaaggaaatc   204720
cccccttttc atgtattcct tggtttgagg acatgactcc tgtaagggag aggaaaggga    204780
gatgcttcct gtttgaactg cagtgaattc acggttcctg tttcaccact ccaaacctta   204840
tggcgactca cacacacatt cctctttct gttactgcca aaggttcggg tttagtacac     204900
ttcagttcca ctcaagcatt gaaaaggttc tcgtggagtc tggggcgtgc ccagtgaaaa   204960 gatgggggact ttttaattgt ccacagacct ctctatacct gctttgcaaa aattacaatg  205020
gagtaactat ttttaaagct tatttttcaa ttcataaaaa agacatttat tttcagtcaa   205080
atggatgatg tctccctctt ttcccctatt ctcaatgttt gcttgaatct tttattattt   205140 ttttttaattc tccccccatac ccacttcctg atactttggt tctctttcct gctcaggtcc 205200
cttcatttgt actttggagt ttttctcatg taaatttgta taacagaaaa tattgttcag  205260
tttggataga aagcatggag aataaaaaaa gatagctgaa attcagattg aagaaattta   205320
tttctgtgta aagttattta aaaactgtat tatataaaag gcaaaaaaag ttctatgtac   205380
ttgatgtgaa tatgcgaata ctgctataat aaagattgac tgcatggaga agtcttcatc   205440
aagactattt ttctaacacg attacattca gtaacaaaag tagtcagcag ttttaacagt   205500
ttttctagac aatggagaga ctgagaaatg tacattttgt ttcatacata atgttggtta   205560
ctgcttagtg ggtagaagtt caagtaagtt gtcaagtttc atgcatggta ggttatacgt   205620
gctatacaac ttgcagtggc aacagtcgtt tgtcaggtgt tggtgatgac ccttaaatat   205680
ttgagatgtt gtgacctgat gtatctttag tttcaaacca ctgctttcct ccatgtggtt    205740
cagttggagt atgtgctcta ctttagtcat gtttaaagtt tatctgcaga aactcacctt   205800
agaattgtat ttttttcaaac ttttgacagc ttacattttc tatagcaaca cagcacacgc  205860
acgctaacat ttacttgaaa ctatgcactc atgttttcta cttcattttt ttttatgctg  205920
gttacctcag tgagttgatt ttctgcattt gatttcatga cccttcccca aataaaattc   205980
actgaagtct gaaaaactcc tagagtatct tcagacaaaa tatatcaaat tactgggcag   206040
agtttccaga aaggaagtaa accgttttaa aactcatctg cagccaggtg cagtggctca  206100
cgcctgtaat cccagcaatt tgggaggccg aggcgggtgg atcacctgag gtcaggagtg  206160
```

```
gagactagcc tgaccaacat ggtgaaactg tctctactaa aaaatacaaa aattaggcca   206220
ggtgtggtgg ctcacgcctg taatcccagc actttgggag gccaaggcag gcagatcacc   206280
tgaggttagg agttcgagac cagcctgacc aacatggaga aaccccctct ctcctaaaaa   206340
tacaaaatta tccggctgtg gtggcgcatg cctgtaattc cagctactca ggaggctgag   206400
gcaggagaat cgcttgaacc cgggagtgag ccgaccgaga ttgtgccatt gcactccagc   206460
ctgggcaaca agagcaaaac tccatctcag aaagaaataa aaaaaagctg ggcatggtgg   206520
ccagcacctg taatcccagc tactcgggag gctgaggcag gagaatcgct tgaacctggg   206580
aggcggaggt tgcagtgagc tgagatcacg ccattgcact ctagcctggg caacagagcg   206640
agactctgtc tcaaaaaaaa cacttcacct gtttatcctt atgtctgaga ataatatgaa   206700
ggaacagaaa agcctaaaaa gggcttgtgc ctgaggaatc tggtttcacc cctcctccca   206760
aacaataaaa tgttatcaag acttaaaagg ctaaggcagg aggattgctt gagcccagga   206820
gtttgaggca agccagggca atatagcaag acacccacgc taaaaataaa aataaatgtc   206880
aagacttaat ttcctatgaa ctgcagtttt tctcttctga aaatggtaat tctataatat   206940
aaacatcata gaaattcatt ttctaaacct tcatgtgtga ttacaacaga gtagatgtgg   207000
ctttaagaac atactatacc atatatgtga ggttttcctt aaaatttagc ccagaactat   207060
ggacactttg gttattataa agttgtatta taaagaactc taccacacta gctcttctga   207120
aattttatca ggggctgtga cacttggacc tactgtcttt tgagttatat agttctccta   207180
gactcaaaat gttagggcaa aaagtgttct taacactgag ttgggctcaa tggctcacgc   207240
ctaaatccca gcactttggg aggctaaagt gggaggatca cttgaagcca ggagttccag   207300
accagcctgg ccaaaaaaaa aatttaatta gctgggcatg gtgtcacgca cctgtgatcc   207360
cagctgaggt cggggggagac tgcttgagcc tgggaggtca aggctgcagt gagctgtgat   207420
tgcaccactg cactgcagcc tgggcggcag agcaagaccc tgtttcagag aaaaaaaaaa   207480
actggtccaa ctcctctcct atcagttgct gaatatgcag ccccaaagga tatgactcgc   207540
taggcttatg tagccaggac ccaagatctg taacatgcat tttacatagg tatatattac   207600
agatatataa ttttgtcacg atggctgtaa cgagatttgg atagaaatgg gtattgactc   207660
catgacagtg agttcatagc cagaaatggt tgttgtgtta ggcatgctcc acttgtccct   207720
actgttgtca tcaccaatct gggaagacac tgctagtgta aacaaaaggc acctgctgag   207780
gcaggtccac acgccacctc agggagctcc catttccctg acactgcacg ttggtgtttc   207840
ccaccattgc tcctggtgaa atggttgcag caggcgacag ggtcaacctc ttctataaaa   207900
tagttctagg ggcaattgga accaagatga cttctgtatc ttcctataac atgcatataa   207960
cagctgttct tctgcaacac ctctcatctc aaactttatt agacaactaa ttgtggtatt   208020
tacattaagg ttccctagga aactaacaaa gttacaaacg tgtgtgctaa aatttaacac   208080
tggacctctg ttgccatttg aggccatacc ctaaaactta actttgaatg tacttgtagc   208140
tgctcatcag gaagagagga acagatactg taaatgtgtt ttttttgcttt ggcatatttt   208200 tgacgggagg ggtggcactg cgtctgctgg aatatgttta caatctggtc tatctggaag   208260 ttttttctata aaaatcaaac tgggatccca gggtcactac acttagctta ggtccaatgg   208320
tctagaaata acaactgatt caatttagag agtatttcat tcaggccagg cctagttcta   208380
agagctttac ctaactaact catttaacct ttttaatcca ttctacaaat taggacatta   208440
aggtacagat caaagttatt tgcccaaact catagcaagc aaatggtaga gctcctagtc   208500
agatccagca agtctgactc caacagcctg agttctggaa gcattacacc agcttttcaa   208560
```

```
atgtcagatt gagacaactt agtaggctgt aaaatcagtt taggaggtct caactggcca   208620
ttcttcttta gtatgtagaa taaaatgaaa atagtgtgca tcatggtaaa tactgttttg   208680
tgaacttttg gtttgatata tgtgtacaca agtatattta tatgctaggt aatatgaaat   208740
tcttaaactg tgatcaaaaa ggctgacacc aagctgtgtt gactcagatc atctgactcc   208800
gcctagaaca agac                                                     208814

<210> SEQ ID NO 3
<211> LENGTH: 21
<212> TYPE: DNA
<213> ORGANISM: Artificial Sequence
<220> FEATURE:
<223> OTHER INFORMATION: Synthetic primer

<400> SEQUENCE: 3
tccagacaac tgttcaaact g                                                  21

<210> SEQ ID NO 4
<211> LENGTH: 21
<212> TYPE: DNA
<213> ORGANISM: Artificial Sequence
<220> FEATURE:
<223> OTHER INFORMATION: Synthetic primer

<400> SEQUENCE: 4
ctcttcataa tgcttgctct g                                                  21

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
ggcaaataca cagaggaagc                                                    20

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6 accccccagga ttcttacaga                                                   20
```

MEANS AND METHODS FOR STAGING, TYPING AND TREATING A CANCEROUS DISEASE

This application is a national phase application under 35 U.S.C. § 371 of International Application No. PCT/EP2017/051789, filed Jan. 27, 2017, which claims benefit of European Application No. 16152883.1, filed Jan. 27, 2016, the entire contents of each of which are hereby incorporated by reference.

The present invention relates to methods for diagnosing, staging and treating cancer. In particular, the present invention provides methods for determining the stage/type of a cancerous disease, comprising detecting somatic alterations of the DNA of one or more disseminated cancer cells (DCCs), obtained after homing to a distant organ, such as a lymph node; and determining the somatic evolution of the DCC(s) based on the detected somatic alterations, wherein the somatic evolution is indicative of the stage/type of the cancerous disease.

Cancer staging/typing is the process of determining the extent to which a cancer has developed by spreading. Contemporary practice is to assign a number from I-IV to a cancer, with I being an isolated cancer and IV being a cancer which has spread to the limit of what the assessment measures. Usually, stage IV indicates distant spread of the cancer. The stage generally takes into account the size of a tumor, whether it has invaded adjacent organs, how many regional (nearby) lymph nodes it has spread to (if any), and whether it has appeared in more distant locations (metastasized).

The determined stage of a cancer is generally used to find a suitable strategy for therapy of the cancer, e.g. surgical therapy or drug therapy. However, therapy, in particular drug therapy, is often unsuccessful due to, inter alia, resistance.

In this regard, our inability to cure cancer in many cases is directly linked to the selection of therapy-resistant variants. Insights into cancer drug resistance have been gained by studying advanced metastatic patients, where the total number of cancer cells correlates with the likelihood of resistance; see Holohan et al. (2013) Nature reviews Cancer 13, 714. Consequently, minimal systemic cancer after 'curative' surgery (i.e. the (neo-)adjuvant therapy setting) should be much easier to treat. The time-window after primary surgery and before manifestation of metastasis, i.e. during clinically undetectable minimal residual disease (MRD), defined by disseminated cancer cells (DCCs) and/or circulating tumor cells (CTCs) that are left behind after primary tumor (PT) surgery, may be particularly suitable to prevent lethal metastasis (Aguirre-Ghiso et al. (2013) Nature Med. 19(3):276-7; Polzer and Klein (2013) Nature Med. 19(3):274-5). However, only circumstantial knowledge is available about MRD and consequently (neo-)adjuvant therapies, i.e. the administration of systemic drugs before or after surgery in non-metastatic cancer, improve outcome in only about 20% of patients (Cole et al. (2001) Lancet 358:277-286; Gianni et al. (2011) Lancet Oncol. 12:236-244). Moreover, when targeted therapies with documented efficacy in patients with manifested metastasis were applied in the adjuvant therapy setting, success was disappointingly low (Polzer and Klein (2013) Nature Med. 19(3):274-5). This clinical situation indicates that our current understanding of early systemic cancer is insufficient to successfully prevent metastasis.

First direct evidence for a characteristic biology of early-disseminated cancer cells and MRD came from the analysis of DCCs isolated from bone marrow of breast cancer patients before and after manifestation of metastasis. Genetic data indicated that DCCs from the two stages of metastatic spread differ (Klein et al. (2002) Lancet 360:683-689) Schmidt-Kittler et al. (2003) PNAS 100:7737-7742) and it was suggested that they might have disseminated early and evolved in parallel to the primary tumor (Klein (2009), Nat Rev Cancer 9:302-312). Subsequently, studies in transgenic mouse models (Eyles et al. (2010) J Clin Invest. 120:2030-2039; Husemann et al. (2008) Cancer Cell 13:58-68; Rhim et al. (2012) Cell 148:349-361) and in patients with pre-malignant lesions or in-situ carcinomas (Bangs et al. (2012) Breast Cancer Res Treat. 131:801-808; Husemann et al. (2008) Cancer Cell 13:58-68; Sänger et al. (2011) Int J Cancer 129:2522-2526) corroborated this concept. Evidence for both the early and late dissemination models is available but inconclusive. Cancer of unknown primary (CUP), i.e. metastasis without primary tumor, comprises about 5% of cancer patients and proves that large advanced primary tumors are not needed for metastasis. Similarly, epidemiological data support dissemination of cancer cells and initiation of metastasis years before diagnosis (Engel et al. (2003) Eur J Cancer 39:1794-1806). Genetic data such as comparative sequencing studies of matched primary tumors and metastasis provide examples for both scenarios (Klein (2013) Nature 501:365-372). However, sequencing studies may be misleading or inconclusive as iatrogenic selection over several lines of systemic therapies may shift cancer populations significantly. In summary, clinical and patient-derived ex vivo data seem to support early dissemination and ectopic progression, whereas most experimental models assume and use late-arising, fully malignant metastatic cells. In this regard, many reports use patient material derived from blood samples whereas samples derived from lymph nodes are considered a less preferred source, as for example described in WO 02/37113. Preference for plasma or blood samples is also disclosed in EP 2 503 009, which relates to a method for diagnosing tumors based on copy number of the ErbB2 gene and its expression profile. Experiments are done using exclusively serum or plasma samples of patients. As current clinical practice is based on a late-dissemination and intratumoral progression model (as opposed to a parallel progression model), consideration of a parallel progression model would fundamentally imply the need for novel diagnostic tools, for improved and more accurate determination of the stage/type of cancer and improved cancer therapy, in particular adjuvant therapy.

Thus, the technical problem underlying the present invention is the provision of accurate methods for the early determination of the stage/type of a cancerous disease and corresponding improved means and methods for treating a cancerous disease.

The solution is provided by the embodiments as defined herein below and as characterized in the claims.

The invention, accordingly, relates to a method for staging and/or typing of a cancerous disease, said method comprising the following steps:

(a) detecting somatic alterations of the DNA of one or more disseminated cancer cell(s) DCC(s) obtained from one or more lymph node(s); and
(b) determining the somatic evolution of the DCC(s) based on the detected somatic alteration(s) in step (a), wherein the somatic evolution of the DCC(s) is indicative of the stage/type of the cancerous disease.

In a particularly preferred embodiment, the cancerous disease to be staged/typed is melanoma. Thus, the invention relates to a method for staging and/or typing of a cancerous disease, said method comprising the following steps:

(a) detecting somatic alterations of the DNA of one or more disseminated cancer cell(s) DCC(s) obtained from one or more lymph node(s); and
(b) determining the somatic evolution of the DCC(s) based on the detected somatic alteration(s) in step (a), wherein the somatic evolution of the DCC(s) is indicative of the stage/type of the cancerous disease, wherein the cancerous disease is melanoma.

The illustrative appended Examples demonstrate that DCCs acquire alterations that are critical for metastatic progression within lymph nodes. This indicates that parallel progression of the primary tumor and DCCs takes place (as opposed by intratumoral progression of DCCs). Parallel progression of the primary tumor and DCCs means that analysis of the primary cancer cannot be used to evaluate whether DCCs progress to metastases. Parallel progression of the primary tumor and DCCs also means that progression of DCCs to metastasis cannot be prevented by resection of the primary cancer. Furthermore, parallel progression means that analysis of the primary cancer cannot be used to determine whether the metastases respond to a certain therapy.

In context of the present invention it has surprisingly been found that before progression to metastases DCCs show a metastasis signature (i.e. particular genetic alterations indicating that the DCCs will progress to metastases). According to the present invention this metastasis signature can advantageously be used to evaluate whether the DCCs will form metastases. In addition, this metastases signature can be used in order to evaluate whether the metastases will respond to a certain therapy.

Thus, the present invention relates to a method for identifying the metastasis signature of one or more DCC(s) (i.e. for staging and/or typing of a cancerous disease) said method comprising the following steps:
(a) detecting somatic alterations of the DNA of one or more DCC(s) obtained from one or more lymph node(s); and
(b) determining the metastasis signature (i.e. the somatic evolution) of the DCC(s) based on the detected somatic alteration(s) in step (a).

In this method the metastases signature of the DCC(s) is indicative of the stage/type of the cancerous disease.

In a particularly preferred embodiment, the cancerous disease is melanoma.

According to the present invention the stage/type of a cancerous disease can be used to evaluate whether the cancerous disease (preferably a melanoma) responds to a certain therapy. Therefore, the method of the present invention is useful to determine whether a certain therapy should be initiated, continued or discontinued.

Thus, another embodiment of the present invention relates to a method for treating a cancerous disease, said method comprising the following steps:
(a) detecting somatic alterations in the DNA of one or more DCC(s) obtained from one or more lymph node(s) of a subject;
(b) determining the somatic evolution of the DCC(s) based on the detected somatic alteration(s) in step (a); and
(c) determining the stage/type of the cancerous disease based on the somatic evolution of the DCC(s) determined in step (b), wherein the stage/type of the cancerous disease is used to initiate, continue or discontinue therapy of said cancerous disease.

In a particularly preferred embodiment, the cancerous disease is melanoma.

The invention also relates to a pharmaceutical composition for use in treating a cancerous disease in a subject, wherein treatment is initiated, continued or discontinued based on the stage/type of said cancerous disease, wherein said stage/type of said cancerous disease is determined by:
(a) detecting somatic alterations in the DNA of one or more DCC(s) obtained from one or more lymph node(s) of a subject;
(b) determining the somatic evolution of the DCC(s) based on the detected somatic alteration(s) in step (a); and
(c) determining the stage/type of the cancerous disease based on the somatic evolution of the DCC(s) determined in step (b).

In a particularly preferred embodiment, the cancerous disease is melanoma.

Said pharmaceutical composition may be any type of medicament for the treatment of a cancerous disease, including composition comprising a chemotherapeutic drug or a composition comprising a drug for immunotherapy.

One embodiment of the present invention relates to the methods or pharmaceutical composition of the invention, further comprising determination of the DCC density (DCCD), wherein the DCCD is the number of DCCs per million cells in the lymph node used to obtain the DCCs, wherein the DCCD is indicative of the stage/type of the cancerous disease. The appended Examples show that DCCs from lymph nodes with a DCCD of >100 are able to grow to a colony and to develop to tumors in a xenograft experiment, in particular for melanoma. Therefore, one aspect of the present invention relates to the herein provided methods, or the herein provided pharmaceutical composition, wherein a DCCD of >100 is indicative for the development of metastases, in particular in the case of melanoma.

In addition, it has been surprisingly found that immunological changes (i.e. signs of T cell exhaustion indicating a blunted T cell response and DCCs progressing to metastases) are locally observed and depend on the local tumor cell load. This information can be used to determine whether therapies targeting the microenvironment will be effective, in particular therapy targeting cells of the immune system. This is because the tissue origin of the primary tumor and target site of dissemination and metastasis differ. Thus, analysis of the microenvironment (e.g. immune cells) of the primary tumor may be less suited to evaluate whether the microenvironment at the target site of dissemination and metastasis is affected or whether a certain therapy targeting the microenvironment of DCC(s) and metastases will be effective. Rather, as is shown herein, the microenvironment in lymph nodes is indicative of the stage/type of the cancerous disease outside the primary tumor. Thus, it has been surprisingly found that, as is further demonstrated in the appended Examples, a DCCD of >2000, in particular in the case of melanoma, is indicative of a yet further advanced stage/type of the cancerous disease, in particular melanoma. Specifically, the appended Examples show that the number of antigen-experienced CD8 T cells increases with increasing DCCD, which is indicative of T cell activation related to tumor cell growth and metastases formation. In particular, PD-1 high expressing CD8 T cells are significantly enriched in lymph nodes with a DCCD at about 2000, i.e. at a value 20× higher than the DCCD>100 which is indicative of metastasis development. PD-1 high CD8 T cells are considered as terminally exhausted T cells. These cells co-express Tim-3, another marker of exhausted T cells and have an impaired ability for cytokine production. Exhausted T cells lose effector functions in a hierarchical manner: IL-2 production, high proliferative capacity and cytolytic activity are lost first, followed by impaired cytokine production. PD-1 expressing CD8 T cells isolated from tumor tissue of metastatic melanoma patients were shown to be tumor-reactive. An increase in MDSCs (myeloid derived suppressor cells) was concomitant with the increase with PD-1 high expressing CD8 T cells. MDSCs are immunosuppressive immune cells and cancer tissues with high infiltration of MDSCs are associated with poor patient prognosis and resistance to therapies. Also, the percentage of MDSC is increased in patients with a DCCD at about 2000, whereas the percentage of cytolytic CD56dim NK cells is decreased in lymph nodes with a high DCCD. CD56dim NK cells possess high cytolytic function and therefore can kill tumor cells. All together the appended Examples demonstrate that changes in the local immune microenvironment in the target organ of dissemination are associated with metastatic outgrowth, for which the DCCD gives an indicative measurement. The DCCD alone or in combination with information about changes in the immune microenvironment is indicative of the stage/type of the cancerous disease and/or is used to initiate, continue or discontinue therapy of said cancerous disease. Thus, in one embodiment, the methods or pharmaceutical composition of the invention, further comprise determination of the DCC density (DCCD), wherein the DCCD is the number of DCCs per million cells in the lymph node used to obtain the DCCs, wherein the DCCD is indicative of the stage/type of the cancerous disease, wherein a DCCD of >100 is indicative for the development of metastases and/or wherein a DCCD of >2000 is indicative of the immune system being unable to inhibit metastatic growth. Thus, where the DCCD is >2000, in particular in melanoma, treatment may further comprise immune therapy specifically addressing immune cells and their ability to inhibit metastasis growth.

As indicated above, the appended Examples show that depending on the metastasis signature (i.e. the type of somatic alterations) patient-derived DCCs are able to form tumors in mice. In particular, all DCCs that were able to form tumors had either a BRAF mutation, a loss of chromosome 9p11-13, a loss of chromosome 9p21-24, a gain of chromosome 7q21-36, or a NRAS mutation. In this regard, deletions of 9p11-13 and/or 9p21-24 are observed in about 90% of cells carrying more than one somatic alteration. All together, in about 20% of the samples, a loss of 9p11 was observed in combination with a loss of 9p24. About 50% have a loss of 9p11 and/or 9p24 in combination with a further alteration (BRAF, NRAS or gain on chromosome 7q21. Only about 20% have a loss of 9p11 and/or 9p24 plus a gain on chromosome 7q21 together with a mutation of BRAF or NRAS.

Therefore, one aspect of the present invention relates to the methods of the invention, or the pharmaceutical composition of the invention, wherein the somatic alterations comprise at least one of the somatic alterations selected from the group consisting of a BRAF mutation, a loss of chromosome 9p11-13, a loss of chromosome 9p21-24, a gain of chromosome 7q21-36, and a NRAS mutation. According to the present invention the somatic alterations may also comprise at least two, three, four or all of the somatic alterations selected from the group consisting of a BRAF mutation, a loss of chromosome 9p11-13, a loss of chromosome 9p21-24, a gain of chromosome 7q21-36, and a NRAS mutation. In the methods of the invention or in context of the pharmaceutical composition of the invention, a BRAF mutation, a loss of chromosome 9p11-13, a loss of chromosome 9p21-24, a gain of chromosome 7q21-36, and/or a NRAS mutation indicates that the DCC(s) will develop to metastases.

However, according to the present invention also the proliferation activity of DCC(s) may be used in order to determine whether these cells will develop to metastases. Thus, another embodiment of the present invention relates to the methods of the invention, or the pharmaceutical composition of the invention, wherein step (a) further comprises evaluating the proliferation of the DCC(s), wherein in step (b) an increased proliferation of the DCC(s) indicates that the DCC(s) will develop to metastases. The proliferation can be measured, e.g., by analyzing the amount of proliferation markers such as the proliferation marker Ki-67. The frequency of Ki-67 positive cells can be determined by assessing the percentage of cells that stain positive for the marker, e.g. by immunohistochemistry, immunofluorescence. This percentage provides an estimate of cells in the cell cycle, i.e. the percentage of proliferating cells.

As indicated above, the stage/type of a cancerous disease can be used to evaluate whether the cancerous disease (preferably a melanoma) responds to a certain therapy. In particular, the presence or absence of genetic alterations within DCCs also indicates whether a certain treatment is to be initiated, continued or discontinued. In particular, one embodiment of the present invention relates to the methods of the invention, or the pharmaceutical composition of the invention, wherein if the DCC(s) are found to carry a BRAF mutation, a treatment that is directed against cells carrying said mutation is to be initiated or continued. However, if the DCC(s) were found to not carry a BRAF mutation, a treatment that is directed against cells carrying said mutation might be harmful to the patient. Similarly, if the DCC(s) are found to carry a NRAS mutation, a treatment that is directed against cells carrying said mutation is to be initiated or continued. However, if the DCC(s) are found to not carry a NRAS mutation, a treatment that is directed against cells carrying said mutation might be harmful to the patient. If PD-1 high expressing T cells, which are thought to not respond to PD-1 blockade (PMID: 25797516), i.e. regain functionality, are found in increasing numbers in lymph node(s) harboring DCC(s), no therapy response might be observed under therapeutically PD-1 or PD-L1 blockade or the therapy might be even harmful to the patient (i.e. autoimmunity without anti-cancer response).

As described below in more detail, in the methods and pharmaceutical composition of the present invention, the type of cancerous disease is not particularly limited as long as the disease involves the dissemination of cells from a primary disease site into lymph node(s) and/or other tissue, for example bone marrow. It is preferred that the cancerous disease is a melanoma.

Accordingly, the present invention relates to a method for staging and/or typing of a cancerous disease, a method for treating a cancerous disease and a pharmaceutical composition for use in treating a cancerous disease, in particular cancer. In this regard, it was surprisingly and unexpectedly found that the stage/type of a cancerous disease, in particular cancer, can be determined by detecting the somatic alterations, in particular genetic and/or epigenetic alterations, in the DNA of disseminated cancer cells (DCCs) obtained from a tissue sample of a subject, in particular obtained from one or more lymph node(s) of a subject, in particular draining and/or regional lymph node(s) and/or sentinel lymph node(s).

Also provided herein are methods for staging and/or typing of a cancerous disease by detecting the somatic alterations, in particular genetic and/or epigenetic alterations, in the DNA of circulating tumor cells (CTCs). Accordingly, the present invention provides a method for staging and/or typing of a cancerous disease, a method for treating a cancerous disease and a pharmaceutical composition for use in treating a cancerous disease, in particular cancer where the stage/type of a cancerous disease, in particular cancer, is determined by detecting the somatic alterations, in particular genetic and/or epigenetic alterations, in the DNA of one or more CTC(s) obtained from blood of a subject, in particular obtained from a blood sample obtained from a subject or obtained using an in vivo CTC-capturing-device. That is, the embodiments provided herein may also be applied to CTC(s), unless indicated otherwise, instead or in addition to DCC(s). The skilled person is readily aware how to adapt the teaching provided herein for DCC(s) to CTC(s) accordingly.

The inventors determined the time point of metastatic seeding of melanoma relative to the depth of dermal invasion and characterized ectopic molecular evolution in cancer, in particular melanoma; see inter alia Example 1 and FIG. 1. More specifically, as also large melanomas may be non-invasive, the time point of metastatic seeding of melanoma relative to the depth of dermal invasion (not relative to the total size) of the melanoma was analyzed. Dissemination to lymph nodes preferentially occurred around 0.4 mm (95% CI 0.04-0.75 mm) before intradermal expansion. Disseminated cancer cells (DCCs) lacked typical driver changes before lymphatic colony formation regardless of primary tumor thickness; see inter alia Example 5 and FIGS. 2, 3 and 4. However, driver mutations in BRAF or NRAS and signature chromosomal rearrangements became significantly enriched in colony-forming DCCs and/or xenografts from DCCs and put patients at high risk for death. Thus, in cancerous diseases, in particular cancer, DCCs leave primary tumors early and evolve at different sites in parallel; see inter alia Example 6 and FIG. 5. Accordingly, staging and/or typing of cancerous diseases, in particular cancer, can be improved, in particular a more accurate method of staging and/or typing of cancerous diseases can be provided, by using information from cells derived from primary tumors, in particular DCCs obtained from different sites where cells evolve, i.e. sites where DCCs migrate, like for example lymph nodes, or sites where cells, in particular CTCs derived from a primary tumor circulate, for example blood. In this regard, the inventors surprisingly found that the somatic evolution of said DCCs or CTCs, respectively, determined based on somatic, in particular genetic and/or epigenetic alterations detected in the DNA of said DCCs or CTCs, respectively, can be used to stage/type a cancerous disease, in particular cancer. These surprising and unexpected findings led to the present invention, in particular more accurate means and methods for staging and/or typing of cancerous diseases, which are based on a novel model of cancerous diseases, in particular cancer.

As outlined further above, the stage of a cancerous disease is usually determined using, for example, the TNM staging system. The TNM Classification of Malignant Tumours (TNM) is a cancer staging notation system that gives codes to describe the stage of a patient's cancer, wherein T describes the size of the original (primary) tumor and whether it has invaded nearby tissue, N describes nearby (regional) lymph nodes that are involved, and M describes distant metastasis (spread of cancer from one part of the body to another). With particular regard to the tumour, i.e. parameter T, there are several stages: Tx: tumor cannot be evaluated, Tis: carcinoma in situ, T0: no signs of tumor, and T1, T2, T3, T4: size and/or extension of the primary tumor. As it was found by the present inventors, the above stages of cancerous diseases, in particular cancer, for example melanoma, are in many cases insufficient to determine a suitable strategy for therapy of a cancerous disease. Therefore, a new model was found, which uses the somatic evolution of cells, in particular DCCs obtained from one or more lymph node(s) of a subject, in particular draining and/or regional lymph node(s) and/or sentinel lymph node(s), but also, if available, DCCs from other organs than lymph nodes, such as bone marrow or liquor, informing about the molecular state of brain DCCs. The somatic evolution of cells may also be determined using CTCs obtained from blood of a subject. Accordingly, in contrast to classical staging/typing of cancerous diseases, which mainly depends on phenotypic assessment of a primary tumor, the novel and inventive methods of the present invention use the somatic evolution of cells, in particular DCCs and/or CTCs, as indicator of the stage/type of a cancerous disease, in particular cancer.

DCCs are cells that disseminated from a primary tumor site before surgery and spread lymphatically or hematogeneously. They may be detected using epithelial cell markers or melanocytic markers in case of melanoma, which are not found on the surface of lymphatic cells or cells found in bone marrow. For example, EpCAM and/or cytokeratins are cell markers that may be targeted in the detection of DCCs (Klein (2009), Nat Rev Cancer 9:302-312), in particular in the case of carcinomas. The targeting cell markers can be expressed and/or located intracellularly and/or at the surface of the cell. Preferably, DCCs from melanoma may be detected by using gp100 and/or MCSP (melanoma-associated chondroitin sulfate proteoglycan) and/or Melan A (MART-1), and/or CD146 as targeting cell markers. DCCs can be detected and isolated for example from bone marrow aspirates or lymph nodes. After disaggregating and/or processing into single cell suspension, the DCCD can be determined by immunocytology. In particular, the single cell suspension may be stained with antibodies against the said targeting cell markers such as EpCAM (Guzvic et al. (2014) Cancer Res. 74:7383-7394), cytokeratin (Schardt et al. (2005) Cancer Cell 8:227-239, gp100 or MCSP (Ulmer et al. (2014) PLoS Med. 11:e1001604. The number of cells positive for the targeting cell marker per million of cells (preferably lymph node cells) that were stained defines the DCC-density (DCCD).

CTCs are cells that are also derived from a primary tumor site before surgery, but that circulate in the blood system. After primary tumor surgery they may be derived from latent or manifest metastatic colonies. They may be detected and isolated using EpCAM as targeting cell marker, but are not limited to this targeting cell marker. Enrichment and detection markers are similar to those used for detection in other mesenchymal organs (bone marrow, lymph nodes) and include for example EpCAM and Cytokeratins for epithelial markers and the mentioned melanocytic markers in melanoma. CTCs may be obtained from blood (e.g. from leukapheresis products) (Fischer et al. (2013) PNAS 110: 16580-16585) using methods well-known in the art, in particular FDA-cleared Cell Search® system (Veridex LLC), DEPArray™ technology or flowcytometry, but CTC-isolation is not limited to these systems (Polzer et al. (2014) EMBO Mol Med. 6:1371-138) and may comprise a variety of novel devices such as CellSieve or Parsortix. In vivo CTC-capturing-devices may also be used. Examples for such devices are Gilupi, CellCollector (Gorges et al. (2015) ClinCancer Res. 1416.2015, Epub ahead of print), cancer cell binding nanoparticles Galanzha et al. (2011) Cytometry 79:814-824) or medical wires (Saucedo-Zeni et al. (2012) Int J Oncol. 41:1241-1250), but are not limited to these. Such devices or particles are implanted or infused into a subject/patient to capture and enrich CTCs in the body of the subject/patient. The CTCs can then be retrieved from the CTC-capturing-device or -particles ex vivo or in vivo.

In this regard, the term "somatic evolution" as used herein relates to the accumulation of alterations in cells, in particular cancerous disease cells, in particular DCCs, during a lifetime, and the effects of those alterations on the fitness of those cells. Somatic evolution of cancer cells is due to spontaneous or induced genetic/epigenetic alterations and subsequent natural selection during clonal expansion, which selects cells according to fitness, proliferation rate, apoptosis rate and the like. In addition, cancer therapy acts as a form of artificial selection, killing sensitive cancer cells, but leaving behind resistant cells. Often the tumor will regrow from those resistant cells, the patient will relapse, and the therapy that had been previously used will no longer be effective. Thus, somatic evolution is an ongoing process during the development of cancerous diseases and/or therapy of a cancerous disease. In this regard, there are multiple levels of genetic heterogeneity associated with somatic evolution in cancerous diseases. In the methods of the present invention, somatic evolution is determined based on somatic alterations, including epigenetic alterations and/or genetic alterations. Therefore, based on the number and/or nature of somatic alterations, including epigenetic alterations and/or genetic alterations, the somatic evolution of a cell, in particular a DCC, can be determined.

The term "somatic alterations" as used herein includes any alteration of nucleic acids, in particular DNA, comprised in a cell, in particular a DCC. Alteration means a deviation from a reference state like for example a state at a given point of time in a reference sample obtained from a subject, for example in a sample obtained from a subject comprising cells derived from other tissue than the sample to be analyzed in the methods of the present invention and/or comprising stem cells of the subject, or a state generally taken as reference with regard to a particular segment of DNA, for example a DNA sequence taken from a sequence database or a known pattern of epigenetic alterations such as a methylation pattern. Accordingly, a somatic alteration may be detected by comparing an observed state with a reference state. Any observed deviation may then be categorized as somatic alteration. In a second phase, said alteration may be categorized as real somatic alteration or an error introduced by the employed detection method, for example sequencing method. In this regard, the present invention discloses means and methods particularly useful for error-free detection of somatic alterations. Such methods are preferred to be used in the methods of the present invention. Somatic alterations within the meaning of the present invention include epigenetic and/or genetic alterations. Genetic alterations include alterations on the level of the sequence of the DNA, i.e. the succession of nucleotides comprised in DNA, and alterations of the relative abundance of segments of the DNA comprised in the sample to be analyzed. Accordingly, genetic alterations within the meaning of the present invention may include, inter alia, single nucleotide variations (SNV), sequence mutations, Microsatellite shifts and instability, Loss of heterozygosity (LOH), copy number alterations, karyotypic variations including chromosome structural aberrations and/or aneuploidy. Epigenetic alterations include chemical alterations of DNA that are not on the level of the DNA sequence and alterations of external factors involved in DNA structure formation, processing and the like. Accordingly, epigenetic alterations within the meaning of the present invention may include, inter alia, methylation, in particular methylation of CG pairs, deficiencies of DNA repair proteins, and/or alterations in histone architecture or structure like methylation, acetylation, sumoylation, activating or inactivating histone marks and/or alterations in chromatin architecture like for example in eu- or hetero-chromatin and the like.

In one aspect of the invention, somatic alterations, in particular genetic alterations, comprise one or more driver mutation(s) and/or passenger mutation(s). The term "driver mutation" refers to mutations that give a selective advantage to a clone in its microenvironment, through either increasing its survival or reproduction. Driver mutations tend to cause clonal expansions. Accordingly, the somatic alterations, in particular genetic alterations, determined in the methods of the present invention may comprise one or more driver mutation(s). In this regard, one common feature of cellular, in particular DCC progression is the expansion of a clone with a somatic alteration, in particular a genetic and/or epigenetic alteration. This is generally due to the expanding clone having a competitive advantage (either a reproductive or survival advantage) over other cells in the respective tissue. Since expanding clones often have more than one somatic alteration, in particular genetic and/or epigenetic alteration, in their genomes, it is often not clear which of those alterations cause a reproductive or survival advantage and which other alterations are simply hitchhikers or passenger mutations on the clonal expansion. However, several driver mutations are known in the art. For example, driver mutations may be, inter alia, mutations in known oncogenes. Oncogenes are genes known to be associated with the development of a cancerous disease, in particular cancer. Thus, driver mutation(s) within the meaning of the present invention include, but are not limited to, mutations in known oncogenes. For examples, the genes coding for the neuroblastoma RAS viral oncogene homolog (NRAS) or BRAF are known oncogenes. Further known oncogenes are reported in databases such as the COSMIC database by Forbes et al. (2014) Nucleic Acid Res. 43, D805-811, or in reports by Vogelstein et al. (2013) Science 339(6127):1546-58, Akagi et al. (2004) Nucleic Acid Res. 32, D523-7 or Huret et al. (2000) Nucleic Acid Res. 28(1):349-51. Such databases are constantly updated for oncogenes and known driver mutations. Accordingly, any of the therein reported driver mutations may be detected in the methods of the present invention. In this regard, the methods used in the present invention for detecting the somatic alterations, in particular genetic and/or epigenetic alterations, in oncogenes are suitable for simultaneous detection of somatic alterations in multiple oncogenes. Particular driver mutations that may be detected in the methods of the present invention comprise driver mutations in the gene coding for NRAS comprising, inter alia, the exon 3 mutation c181C>A. Accordingly, the present invention relates to a method for staging and/or typing of a cancerous disease, the method comprising the steps of detecting somatic alterations of the DNA of one or more DCC(s) obtained from a tissue sample, in particular one or more lymph node(s); and determining the somatic evolution of the DCC(s) based on the detected somatic alteration(s) in the DNA of the one or more DCC(s), wherein the somatic evolution of the DCC(s) is indicative of the stage/type of the cancerous disease, wherein detection of somatic alterations comprises detection of the nucleotide at position 2986 of SEQ ID NO:1, wherein a cytosine at position 2986 of SEQ ID NO:1 is indicative of a non-diseased stage/type and an adenine at position 2986 of SEQ ID NO:1 is indicative of a diseased stage/type. Furthermore, a guanine at position 2987 of SEQ ID NO:1 or a thymine at position 2987 of SEQ ID NO:1 is indicative of a diseased stage. The present invention furthermore relates to a method for treating a cancerous disease, the method comprising the steps of detecting somatic alterations in the DNA of one or more DCC(s) obtained from a tissue sample, in particular one or more lymph node(s) of a subject; determining the somatic evolution of the DCC(s) based on the detected somatic alteration(s) in the DNA of the one or more DCC(s); and determining the stage/type of the cancerous disease based on the somatic evolution of the cancerous disease determined based on the detected somatic alterations in the DNA of the one or more DCC(s), wherein the stage/type of the cancerous disease is used to initiate, continue or discontinue therapy of said cancerous disease, wherein detection of somatic alterations comprises detection of the nucleotide at position 2986 of SEQ ID NO:1, wherein a cytosine at position 2986 of SEQ ID NO:1 is used to discontinue therapy and an adenine at position 2986 of SEQ ID NO:1 is used to initiate or continue therapy of the cancerous disease. Furthermore, a guanine at position 2987 of SEQ ID NO:1 or a thymine at position 2987 of SEQ ID NO:1 is used to initiate or continue therapy of the cancerous disease.

The invention furthermore relates to a pharmaceutical composition for use in treating a cancerous disease in a subject, wherein treatment is initiated, continued or discontinued based on the stage/type of the cancerous disease, wherein the stage/type of the cancerous disease is determined by detecting somatic alterations in the DNA of one or more DCC(s) obtained from a tissue sample, in particular one or more lymph node(s) of a subject; determining the somatic evolution of the DCC(s) based on the detected somatic alteration(s) in the DNA of the one or more DCC(s); and determining the stage/type of the cancerous disease based on the somatic evolution of the cancerous disease determined based on the detected somatic alterations in the DNA of the one or more DCC(s), wherein detection of somatic alterations comprises detection of the nucleotide at position 2986 of SEQ ID NO:1, wherein a cytosine at position 2986 of SEQ ID NO:1 is used to discontinue treatment and an adenine at position 2986 of SEQ ID NO:1 is used to continue or initiate treatment. Furthermore, a guanine at position 2987 of SEQ ID NO:1 or a thymine at position 2987 of SEQ ID NO:1 is used to continue or initiate treatment of the cancerous disease. The detection of somatic alterations may comprise the detection of genetic and/or epigenetic alterations of one or more oncogenes.

As outlined above, the detection of somatic alterations, including genetic and/or epigenetic alterations, may comprise the detection of somatic alterations in known oncogenes. As described above for NRAS, known driver mutations may also be detected in BRAF, another known oncogene encoding a protein involved in directing cell growth. As such, several genetic alterations, in particular (driver) mutations, are described in the art to cause a constitutively active form of BRAF, which is associated with the development of cancer. In view of its role in disease, several BRAF inhibitors directed to the native and mutated form have been described; see e.g. Wan et al. (2004) Cell 116 (6): 855-67; Tsai et al. (2008) PNAS 105 (8): 3041-6; and Bollag et al. (2010) Nature 467 (7315): 596-9. For example, sorafenib is a small molecular kinase inhibitor drug approved for the treatment of primary kidney cancer (advanced renal cell carcinoma), advanced primary liver cancer (hepatocellular carcinoma), and radioactive iodine resistant advanced thyroid carcinoma. Sorafenib inhibits, inter alia, wild-type and mutant BRAF. A further exemplary BRAF inhibitor is vemurafenib, which is a selective inhibitor of the V600E mutated BRAF protein responsible for an aggressive form of melanoma. It has also been shown to be an effective inhibitor of V600K mutated BRAF protein. In melanoma patients having wild-type BRAF, vemurafenib promotes tumor growth; see Hatzivassiliou et al. (2010) Nature 464 (7287): 431-5 or Halaban et al. (2010) Pigment Cell Melanoma Res. 23(2): 190-200. However, classical melanoma diagnosis does not comprise determination of the mutational state of patients with regard to the BRAF oncogene. Moreover, as it has been surprisingly found by the present inventors, the herein described new model of parallel evolution of cells in the primary tumor and DCC(s) indicates that detection of the mutational state in the primary tumor is insufficient for determination of the best suitable therapy of melanoma patients. Accordingly, the herein provided more accurate methods of cancer staging/typing may comprise a step of detecting the mutational state of the BRAF oncogene. Therefore, the present invention relates to a method for staging and/or typing of a cancerous disease, the method comprising the steps of detecting somatic alterations of the DNA of one or more DCC(s) obtained from a tissue sample, in particular one or more lymph node(s); and determining the somatic evolution of the DCC(s) based on the detected somatic alteration(s) in the DNA of the one or more DCC(s), wherein the somatic evolution of the DCC(s) is indicative of the stage/type of the cancerous disease, wherein detection of somatic alterations comprises detection of the nucleotide triplet at positions 171428 to 171430 of SEQ ID NO:2, wherein a nucleotide triplet guanine at position 171428, tyrosine at position 171429 and guanine at position 171430 of SEQ ID NO:2 is indicative of a non-diseased stage/type and a nucleotide triplet guanine at position 171428, adenine at position 171429 and guanine at position 171430 of SEQ ID NO:2 is indicative of a diseased stage/type. Furthermore, a nucleotide triplet adenine at position 171428, adenine at position 171429 and guanine at position 171430 of SEQ ID NO:2 and a nucleotide triplet adenine at position 171428, guanine at position 171429 and guanine at position 171430 of SEQ ID NO:2 is indicative of a diseased stage/type. The present invention furthermore relates to a method for treating a cancerous disease, the method comprising the steps of detecting somatic alterations in the DNA of one or more DCC(s) obtained from a tissue sample, in particular one or more lymph node(s); determining the somatic evolution of the DCC(s) based on the detected somatic alteration(s) in the DNA of the one or more DCC(s); and determining the stage/type of the cancerous disease based on the somatic evolution of the cancerous disease determined based on the detected somatic alterations in the DNA of the one or more DCC(s), wherein the stage/type of the cancerous disease is used to initiate, continue or discontinue therapy of said cancerous disease, wherein detection of somatic alterations comprises detection of the nucleotide triplet at positions 171428 to 171430 of SEQ ID NO:2, wherein a nucleotide triplet guanine at position 171428, tyrosine at position 171429 and guanine at position 171430 of SEQ ID NO:2 is used to discontinue treatment and a nucleotide triplet guanine at position 171428, adenine at position 171429 and guanine at position 171430 of SEQ ID NO:2 is used to continue or initiate treatment. Furthermore, a nucleotide triplet adenine at position 171428, adenine at position 171429 and guanine at position 171430 of SEQ ID NO:2 and a nucleotide triplet adenine at position 171428, guanine at position 171429 and guanine at position 171430 of SEQ ID NO:2 is used to initiate or continue treatment. It is preferred that treatment comprises the use of an inhibitor of BRAF. Accordingly, treatment preferably comprises the use of sorafenib or vemurafenib. Moreover, it is preferred that the cancerous disease is melanoma. The invention furthermore relates to a pharmaceutical composition for use in treating a cancerous disease in a subject, wherein treatment is initiated, continued or discontinued based on the stage/type of the cancerous disease, wherein the stage/type of the cancerous disease is determined by detecting somatic alterations in the DNA of one or more DCC(s) obtained from a tissue sample, in particular one or more lymph node(s) of a subject; determining the somatic evolution of the DCC(s) based on the detected somatic alteration(s) in the DNA of the one or more DCC(s); and determining the stage/type of the cancerous disease based on the somatic evolution of the cancerous disease determined based on the detected somatic alterations in the DNA of the one or more DCC(s), wherein detection of somatic alterations comprises detection of the nucleotide triplet at positions 171428 to 171430 of SEQ ID NO:2, wherein a nucleotide triplet guanine at position 171428, tyrosine at position 171429 and guanine at position 171430 of SEQ ID NO:2 is used to discontinue treatment and a nucleotide triplet guanine at position 171428, adenine at position 171429 and guanine at position 171430 of SEQ ID NO:2 is used to continue or initiate treatment. Furthermore, a nucleotide triplet adenine at position 171428, adenine at position 171429 and guanine at position 171430 of SEQ ID NO:2 and a nucleotide triplet adenine at position 171428, guanine at position 171429 and guanine at position 171430 of SEQ ID NO:2 is used to initiate or continue treatment. It is preferred that the pharmaceutical composition comprises an inhibitor of BRAF. Accordingly, it is preferred that the pharmaceutical composition comprises sorafenib or vemurafenib. Moreover, it is preferred that the cancerous disease is liver cancer, kidney cancer or melanoma. It is more preferred that the cancerous disease is melanoma. Accordingly, the present invention relates to, inter alia, a pharmaceutical composition comprising a BRAF inhibitor, preferably sorafenib or vemurafenib, for use in treating a cancerous disease in a subject, wherein treatment is initiated, continued or discontinued based on the stage/type of the cancerous disease, wherein the stage/type of the cancerous disease is determined by detecting somatic alterations in the DNA of one or more DCC(s) obtained from a tissue sample, in particular one or more lymph node(s) of a subject; determining the somatic evolution of the DCC(s) based on the detected somatic alteration(s) in the DNA of the one or more DCC(s); and determining the stage/type of the cancerous disease based on the somatic evolution of the cancerous disease determined based on the detected somatic alterations in the DNA of the one or more DCC(s), wherein detection of somatic alterations comprises detection of the nucleotide triplet at positions 171428 to 171430 of SEQ ID NO:2, wherein a nucleotide triplet guanine at position 171428, tyrosine at position 171429 and guanine at position 171430 of SEQ ID NO:2 is used to discontinue treatment and a nucleotide triplet guanine at position 171428, adenine at position 171429 and guanine at position 171430 of SEQ ID NO:2 is used to continue or initiate treatment. Furthermore, a nucleotide triplet adenine at position 171428, adenine at position 171429 and guanine at position 171430 of SEQ ID NO:2 and a nucleotide triplet adenine at position 171428, guanine at position 171429 and guanine at position 171430 of SEQ ID NO:2 is used to initiate or continue treatment. The cancerous disease is preferably liver cancer, kidney cancer or melanoma. It is more preferred that the cancerous disease is melanoma.

In accordance with the above, the invention provides means and methods of treating a cancerous disease, in particular cancer. Accordingly, the present invention, inter alia, relates to a method of treating a cancerous disease, in particular cancer, comprising obtaining and analyzing a sample from a patient suspected of having or having a cancerous disease, in particular cancer; wherein analyzing comprises sequencing of the DNA of DCC(s) comprised in the sample; detecting the presence or absence of somatic alterations, in particular genetic and/or epigenetic alterations, in the DNA, wherein the presence of somatic alterations indicates that an effective amount of a pharmaceutical composition has to be administered to the patient. The invention furthermore relates to a method of diagnosing a cancerous disease, comprising obtaining and analyzing a sample from a patient suspected of having a cancerous disease, in particular cancer; wherein analyzing comprises sequencing of the DNA of DCC(s) comprised in the sample; detecting the presence or absence of somatic alterations, in particular genetic and/or epigenetic alterations, in the DNA, wherein the presence of somatic alterations indicates a patient has, or is likely to have, a cancerous disease and the absence of somatic alterations indicates the patient does not have, or is not likely to have, a cancerous disease.

Somatic alterations, in particular genetic alterations, determined in the methods of the present invention may also comprise one or more passenger mutations. A passenger mutation is a mutation that has generally no or only little effect on the fitness of a clone but may be associated with a clonal expansion because it occurs in the same genome with a driver mutation. In this regard, it is important to recognize that a passenger mutation may have no or only little effect on the fitness of a cell within a particular tissue while the same mutation may have drastic effect on the fitness of a cell within another tissue. However, within the meaning of the present invention, passenger mutations may be those mutations that are known to have a higher probability to be found in a genome where a driver mutation occurred or is likely to occur in the future.

Somatic alterations, in particular genetic or epigenetic alterations, determined in the methods of the present invention may also comprise one or more copy number alterations. Copy-number alterations are alterations of the DNA of a genome that result in the cell having an abnormal or, for certain genes, a normal variation in the number of copies of one or more sections of the DNA. A copy number alteration may correspond to parts of the genome that have been deleted (fewer than the normal number) or multiplied (more than the normal number).

Each alteration may correspond to the deletion or gain, in particular duplication, of a genomic region, which may range from about one kilobase (1,000 nucleotide bases) to several megabases (1,000,000 nucleotide bases) in size. Copy number alterations have been associated with susceptibility or resistance to disease. For example, gene copy number can be elevated in cells associated with cancer, e.g. in DCCs. Accordingly, copy number alterations may also be determined in the methods of the present invention in order to determine the somatic evolution of a cell, in particular of a DCC. The somatic evolution may then be used to determine the stage/type of a cancerous disease, in particular cancer. Particular copy number alterations determined in the methods of the present invention comprise loss of chromosome 9p11-13, loss of chromosome 9p21-24 and/or gain of chromosome 7q21. Accordingly, the present invention relates to the methods or pharmaceutical compositions of the invention, wherein the somatic alterations of the DNA comprise at least one of the alterations selected from a loss of chromosome 9p11-13, a loss of chromosome 9p21-24 and gain of chromosome 7q21.

In addition or alternatively to the nature/type of somatic alterations, in particular genetic and/or epigenetic alterations, detected in the methods of the present invention, the number of somatic alterations, in particular genetic and/or epigenetic alterations, may also be determined in order to determine the somatic evolution of a cell, in particular a DCC. In this regard, it can generally be assumed that the higher the number of accumulated somatic alterations, the more advanced the somatic evolution of the cells, in particular the DCCs. While there are driver mutations, as described above, whose presence is indicative of an advanced stage/type of the cancerous disease, in particular the cancer, the overall number of accumulated somatic alterations may also achieve a threshold value, which is indicative of an advanced stage of the cancerous disease, in particular the cancer; see e.g. Shain et al. (2015) N Engl J Med 373; 20:1926.

The accuracy of the methods of the present invention may be further increased by using additional parameters to determine the overall somatic evolution of a cell population, in particular DCCs comprised in a lymph node of a subject or derived from other tissue (early) invaded by cancer cells, e.g. bone marrow or brain. In this regard, it was surprisingly found that at a specific cell density, cells, in particular DCCs, form cell-cell contacts leading to DCCs being organized in small nests of cells rather than isolated cells. Moreover, it was surprisingly found that in xenotransplanation experiments, only mice transplanted with cells, in particular DCCs, derived from lymph nodes of patients in which said cells, in particular DCCs, were present at a cell density above a specific threshold value gave rise to a tumor in transplanted mice; see FIG. 5C. From these experiments, it was deduced that the overall cell number of DCCs observed in the respective tissue sample, e.g. a sample derived from a lymph node or a bone marrow sample, may serve as additional parameter to further increase accuracy of the methods of the present invention. Based on these experiments, the threshold value indicative for a high probability that cells accumulated important driver mutations in their genome so that an advanced stage/type of the cancerous disease, in particular cancer, is determined to be in the range of about 50 or more, preferably 60, 70, 80, 90 or more, most preferably 100 cells per one million cells in the respective tissue sample. Accordingly, a DCCD between about 50 and about 100, preferably between about 60 and about 100, preferably between about 70 and about 100, preferably between about 80 and about 100 and most preferably between about 90 and about 100 is indicative of an advanced stage/type of a cancerous disease, in particular cancer. In accordance with the above, based on the number of cells found in the tissue sample obtained from a patient, the cell density can be calculated with respect to the overall number of cells in the obtained sample or with respect to another cell population found in the obtained sample. In this regard, it is preferred that the DCC cell population comprised in the tissue sample obtained from a patient is detected using a marker, e.g. EpCAM and/or cytokeratins. The DCC cell population comprised in a melanoma tissue sample obtained from a patient is preferably detected using gp100 as a marker. However, alternative DCC markers may also be used, which may cause alternative threshold values corresponding to an advanced stage/type of the cancerous disease, as the person skilled in the art will appreciate. Accordingly, it should be recognized that the determined DCCD in a tissue sample, in particular lymph node sample or bone marrow sample obtained from a patient, which is used as an indicator of the stage/type of a cancerous disease, in particular cancer, can vary based on the method used to determine the cell density. In this regard, it is preferred that gp100 is used as a marker to determine the number of DCCs comprised in the obtained sample, wherein DCCs are gp100 positive. Accordingly, it is preferred that the methods of the present invention, in addition to determination of somatic alterations, in particular genetic and/or epigenetic alterations, comprised in one or more DCCs obtained from one or more lymph nodes of a patient, comprise a step of determining the DCCD in the lymph node used to obtain the DCCs, in particular the lymph node obtained from a patient.

Where the stage/type of a cancerous disease is determined based on the somatic evolution of CTCs, the methods of the present invention may further comprise a step of determining the CTCD in order to improve accuracy. Accordingly, it is preferred that, in addition to determination of somatic alterations, in particular genetic and/or epigenetic alterations, comprised in one or more CTCs from a patient, in particular retrieved from blood samples or in vivo CTC-capturing-devices, comprise a step of determining the CTC density (CTCD). In this regard, the CTCD is the number of CTCs per one million cells in the blood sample obtained from a patient, or in the case of an in vivo capturing-device by some parameter that relates the CTC number to the filtered blood volume (blood volume or filtering time as surrogate). At a specific threshold value that may be determined based on the used detection method of CTCs, for example comprising the use of MCSP or EpCAM as a marker, but not limited to this, an advanced stage/type of the cancerous disease may be determined.

In the methods of the present invention, the one or more cell(s), in particular the one or more DCC(s) is/are preferably obtained from one or more lymph node(s). Lymph nodes are oval-shaped organs of the lymphatic system, distributed widely throughout the body including the armpit and stomach and linked by lymphatic vessels. Lymph nodes are major sites of B, T, and other immune cells. Lymph nodes are important for the proper functioning of the immune system, acting as filters for foreign particles and cancer cells. Lymph nodes are known to have clinical significance. They become inflamed or enlarged in various infections and diseases, which range from throat infections to cancer. It is furthermore preferred that the one or more lymph node(s) is/are regional lymph node(s), wherein a regional lymph node is a lymph node close to a site being in a status of developing a disease, in particular a site susceptible to developing a cancerous disease, in particular cancer or a site that has developed a cancerous disease, in particular cancer. In particular, in the context of cancer, the regional lymph node is a lymph node anatomically close to a cancer site, for example a tumor. It is more preferred that the one or more lymph node used in the methods of the invention is/are (a) draining lymph node(s). Draining lymph nodes are lymph nodes to which cells migrate. Often, the draining lymph node(s) of a diseased site or a site susceptible of developing a disease is/are the first lymph node(s) invaded by cells migrating from said site. Such lymph node(s) is/are also called sentinel lymph node(s), i.e. the hypothetical first lymph node or group of nodes draining a cancerous disease, in particular a cancer. In case of established cancerous dissemination the sentinel lymph node/s is/are the target organs primarily reached by metastasizing cancer cells from the tumor. Thus, sentinel lymph nodes can be totally void of cancer because they were detected prior to dissemination. Accordingly, it is most preferred that the DCCs used in the methods of the present invention are derived from one or more sentinel lymph node(s) in order to determine whether a subject is susceptible to develop a cancerous disease, in particular cancer, or determine the stage/type of a cancerous disease, in particular cancer.

The person skilled in the art is well-aware of methods how to obtain lymph node(s) from a subject, in particular a human subject. As used herein, the term "sample obtained from one or more lymph node(s)" refers to a sample of cells, tissue or fluid that is removed from a subject for the purpose of determining if the sample contains cancerous tissue, in particular DCC(s), and/or for determining the somatic evolution of said cells. In some embodiments, such a sample is obtained because a subject is suspected of having cancer due to an earlier diagnosis and/or a predisposition. The sample may then also be examined for the presence or absence of cancer, cancer stem cells, and/or cancer stem cell gene signature expression using methods known in the art. For example, the lymph node samples used in the methods of the present invention may be obtained by lymph node biopsy, for example needle biopsy or open biopsy as described in the art; see e.g. Chang K L et al. (2009) Modern Surgical Pathology. 2nd ed. Philadelphia, Pa.: Saunders Elsevier; 2009:chap 41.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject. Accordingly, it is preferred that the one or more DCC(s) are obtained from a human subject, more preferred a human patient, wherein the subject/patient may be suspected of having cancer or may be susceptible to a cancerous disease, in particular cancer.

As used herein, the term "subject suspected of having cancer" or "patient susceptible to a cancerous disease" refers to a subject/patient that presents one or more symptoms indicative of a cancer (e.g., a noticeable lump or mass) or is being screened for a cancer (e.g., during a routine physical). A subject suspected of having cancer or a patient susceptible to a cancerous disease, in particular cancer, can also have one or more risk factors. A "subject suspected of having cancer" or "patient susceptible to a cancerous disease" encompasses an individual who has received an initial diagnosis but for whom the stage of cancer is not known. The term further includes people who once had cancer (e.g., an individual in remission). The term also refers to a subject with one or more risk factors for developing a specific cancer. Risk factors include, but are not limited to, gender, age, genetic predisposition, environmental exposure, previous incidents of cancer, preexisting non-cancer diseases, and lifestyle.

The methods of the present invention are for staging and/or typing and/or predicting outcome and/or treating a cancerous disease, in particular cancer. In the methods of the present invention, the type of cancerous disease is not particularly limited as long as the disease involves the dissemination of cells from a primary disease site into lymph node(s) and/or other tissue, for example bone marrow. Generally, dissemination relates to the process of migration by active migration or passive transport by body fluids from a primary disease site to a secondary site, for example a lymph node or bone marrow or blood. Accordingly, the methods of the present invention are for staging/typing of a cancerous disease, in particular a cancerous disease involving dissemination of cells, preferably involving lymphatic dissemination. Thus, the methods of the present invention are preferably for staging and/or typing and/or predicting outcome and/or treating of solid cancer. As used herein, a "solid cancer" refers to one or more cells which are growing or have grown in an uncontrolled manner to form cancer tissue. As used herein, the term "solid cancer" includes, but is not limited to "carcinomas", "adenocarcinomas" and "sarcomas". "Sarcomas" are cancers of the connective tissue, cartilage, bone, muscle, and the like. "Carcinomas" are cancers of epithelial (lining) cells. "Adenocarcinoma" refers to carcinoma derived from cells of glandular origin. The terms "cancer" and "tumor" are used interchangeably throughout the subject specification.

Solid cancers may arise in nearly any tissue of the body and the methods of the present invention may be used for staging and/or typing and/or predicting outcome and/or treating of any of these cancers. Exemplary "solid cancers" which may be staged and/or typed and/or whose outcome may be predicted and/or which may be treated in accordance with the present invention include acoustic neoma, adenocystic carcinoma, adrenocortical cancer, alveolar soft-part sarcoma, anal cancer, angiosarcoma, basal cell carcinoma (bcc), bladder cancer, bone cancers, bowel cancer, brain stem glioma, breast cancer, CNS cancers, carcinoid cancers, cervical cancer, childhood brain cancers, childhood soft tissue sarcoma, chondrosarcoma, choriocarcinoma, colorectal cancers, dermatofibrosarcoma-protuberans, desmoplastic small round cell cancer, ductal carcinoma, endocrine cancers, endometrial cancer, ependymoma, esophageal cancer, Ewing's sarcoma, extra hepatic bile duct cancer, eye cancer, eye: melanoma, retinoblastoma, fallopian tube cancer, fibrosarcoma, gall bladder cancer, gastric cancer, gastrointestinal cancers, gastrointestinal carcinoid cancer, genitourinary cancers, germ cell cancers, gestational trophoblastic disease, glioma, gynecological cancers, head and neck cancer, hepatocellular cancer, hereditary breast cancer, human papillomavirus, hypopharynx cancer, intra-ocular melanoma, Kaposi's sarcoma, kidney cancer, laryngeal cancer, leiomyosarcoma, lip cancer, liposarcoma, liver cancer, lung cancer, male breast cancer, malignant rhabdoid cancer of kidney, medulloblastoma, melanoma, merkel cell cancer, mesothelioma, metastatic cancer, mouth cancer, multiple endocrine neoplasia, nasal cancer, nasopharyngeal cancer, nephroblastoma, neuroblastoma, neurofibromatosis, non-melanoma skin cancer, non-small cell lung cancer (nscic), ocular cancers, oesophageal cancer, oral cavity cancer, oropharynx cancer, osteosarcoma, pancreas cancer, paranasal cancer, parathyroid cancer, parotid gland cancer, penile cancer, peripheral neuroectodermal cancers, pituitary cancer, prostate cancer, rare cancers and associated disorders, renal cell carcinoma, retinoblastoma, rhabdomyosarcoma, salivary gland cancer, sarcoma, skin cancer, small cell lung cancer (scic), small intestine cancer, soft tissue sarcoma, spinal cord cancers, squamous cell carcinoma (scc), stomach cancer, synovial sarcoma, testicular cancer, thymus cancer, thyroid cancer, transitional cell cancer (bladder), transitional cell cancer (renal-pelvis-/-ureter), trophoblastic cancer, urethral cancer, urinary system cancer, uroplakins, uterine sarcoma, uterus cancer, vaginal cancer, vulva cancer, and Wilms' Cancer. It is preferred that the cancer to be staged and/or typed and/or whose outcome may be predicted and/or which may be treated is melanoma. Accordingly, in a preferred embodiment, the present invention relates to a method for staging and/or typing of melanoma, said method comprising the steps of detecting somatic alterations of the DNA of one or more DCC(s) obtained from one or more lymph node(s); and determining the somatic evolution of the DCC(s) based on the detected somatic alteration(s) in the DNA of the one or more DCC(s), wherein the somatic evolution of the DCC(s) is indicative of the stage/type of melanoma. In a further embodiment, the present invention relates to a method for treating melanoma, said method comprising the steps of detecting somatic alterations in the DNA of one or more DCC(s) obtained from lymph node(s) of a patient; determining the somatic evolution of the DCC(s) based on the detected somatic alteration(s) in the DNA of the one or more DCC(s); and determining the stage/type of melanoma of said patient based on the somatic evolution of melanoma determined based on the detected somatic alteration(s) in the DNA of the one or more DCC(s), wherein the stage/type of melanoma is used to initiate, continue or discontinue melanoma therapy. Furthermore, the present invention relates to a therapeutic intervention, preferably a pharmaceutical composition, for use in treating melanoma in a patient, wherein treatment is initiated, continued or discontinued based on the stage/type of melanoma, wherein said stage/type of melanoma is determined by detecting somatic alterations in the DNA of one or more DCC(s) obtained from lymph node(s) or liquor (preferably form lymph node(s), more preferably from a sentinel lymph node) of said patient; determining the somatic evolution of the DCC(s) based on the detected somatic alteration(s) in the DNA of the one or more DCC(s); and determining the stage/type of melanoma of said patient based on the somatic evolution of melanoma determined by detecting somatic alterations in the DNA of one or more DCC(s) obtained from lymph node(s) or liquor of said patient.

In a further preferred embodiment, the invention relates to a method for staging and/or typing of melanoma, said method comprising the steps of detecting somatic alterations of the DNA of one or more CTC(s) obtained from blood; and determining the somatic evolution of the CTC(s) based on the detected somatic alteration(s) in the DNA of the one or more CTC(s), wherein the somatic evolution of the CTC(s) is indicative of the stage/type of melanoma. As described herein above, for obtaining the CTCs from blood, in vivo CTC-capturing-devices may be used. In a further embodiment, the present invention relates to a method for treating melanoma, said method comprising the steps of detecting somatic alterations in the DNA of one or more CTC(s) obtained from blood of a patient; determining the somatic evolution of the CTC(s) based on the detected somatic alteration(s) in the DNA of the one or more CTC(s); and determining the stage/type of melanoma of said patient based on the somatic evolution of melanoma determined based on the detected somatic alteration(s) in the DNA of the one or more CTC(s), wherein the stage/type of melanoma is used to initiate, continue or discontinue melanoma therapy. Furthermore, the present invention relates to a pharmaceutical composition for use in treating melanoma in a patient, wherein treatment is initiated, continued or discontinued based on the stage/type of melanoma, wherein said stage/type of melanoma is determined by detecting somatic alterations in the DNA of one or more CTC(s) obtained from blood of said patient; determining the somatic evolution of the CTC(s) based on the detected somatic alteration(s) in the DNA of the one or more CTC(s); and determining the stage/type of melanoma of said patient based on the somatic evolution of melanoma determined by detecting somatic alterations in the DNA of one or more CTC(s) obtained from blood of said patient.

The methods of the present invention comprise a step of detecting somatic alterations of the DNA of one or more DCC(s) or CTC(s), respectively, obtained from a tissue sample, in particular a lymph node sample or bone marrow sample or blood. In this regard, the person skilled in the art is well-aware of methods suitable for detecting somatic alterations of DNA. As explained further above, somatic alterations may comprise epigenetic and/or genetic alterations.

With regard to epigenetic alterations, the person skilled in the art is well-aware of methods capable of detecting epigenetic alterations with regard to a reference sample or with regard to a reference standard known in the art. As explained above, epigenetic alterations to be detected in the DNA of one or more DCC(s) may include methylation, in particular methylation of CpG(s), deficiencies of DNA repair proteins, and/or alterations in histone architecture or structure like methylation, acetylation, sumoylation, activating or inactivating histone marks and/or alterations in chromatin architecture like for example in eu- or hetero-chromatin and the like. Accordingly, in the methods of the present invention a step of DNA methylation analysis may be included. It is known that epigenetic mechanisms play important roles during normal development, aging and a variety of disease conditions. Hypermethylation of CpG islands located in the promoter regions of tumor suppressor genes is firmly established as a frequent mechanism for gene inactivation in cancers (Hansen et al. 2011. Nat. Genet. 43, 768-775). Methylation of the 5' carbon of cytosine is a form of epigenetic modification that does not affect the primary DNA sequence, but affects secondary interactions that play a critical role in the regulation of gene expression. Aberrant DNA methylation may suppress transcription and subsequently gene expression. Methylation analysis as in the methods of the present invention may comprise selective modification of the target DNA. Such modification may comprise the addition of methylation-dependent restriction enzymes (MDREs) or methylation-sensitive restriction enzymes (MSREs), preferably MDREs. Selective modification of the target DNA may also comprise addition of a chemical agent that is able to selectively differentiate between methylated or unmethylated nucleotides. In particular, methylation analysis as employed in the methods of the present invention may be able to selectively identify methylated cytosines that may later be read-out using methods known in the art, e.g. methods described in WO 2015/118077 or WO 2000/017390. For example, treatment with bisulfite is known to convert unmethylated cytosines (C) to uracil (U) while methylated cytosines are not converted (Frommer et al. 1992. Proc. Natl. Acad. Sci. USA 89, 1827-1831). Sequencing of DNA subsequent to treatment with bisulfite may be used to identify methylated nucleotides, in particular cytosines. Treatment with MDREs leads to methylation-dependent restriction of DNA fragments, while treatment with MSREs leads to methylation-dependent inhibition of restriction. Sequencing of DNA subsequent to MDRE/MSRE restriction in addition to MseI restriction may be used to identify methylated nucleotides, in particular cytosines.

Additionally or alternatively, one of the most commonly used techniques for the detection of epigenetic alterations in DNA organized in chromatin may be used, i.e. chromatin immunoprecipitation (ChIP) and related techniques such as ChIP-chip, ChIP-PET, ChIP-Seq, MeDIP, DamID or the like; see Minard et al. (2009) Genesis 47(8), pp. 559-72 and references cited therein. For example, methylation of DNA may genome-wide be detected using MeDIP, MeDIP-chip or MeDIP-seq. Exemplary protocols comprise steps of subjecting purified DNA to sonication to shear it into random fragments. The resulting fragments may range from 300 to 1000 base pairs (bp) in length, preferably between 400 and 600 bp. The DNA fragments are then denatured to produce single-stranded DNA. Following denaturation, the DNA is incubated with 5-methylcytosine (5-mC) antibodies available in the art. The classical immunoprecipitation technique is then applied: magnetic beads conjugated to anti-mouse-IgG are used to bind the anti-5mC antibodies, and unbound DNA is removed in the supernatant. To purify the DNA, proteinase K is added to digest the antibodies and release the DNA, which can be collected and prepared for DNA detection. Subsequent DNA detection is done using methods described further below for detection of genetic alterations. Further experimental protocols are described by Weber M, Davies J J, Wittig D, et al. (August 2005) Nat. Genet. 37 (8): 853-62; Pomraning K R, Smith K M, Freitag M (March 2009) Methods 47 (3): 142-50; Wilson I M, et al. (2005) Cell Cycle 5 (2): 155-8; and Zhang X, Yazaki J, Sundaresan A, et al. (September 2006) Cell 126 (6): 1189-201. For an exemplary MeDIP-chip protocol, the following steps are applied: A fraction of the input DNA obtained after the sonication step above is labeled with cyanine-5 (Cy5; red) deoxy-cytosine-triphosphate while the methylated DNA, enriched after the immunoprecipitation step, is labeled with cyanine-3 (Cy3; green). The labeled DNA samples are cohybridized on a 2-channel, high-density genomic microarray to probe for presence and relative quantities. The purpose of this comparison is to identify sequences that show significant differences in hybridization levels, thereby confirming the sequence of interest is enriched, i.e. methylated. There are additional standard steps required in signal processing to correct for hybridization issues such as noise, as is the case with most array technologies. Additionally or alternatively, the MeDIP-seq approach may be applied, i.e. the coupling of MeDIP with next generation, short-read sequencing technologies such as 454 or Illumina sequencing. The high-throughput sequencing of the methylated DNA fragments produces a large number of short reads (36-50 bp or 400 bp, depending on the technology). The short reads are aligned to a reference genome using alignment software such as Mapping and Assembly with Quality (Maq) which uses a Bayesian approach, along with base and mapping qualities to model error probabilities for the alignments. The reads can then be extended to represent the ~400 to 700 bp fragments from the sonication step. The coverage of these extended reads can be used to estimate the methylation level of the region. A genome browser such as ENSEMBL can also be used to visualize the data. Validation of the approach to assess quality and accuracy of the data can be done using, inter alia, quantitative PCR This is done by comparing a sequence from the MeDIP sample against an unmethylated control sequence. The samples are then run on a gel and the band intensities are compared. The relative intensity serves as the guide for finding enrichment.

ChIP techniques may also be used to detect other epigenetic alterations, such as histone modifications or modifications relating to other proteins bound to DNA. Such techniques are known in the art and extensively described in various standard reference books, such as "Chromatin Immunoprecipitation Assays—Methods and Protocols" by Philippe Collas, Humana Press (2009). However, the person skilled in the art is well-aware that other techniques may also be applied to detect epigenetic alterations of DNA. Accordingly, in the methods of the present invention, any technique suitable for detecting such modifications, in particular epigenetic alterations, may be applied.

However, in the context of the present invention, it is preferred that methods for detecting epigenetic alterations be used that are compatible with methods for detecting genetic alterations, in particular that allow simultaneous detection of genetic and epigenetic alterations. Such methods are described in e.g. WO 2015/118077 or WO 2000/017390. However, alternative methods relying on DNA sequence information in order to detect epigenetic alterations are known to the person skilled in the art. For example, next generation sequencing techniques as marketed by Illumina® are known to the person skilled in the art and are suitable for detecting epigenetic alterations such as methylation, in particular combined with further techniques such as next-generation sequencing, in particular methylation sequencing; and/or for detecting protein-DNA interactions, techniques such as chromatin immunoprecipitation (ChIP) and/or ChIP combined with next-generation sequencing, in particular ChIP-Seq (for example using protocols available for Illumina® sequencing machines).

A preferred example of a method suitable for isolated and/or simultaneous detection of epigenetic and/or genetic alterations is a method comprising the steps of providing a sample comprising DNA, in particular a sample derived from one or more lymph node(s) or a bone marrow sample comprising one or more DCC(s) or CTC(s); adding an agent to said DNA that selectively recognizes epigenetically modified nucleic acids, in particular methlylated nucleic acids, e.g. bisulfite; digesting the DNA with a restriction endonuclease under conditions suitable to obtain DNA fragments of similar length, wherein said restriction endonuclease is capable of providing 5' overhangs, wherein the terminal nucleotide of the overhang is phosphorylated or, wherein said restriction endonuclease is capable of providing 3' overhangs, wherein the terminal nucleotide of the overhang is hydroxylated on said DNA fragments; annealing a first oligonucleotide to said DNA fragments, wherein a first sequence of said first oligonucleotide is complementary to the 5' or 3' overhang, respectively, of said DNA fragment, and a second sequence of said first oligonucleotide is complementary to a first sequence of a second oligonucleotide, wherein said second oligonucleotide comprises a second and a third sequence, wherein said second sequence of said second oligonucleotide comprises a randomized sequence; ligating said second oligonucleotide to said DNA fragment; filling in of the generated overhangs; amplifying said DNA fragments using a third oligonucleotide comprising a sequence binding to said third sequence of said second oligonucleotide; sequencing said amplified DNA fragments; and identifying methylated nucleic acid residues, wherein when bisulfite is used as agent that selectively recognizes epigenetically modified nucleic acids, a cytosine (C) corresponds to a methylated residue in said DNA sample and an uracil (U) corresponds to an unmethylated residue in said DNA sample. Alternative agents are known to the person skilled in the art in order to detect other epigenetic modifications than methylation, i.e. agents that specifically recognize epigenetically modified nucleic acids. The sequence information obtained in the last step of the above described method may be used to simultaneously detect genetic alterations. The obtained sequence information may, for example, be used in methods for DNA sequence analysis like whole genome sequencing, whole exome sequencing, whole regulome sequencing, sequencing-based methylation analysis, sequencing-based breakpoint detection, ChIP sequencing, or targeted sequencing and variations thereof.

As explained above, the methods of the present invention comprise a step of detecting somatic alterations of the DNA of one or more DCC(s) or CTC(s), respectively, obtained from a tissue or body fluid sample, in particular a lymph node sample or bone marrow sample or liquor (in the case of DCC(s)), or blood (in the case of CTC(s)), respectively. In this regard, the person skilled in the art is well-aware of methods suitable for detecting somatic alterations of DNA, in particular genetic alterations. An overview of suitable methods is given by Schwartz et al. (2013) JMB 425(21), pp-3914-8. Basically, with completion of the human genome research project, a reference sequence was established to which genetic alterations can be compared. That is, subsequent to sequencing DNA, the resulting sequence may be compared to reference sequences known in the art. With regard to methods for sequencing DNA, any method may be employed within the context of the present invention. However, it is preferred to use methods which are fast, efficient, reliable and only require low input amounts. This is particularly important for detecting DCCs or CTCs in an early phase of cancer spread where only one single cell may be present in a tissue or body fluid sample, in particular a lymph node sample or bone marrow sample or liquor sample, or blood respectively. Thus, in order to detect genetic alterations sequencing methods known in the art may be employed that are particularly suitable for sequencing of low amounts of input DNA, e.g. as described in Mardis (2008) Annu Rev Genomics Hum Genet 9, 387-402. Preferably, error-free sequencing methods of low amounts of input DNA are used, as e.g. described in WO 2015/118077 or WO 2000/017390. Accordingly, a preferred method to be employed in the present invention is a DNA sequencing method comprising the use of endonucleases, oligonucleotides specifically recognizing overhangs created by the endonucleases and further oligonucleotides for amplification. The oligonucleotides may, for example, comprise barcode sequences in order to distinguish between fragments generated by the endonucleases and in order to generate an internal sequencing reference for error-free sequencing. An exemplary and preferred method for DNA sequencing comprises the steps of providing a sample comprising DNA, in particular a sample derived from one or more lymph node(s) or a bone marrow sample or a liquor or blood sample comprising one or more DCC(s) or CTC(s); digesting the DNA with a restriction endonuclease under conditions suitable to obtain DNA fragments of similar length, wherein said restriction endonuclease is capable of providing 5' overhangs, wherein the terminal nucleotide of the overhang is phosphorylated or, wherein said restriction endonuclease is capable of providing 3' overhangs, wherein the terminal nucleotide of the overhang is hydroxylated on said DNA fragments; annealing a first oligonucleotide to said DNA fragments, wherein a first sequence of said first oligonucleotide is complementary to the 5' or 3' overhang, respectively, of said DNA fragment, and a second sequence of said first oligonucleotide is complementary to a first sequence of a second oligonucleotide, wherein said second oligonucleotide comprises a second and a third sequence, wherein said second sequence of said second oligonucleotide comprises a randomized sequence; ligating said second oligonucleotide to said DNA fragment; filling in of the generated overhangs; amplifying said DNA fragments using a third oligonucleotide comprising a sequence binding to said third sequence of said second oligonucleotide; and sequencing said amplified DNA fragments.

Subsequent to detecting somatic alterations, in particular genetic and/or epigenetic alterations, of the DNA of one or more DCC(s) of one or more lymph node(s) or a bone marrow sample or the DNA of one or more CTC(s) from blood, the methods of the present invention comprise a step of determining the somatic evolution based on the detected somatic alterations. As described above, the somatic evolution is determined based on the accumulated somatic alterations during the lifetime of a cell, in particular a DCC or CTC, preferably comprising further parameters such as the DCCD/CTCD. Thus, based on the detected somatic alterations, in particular genetic and/or epigenetic alterations, the somatic evolution may be determined and the stage/type of the cancerous disease, in particular cancer, may be determined, treatment methods may be adjusted and the like. The person skilled in the art will appreciate how to express the determined stage/type of a cancerous disease, using, for example, letter codes, number codes or the like.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

The methods and techniques of the present invention are generally performed according to conventional methods well known in the art and as described in various general and more specific references that are cited and discussed throughout the present specification unless otherwise indicated. See, e.g., Sambrook et al., Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual, Cold Spring Harbor Laboratory Press, Cold Spring Harbor, N.Y. (1990).

While the invention is illustrated and described in detail in the drawings and foregoing description, such illustration and description are to be considered illustrative or exemplary and not restrictive. It will be understood that changes and modifications may be made by those of ordinary skill within the scope and spirit of the following claims. In particular, the present invention covers further embodiments with any combination of features from different embodiments described above and below.

The invention also covers all further features shown in the figures individually, although they may not have been described in the previous or following description. Also, single alternatives of the embodiments described in the figures and the description and single alternatives of features thereof can be disclaimed from the subject matter of the other aspect of the invention.

Furthermore, in the claims the word "comprising" does not exclude other elements or steps, and the indefinite article "a" or "an" does not exclude a plurality. A single unit may fulfill the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

The present invention is also illustrated by the following figures.

FIG. 1: Dissemination of Melanoma Cells as Function of Tumor Thickness (A) Staged function: estimated cumulative probability of dissemination as a function of tumor thickness (Turnbull) (n=1027 patients). Continuous line: Weibull distribution incorporating a fraction of patients without long-term dissemination (95% CI lower dashed lines). Upper dashed line: only 63.5% of melanomas disseminate lymphatically (95% CI 53.5-73.4%). Fifty percent of this value (31.75%) provides the median thickness (0.40 mm, 95% CI 0.04-0.75 mm) of disseminating melanomas (straight dashed line).

(B) Comparative analysis of histopathological and immuncytological lymph node halves. Displayed are representative examples with immunocytological scores of DCCD≤100, 100<DCCD≤1000 and DCCD>1000. Samples LN 72 and LN 89 are stained against melan A LN 10, LN 135 and LN 168 against S100. LN 154 shows a highly pigmented melanoma in H&E staining.

(C) Percentage of DCC-positive patients (n=525) with colonization (DCCD>100) according to the Turnbull estimate (staged line). The percentage of colonization (continuous curve, 95% CI dashed curves) is described by a cumulative Weibull distribution function (median 8.9 mm; 95% CI 6.8-14.3 mm).

(D) Hazard functions for dissemination, and colonization describing the instantaneous risk per unit thickness for an event (dissemination, colonization) for those tumors, for which it has not yet occurred.

(E) Survival analysis of melanoma patients (n=1027) according to T-stage (T1: ≤1 mm; T2: 1.01-2.0 mm; T3: 2.01-4.0 mm; T4: >4 mm thickness).

Figure 2:
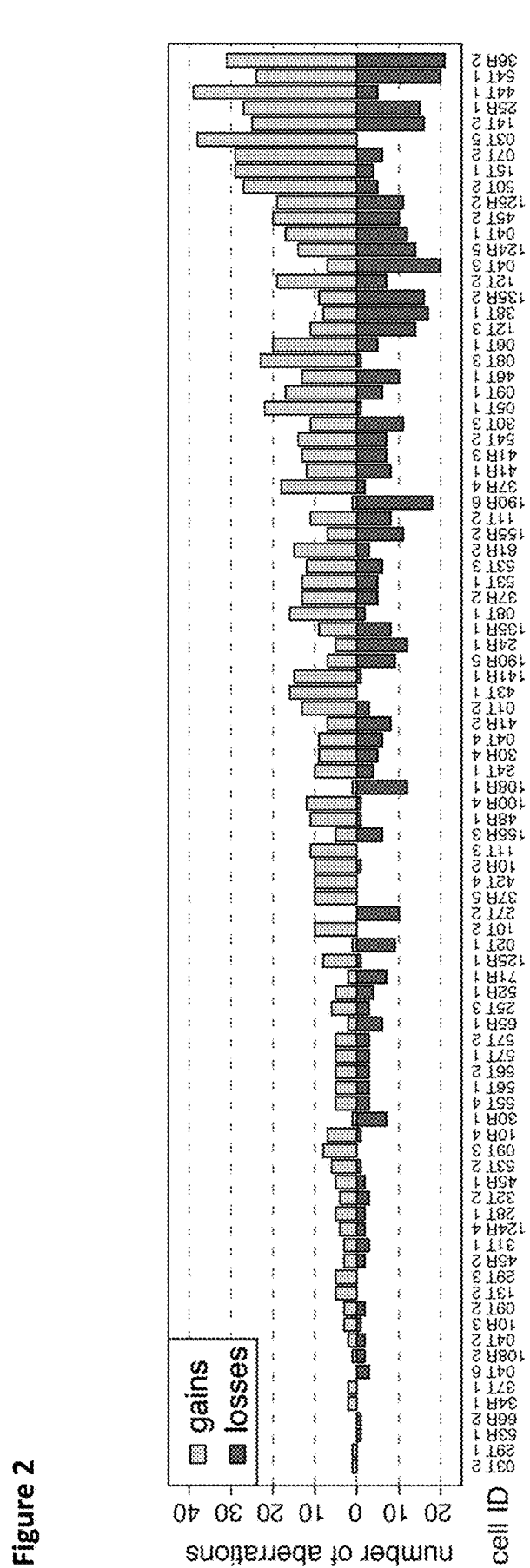

FIG. 2: Gp100-Positive Cells from SLNs Display Multiple CNAs.

Ninety DCCs from the patient collective were selected according to QC criteria (see main text) for CGH and mutation analysis (see below). Histograms depict the genomic gains (light grey) or losses (dark grey) per cell and confirm malignant origin. The identifiers indicate cell ID.

Figure 3:
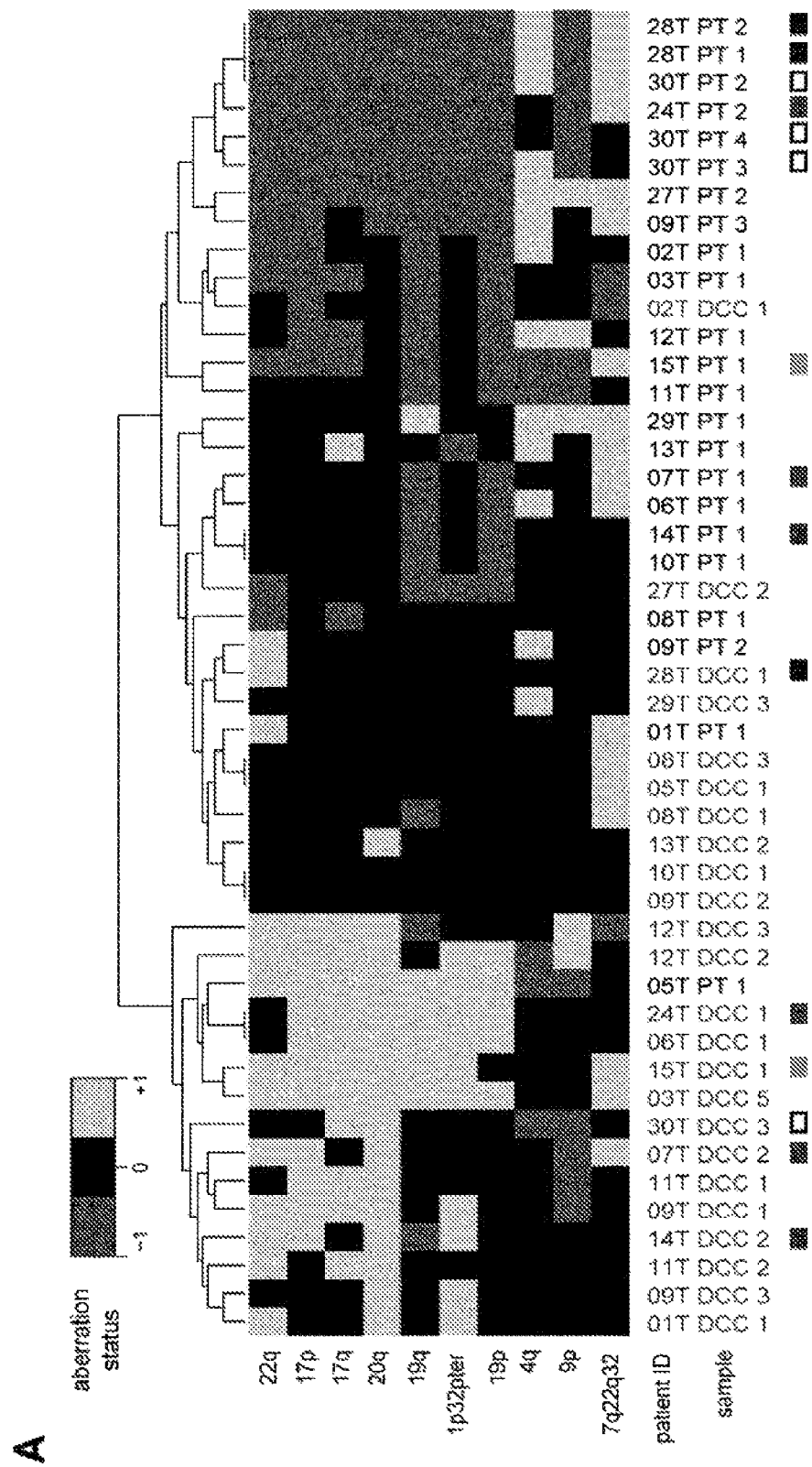
Figure 3:
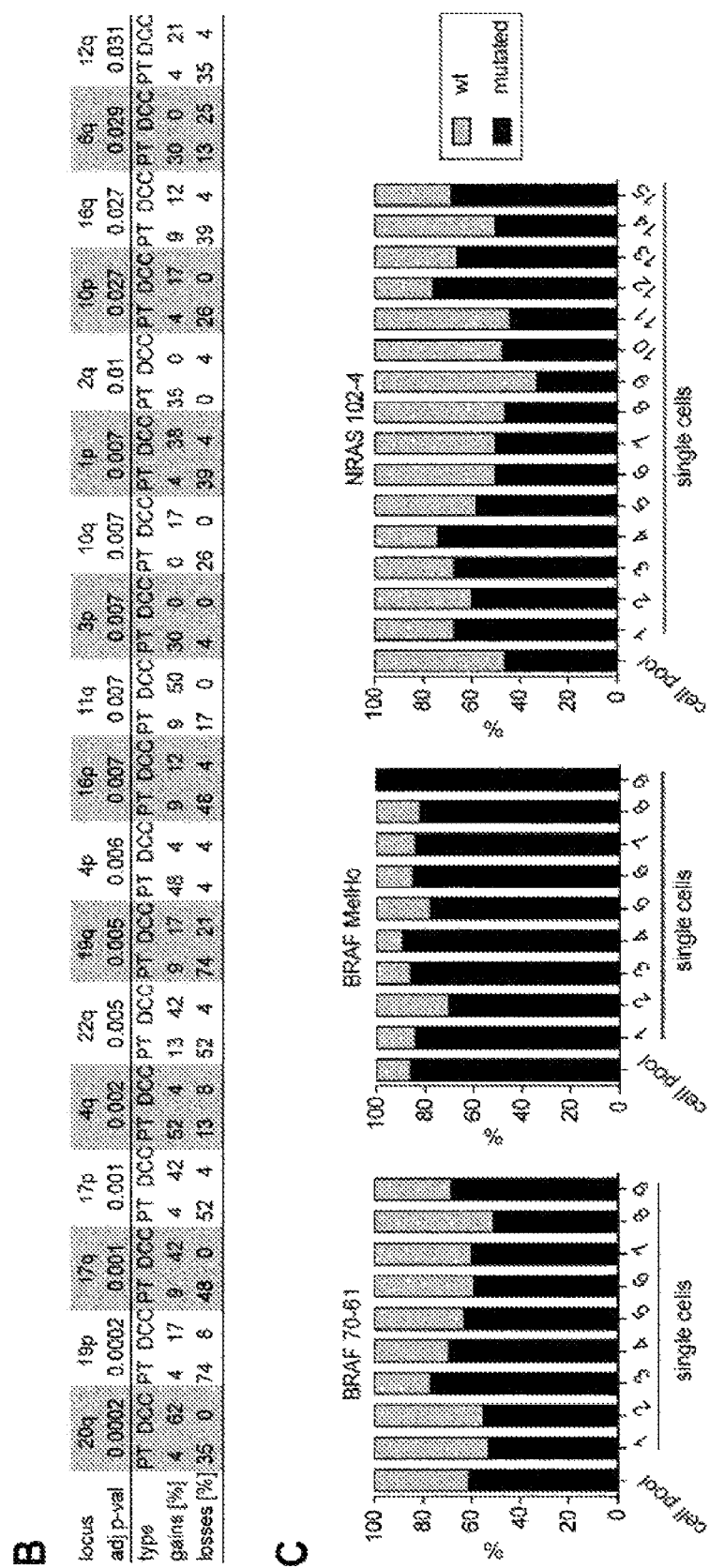
Figure 3:
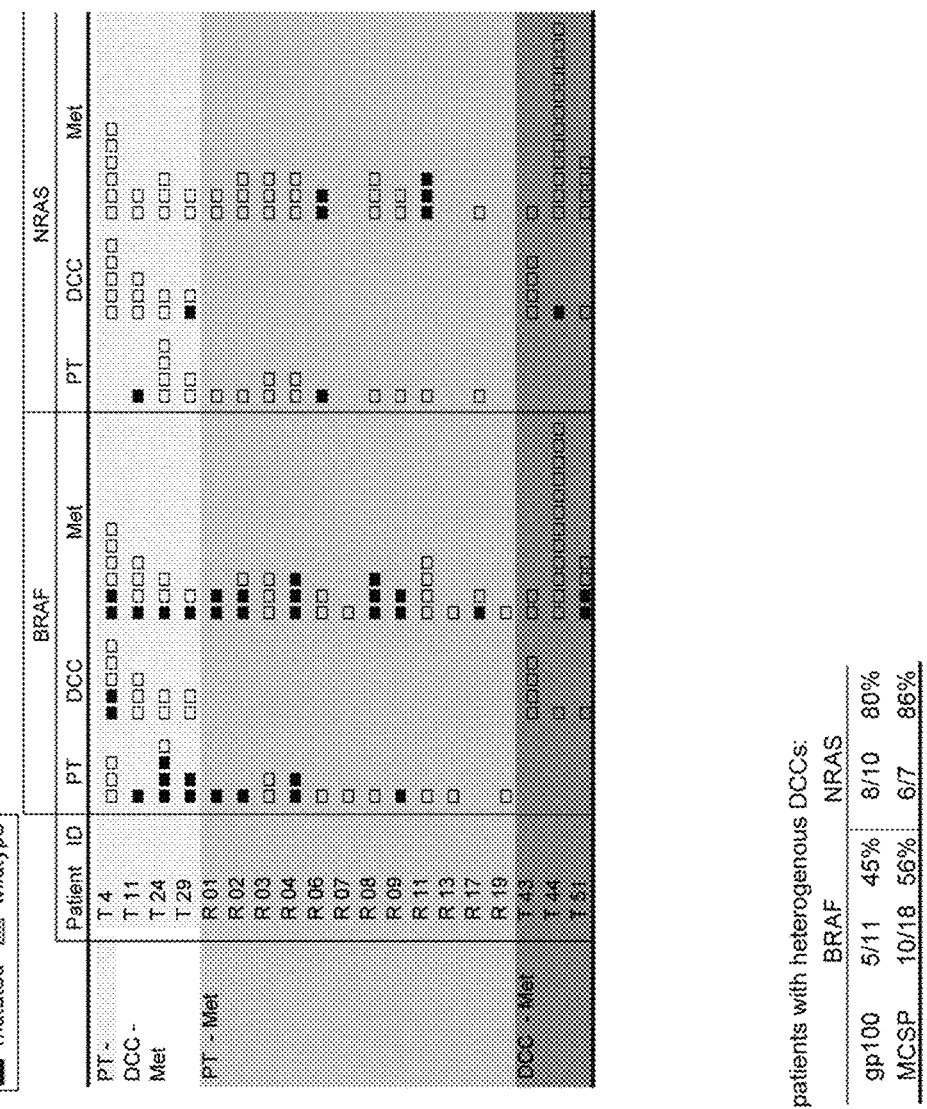
Figure 3:
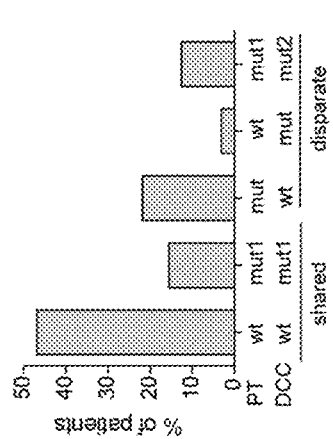
Figure 3:
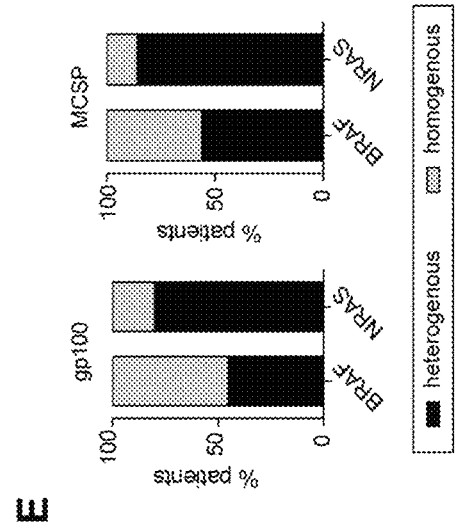

FIG. 3: Genetic Comparison of DCCs and Primary Tumors (A) Cluster analysis of paired primary tumors and DCCs for chromosomal aberrations (gain=+1; loss=−1). Only the ten most variable regions are included. Bottomline identifiers indicate patient ID, sample type (PT, primary tumor; DCC, disseminated cancer cell) and sample index; sideline labels indicate chromosomal regions. Black and white filled squares indicate examples of PT-DCC pairs for which several areas of the primary tumor were available. Examples of paired DCCs and PTs with varying PT-thickness are indicated by squares.

(B) Comparison of paired PTs and DCCs for chromosomal aberrations. Displayed are the 18 chromosomal regions that differ significantly (FDR-adjusted p-value≤0.05) between paired PTs (n=23) and DCCs (n=24) regarding aberration frequency. Gains and losses are given in percent.

(C) Single cell WGA reliably captures wild type and mutated alleles. Exon 15 mutation c1799T>A (BRAF) and Exon 2 mutation c181C>A (NRAS) were detected in all single cells (lanes 1-15) of cell lines with BRAF (cell lines 70-61 and MelHo) or NRAS (cell line 102-4) mutation. The allelic ratio of wt vs. mt alleles of each cell line is provided by pooled DNA. Note that this ratio is preserved in most single cells.

(D) Mutation analysis of BRAF and NRAS for paired PT-DCC samples (n=32 patients). Different mutations (either NRAS or BRAF) are indicated by mut1 and mut2. Fisher's exact test p-values indicate differences in BRAF mutational status between PT and DCC.

(E) Percentage of patients with homogeneous (all cells harboring the mutation) and heterogeneous BRAF NRAS mutational status among DCCs. DCCs were detected using two markers, gp100 or MCSP.

(F) Oncogenic mutations in BRAF and NRAS of paired PT-DCC-metastases triplets, pairs of PT-metastases or pairs of DCC-metastases. Squares indicate areas (PT and metastases) or individual cells (DCCs). Squares indicate areas (PT), individual cells (DCCs) or individual metastases (Met). Black squares indicate mutation was detected and white squares indicate wild type sequence.

Figure 4:
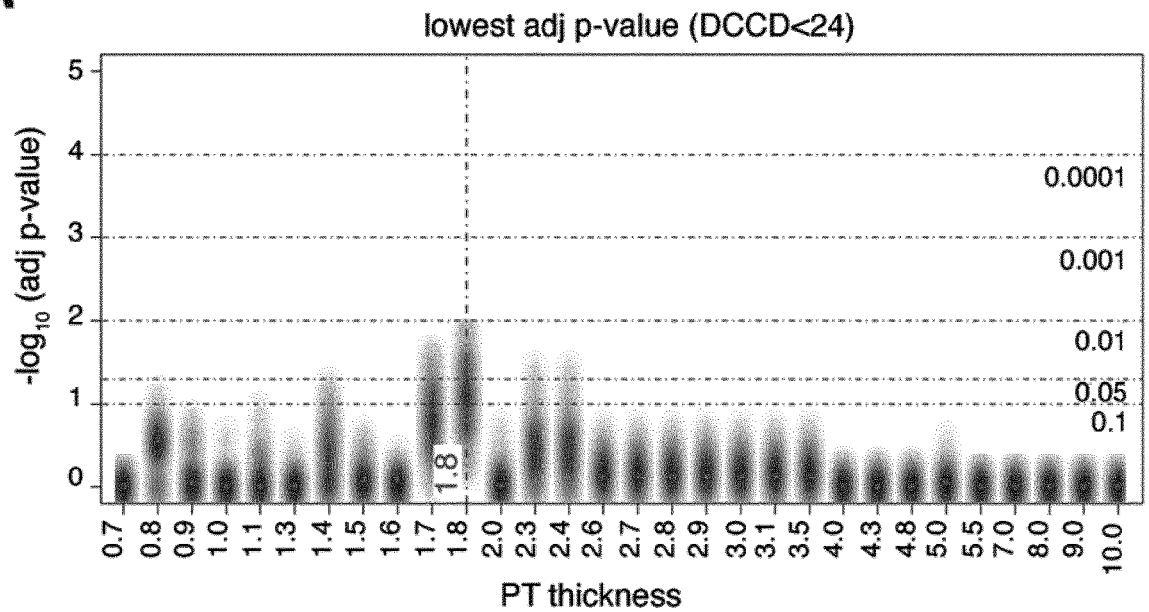
Figure 4:
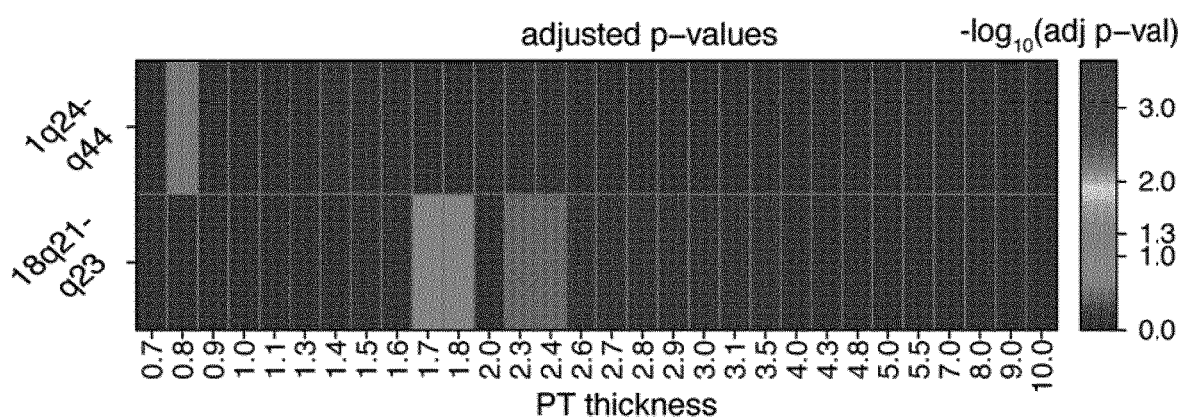
Figure 4:
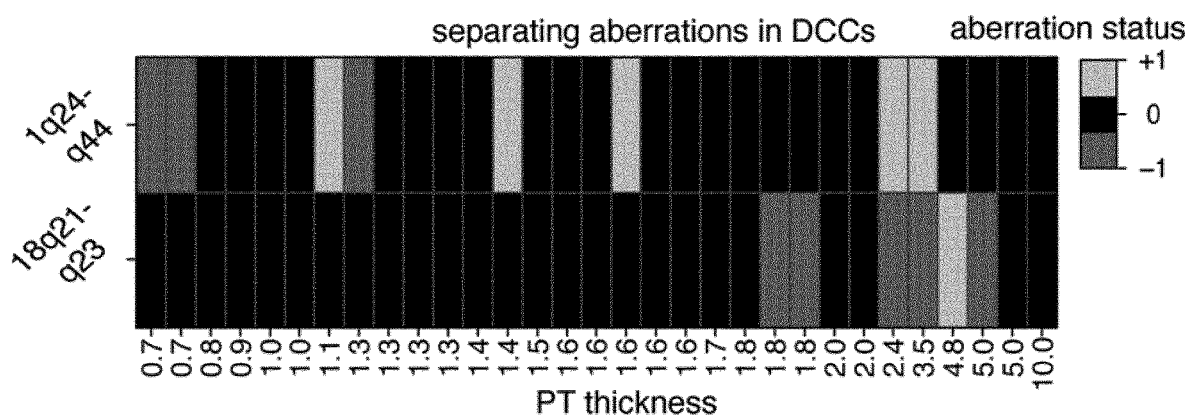
Figure 4:
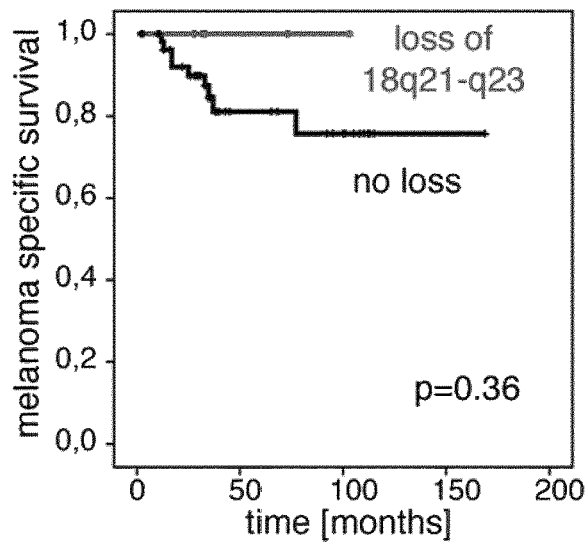
Figure 4:
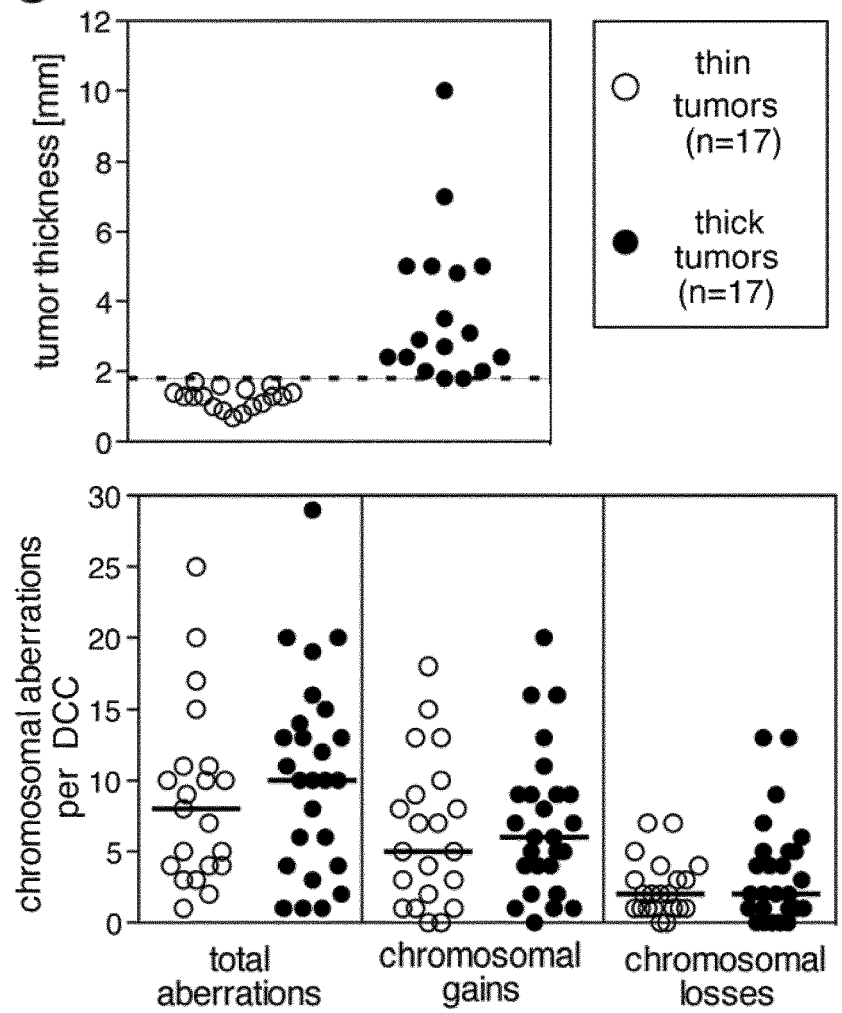

FIG. 4: Molecular Analysis of DCCs at Dissemination.

(A) Top: Samples with DCCD<24 were tested for genomic aberrations that can split DCCs into two groups according to the thickness of their matched PTs. Displayed are lowest (across chromosomal loci) FDR-adjusted p-values as a function of the limiting PT thickness that defines the low and high PT thickness groups. Low p-values (corresponding to high values of $-\log_{10}(p)$) would indicate thickness limits for which there is a significant difference in aberration frequency between DCCs from patients with thin and thick PTs. 5% significance is indicated by $-\log_{10}(0.05) = 1.30$. Red points refer to all 31 cells. Blue clouds represent subsampling-based robustness estimates (Supplemental Methods). Mid: Individual adjusted p-values for the top two loci 18q21-q23 (p=0.051 [1.8 mm] and 0.10 [1.7 mm]) and 1q24-q44 (p=0.26 [0.8 mm]) as a function of limiting PT thickness. Bottom: Aberration status (gain=+1, loss=−1) per cell for both loci listed according to sample PT thickness.

(B) Kaplan-Meier survival analysis of patients with DCCs that display loss (n=5) or no loss (n=56) of 18q21-q23.

(C) Upper: Thickness of thin (<1.8 mm) and thick (≥1.8 mm) tumors, from which DCCs were analyzed. Thin-thick splitting was performed according to the PT thickness 1.8 mm as determined by FIG. 4A. Lower: Number of chromosomal aberrations per cell in DCCs from thin and thick tumors, respectively.

Figure 5:
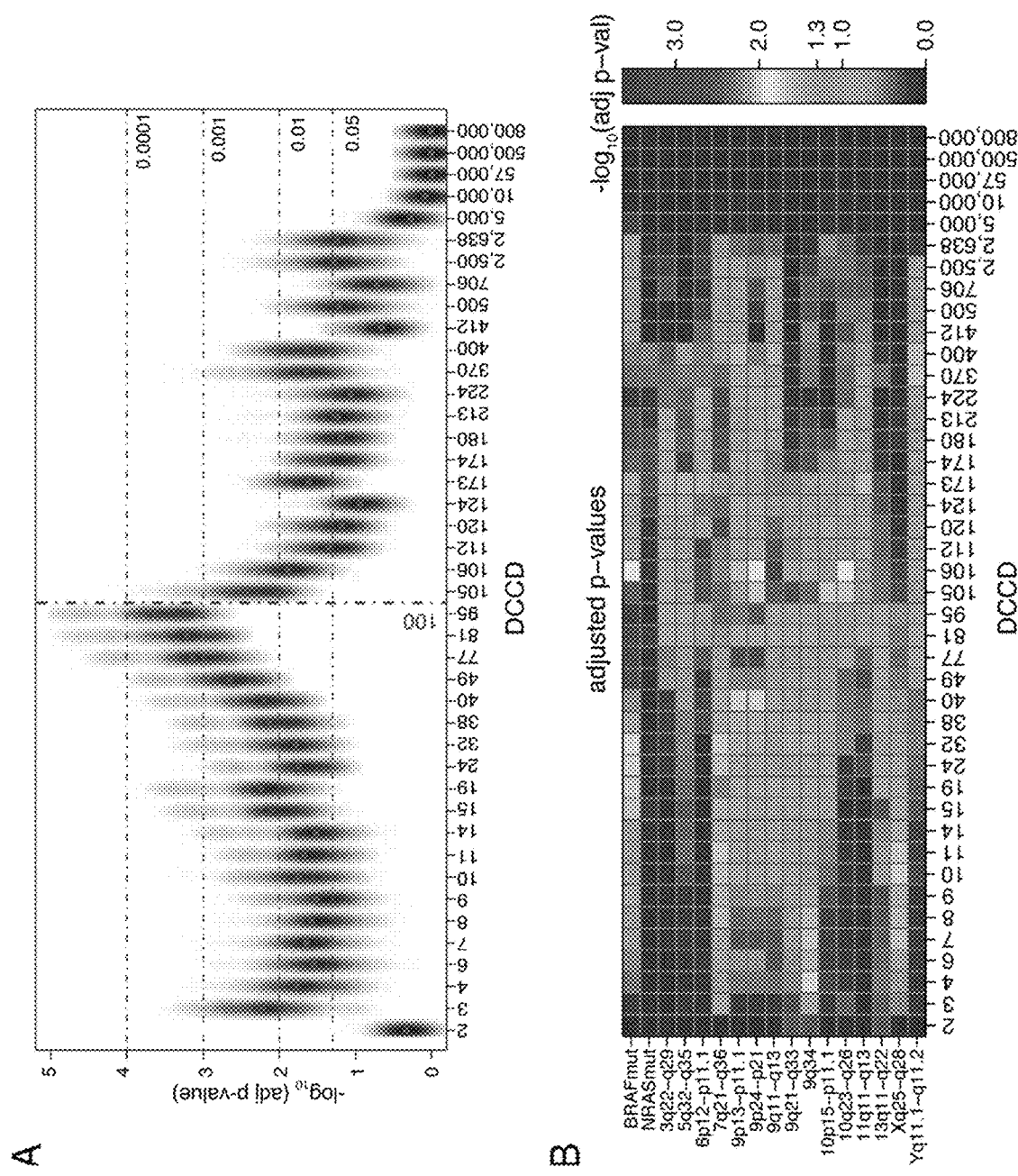
Figure 5:
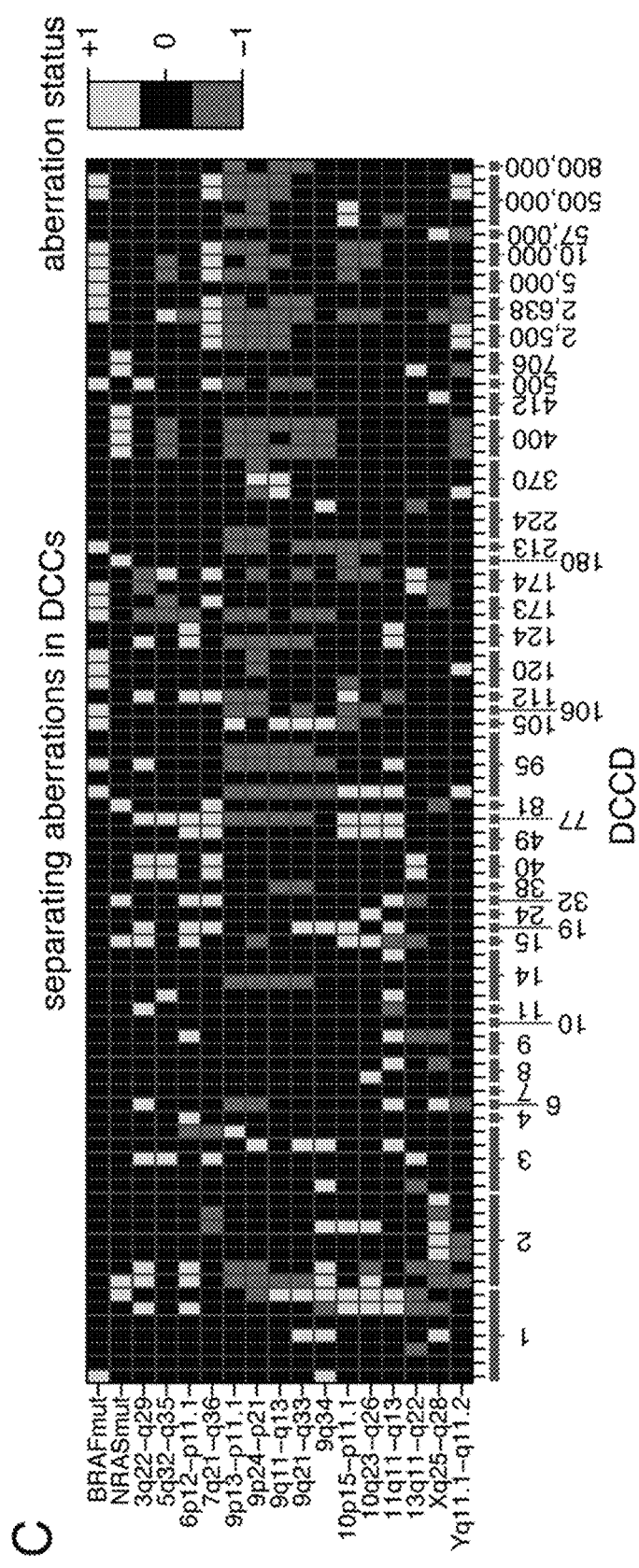

FIG. 5: Colonization-Associated Changes in DCCs.

(A) Samples were tested for genomic aberrations that can split DCCs into two groups according to patient DCCD. Displayed are lowest (across chromosomal loci) FDR-adjusted p-values as a function of the limiting DCCD that defines the low and high DCCD patient groups. Low p-values indicate DCCD limits for which there is a significant difference in aberration frequency between DCCs from patients with low and high DCCD. Red points refer to all 90 cells. Blue clouds are robustness estimates.

(B) Individual, adjusted p-values for all loci reaching 5% significance (indicated by $-\log_{10}(0.05)=1.30$) for at least one DCCD as a function of limiting DCCD (lowest p=0.0002 for BRAF). In addition, NRAS is displayed (lowest p=0.29).

(C) Aberration status (gain=+1, loss=−1) per cell for all panel B genetic loci plus BRAF and NRAS mutational status, listed according to increasing patient DCCD. For BRAF and NRAS aberration status+1 indicates mutation.

(D) Proliferation of DCCs in sentinel nodes. Immunofluorescence of Melan A+ cells in G0-, G1-, G2-phase and mitosis (from left to right). Nucleus, Melan A and Ki-67 are displayed.

Figure 6:
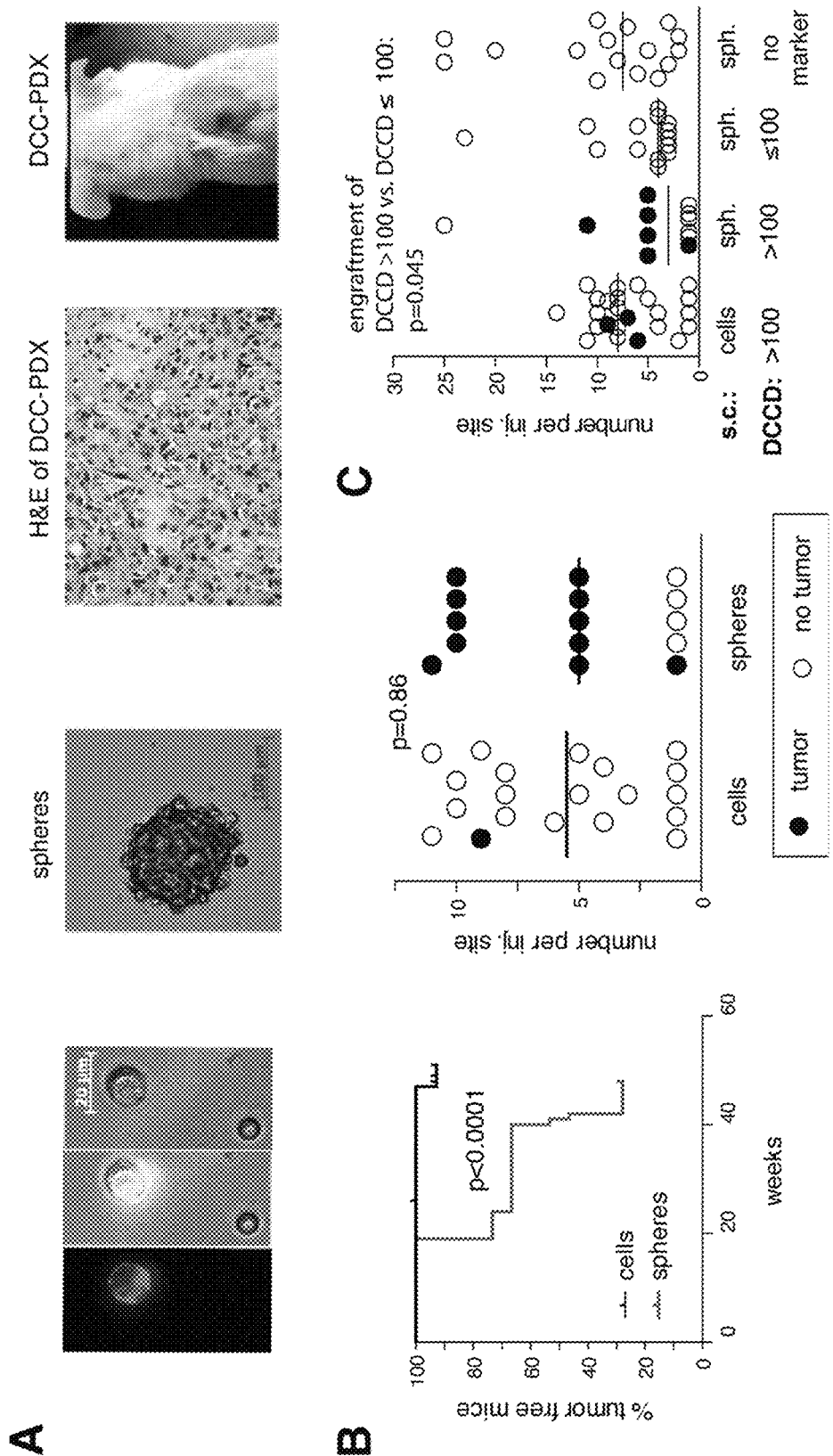
Figure 6:
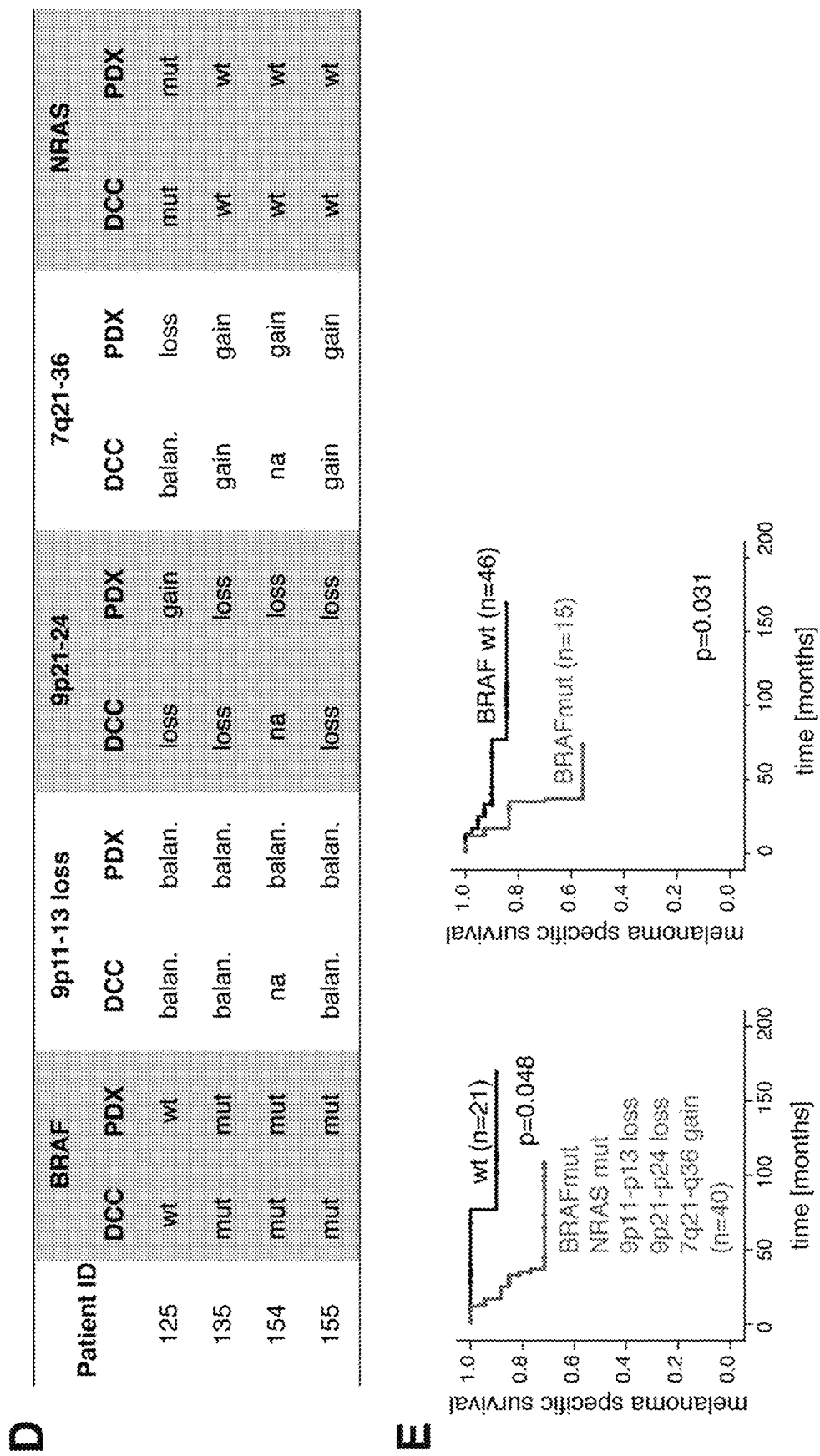

FIG. 6: Tumor-Forming Ability of DCCs Before and After Colonization and Patient Survival (A) Left to right. Isolated MCSP+ DCCs from a patient-SLN: DCC-derived sphere; H&E-staining of a patient DCC-derived xenograft (DCC-PDX); DCC-PDX (7 s.c. injected DCCs).

(B) Side-by-side transplantation of paired MCSP+ DCCs and DCC-derived spheres from the same patient into NSG-mice. Left: Kaplan-Meier analysis of tumor-free mice (p<0.0001, log-rank test). Right: number of injected MCSP+ DCCs and DCC-derived spheres per injection site (p=0.86, Mann-Whitney U test). Black filled circles indicate tumor formation.

(C) Number of MCSP+ DCCs (DCCD>100: n=24 injection sites) or DCC-derived spheres (DCCD>100: n=12 injection sites; DCCD≤100: n=14 injection sites) that were transplanted into NSG-mice. Each circle represents one injection site. Black filled circles indicate tumor formation (engraftment). The p-value (Fisher's exact test) indicates a significant difference in the engraftment rate for samples with DCCD>100 (pooled cells and spheres, n=36) vs. DCCD≤100 (spheres, n=14).

(D) Colonization signature (genetic loci identified in FIG. 5 A-C), BRAF and NRAS mutational status of patient-derived DCCs and their respective xenografts.

(E) Left: Kaplan-Meier survival analysis of patients with DCCs that display at least one of the colonization signature changes (n=40) or not (wt, n=21) or. Right: Kaplan-Meier survival analysis of patients with DCCs that display BRAF mutation (BRAFmut, n=15) or wild type sequence (wt, n=46).

Figure 7:
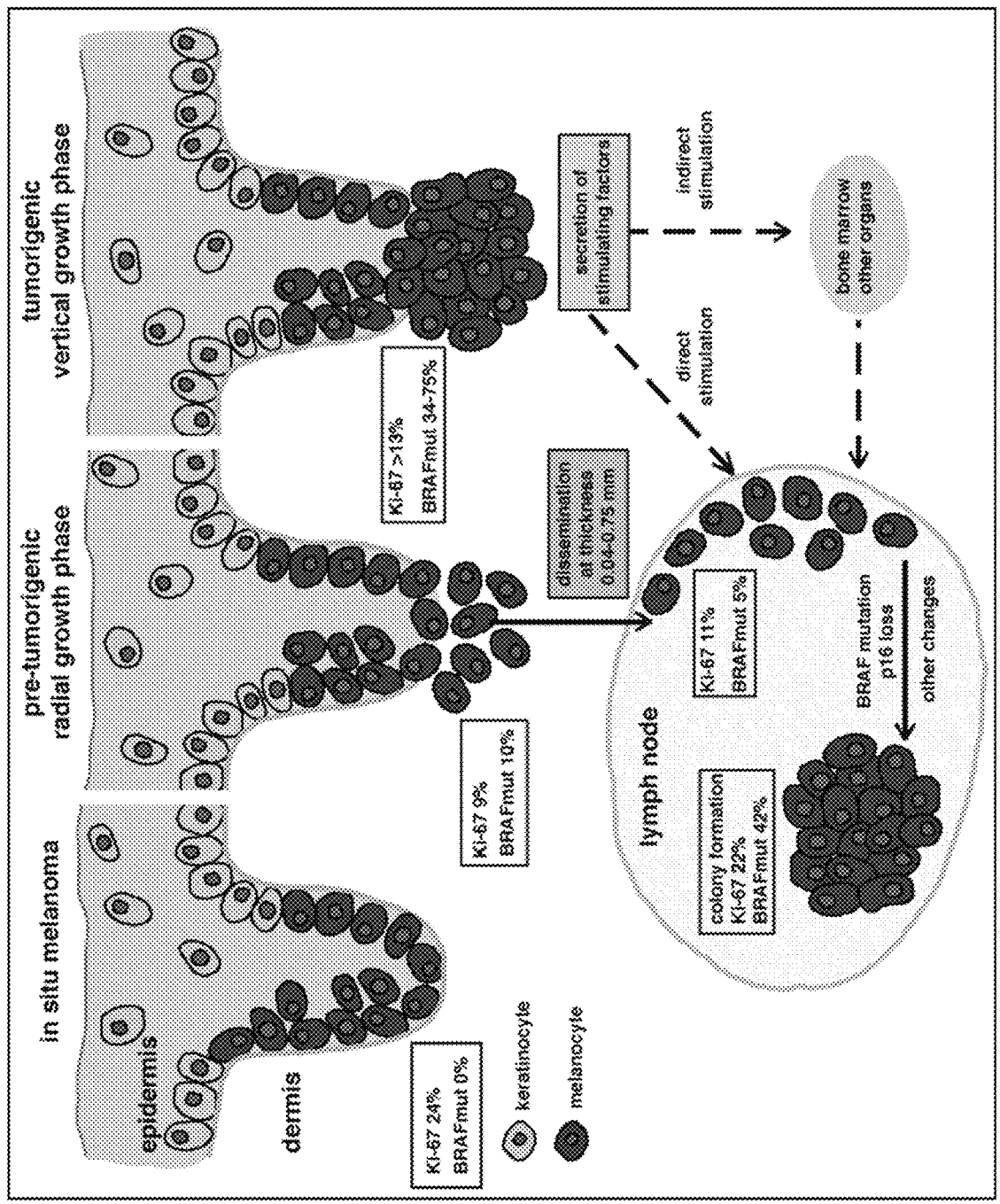

FIG. 7: Model of Melanoma Progression from Local to Metastatic Disease

Histologic appearance, patient-derived dissemination estimate, proliferation rate and BRAF mutational state are integrated into the scheme. Data are taken from this study and from references (Dong (2003) Cancer research 63, 3883-3885; Gimotty (2005) Journal of clinical oncology: official journal of the American Society of Clinical Oncology 23, 8048-8056; Verlinden (2014) Medicine 93, e285).

Figure 8:
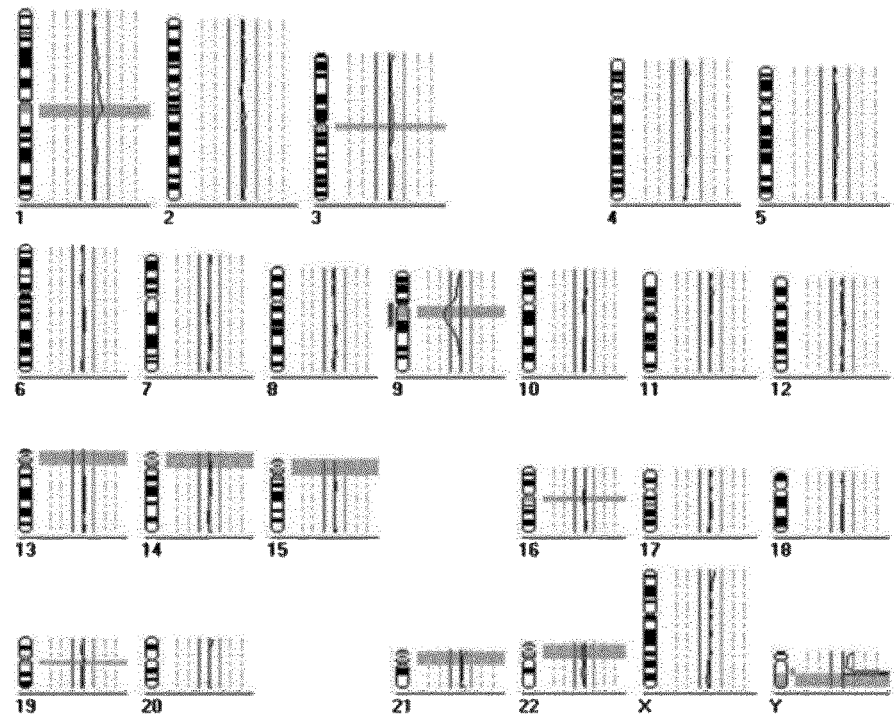
Figure 8:
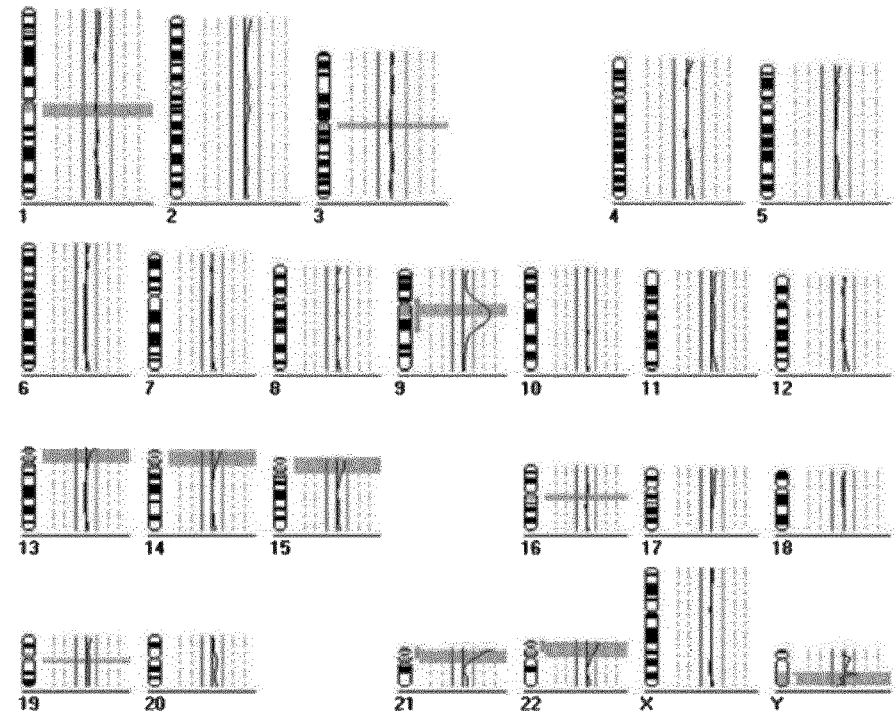
Figure 8:
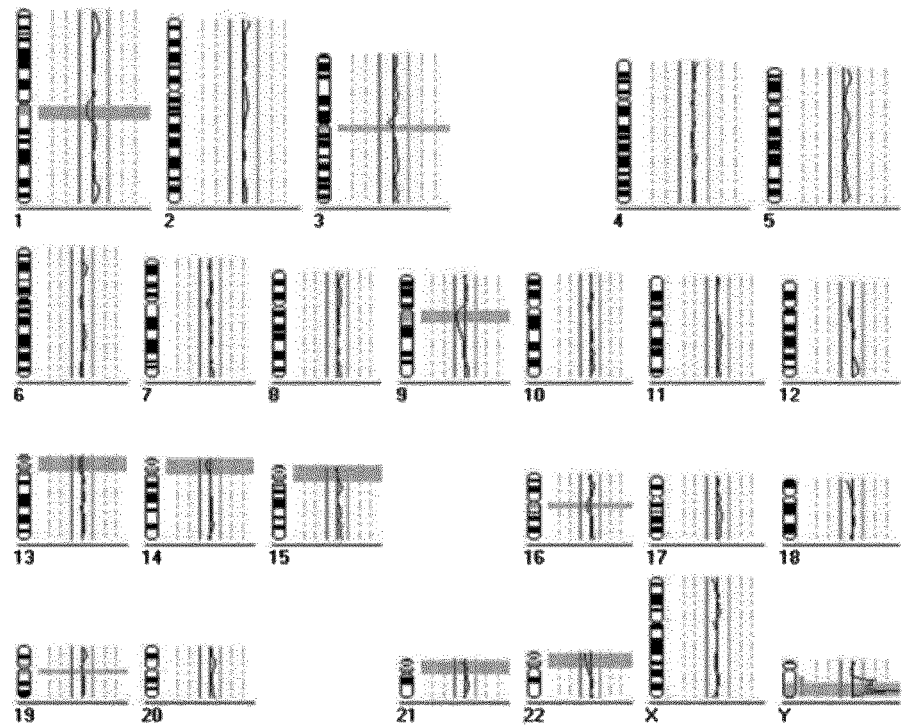
Figure 8:
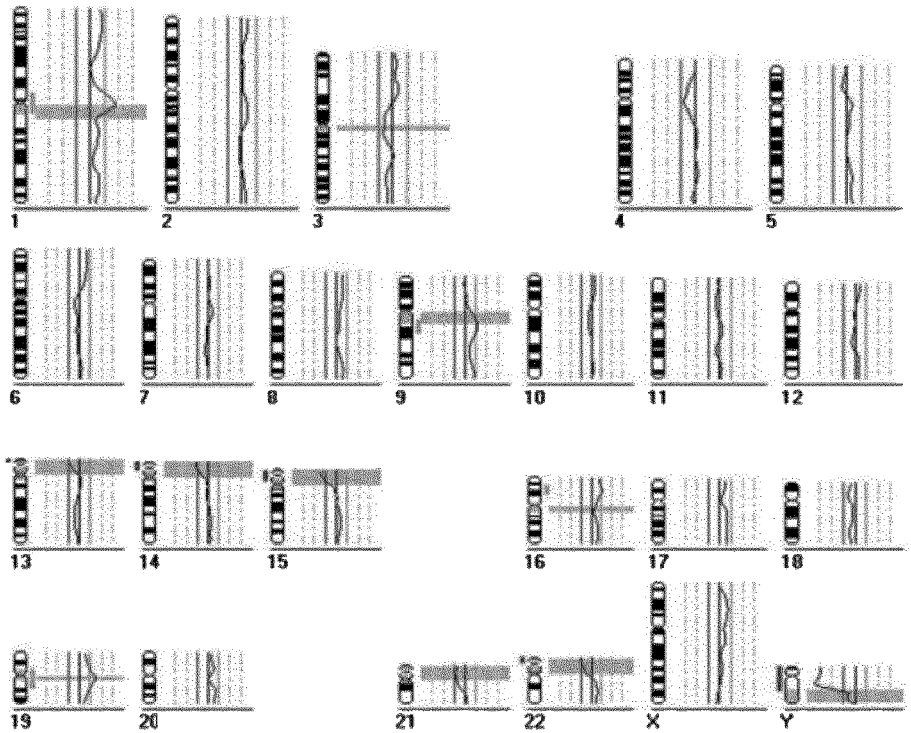
Figure 8:
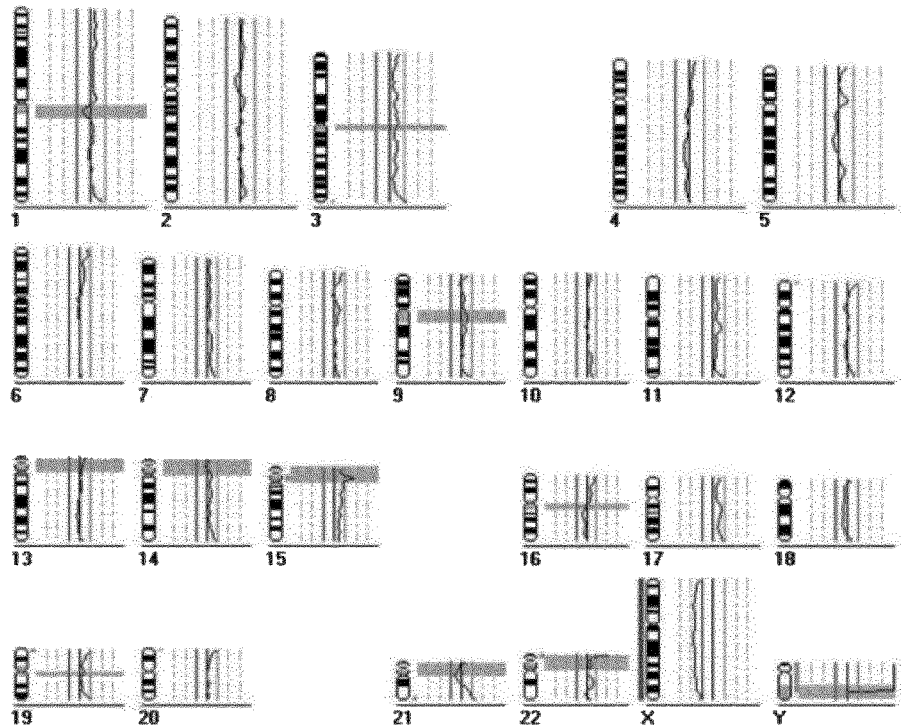
Figure 8:
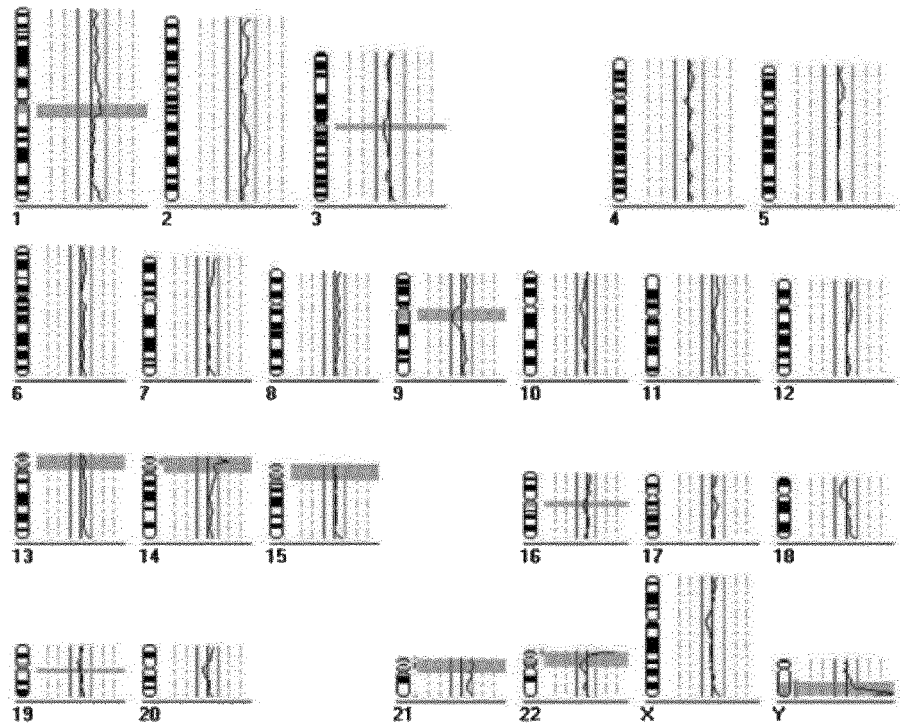
Figure 8:
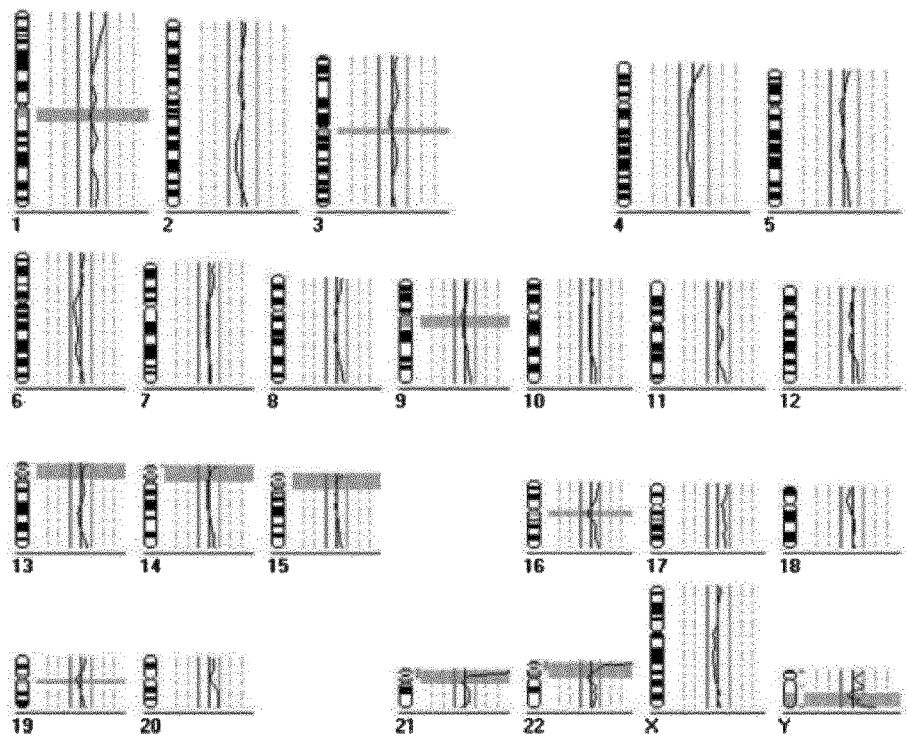
Figure 8:
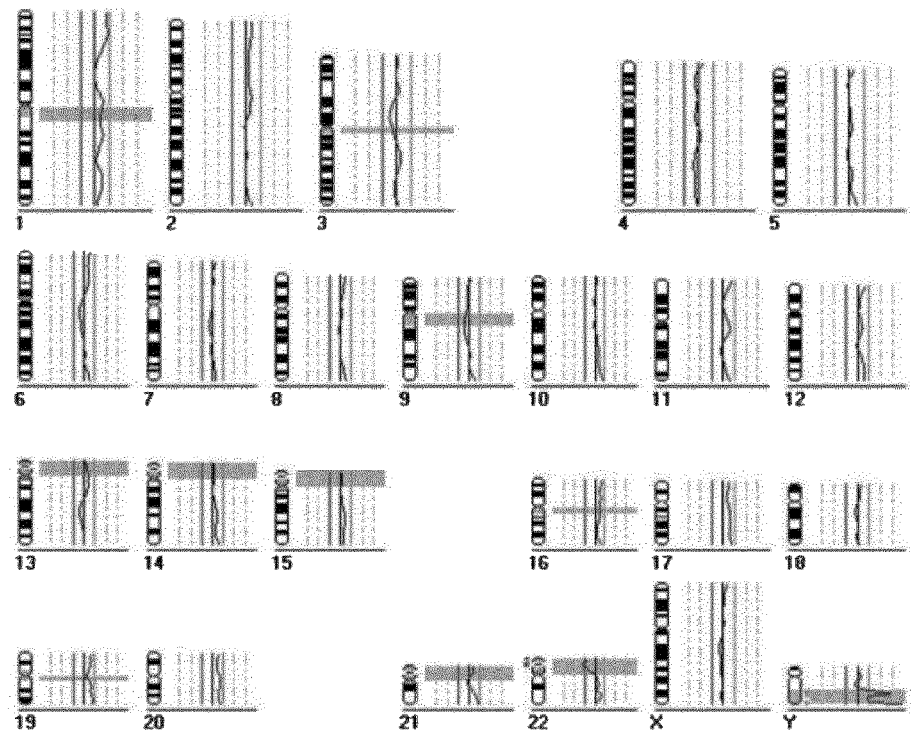
Figure 8:
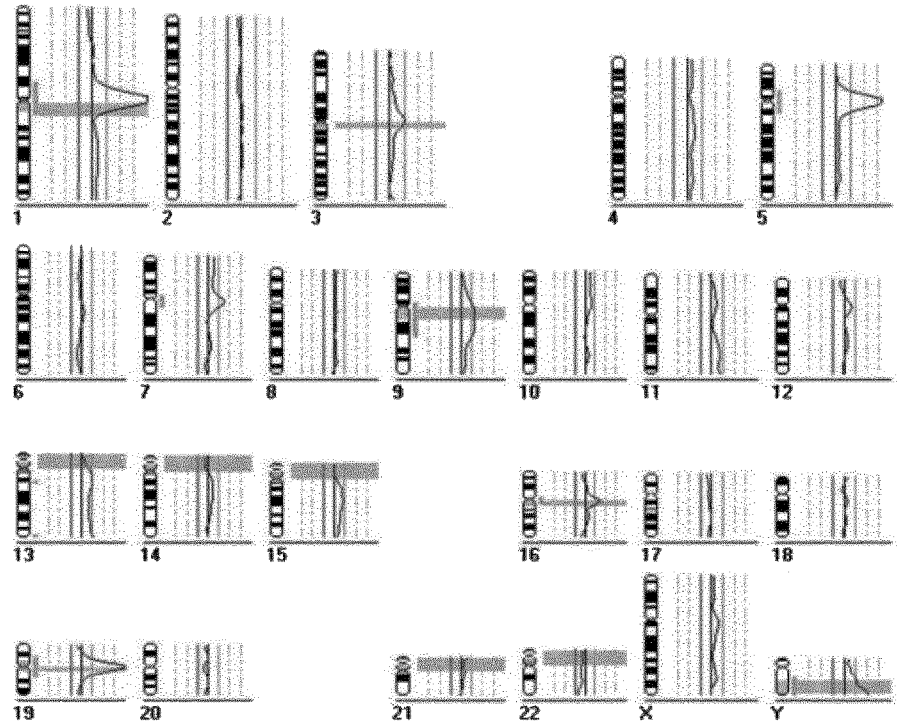
Figure 8:
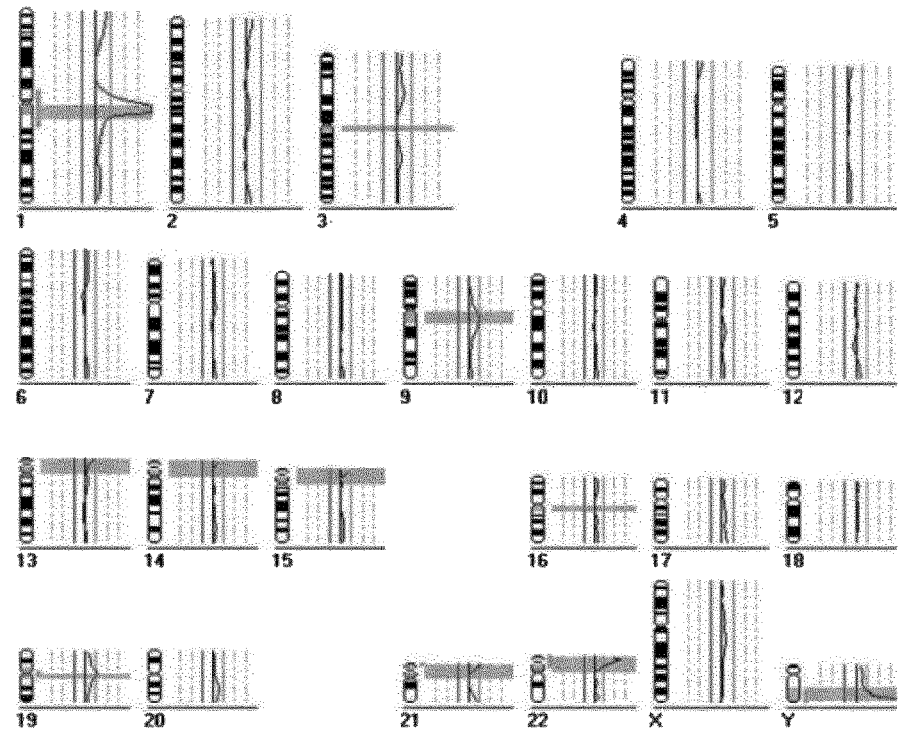
Figure 8:
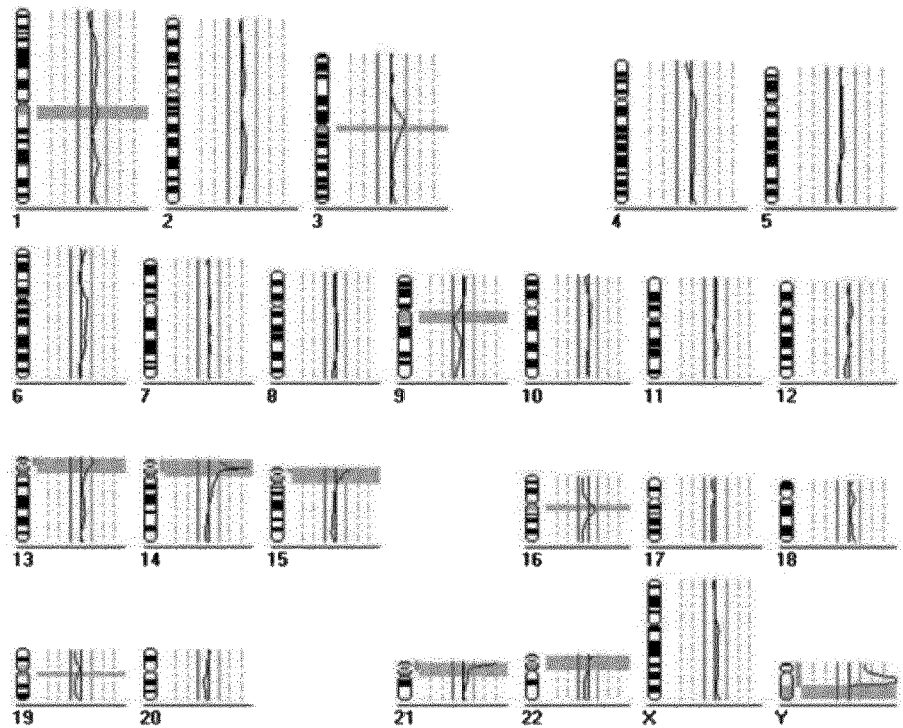
Figure 8:
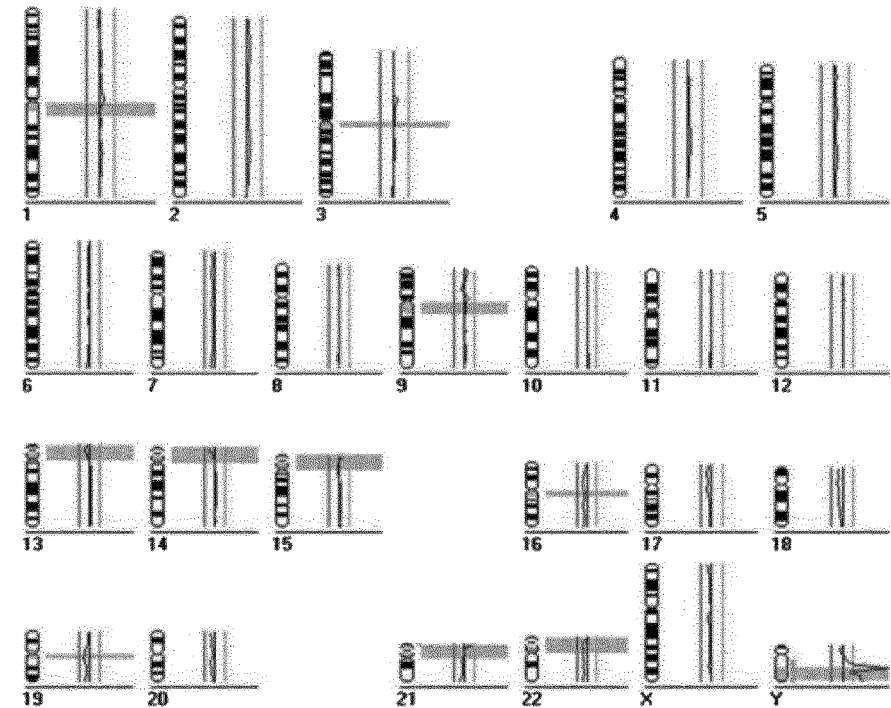
Figure 8:
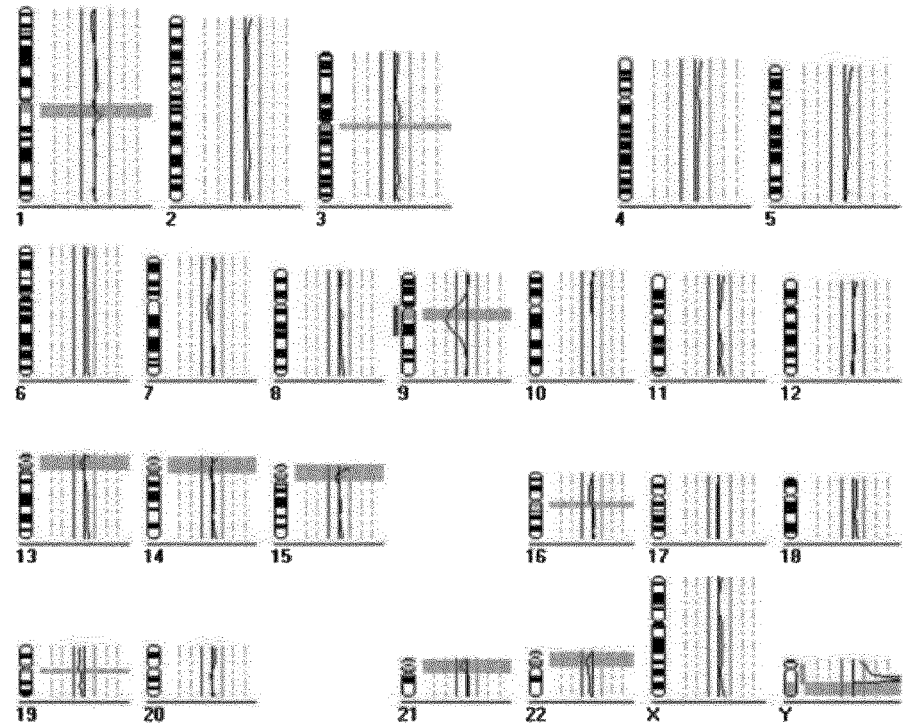
Figure 8:
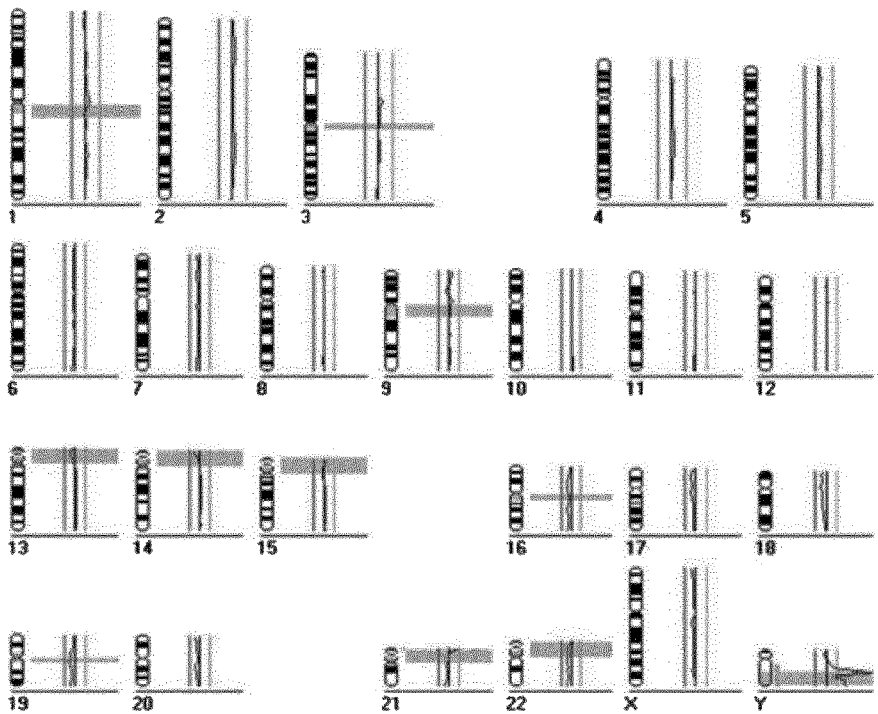
Figure 8:
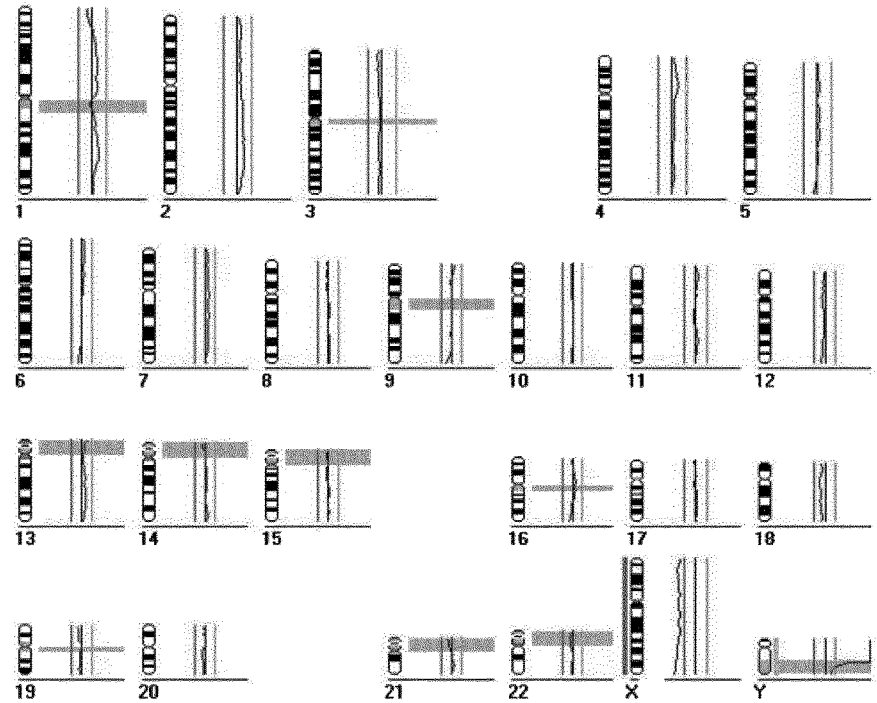
Figure 8:
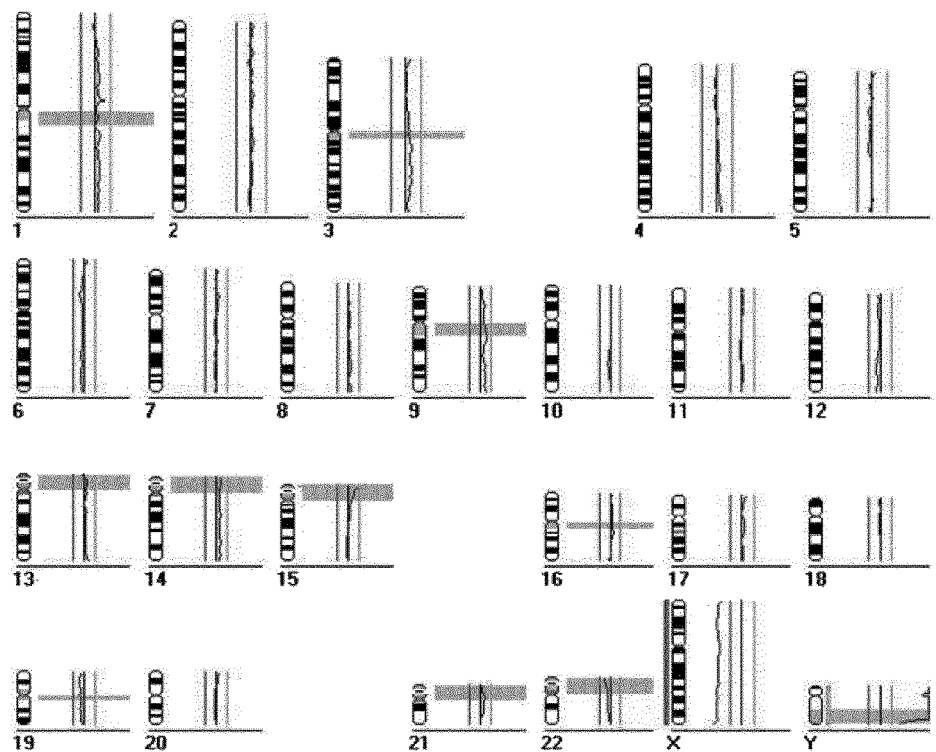
Figure 8:
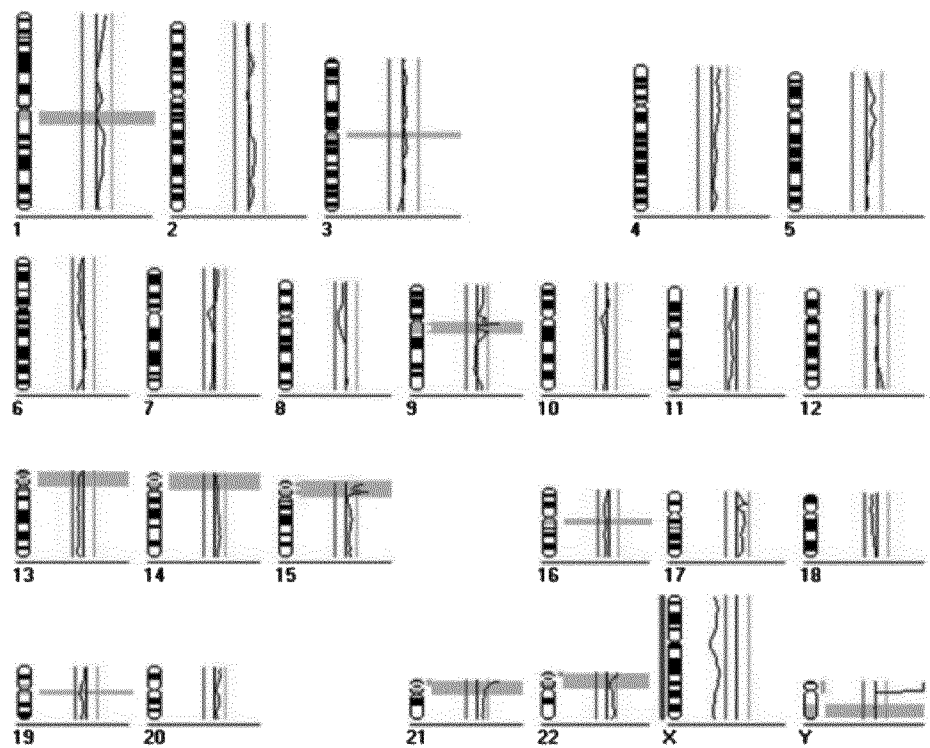
Figure 8:
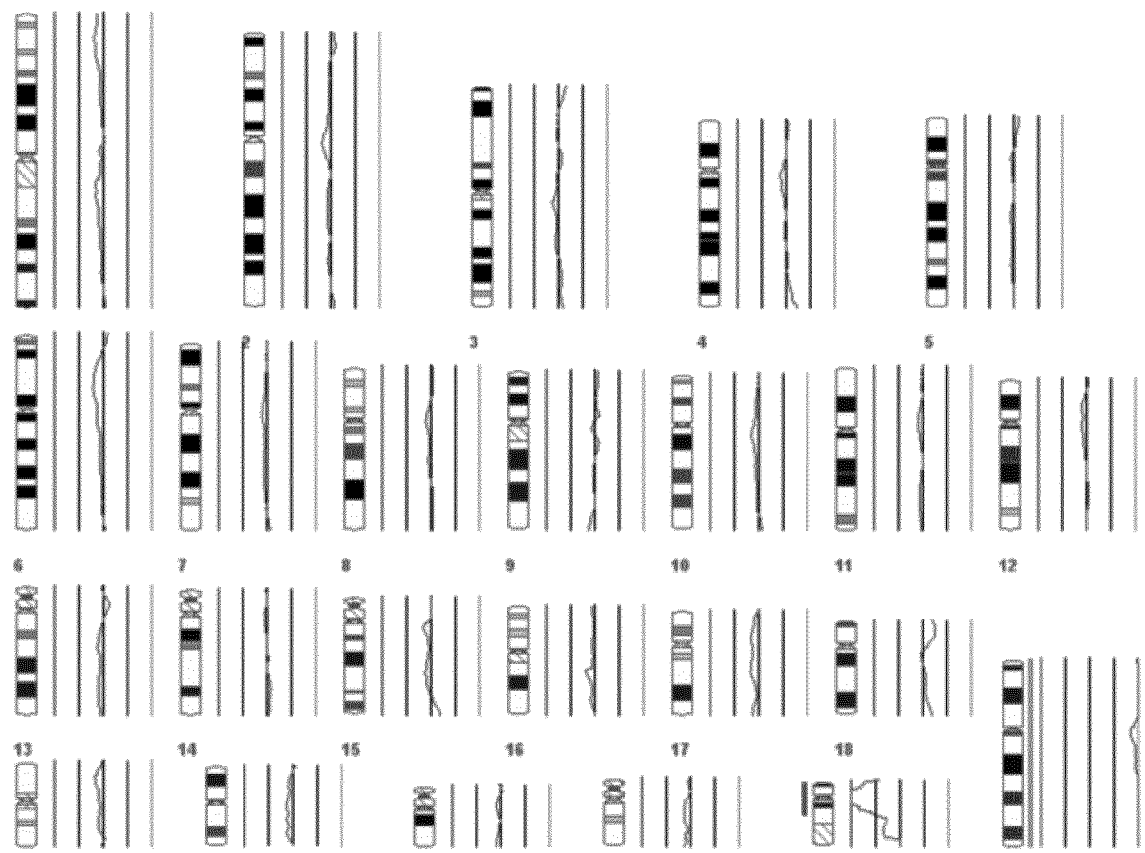
Figure 8:
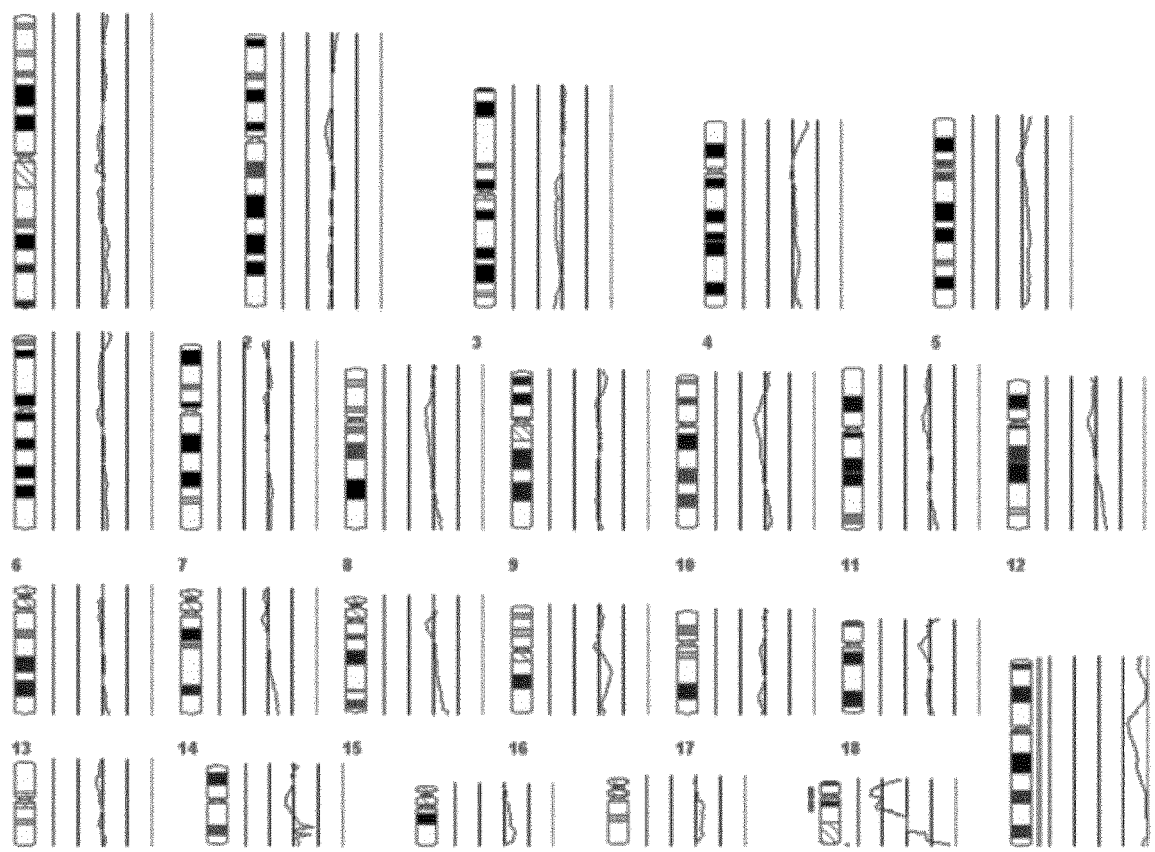
Figure 8:
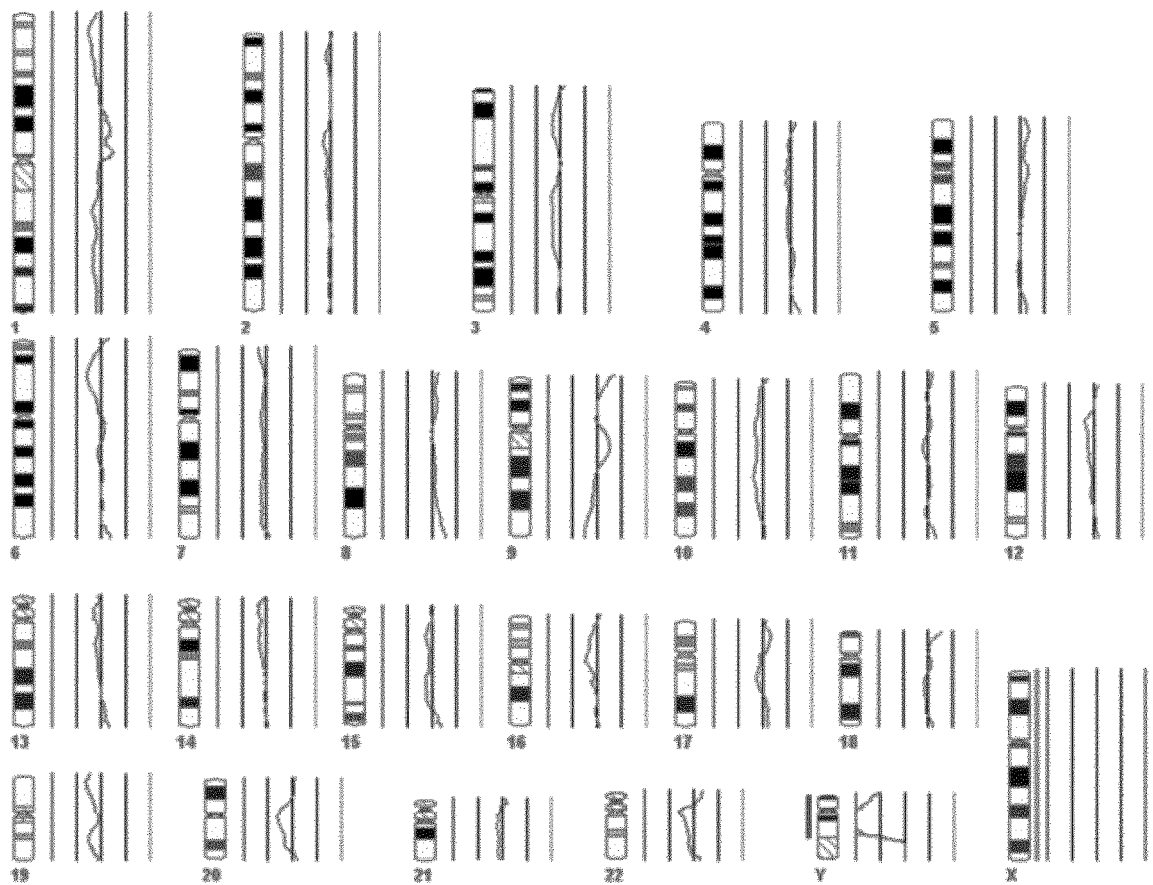
Figure 8:
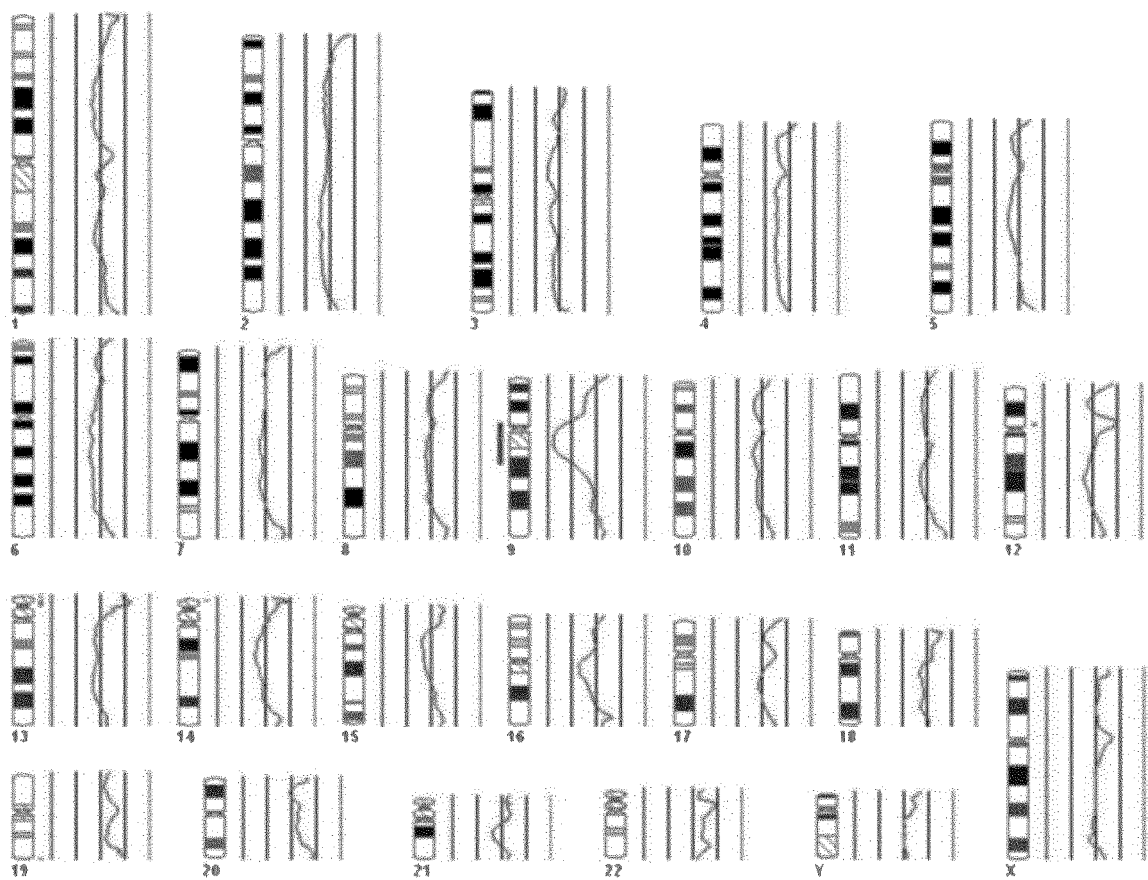
Figure 8:
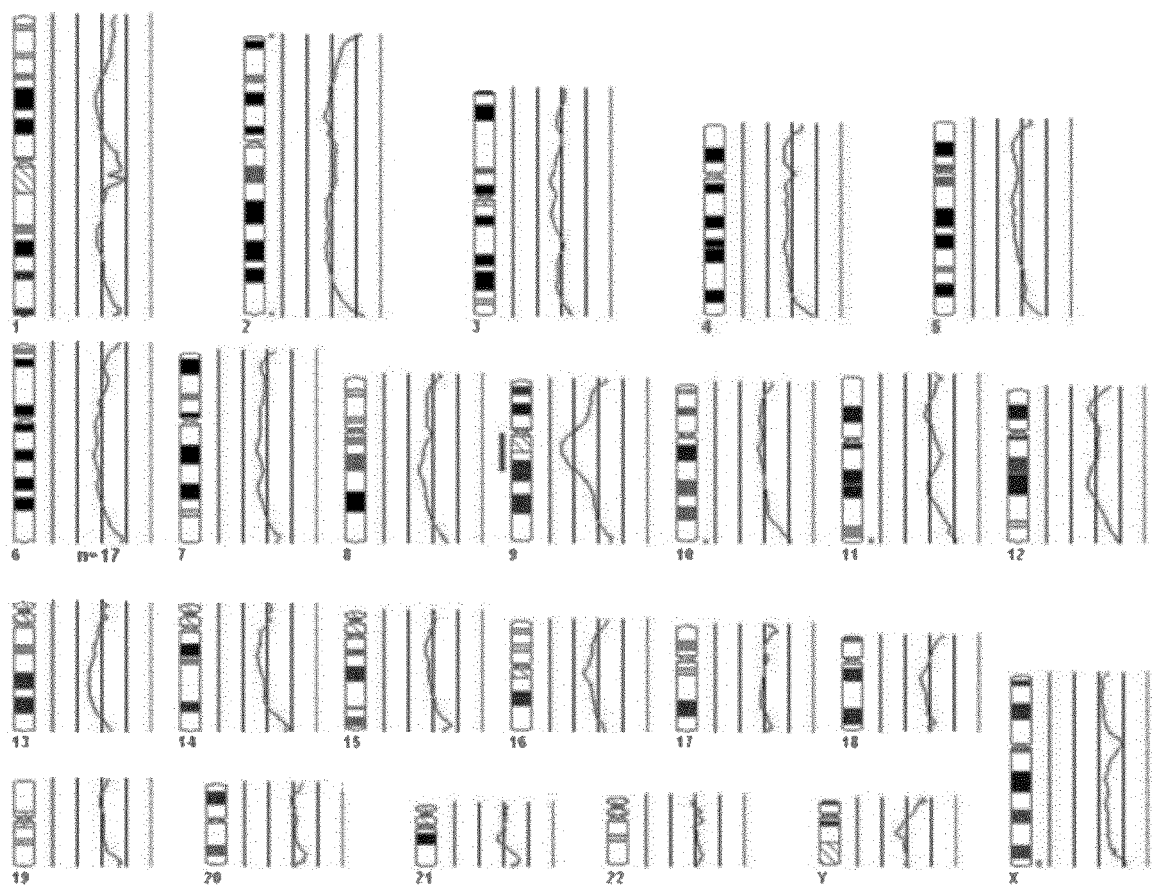
Figure 8:
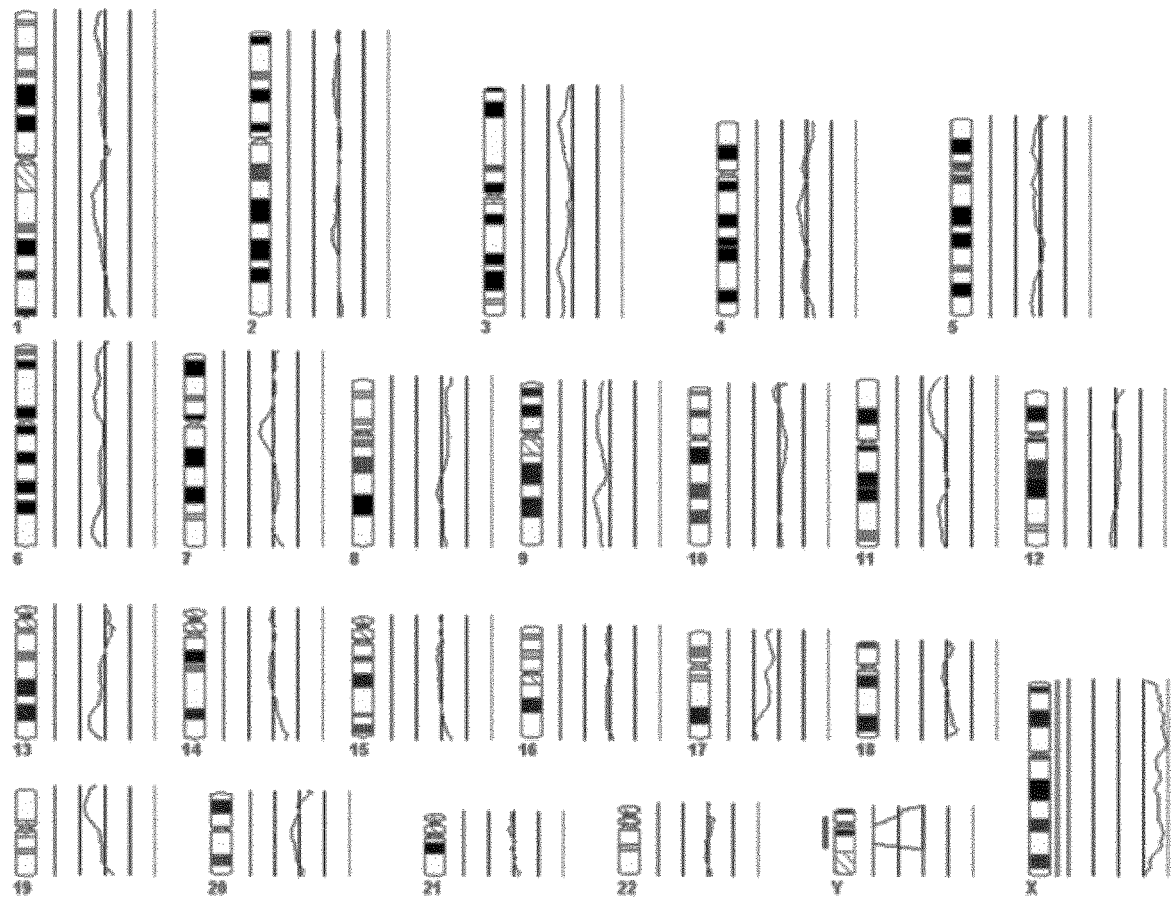
Figure 8:
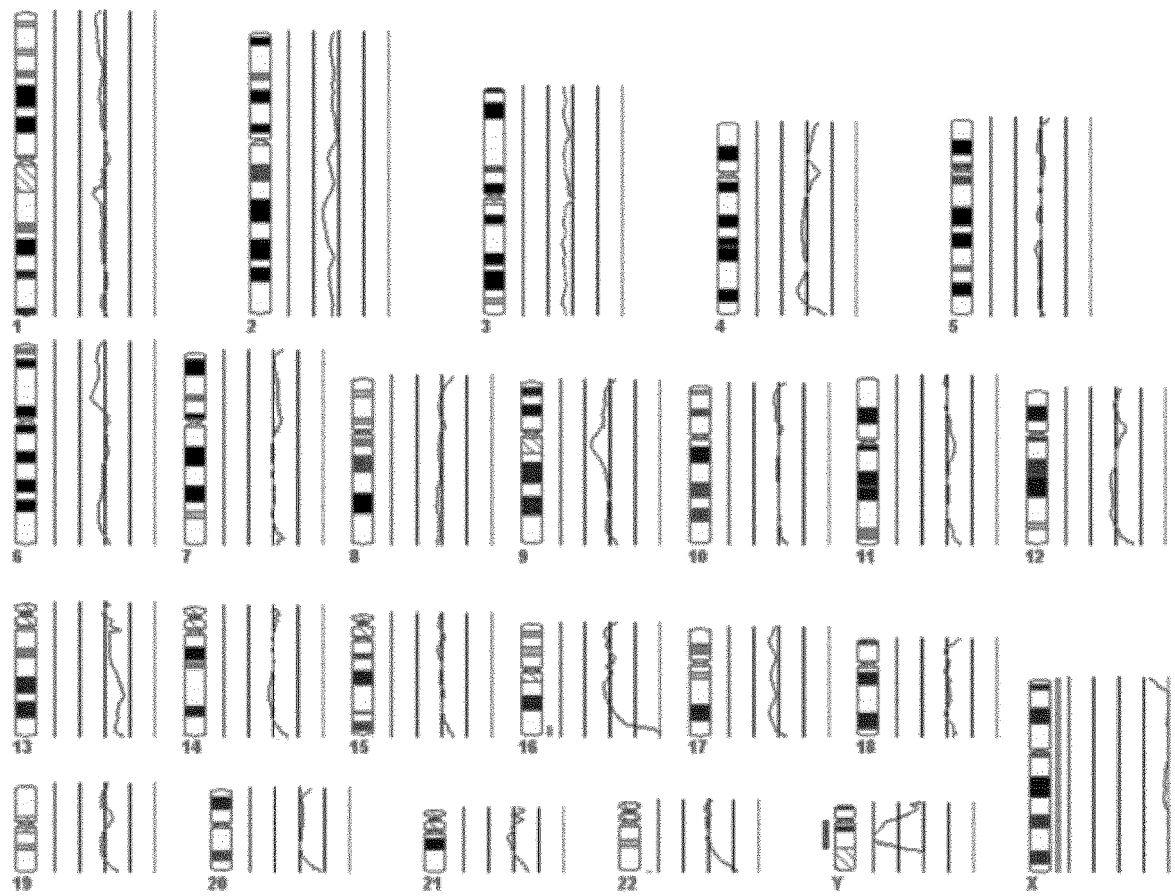
Figure 8:
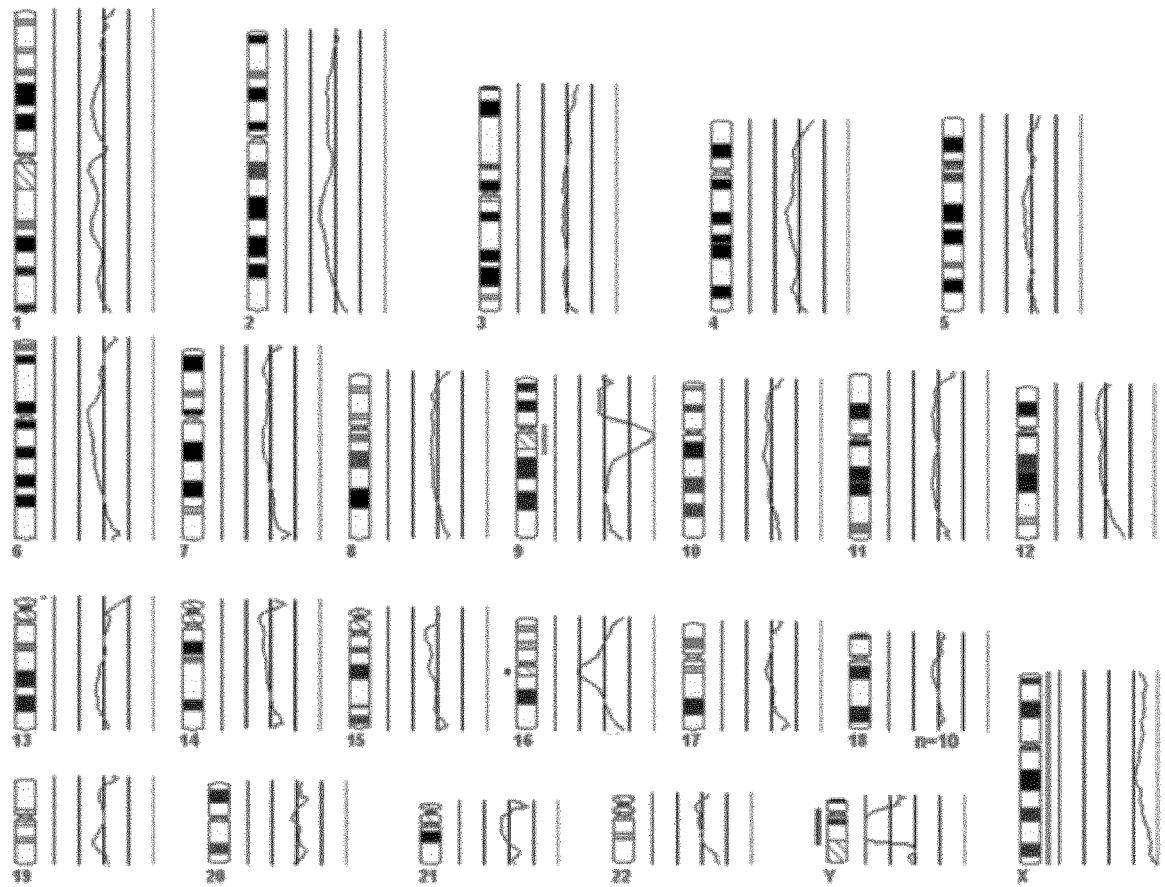
Figure 8:
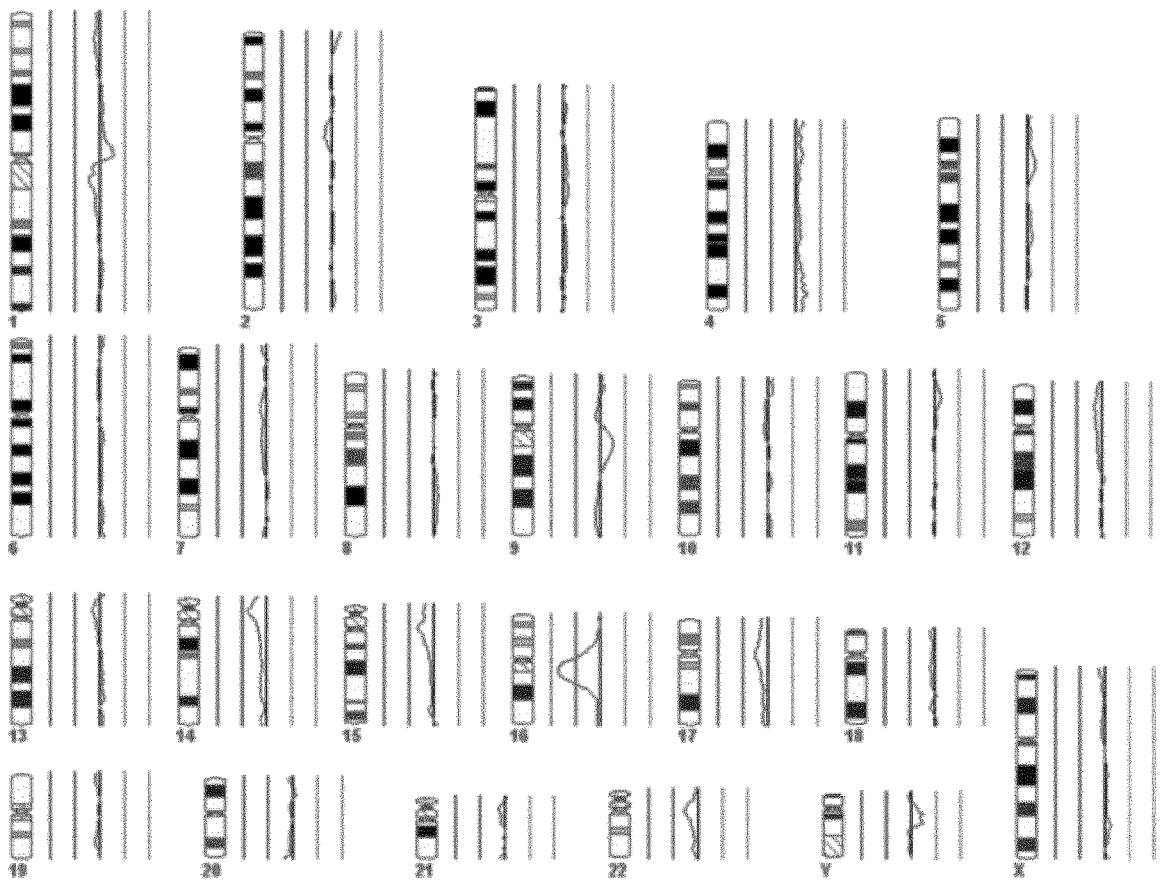
Figure 8:
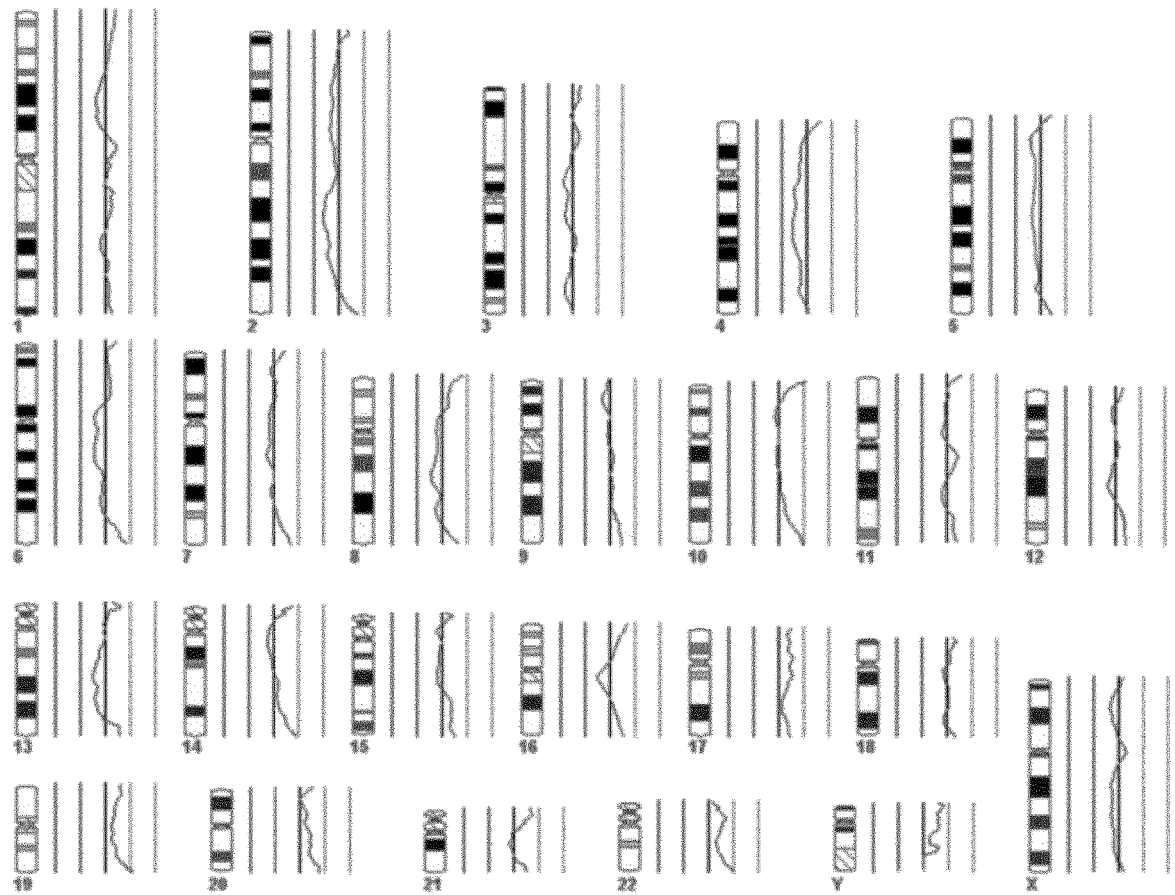
Figure 8:
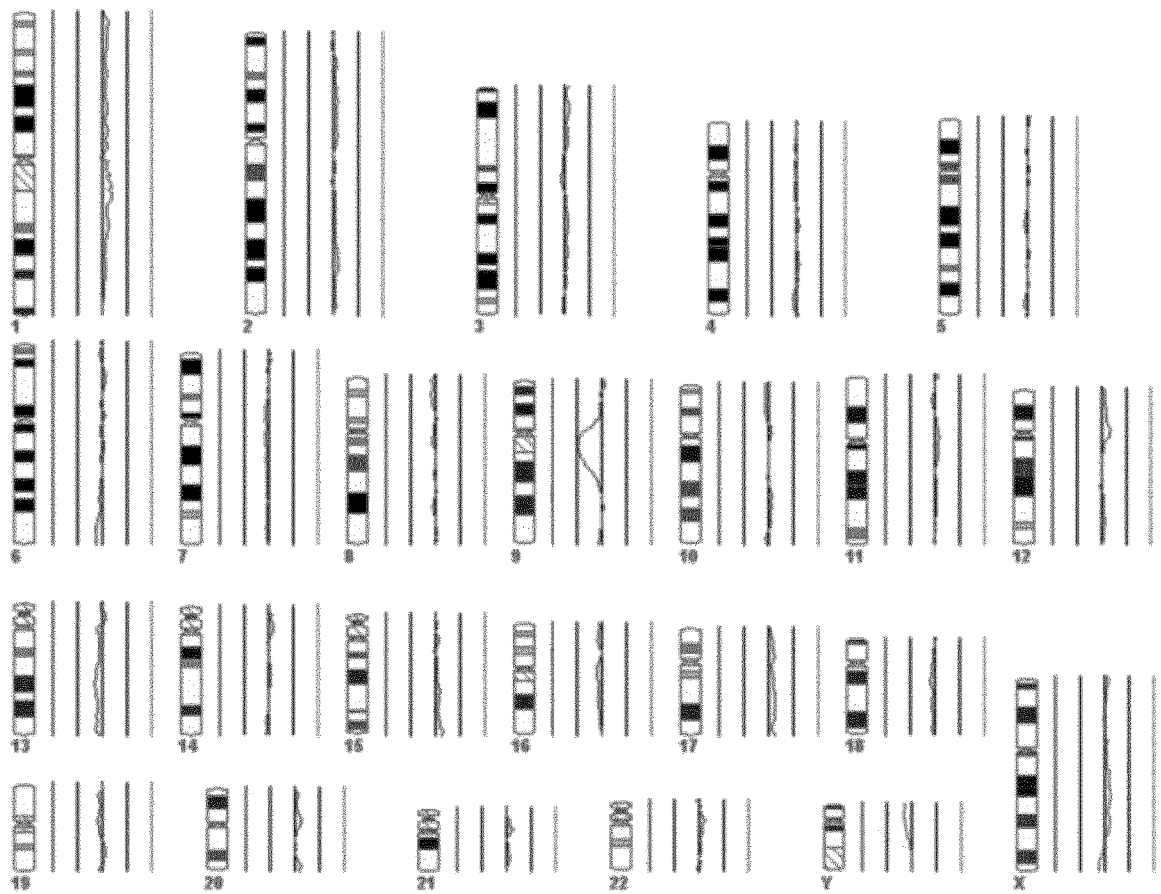
Figure 8:
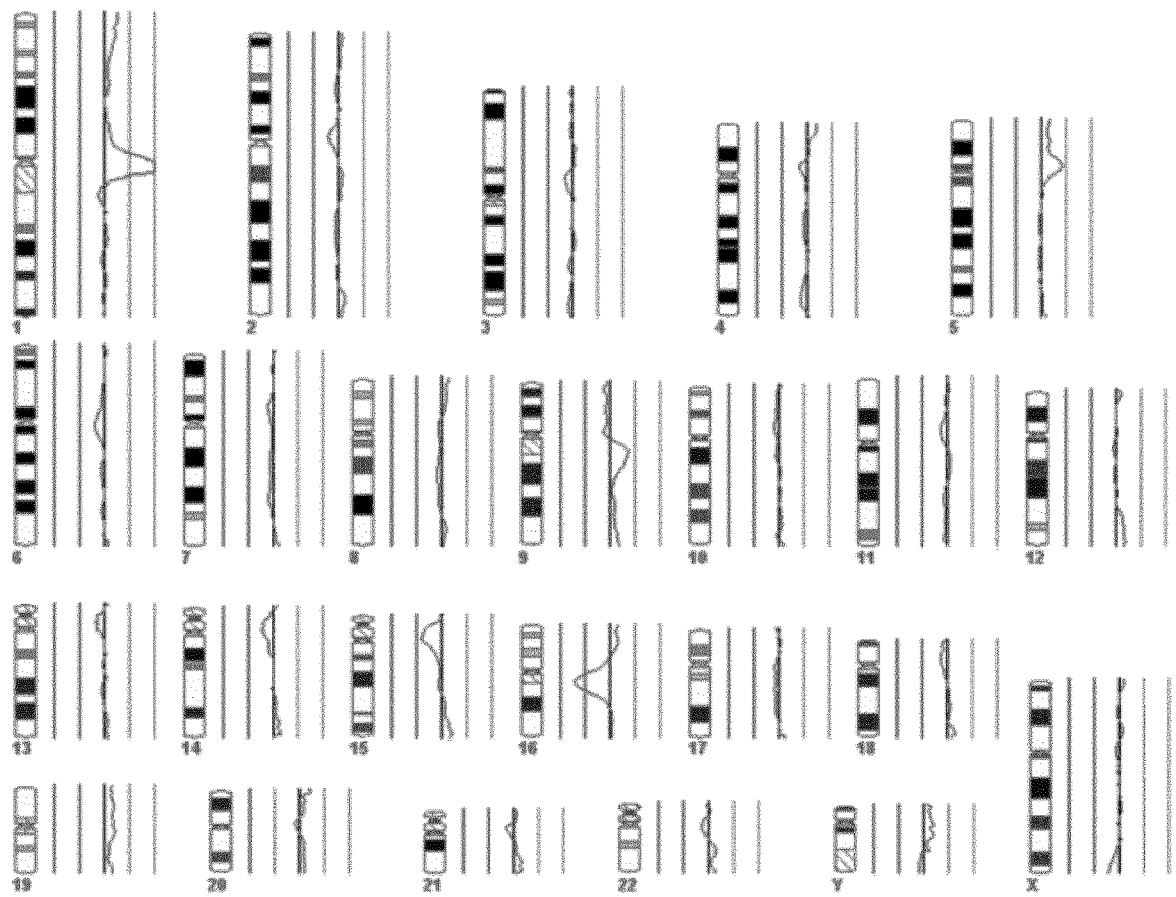
Figure 8:
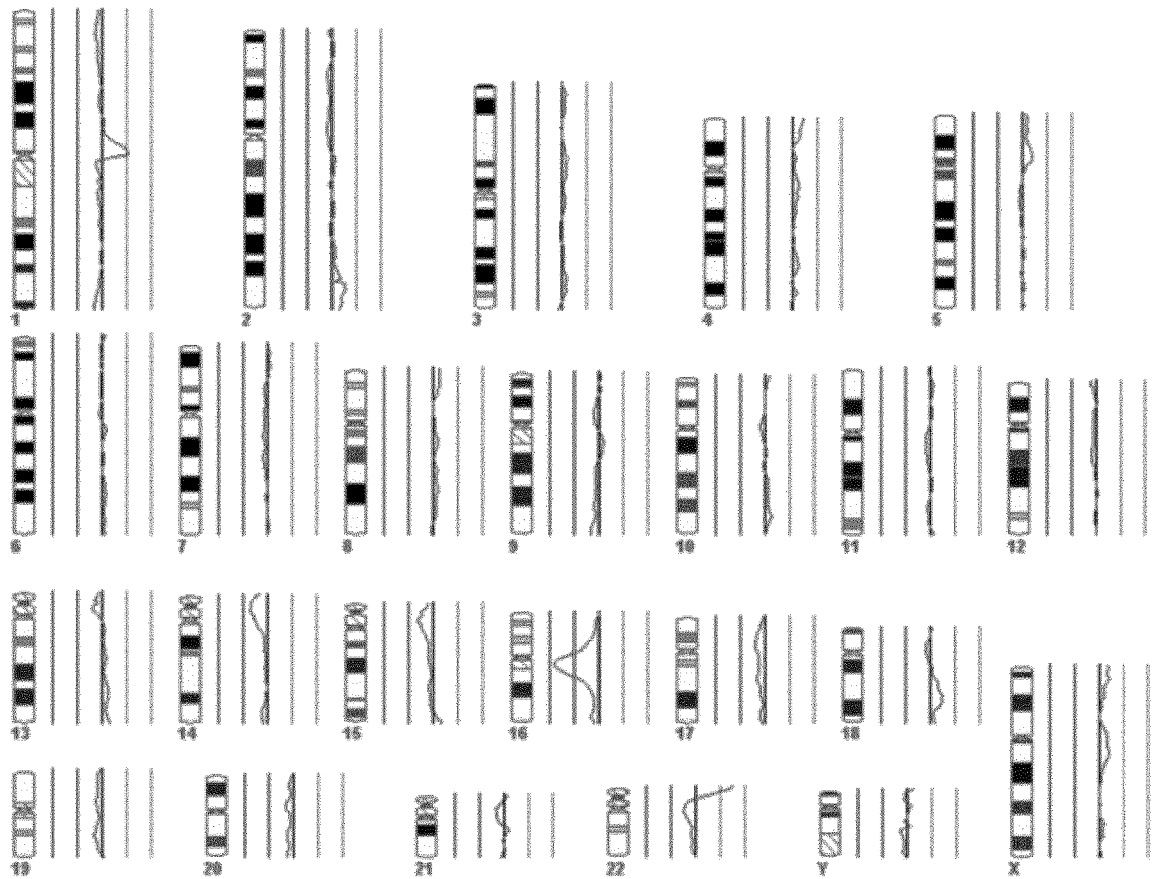

FIG. 8 CGH profiles of 30 control cells isolated from blood, lymph node or bone marrow. Cells were identically isolated and amplified as gp100-positive cells. All chromosomes are depicted. In some cases, we used sex-mismatch control DNA to demonstrate successful hybridization. Colored bars indicate relative gains or losses of the X-chromosome (red, underrepresentation in test cells; green, overrepresentation in test cells) bars next to the ideogram. Chromosomal regions (centromeric regions) marked by gray bars are excluded from analysis as they contain repetitive regions. All cells displayed normal genomes.

Figure 9:
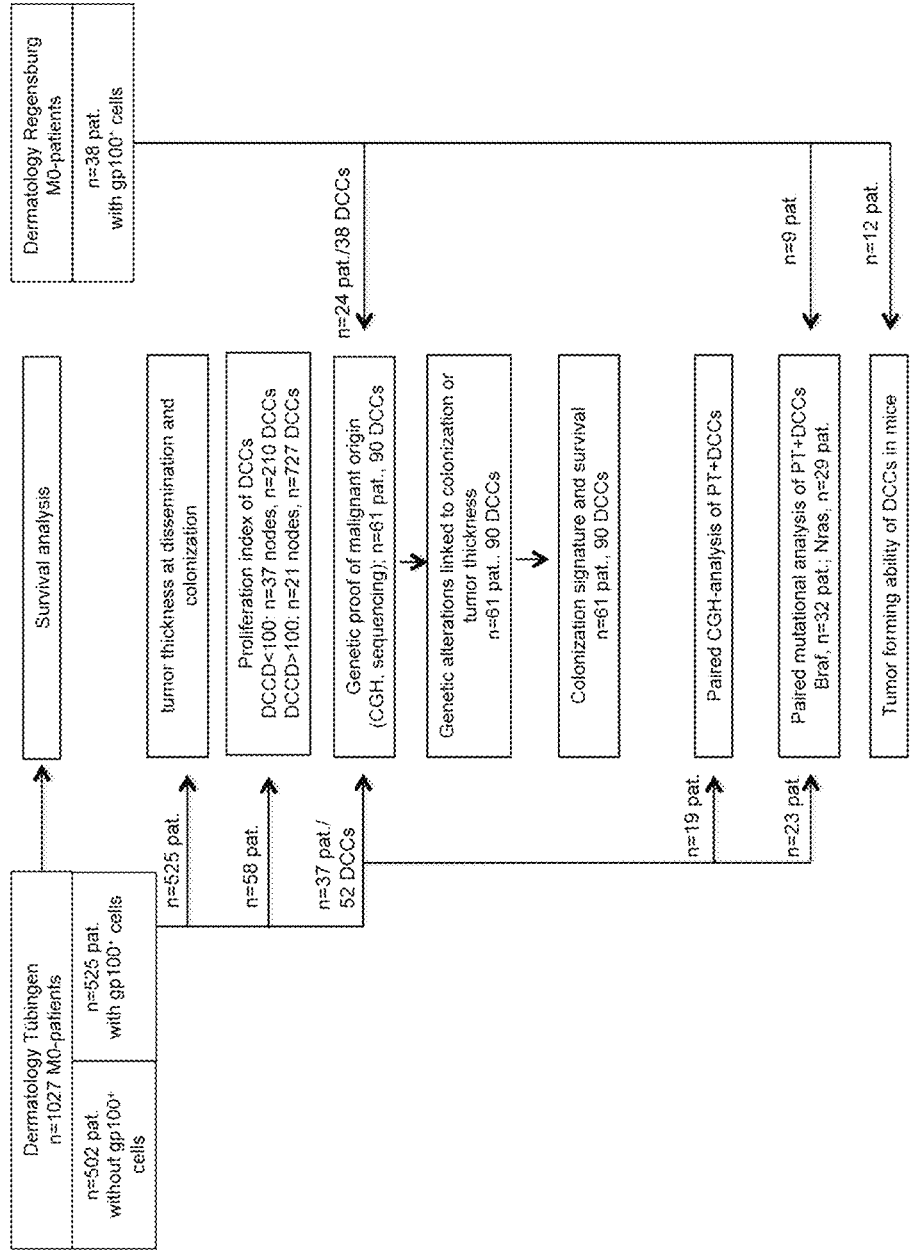

FIG. 9 Overview of Analyzed Patient Samples

Our study focuses on melanoma patients in their earliest disease stages; therefore only non-metastasized (MO) patients with clinically node-negative disease were included. For molecular analysis, samples were included according to availability or DNA-quality. Our criteria for selection of patients/cells for further genomic or functional analysis included:

1) Patients had gp100+ cells in their SLN.
2) Gp100+ DCCs were isolated.
3) DCC-derived DNA passed quality control for CGH analysis (see Polzer et al. 2014).
4) Paraffin-blocks of primary tumors (PTs) could be received from external dermatologists. (Note, that acquisition of primary tumors is extremely difficult as almost all patients are operated outside of the University hospital).
5) Sufficient material of PTs was left and not completely used for diagnosis.
6) DNA from many paraffin-embedded tissues passed the quality control.
7) Sufficient SLN material to allow short-term culture or xenotransplantations.
8) Follow-up was available and of sufficient length.

Figure 10:
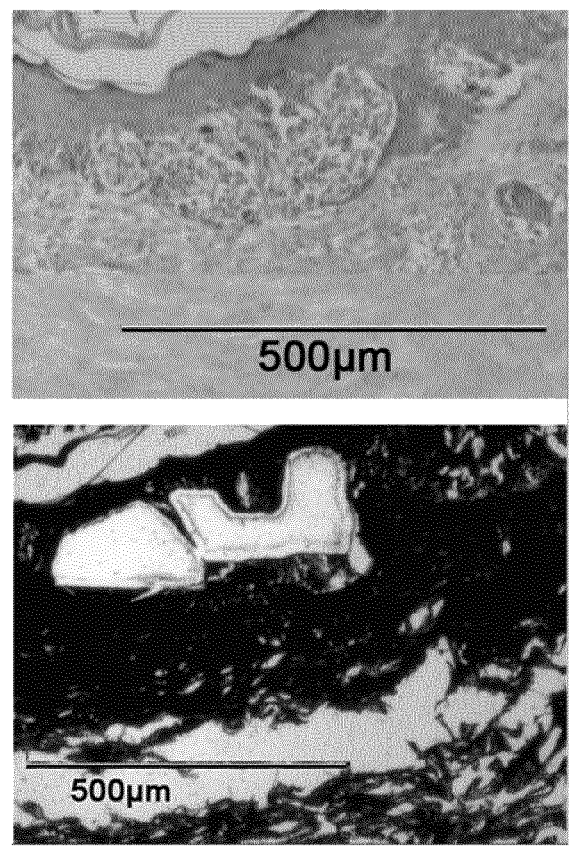

FIG. 10 Microdissection of Paraffin-Embedded Melanoma

Upper: H&E skin staining containing an area of primary melanoma. Lower: Same area after lasermicrodissection. Note the excised area of the melanoma.

Figure 11:
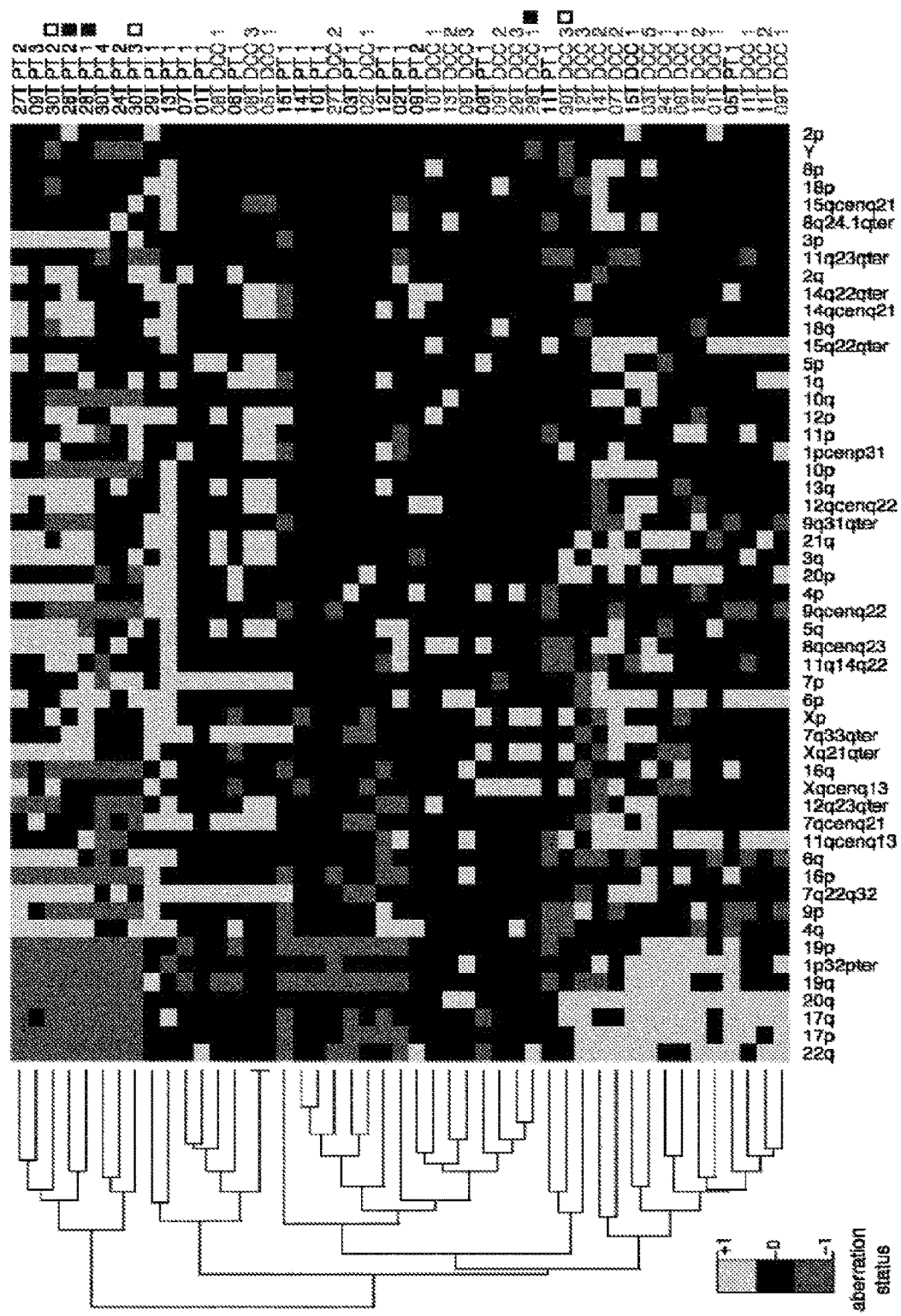

FIG. 11 Genetic comparison of DCCs and primary tumors. Cluster analysis of paired primary tumors (PT) and disseminated cancer cells (DCCs) for chromosomal aberrations (gain=+1; loss=−1). All variable regions are included. The identifiers indicate patient ID, sample type and sample index. Black and white filled squares indicate PT-DCC pairs of which several areas of the primary tumor were available.

Figure 12:
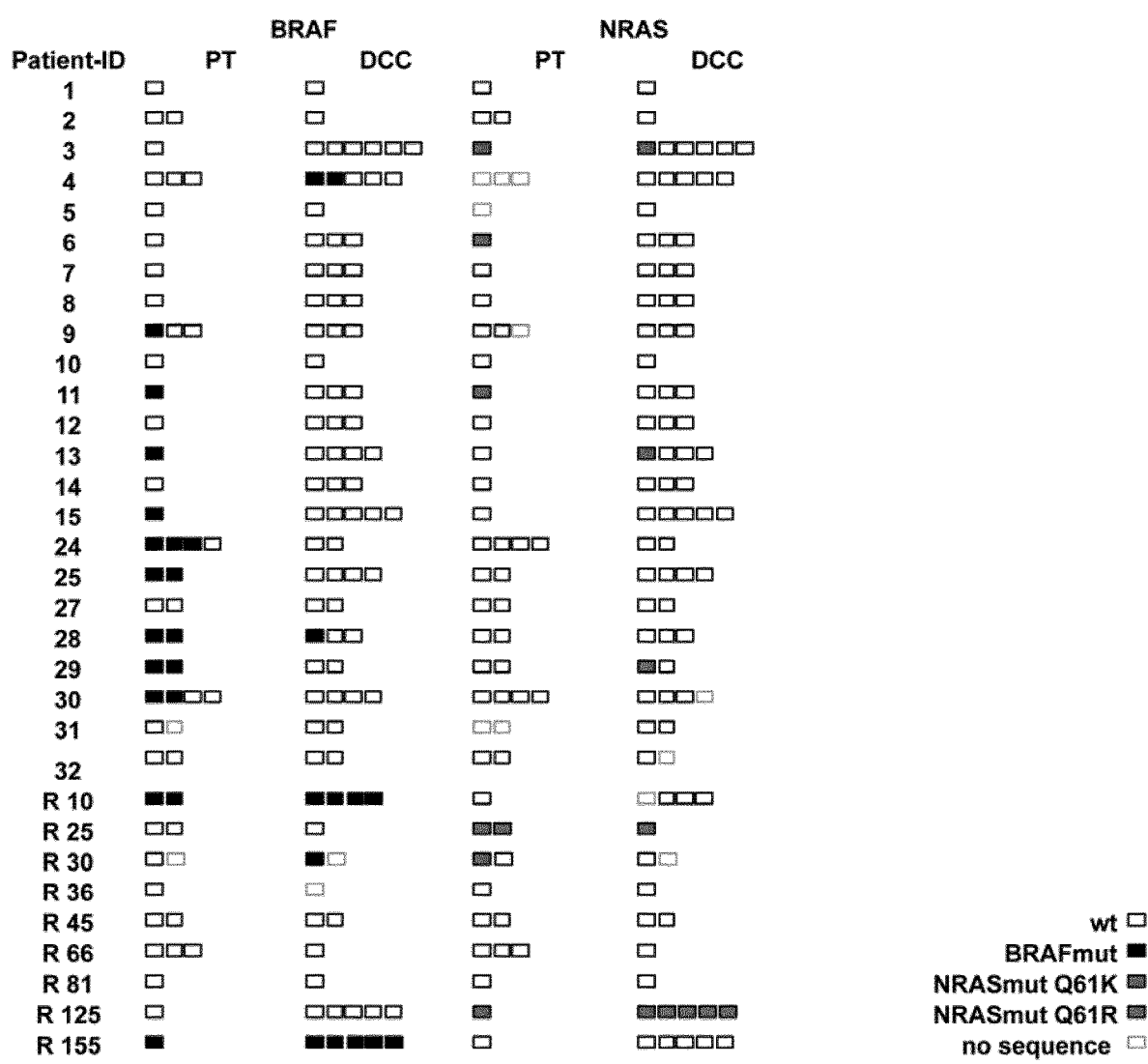

FIG. 12 Oncogenic mutations in BRAF and NRAS of paired primary tumors and DCCs. Squares indicate areas (PT) or individual cells (DCCs). Black filled squares indicate that the mutation was detected and white filled squares indicate wild type sequence. Blue and red filled squares indicate NRASmut Q61K and NRASmut Q61R, respectively. Grey lined squares indicate samples of which no sequence could be obtained.

Figure 13:
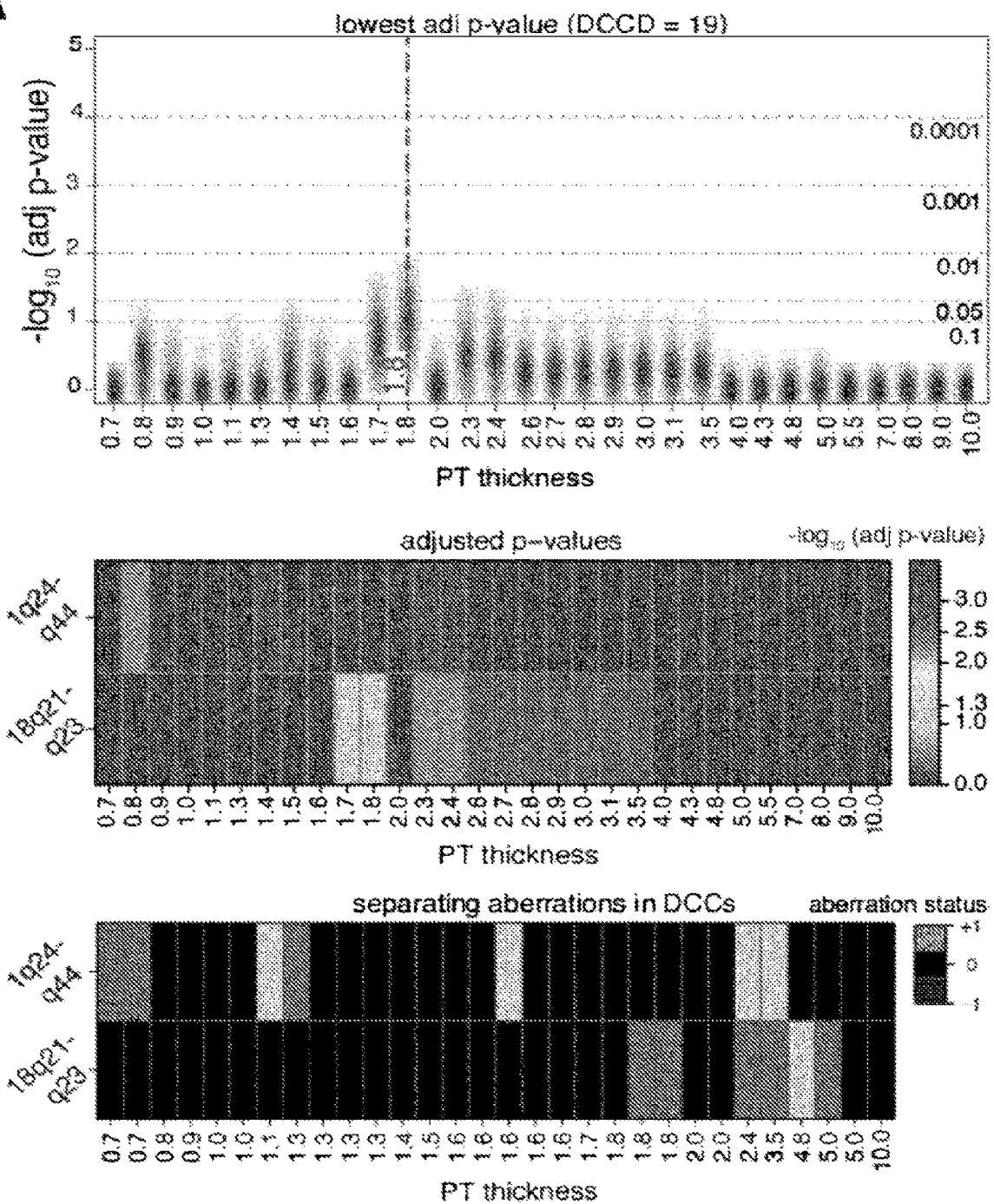
Figure 13:
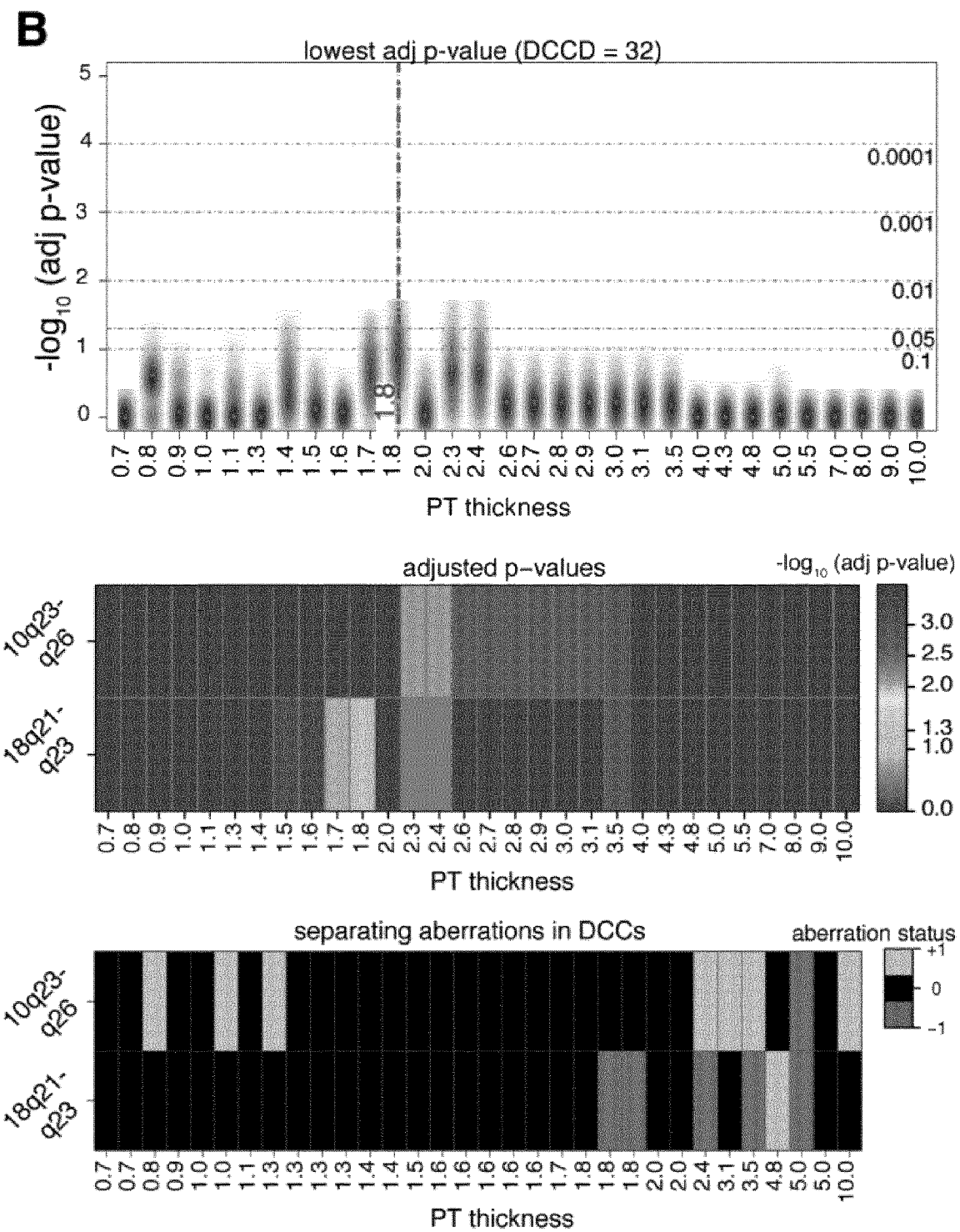
Figure 13:
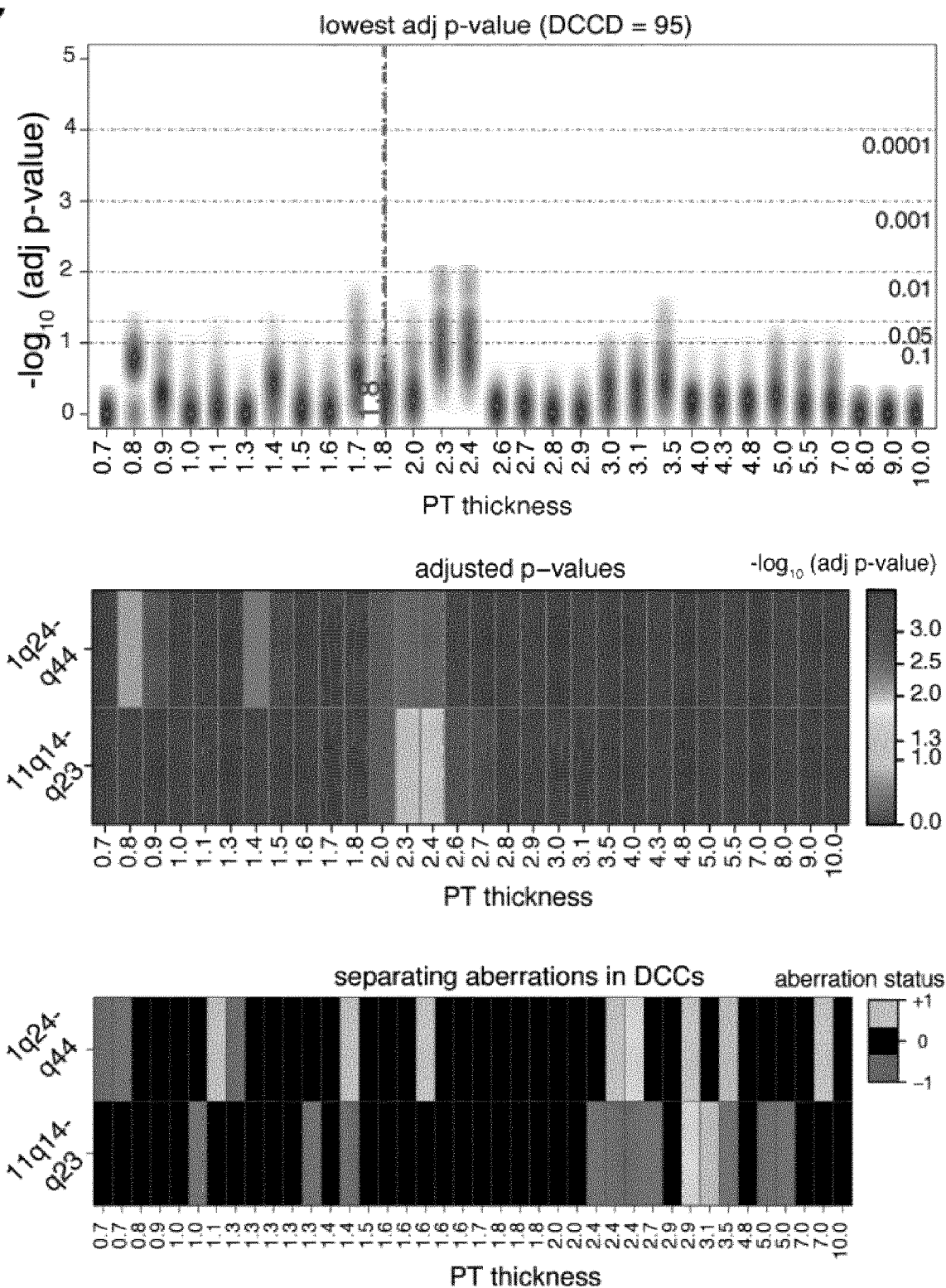

FIG. 13 (A) Top: Lowest FDR-adjusted p-values that identify genetic loci separating DCCs (n=30) from patients with DCCD<19 into two groups according to observed PT thickness. Mid: Adjusted p-values for the top two loci 18q21-q23 (p=0.065 [1.8 mm] and 0.13 [1.7 mm]) and 1q24-q44 (p=0.29 [0.8 mm]). The 5% significance level is indicated by $-\log_{10}(0.05)=1.3$. Bottom: Aberration status (gain=1, loss=−1) per cell for both loci listed according to PT thickness. (B) Same as (A) but for DCCD<32 (n=32). Top two loci: 18q21-q23 (p=0.083 [1.8 mm] and p=0.15 [1.7 mm]) and 10q23-q26 (p=0.19 [2.3, 2.4 mm]). (C) Same as (A) but for DCCD<95 (n=40). Top two loci: 11q14-q23 (p=0.082 [2.3, 2.4 mm]) and 1q24-q44 (p=0.16) [0.8 mm].

Figure 14:
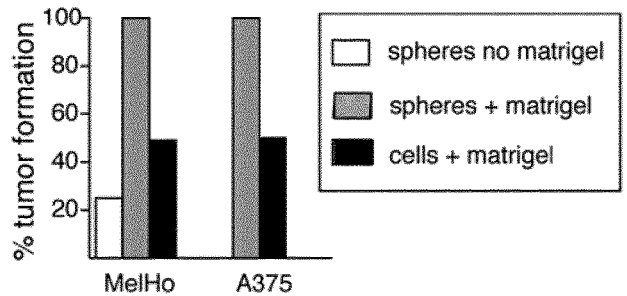
Figure 14:
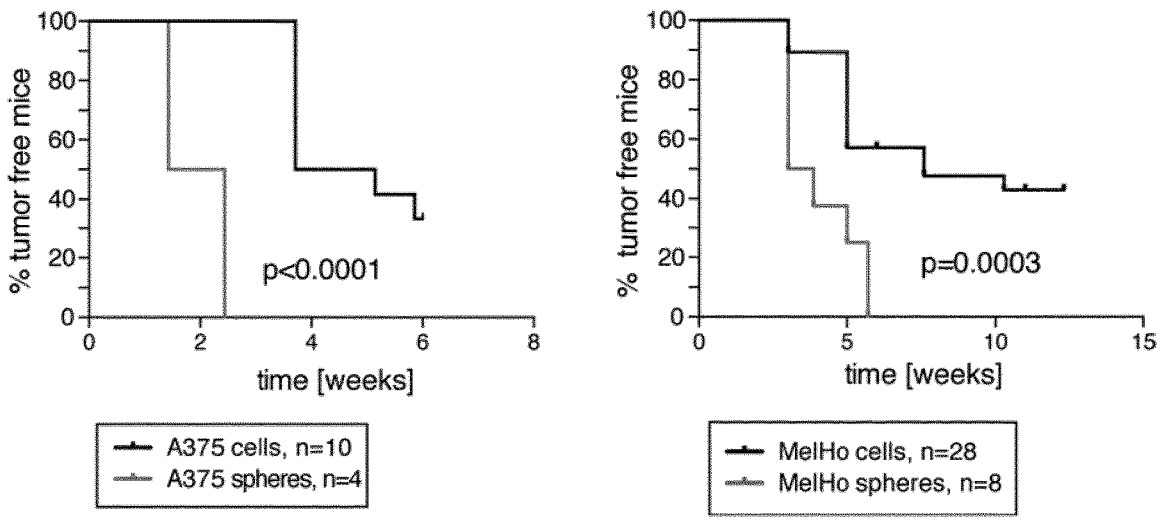

FIG. 14 Xenotransplantation of Single Cells and Spheres from Melanoma Cell Lines.

Figure 15:
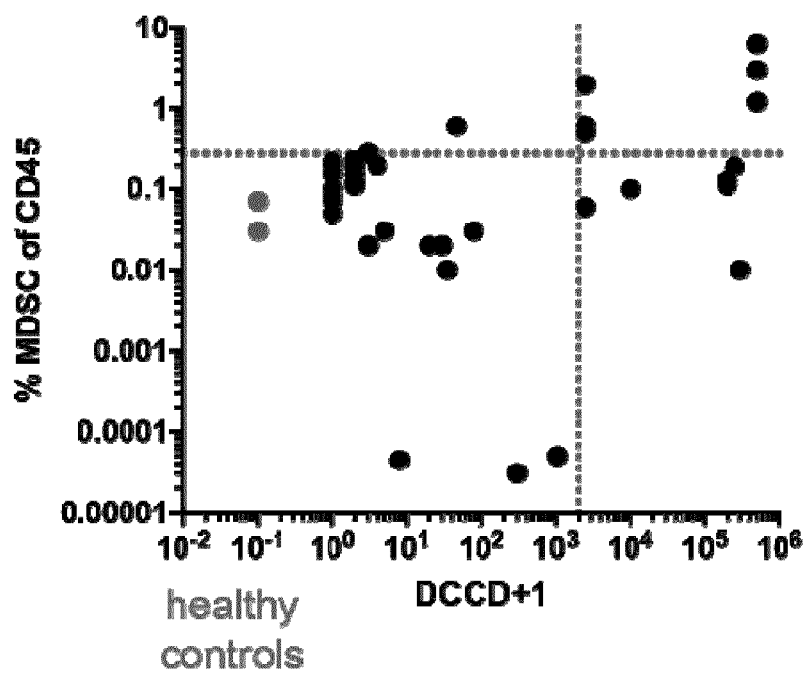
Figure 15:
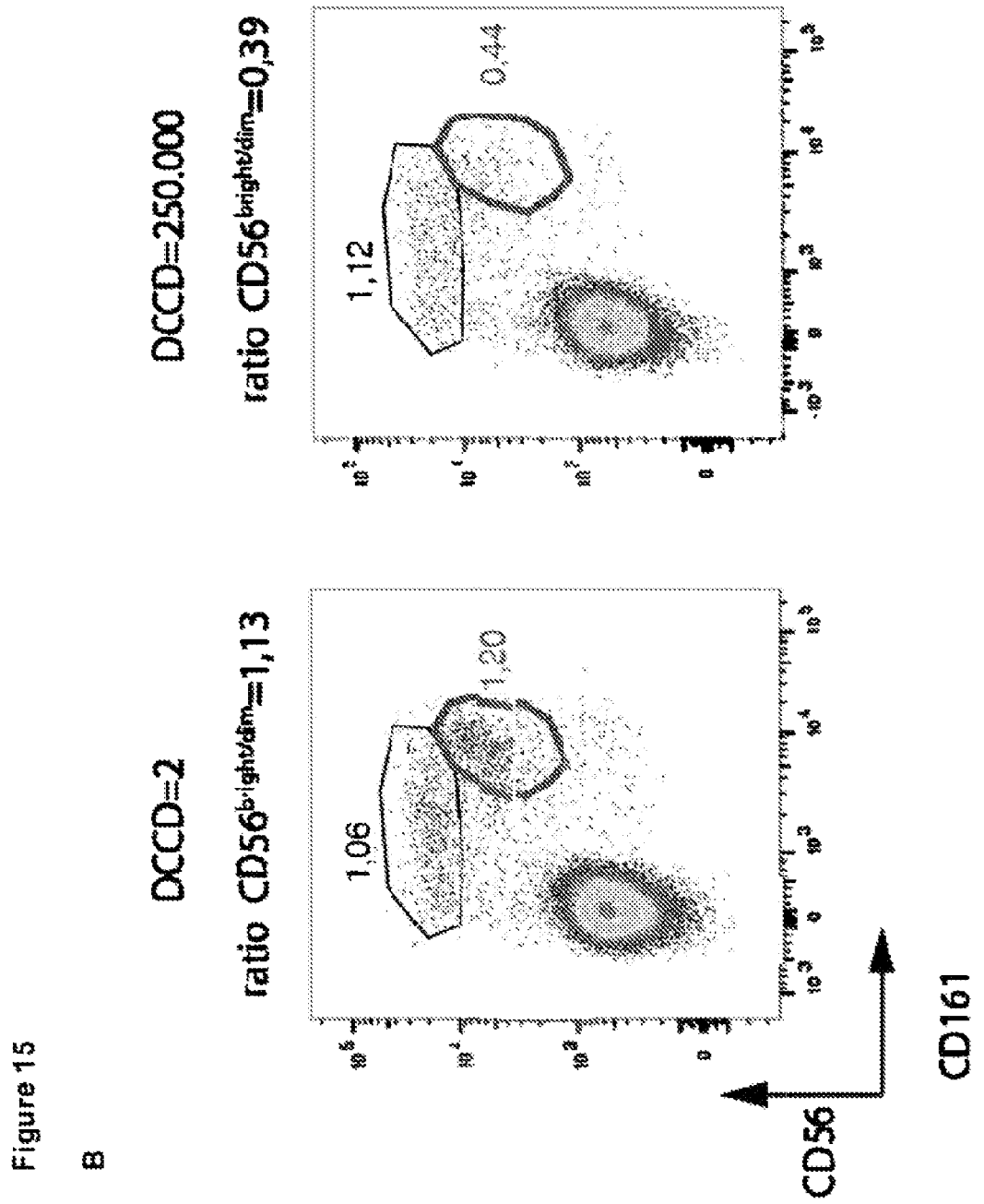
Figure 15:
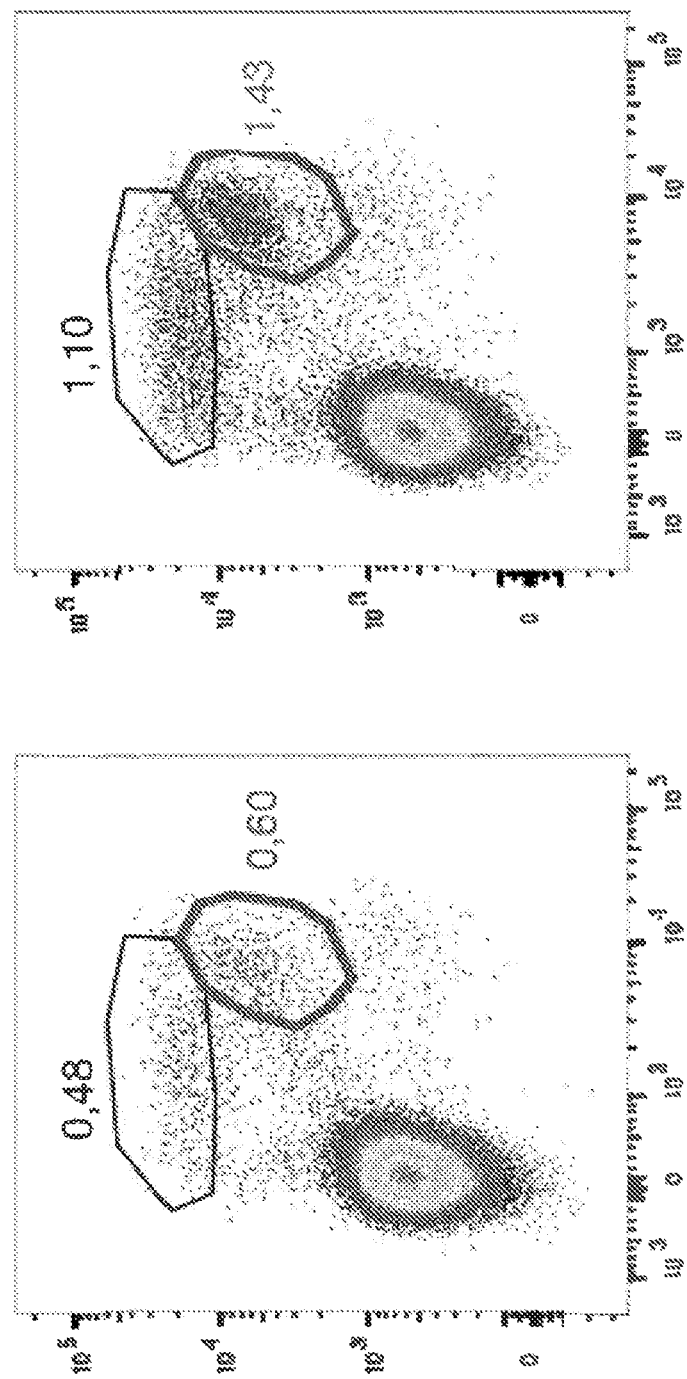

(A) groups of 3-5 spheres with or without matrigel or groups of 5 single cells with matrigel were s.c. transplanted into NSG-mice. The percentage of injection sites with tumor growth was determined. (B) Mice with s.c. injections of groups of 3-5 spheres plus matrigel or groups of 5 single cells plus matrigel were weekly palpated and the time-point of first palpation of the s.c. growing tumor was documented. p-values indicate statistical significance (log-rank test). Numbers of injection sites are given in the figures. (C) Confirmation of patient-origin of spheres/xenografts by STR analysis. All 4/7 xenografts are shown. Xenograft from LN 154 was erroneously FFPE-fixed and could not be analysed thereafter. Tri- as well as quatro-allelic patterns at D21511, D165538 and vWA loci indicate repeat number at these loci. n.d.=not detectable FIG. 15 Colonization is Associated with an Increase in MDSCs and a Decrease in Cytolytic NK Cell Numbers (A) The percentage of MDSCs in the lymph nodes (n=39) of melanoma patients was determined by flowcytometry with regard to the respective DCCD (on a log-scale). Lymph nodes from healthy controls (two patients without cancer) are included. The y-axis cut-off was set according to the highest percentage of MDSCs in lymph nodes with a DCCD of zero (on a log-scale for DCCD+1=1), as the number of control lymph nodes was too low. At a DCCD≥2000 a significantly increased number of samples showed a higher percentage of MDSCs in lymph nodes with a DCCD of zero (y-axis cut off; p<0.007, fisher's exact test). (B) Analysis of NK cells in several lymph nodes of one patient. The respective DCCD of each lymph node is given and the ratio of the percentage of $CD56^{bright}$ over cytolytic $CD56^{dim}$ cells is shown. A decrease in the ratio indicates a reduction in the percentage of cytolytic $CD56^{dim}$ cells versus non-cytolytic $CD56^{bright}$ NK cells.

Figure 16:
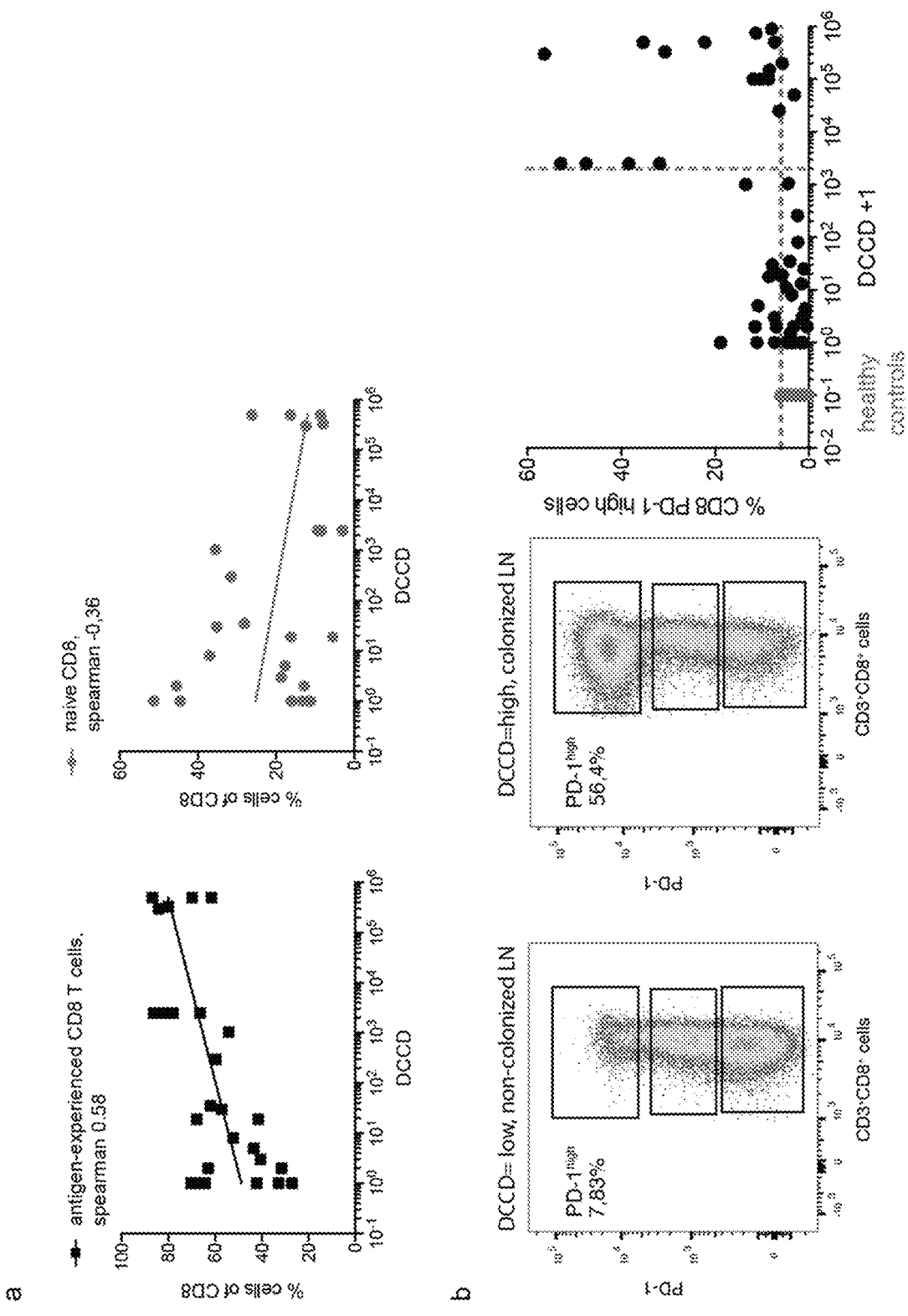
Figure 16:
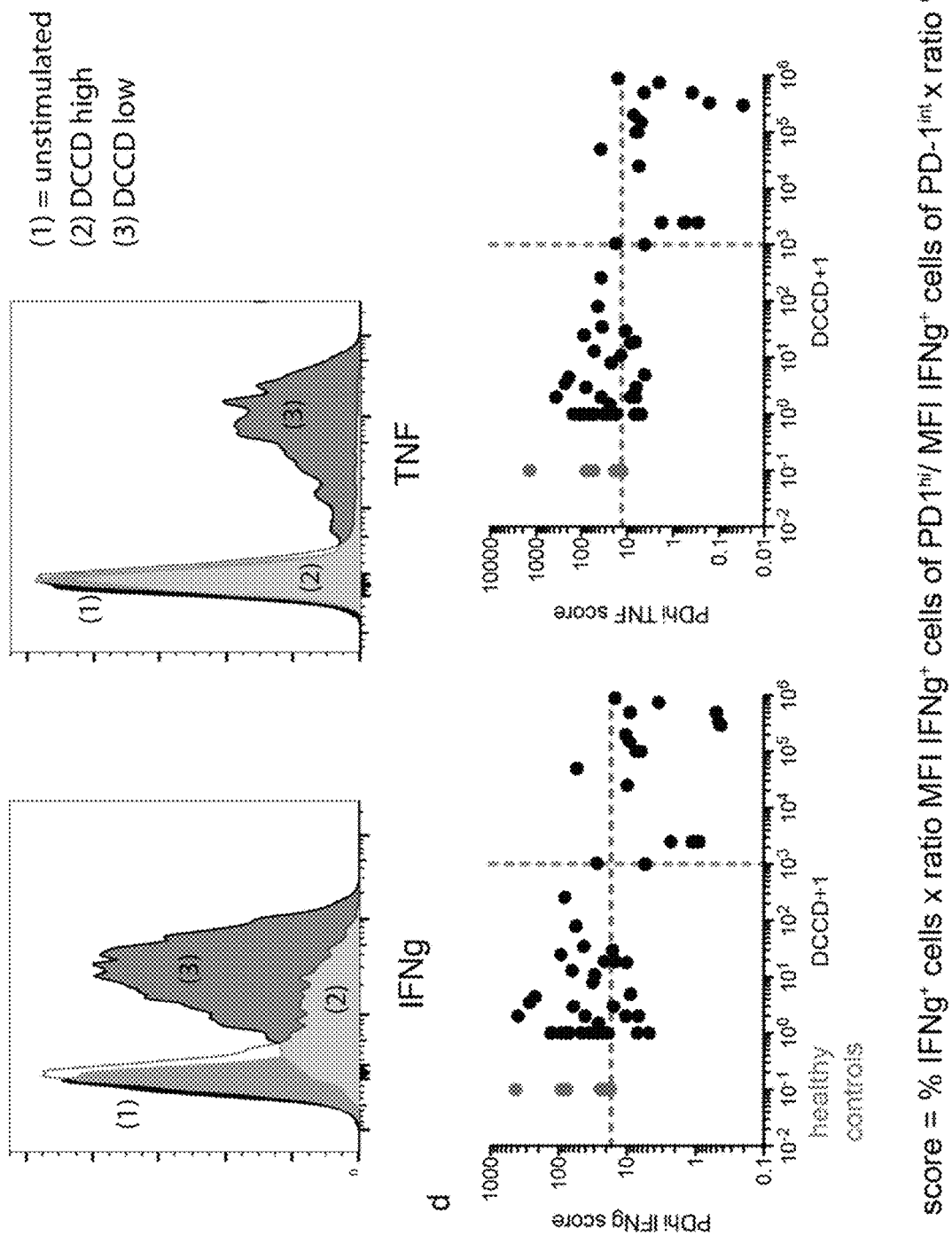

FIG. 16 Colonization of Lymph Nodes is Associated with Functional Impairment of CD8 T Cells.

(A) Lymph nodes were analyzed by flowcytometry and the percentage of antigen-experienced (CD45RA-CCR7+/−) CD8 T cells in lymph nodes of melanoma was determined as a function of DCCD of the LN. The number of antigen-experienced CD8 T cells increases with increasing DCCD (depicted on a log-scale). (B) Lymph nodes were analyzed by flowcytometry and the percentage of PD-1 and Tim-3 expressing CD8 T cells in lymph nodes of melanoma patients was determined as a function of DCCD of the lymph node. Lymph nodes from healthy controls (patients without cancer) were used as controls. The y-axis cut-off was set according to the highest percentage of PD-1 high expressing CD8 T cells in control lymph nodes. At a DCCD≥2000 a significantly increased number of samples showed a higher percentage of PD-1 high expressing CD8 T cells than in healthy controls (y-axis cut off; p<0.004, fisher's exact test). The flowcytometric dot plots illustrate representative examples of PD-1 and Tim-3 expression in lymph nodes with a DCCD<2000 and a DCCD≥2000 (C) Single cell suspensions of lymph nodes were stimulated with PMA/ ionomycin and the percentage of TNF and IFNg expressing PD-1 high and PD-1 intermediate expressing CD8 T cells and their respective median fluorescence intensity (MFI) for TNF and INFg was determined by flowcytometry. PD-1 high cells show a reduced percentage of IFNg and TNF producing cells as well as a reduced MFI for both cytokines. Unstimulated CD8 T cells were used as control and were found to be negative for TNF and IFNg production. (D) The IFNg or TNF score combines the ratio of the percentage of PD-1 intermediate plus negative CD8 T cells to PD-1 high CD8 T cells multiplied with the ratio of the percentage of cytokine producing PD-1 high to PD-1 intermediate CD8 T cells and the ratio of the median cytokine fluorescence intensity of cytokine expressing PD-1 high CD8 T cells to the median fluorescence intensity of PD-1 intermediate expressing cells. IFNg score=ratio % CD8 PD-1 int+ neg/% PD-1 high×% IFNg PD-1 high/% IFNg PD-1 int cells×ratio MFI IFNg+ cells of PD1hi/MFI IFNg+ cells of PD-1 int CD8 T cells. The lower the score the more PD-1 high CD8 T cells with reduced IFNg or TNF secretion are present. Lymph nodes from healthy controls (patients without cancer) were used as a control.

The present invention is additionally described by way of the following illustrative non-limiting examples that provide a better understanding of the present invention and of its many advantages. The following examples are included to demonstrate preferred embodiments of the invention. It should be appreciated by those of skill in the art that the techniques disclosed in the examples which follow represent techniques used in the present invention to function well in the practice of the invention, and thus can be considered to constitute preferred modes for its practice. However, those of skill in the art should appreciate, in light of the present disclosure, that many changes can be made in the specific embodiments which are disclosed and still obtain a like or similar result without departing from the spirit and scope of the invention.

A number of documents including patent applications, manufacturer's manuals and scientific publications are cited herein. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

EXAMPLE 1 TUMOR THICKNESS WHEN CELLS DISSEMINATE AND FORM COLONIES

It was investigated at what tumor thickness melanomas disseminate to the sentinel lymph node(s) (SLN) in patients with clinically node-negative disease as assessed by palpation and ultrasound. A highly sensitive and quantitative gp100-based detection method for single melanoma cells in sentinel nodes (Ulmer et al. (2005), Clin Cancer Res. 11, 5425-5432) was applied in a prospective study on 1027 melanoma patients (Ulmer et al. (2014) PLoS Med. 11:e1001604. Of these, 51% harbored gp100-positive cells (Ulmer et al. (2014) PLoS Med. 11:e1001604, whereas not a single gp100-positive cell among 70 control samples (average number of cells screened per patient $2.3 \times 10^6$). Upon comparative genomic hybridization (CGH) analysis it had been seen that 98% of randomly selected gp100-positive cells from lymph nodes harbor copy number alterations (Ulmer et al. (2014) PLoS Med. 11:e1001604). For control, 30 single leukocytes were isolated and CGH analysis was performed with none of the control cells displaying any aberration (p<0.0001; Fisher's exact test; FIG. 8).

There was a weak positive correlation (Spearman's p=0.18, p<0.0001, n=1027) between primary tumor thickness and disseminated cancer cell density (DCCD; defined as the number of gp100-positive cells per million cells in disaggregated lymph nodes). The percentage of patients with gp100-positive lymph nodes increased only marginally from T1 (≤1 mm) to T4 (>4 mm) tumors (T1: 45.8%, T2: 47.4%, T3: 54.9%, T4: 59.4%), suggesting that dissemination occurs preferentially early. The Turnbull method and a Weibull function were used (see Supplemental Information) to determine thickness at dissemination. These analyses revealed that lymphatic dissemination was restricted to 63.5% of all patients and that in 50% of cases cancer cell spread had occurred before tumors reached a thickness of 0.4 mm (95% CI 0.04-0.75 mm) (FIG. 1A). In sum, these data show that ~⅓ of melanomas disseminate lymphatically at a tumor thickness of <0.4 mm, ~⅓ at a thickness≥0.4 mm, and ~⅓ are not capable of lymphatic spread.

It was then investigated at what tumor thickness disseminated melanoma cells would have grown to a colony in SLN. To establish a DCCD representative for colonization as compared to early dissemination (first arrival) the two halves of a patient's lymph node were compared. In all cases, had lymph nodes were split and one half was analyzed by histopathology (preserving the architecture) and the other by gp100 immunocytology after disaggregation (destroying the architecture but enabling quantification; for details, see (Ulmer et al. (2014) PLoS Med. 11:e1001604). Then the DCCD was compared to histomorphological appearance of the corresponding section. Samples with a DCCD≤100 displayed spotted single cells or small nests of cells in the outer lymphatic sinus, if melanoma cells were detected at all, while at DCCD>100 melanoma cells usually expanded into inner zones of lymph nodes (FIG. 1B). Thus, colonization had probably occurred at a DCCD of ~100 whereas samples with lower DCCD comprise melanoma cells before colony outgrowth. Using a DCCD of 100 as a definition for colony formation it was found that the median tumor thickness of patients with a colonized lymph node was 22 times higher than that at seeding (DCCD≤100; FIG. 1C; 8.9 mm; 95% CI 6.8 to 14.3 mm). The risk of de novo tumor seeding steadily decreased as tumors grew, while the risk of de novo colonization increased (FIG. 1D).

EXAMPLE 2 DISSEMINATION AND SURVIVAL

To explore how the marginal difference (13.6%) in dissemination rates between thin T1 and thick T4 tumors is linked to survival, it was determined how many patients had died during the median follow-up period of 49 months (range 3 to 123 months), with 370 (36%) patients having a follow-up of ≥5 years. Although 38/83 (46%) of T1 stage melanomas harbored DCCs in the sentinel, only one patient died, consistent with previous studies (Balch et al. (2009), JCO 27, 6199-6206); Leiter et al., (2004) JCO 22, 3660-3667). In contrast 47/133 (35%) patients with T4 melanomas died (FIG. 1E; 9-year survival 88.9% for T1, and 45.9% for T4; $p<0.0001$, log-rank test). Thus, there is a discrepancy between T1 and T4 melanomas regarding seeding and death.

To address this difference, the genomic evolution of disseminating melanoma cells in a subset of 61 patients was assessed. To focus on melanoma patients in their earliest disease stages, only patients with clinically node-negative disease (no lymph node involvement by palpation and ultrasound) and no distant metastasis were included. From these patients samples for molecular analysis were taken according to availability or DNA-quality. Specifically, the selection criteria for patients and cells to be subjected to genomic and functional analysis were: (i) successful isolation and whole genome amplification of gp100+ DCCs, (ii) DCC-derived DNA passed quality control for comprehensive genomic analysis (Polzer et al. (2014) EMBO Mol Med. 6:1371-138), and (iii) sufficient follow-up time for survival analysis. The clinical baseline characteristics of these patients are provided in Table 1 (for further details on clinical sample acquisition see FIG. 9). From these patients, 90 individual cells were obtained and c their malignant origin was confirmed by CGH (FIG. 2). These DCCs displayed a large range of copy number variations ranging from 1 to 52 per cell (median=14; interquartile range=14.8). It was noted that genomic gains per cell (median=9; range=0 to 39) were more frequent than losses (median 3.5; range=0 to 21).

TABLE 1

Baseline characteristics of melanoma patients.

|  | number of patients | percentage [%] | median | range | interquartile range |
|---|---|---|---|---|---|
| gender |  |  |  |  |  |
| female | 25 | 41 |  |  |  |
| male | 36 | 59 |  |  |  |
| age [years] |  |  | 61 | 20-78 | 47.5-70 |
| Breslow's thickness [mm] |  |  | 2.35 | 0.6-10.0 | 1.3-4.08 |
| Ulceration |  |  |  |  |  |
| no | 32 | 63.9 |  |  |  |
| yes | 19 | 31.2 |  |  |  |
| not specified | 3 | 4.9 |  |  |  |

TABLE 1-continued

Baseline characteristics of melanoma patients.

|  | number of patients | percentage [%] | median | range | interquartile range |
|---|---|---|---|---|---|
| localization |  |  |  |  |  |
| extremities | 32 | 52.5 |  |  |  |
| trunk or head | 29 | 47.5 |  |  |  |
| nodal status histopathology |  |  |  |  |  |
| negative | 37 | 60.7 |  |  |  |
| positive | 24 | 39.3 |  |  |  |
| DCCD |  |  | 32 | 1-800000 | 3-177 |
| clinical stage |  |  |  |  |  |
| IA | 4 | 6.5 |  |  |  |
| IB | 15 | 24.6 |  |  |  |
| IIA | 7 | 11.5 |  |  |  |
| IIB | 5 | 8.2 |  |  |  |
| IIC | 2 | 3.3 |  |  |  |
| IIIA | 11 | 18.0 |  |  |  |
| IIIB | 13 | 21.3 |  |  |  |
| IIC | 4 | 6.5 |  |  |  |

EXAMPLE 3 GENETIC LINEAGES OF PRIMARY TUMORS AND DCCS

The standard approach to addressing outcome-associated differences between T1 and T4 melanomas employs primary tumor tissue. It assumes that the molecular characteristics of metastasis-initiating DCCs can be identified within the primary tumor, because primary tumors and DCCs are thought to be largely identical. To test this assumption, investigated the genomic profiles of primary tumors and their matched DCCs was investigated.

Primary tumors were isolated by laser microdissection (FIG. 10) and whenever possible several areas were analyzed. However, compared to other cancers such as kidney cancer (Gerlinger et al., (2012) The New England journal of medicine 366:883-892), early stage melanomas are very small, mostly precluding the assessment of subclones from different areas. Microdissected primary tumor samples (n=23, 19 patients) and micromanipulator-isolated single DCCs (n=24, 19 patients) were analyzed by CGH. Regardless of melanoma thickness, there was a striking disparity between primary tumors and matched DCCs. Unexpectedly, primary tumors from different individuals clustered closer together than individual pairs of primary tumors and their matched DCCs (FIG. 3A and FIG. 11). Primary tumors contained significantly more deletions than DCCs (FIG. 3B; p=0.003, Mann-Whitney U test) while the corresponding difference in gains was clearly non-significant (p=0.66, Mann-Whitney U test). When several areas from the same primary tumors were available, genomic heterogeneity was noted, while still clustering together (for example T28, T30 in FIG. 3 and FIG. 11) apart from their paired DCCs. These data show that DCCs disseminated before most deletions occurred and that unrelated melanomas growing in the skin converge on similar chromosomal losses.

Since BRAF and NRAS mutations are frequent (in respectively 40% and 21% of cases on average) in melanoma (Platz et al., (2008) Mol Oncol 1:395-405), it was investigated whether these mutations are transmitted from the primary tumor to DCCs. Both alleles (wild type and mutant) could reliably be retrieved from single cells with heterozygous BRAF and NRAS mutations (FIG. 3C). In paired patient samples, BRAF was mutated more frequently in primary tumors (34%) than in DCCs (15%; p=0.012, Fisher's exact test; n=32 patients; FIG. 3D and FIG. 12), whereas no significant difference was observed for NRAS mutations (15% mutated primary tumors and 11% DCCs; p=0.58; n=29 patients). For these two oncogenes, a shared wild type in 47%, a shared mutated status in 16%, and disparate mutational states in 37% of cases (FIG. 3D) was found. Among patients with mutated primary tumors, matched DCCs were mostly not sharing these mutations (shared in 3/11 for BRAF and 3/6 for NRAS), indicating that hey had disseminated before fixation within the primary site.

BRAF and NRAS mutations have been suggested to initiate melanoma (Shain, et al., (2015) The New England Journal of Medicine 373, 1926-1936) and consequently to be fully clonal. We therefore sequenced individual DCCs from patients with BRAF or NRAS mutant gp100$^+$ DCCs where we had isolated more than one DCC and tested if all sibling cells harbor the mutation. We found that gp100+ DCCs are heterogeneous in 45% and 80% for BRAF and NRAS mutations, respectively (FIG. 3E). To rule out a selective effect of the detection marker gp100, additional MCSP$^+$ melanoma DCCs we analyzed and similar results were obtained. These findings were compared with control cells (FIG. 3C) and it was noted that the expected mutant allele was not detected in a significant number of gp100$^+$ DCCs (BRAF (n=43 cells): one-sided Fisher's exact test p=0.02; NRAS (n=44): p<0.0001) and MCSP$^+$ DCCs (BRAF (n=61): p=0.003; NRAS (n=30): p=0.02). Finally, when the mutational state for primary tumor-DCC-metastases triplets or pairs of primary tumors-metastases or pairs of DCC-metastases was compared, it was found that DCCs with and without BRAF/NRAS mutations were able to form manifest metastases (FIG. 3F).

In summary, both copy number alterations and targeted mutation analysis demonstrated that primary melanomas and their paired DCCs are largely genetically disparate implying early evolutionary branching.

EXAMPLE 4 MOLECULAR CHARACTERISTICS OF DCCS AT EARLY LYMPHATIC ARRIVAL

DCCs from thick melanomas could harbor characteristic alterations responsible for the prognostic relevance of high T stage, which are absent in DCCs from thin melanomas. Therefore, a focus was set on DCCs before evident lymph node colonization as being representative of the time of arrival and their genomic profile was investigated.

Colony formation became clearly apparent at a DCCD>100 (FIG. 1B). To determine a DCCD representative for the time of arrival, i.e. clearly before colony formation, all patient samples with DCCD values below 100 were tested to define a thickness threshold at which genetic alterations characteristic for DCCs from "thick" (defined by the tested threshold) could be identified. In other words, for all samples available at a tested DCCD ranging from 1-99, it was searched for genomic aberrations that could split DCCs into two groups characterized by origin no statistical differences (p>0.05, Fisher's exact test) could be found for any tumor thickness. The lowest p-value (p=0.051; loss of 18q21-23; FIG. 4A, FIG. 13) was obtained for a DCCD of 24 and a thickness of 1.8 mm (FIG. 4A, upper), suggesting a DCCD of up to 24 that defines early arriving DCCs and 1.8 mm indicating the thickness at which melanoma cells had acquired loss of 18q21.23 within the primary site. However, survival did not correlate with loss of 18q21-23 (FIG. 4B), indicating that this change is unrelated to the impact of T stage on survival. It was also noted that the number of copy number alterations (CNAs) did not differ between DCCs arriving from thick and thin melanomas (FIG. 4C).

EXAMPLE 5 MOLECULAR CHARACTERISTICS OF COLONIZING DCCS

These data are difficult to reconcile with a model in which dissemination occurs late and genetic aberrations acquired at high tumor thickness render DCCs more metastatic. It was therefore considered the possibility that DCCs that disseminate early to the SLN, are genetically "immature", and acquire further genetic alterations during metastatic colony formation. Thus, the genetic alterations that mark the transition from immature DCCs to colony-forming DCCs in the sentinel node was investigated. It was analyzed at which DCCD DCCs could be classified in two groups according to their genetic alterations. The greatest significance (p<0.001, Fisher's exact test) was achieved for 77≤DCCD≤95 (FIG. 5A), close to the DCCD of 100, at which colonization became evident in histopathological analyses (FIG. 1B). DCCs acquired three genetic alterations including BRAF mutations, loss of chromosome 9p11-13 and loss of chromosome 9p21-24, which comprises the melanoma suppressor gene, p16 (FIG. 5B). Strikingly, BRAF mutations were observed in 1/43 (2%) cells with DCCD<95 and in 20/47 cells (42%) for DCCD≥95 (FIG. 5C; p<0.0001). Two additional significant splits were observed: at DCCD=3, involving chromosome Xq25-28 and at DCCD=19, involving 7q21-36. While Xq25-28 was frequently altered in a non-directional way, i.e. either gain or loss, in DCCs from patients with DCCD<3 (FIG. 5C), samples with a DCCD≥19 enriched the amplification (gain) of 7q21-36 (FIG. 5B, C), which harbors the MET oncogene.

Since acquisition of genetic alterations often occurs during cell division, labeling indices for the proliferation marker Ki-67 in sentinel node DCCs from patients with DCCD≤100 and DCCD>100 were compared, i.e. before and after colony formation (FIG. 5D). As double staining of MIB-1 (anti-Ki-67) and HMB45 (anti-gp100) was unsuccessful, gp100 was replaced with the melanoma-associated marker MelanA (Ulmer et al. (2005), Clin Cancer Res. 11, 5425-5432). Ki-67 expression was assessed in 37 nodes with DCCD≤100 (Group A) and 21 nodes with DCCD>100 (Group B) involving evaluation of 937 cells in total. In Group A 11.4% of cells were clearly mitotic, whilst in Group B 22.0% were dividing (p=0.0005; Fisher's exact test, FIG. 5D). Thus, a basal proliferation rate of 11% may initially enable acquisition of genetic alterations, which subsequently accelerate outgrowth.

EXAMPLE 6 COLONIZATION-ASSOCIATED ALTERATIONS, XENOTRANSPLANTATION AND PATIENT SURVIVAL

Cancer cells forming a lymph node colony displayed a characteristic signature of alterations. To test whether DCCs have tumor-initiating ability, they were transplanted into NSG-mice. First conditions for xenotransplantation of rare melanoma cells were evaluated (Quintana (2008) Nature 456, 593-598). For cell line cells and patient DCCs two approaches were compared: direct transplantation of groups of DCCs and transplantation of DCC-spheres after brief culture under melanosphere conditions. Melanospheres formed tumors in immunodeficient NSG mice more frequently than groups of single cells (p<0.0001, log-rank test; FIG. 6A, B and FIG. 14). The applied conditions supported growth from as few as one transplanted sphere (FIG. 6B) or a group size of 7 DCCs (FIG. 6C). Therefore, when the tumor-initiating ability of DCCs from SLNs was compared with a DCCD≤100 to those with a DCCD>100, spheres from samples with a DCCD≤100 and spheres or groups of single DCCs from samples with a DCCD>100 were transplanted. The number of spheres per injected site was similar for both, DCCD≤100 and >100 (p=0.27, Mann-Whitney U test; FIG. 6C). Strikingly, it was found that DCCD>100 was predictive for successful xenotransplantation (9/36 transplantations gave rise to tumors in 4/7 patients; FIG. 6C) while samples with DCCD≤100 never established tumors (0/14 injection sites in 0/5 patients). Genetic fingerprinting confirmed patient origin in all cases (FIG. 14). Furthermore, in all patient-derived xenografts either BRAF mutation, loss of 9p11-13 or 9p21-24, or gain of 7q21-36 was present (FIG. 6D). In one case, successful outgrowth was linked to the presence of a NRAS mutation.

Finally, it was investigated whether the genetic aberrations associated with colony-formation in the SLN or with tumor formation in mice were associated with clinical outcome. For this, we tested whether BRAF mutation, loss of 9p11-13/9p21-24, gain of 7q21-36, or NRAS mutation in single DCCs increased the risk for death. Indeed, this combined colonization and engraftment signature was present in 8/9 (89%) patients dying from melanoma (p=0.048, log-rank test; FIG. 6E), with BRAF mutation being the most relevant single indicator (p=0.031).

EXAMPLE 7

Colonization-Associated Alterations of the Immune Cell Microenvironment

Flowcytometric analysis of lymph node suspensions showed a correlation (Spearman's ρ=0.58, p<0.002) between the percentage of antigen-experienced CD8 lymphocytes and the DCCD indicating the presence of a tumor-cell related CD8 T cell response (FIG. 16A). However, detailed analysis of the phenotype of CD8 T cells with regard to the DCCD of the respective lymph node revealed a significantly increased percentage of PD-1 high expressing CD8 T cells at a DCCD≥2000 (FIG. 16B; p<0.0004, fisher's exact test, n=50 lymph nodes from melanoma patients, 6 control lymph nodes from healthy controls). PD-1 is induced on T cells in response to T cell activation, but is downregulated once the immune response has eliminated the antigen. If the antigen does not vanish, as is the case during chronic viral infections, PD-1 is not downregulated and T cells lose effector functions in a hierarchical manner: IL-2 production, high proliferative capacity and cytolytic activity are lost first, followed by impaired cytokine production. In this regard, CD8 T cells expressing high levels of PD-1 are considered as terminally exhausted T cells. These cells co-express Tim-3 (FIG. 16B), another marker of exhausted T cells and have an impaired ability for cytokine production. Furthermore, the percentage of cells that are able to produce IFNg and TNF was reduced in the PD-1 high population as compared to the PD-1 intermediate expressing population, demonstrating that PD-1 high cells are exhausted CD8 T cells (FIG. 16C). Analysis of 50 lymph nodes from 26 melanoma and 6 lymph nodes from 6 non-tumor patients, showed that the score for IFNg and TNF was significantly decreased at a DCCD≥2000 (FIG. 16D; both p<0.0001, fisher's exact test). The IFNg or TNF score combines the ratio of the percentage of PD-1 intermediate and negative CD8 T cells to PD-1 high CD8 T cells multiplied with the ratio of the percentage of cytokine producing PD-1 high to PD-1 intermediate CD8 T cells and the ratio of the median cytokine fluorescence intensity of cytokine expressing PD-1 high CD8 T cells over the median fluorescence intensity of PD-1 intermediate expressing cells. A decrease in the score indicates an increased number of exhausted CD8 T cells and consequently a loss of CD8 T cell function. The presence of PD-1 high CD8 T cells was directly linked to the local number of DCCs in the lymph node as several lymph nodes of the same patient with a DCCD<2000 did not show this increase in exhausted CD8 T cells. In addition to the loss of CD8 T cell function, the local functional impairment of anti-tumoral immune responses was reflected at the level of recruitment of immune suppressive immature MDSCs (FIG. 15A) and loss of cytolytic NK cell function (FIG. 15B). Specifically a significantly increased percentage of immature MDSCs was observed in lymph nodes with a DCCD≥2000 (FIG. 15A; p<0.007, fisher's exact test, n=39 lymph nodes from melanoma patients, 2 control lymph nodes from healthy controls). As for the loss of CD8 T cell function, the loss of cytolytic NK cell function evident by a decrease in the ratio of non-cytolytic CD56bright to cytolytic CD56dim cells, was directly linked to the local DCCD in the respective lymph node, as revealed by side-by-side comparison of several lymph nodes of one patient. In summary these data show that the observed changes in the CD8 T cell and NK cell function as well as the recruitment of MDSCs resemble a local reaction to the local tumor cell load.

Methods

Patients

We used data from 1027 melanoma patients from Tubingen with clinically node negative (as assessed by palpation and ultra-sound) melanoma who underwent sentinel node biopsy to describe the association between thickness and melanoma spread (Ulmer (2014) PLoS Med 11, e1001604). Molecular studies and BRAF/NRAS mutational survival analysis included patients recruited in Tubingen and Regensburg. Informed written consent was obtained from all patients. The study was approved by the ethics committees of the Universities Tubingen (ethics vote number 5/99) and Regensburg (07-079).

For assessment of microenvironmental changes data was obtained from patients from Regensburg who underwent complete lymph node dissection.

Cell Lines

The melanoma cell lines A375 and MelHo were used (obtained from the Leibniz Institute DSMZ-German Collection of Microorganisms and Cell cultures). MelHo is listed in the ICLAC-database for mis-identified cell lines due to unclear patient-origin, but was used as the cell line is heterogenic for the exon 15 mutation c1799T>A (BRAF). The origin of the cell lines was verified by short tandem repeat (STR) analysis (Cell-ID™, Promega). The cell lines 70-61 and 102-4 were developed from DCC-derived xenografts and are exon 15 mutation c1799T>A (BRAF) and exon 3 mutation c181C>A (NRAS) mutated, respectively, as determined by Sanger sequencing (Sequiserve, Vaterstetten, Germany). Their patient-origin was verified by short tandem repeat (STR) analysis (Cell-ID™, Promega), their melanoma-origin by a human pathologist and their aberrant genotype by CGH. A375 and MelHo were maintained in DMEM, 10% FCS, 0.5× Pen/Strep; 102-4 and 70-61 in RPMI, 10% FCS, 0.5× Pen/Strep. All cell lines were routinely tested for mycoplasma and were found to be negative.

Controls

Control lymph nodes (n=70) were obtained from 60 non-melanoma patients (47 skin-draining nodes from non-malignant conditions, 6 sentinel nodes from non-melanoma skin cancer patients, and 17 nodes from non-small cell lung cancer patients) and disaggregated, stained and evaluated identically to the melanoma-derived lymph nodes. After screening $2\times10^6$ lymphocytes, the control lymph node status was revealed to the observer, and screening of the samples was continued until completion, unlike to the melanoma patient samples.

Lymph Node Disaggregation and Immunocytology

Quantitative immunocytology was performed as described (Ulmer (2014) PLoS Med 11, e1001604 and Ulmer (2005) Clinical cancer research: an official journal of the American Association for Cancer Research 11, 5425-5432) after sentinel node biopsy using unfixed lymph node tissue. Briefly, the lymphatic tissue was cut into 1-mm pieces and disaggregated mechanically into a single-cell suspension by rotating knives (DAKO Medimachine, DAKO), washed with HBSS (Life Technologies, Heidelberg, Germany) and centrifuged on a density gradient made of a 60% Percoll solution (Amersham, Uppsala, Sweden). Cells were counted using a Neubauer counting chamber. Per slide, $10^6$ cells from the interphase were then given onto adhesion slides (Menzel, Braunschweig, Germany) in a volume of 1 mL PBS. After sedimentation for 1 hour, the slides were air-dried overnight. Immunocytological staining was carried out with the alkaline phosphatase/anti-alkaline phosphatase method using primary antibodies against gp100 (HMB45, DAKO) and as primary antibody and 5-bromo-4-chloro-3-indolyl phosphate/NBT (DAKO) as substrate, yielding a blue reaction product. A lymph node was defined as gp100 positive if it contained at least one gp100-positive cell. The number of positive cells per million lymphocytes was recorded. Positive samples were stored for a maximum of 4 days in PBS at 4° C. until cell isolation for whole genome amplification. For the isolation of living DCCs, single cells were stained with an anti-human MCSP (melanoma chondroitin sulfate proteoglycan, clone 9.2.27, BD Pharmingen) according to the manufacturers recommendations and detected by indirect immunofluorescence (goat anti-mouse-Cy3, Jackson). After washing, MCSP$^+$ cells were isolated using a micromanipulator (Eppendorf Patch-Man NP2) and transplanted.

Flowcytometric Assessment of Microenvironmental Changes

Single cells of disaggregated lymph nodes were stained with viability dye eFlour 780 (ebioscience) for live/dead cell discrimination. To reduce non-specific binding single cell suspensions were incubated for 10 min at 4° C. with PBS/10% AB-serum (Bio-Rad, subsequently stained with fluorescence-labeled antibodies for 30 min at 4° C., washed two times with PBS/2% FCS/0.01% NaN$_3$ and fixed with Fluoro-Fix buffer (Biolegend). Cells were analyzed on a LSR II machine equipped with FACS DIVA 5.03 software (BD Bioscience) and data was analyzed with FloJo 8.8.6 (Treestar). The cells were stained using the following antibodies (Biolegend). For MDSC identification: CD45 (HI30), CD3 (HIT3a), CD19 (HIB19), CD56 (HDC56), HLA-DR (L243), CD33 (WM53), CD11b (ICRF44). For NK cell identification: CD45 (HI30), CD3 (Sk7), CD56 (HDC56), CD161 (HP-3610). For CD8 T cell identification: CD45 (HI30), CD3 (Sk7), CD8 (HIT8a), CD45RA (HI100), CCR7 (G043H7), PD-1 (EH12.2H7), Tim-3 (F38-2E3), TNF (Mab11), IFNg (4S.B3).

For measurement of IFNg and TNF production single cells of disaggregated lymph nodes were stimulated for 4 hours with PMA (long/ml, Sigma) and ionophore (1 μg/ml, Sigma) in the presence of 1× Brefeldin A (Biolegend). Single cells of disaggregated lymph nodes were stained with viability dye eFlour 780 (ebioscience) for live/dead cell discrimination. To reduce non-specific binding single cell suspensions were incubated for 10 min at 4° C. with PBS/10% AB-serum (Bio-Rad), subsequently stained with fluorescence-labeled antibodies for 30 min at 4° C., washed two times with PBS/2% FCS/0.01% NaN$_3$, fixed and permeabilized with Fixation buffer (Biolegend) and Perm Wash Buffer (Biolegend), respectively. To reduce non-specific binding single cell suspensions were incubated again for 10 min at 4° C. with PBS/10% AB-serum and subsequently stained with fluorescence-labeled antibodies for INFg and TNF in Perm Wash Buffer for 30 min at 4° C. and washed two times with Perm Wash buffer.

Comparison Between Single Cells and Sphere Transplantations

Single cells of disaggregated sentinel lymph nodes were plated in 6 cm poly-HEMA (12 mg/mL, Sigma-Aldrich) coated cell culture plates (Sigma-Aldrich) at a density of 200,000 viable cells/mL. Cells were grown in a serum-free DMEM/Ham's F12 basal medium (PAN Biotech GmbH), supplemented with 0.5× Pen/Strep (PAN Biotech GmbH), 0.5% BSA (VWR-Biochemical), 10 μg/mL insulin (Sigma-Aldrich), 10 nM HEPES (Sigma-Aldrich), 1× B27 (Life Technology GmbH), 10 ng/mL EGF (Sigma-Aldrich) and 10 ng/mL bFGF (Sigma-Aldrich), 4 μg/mL heparin (Sigma-Aldrich), 5 ng/mL GRO-α (R&D Systems), 20 ng/mL HIL-6 (kindly provided by S. Rose-John) and 0.2% Methylcellulose (Sigma-Aldrich). Cultures were incubated at 37° C. and 5% CO$_2$ and 7% O$_2$. Sphere growth was weekly monitored. To generate spheres from melanoma cell lines (MelHo, A375 maintained in DMEM, 10% FCS, 0.5× Pen/Strep), single cells were plated at a density of 10,000 viable cells/mL on poly-HEMA coated cell culture plates in the same medium as for sentinel lymph node cells, but without HIL-6 and GRO-α. Spheres were isolated manually.

Xenotransplantation

Spheres or MCSP cells from disaggregated sentinel lymph nodes were collected using a micropipettor or micromanipulator and pooled in a microwell (volume 10-15 μl, Terasaki). Microwells were pre-coated over night with 12 mg/mL poly-HEMA (Sigma-Aldrich) at RT. Single cells were transplanted in a final volume of 30 μl and 25% high-concentration matrigel (BD Biosciences) as published before (Quintana (2008) Nature 456, 593-598). Cells were injected with an insulin syringe (Microfine, 29G, U-50, BD Biosciences) sub-cutaneously into NOD.Cg-Prkdc$^{scid}$ IL2rγ$^{tmWjl/Sz}$(NSG, 6-8 weeks old, males and females). Mice were purchased from the Jackson Laboratory and maintained under specific-pathogen free conditions, with acidified water and food ad libitum in the research animal facilities of the University of Regensburg, Germany. All approved experimental animal procedures were conducted to German federal and state regulations. Mice were palpated every week at the site of injection. Melanoma-origin of xenografts was verified by a human pathologist and patient-origin was authenticated using short tandem repeat (STR) analysis (Cell-ID™, Promega). Due to the whole genome amplification (Klein et. al. 1999) of samples prior to STR analysis, which includes restriction digest by Mse I, only the STR loci TH01, D21S11, D5S818, D13S317, D16S538 and vWA can be used for detection. Amplified fragments were detected using 3100-Avant Genetic Analyzer (Applied Biosystems). Fragment sizes were determined manually using Cell™ ID Allelic Ladder and Cell™ ID Bins 1.0 provided by Promega.

Ki-67 Labeling of DCC

For immunofluorescence staining cells were incubated with primary antibodies against Melan A/MART-1 (Epitomics rabbit monoclonal dilution 1:100) and Ki-67 (DAKO MIB-1 mouse monoclonal 1:50) overnight at 4° C. As secondary antibodies we used Alexa Fluor 555 (Invitrogen, donkey anti-rabbit) and Alexa Fluor 488 (Invitrogen, donkey anti mouse). The nucleus was stained with DAPI (blue), Melan A with Alexa Fluor 555 (red) and Ki-67 with Alexa Fluor 488 (green). Counterstaining was performed with 4'd-diamidino-2-phenylindole (DAPI) in mounting medium (Vector, Vectashield).

DNA Extraction and Microdissection of Primary Tumor Areas

DNA was extracted from paraffin-embedded tumor blocks after highlighting tumor areas by a pathologist (P.R.). The PALM Microbeam system (Bernried) was used for microdissection and catapulting. DNA was processed as previously described (Klein (2002) Lancet 360, 683-689; Klein (2002) J Exp Med 196, 359-368).

Whole Genome Amplification and Single Cell Comparative Genomic Hybridization

Whole genome amplification (WGA) was performed as previously described by Klein (2002) Lancet 360, 683-689; Klein (2002) J Exp Med 196, 359-368 and Klein (1999) PNAS 96, 4494-4499). The method is now commercially available as kit (Ampli1, Silicon Biosystems).

Single Cell Comparative Genomic Hybridization

Single cell CGH was performed as previously described by Czyz (2014) PloS one 9, e85907; Klein (2002) Lancet 360, 683-689; Klein (2002) J Exp Med 196, 359-368). For most samples we used chromosomal CGH, as it is a very robust method, well established for single cells. We carefully compared both methods. We found a good agreement between array CGH and chromosomal CGH when applied to same samples (see Czyz et al., 2014). While aCGH may detect more changes (mainly for aberrations <10 Mb), the overall picture for aCGH and cCGH is very similar. For cases where we used aCGH, the resolution was adjusted to that of cCGH.

Mutation Analysis of BRAF and NRAS

Mutations in NRAS and BRAF genes were detected using Sanger sequencing (Sequiserve, Vaterstetten, Germany) after gene specific amplification from WGA samples. The primers for BRAF exon 15 analysis were as follows: forward 5'-TCCAGACAACTGTTCAAACTG (SEQ ID NO: 3) and reverse 5'-CTCTTCATAATGCTTGCTCTG (SEQ ID NO: 4), encompassing the mutations of codon 600 (V600E, previously called V599E; V600K, V600R). Cycling temperatures were set to 94° C. (2 min), 60° C. (30 sec) and 72° C. (2 min) for one cycle; 94° C. (15 sec), 60° C. (30 sec) and 72° C. (20 sec) for 14 cycles; 94° C. (15 sec), 60° C. (30 sec) and 72° C. (30 sec) for 24 cycles and an additional final extension step at 72° C. (2 min). The PCR primers for NRAS exon 3 codon 61 analysis were: forward 5'-GGCAAATA-CACAGAGGAAGC (SEQ ID NO: 5) and reverse 5'-ACCCCCAGGATTCTTACAGA (SEQ ID NO: 6) encompassing the common mutations of codon 61: Q61K and Q61R. The PCR cycler was set to 94° C. (2 min), 63° C. (30 sec) and 72° C. (2 min) for one cycle; 94° C. (15 sec), 63° C. (30 sec) and 72° C. (20 sec) for 14 cycles; 94° C. (15 sec), 63° C. (30 sec) and 72° C. (30 sec) for 24 cycles and an additional final extension step at 72° C. (2 min). PCR products were sent for sequencing to Sequiserve, Vatterstetten. The mutation assay was established using single cells or genomic DNA of cell lines with known exon 15 mutation c1799T>A (BRAF) and exon 3 mutation c181C>A (NRAS). The mutant BRAF allele was detected in 62% (70-61), 84% (MelHo) of detected sequences over all analyzed single cells and in 61% (70-61) and 86% (MelHo) in bulk genomic DNA. The mutation NRAS allele was present in 59% of all single cells and 46% of the bulk genomic DNA. When several areas of the primary tumor were microdissected or several DCCs were isolated, the primary tumor or DCCs were called positive if one of the areas or DCCs harbored the BRAF or NRAS mutation.

Statistical Analysis

Unless otherwise stated, statistical significance was assumed for $p<0.05$, with all tests performed two-sided.

Thickness when Tumor Cells Disseminate

Using Turnbull's method we determined that 42.3% of all melanomas had disseminated before reaching a thickness of 0.4 mm (FIG. 1B). Regardless of tumor thickness, dissemination was restricted to 63.5% of melanoma. A modified Weibull model with an upper limit less than 100% (FIG. 1B) predicted an asymptote of 63.5% (95% CI 53.5 to 73.4%) and revealed that 50% of seeding tumors had spread before 0.4 mm (95% CI 0.04-0.75 mm).

To determine the proportion of disseminating and colonizing tumors as a function of tumor thickness the data were fitted non-parametrically by maximum-likelihood according to the iterative method of Turnbull (42) for interval-censored data. Since it is unknown, at which tumor thickness an event occurred or will occur, all data are either left or right censored. For dissemination the obtained estimate is fitted with the maximum-likelihood-method by a Weibull distribution with a fraction of patients without dissemination in order to obtain interpretable parameter estimates for the asymptotic proportion of disseminating tumors and the median thickness of disseminating tumors.

Tumor Thickness when DCCs Colonize

Of the 525 DCC-positive patients, the number of samples with a DCCD>100 increased with tumor thickness as a Weibull cumulative distribution function with a median of 8.9 mm (95% CI 6.8 to 14.3 mm), i.e. 22 times higher than the median thickness at seeding (FIG. 1C). For colonization the obtained estimate is fitted by a Weibull distribution. Explicit formulas for the Weibull distribution were used to calculate the hazard rates. The hazard function describes the instantaneous risk per unit thickness for an event (dissemination, colonization) for those tumors, for which the event has not yet occurred. For example, the hazard rate of 1 per mm (0.2 per mm) indicates that the tumor needs to grow 1 mm (5 mm, respectively) on average for the event to occur.

Comparison of Primary Tumors and DCCs

The frequency statistics of gains and losses between primary tumors and DCCs were determined with a Mann-Whitney U test. Statistic significance for BRAF/NRAS mutations in paired primary tumors and DCCs was determined with Fisher's exact test.

Identification of Mutational Patterns

Mutational patterns that discriminate between primary tumors and DCCs, DCCs from patients with thin and thick melanomas and low and high DCCD, as well as with and without BRAF/NRAS mutations were identified by Fisher's exact test. Only loci with high enough cross-sample standard deviation (>0.25) allowing for sufficient class discrimination were considered. In FIG. 2A only the ten most variable loci in terms of the maximum variance across samples without accounting for primary tumor/DCC class labels were included. Multiple testing corrections were derived according to Benjamini and Hochberg (FDR).

Identification of Discriminating Mutations

To identify the thickness at which critical alterations may have been acquired within the primary tumor, we split DCCs of samples with a DCCD≤100 into two groups according to observed different thickness values and identified genomic alterations that clearly showed non-random distributions across these groups, i.e. lead to low Fisher's test p-values. DCCD- and thickness thresholds associated with low p-values might indicate primary tumor sizes and genomic alterations that facilitate direct dissemination to lymph nodes.

We tested all DCCD thresholds below 100 to define the population of DCCs before colonization and found evidence for statistical differences for certain thickness thresholds for DCCD limits 19, 24, 32, and 95; however, none reached 5% significance.

A similar approach was taken to determine limiting DCCD thresholds and genetic alterations that mark the transition from early DCCs to colony-forming DCCs in the sentinel node. We asked for all genetic regions at which DCCD they would split the DCCs into two groups. This DCCD would then separate DCCs with and without that specific alteration and indicate the number of cells at which an alteration critical for disease progression has been acquired.

Robustness of results with respect to sample size was estimated by systematically excluding two cells from the analysis (subsampling with enumeration of all cases). The respective adjusted p-value distributions were kernel density-smoothed and plotted in 2D. Hierarchical cluster analyses were performed using euclidean distance and complete linkage. Analyses were conducted using R (available on the world wide web at R-project.org) or JMP (available on the world wide web at jmp.com).

Survival Analysis

All survival statistics and tumor-free time of xenografts were calculated using a log-rank test (JMP, IBM SPSS Statistics 20 for Windows or GraphPad Prism 6.0 software for OSX).

Results

This study provides a compelling molecular model that accounts for the ectopic evolution in the spread of early systemic cancer. For the first time the the tumor extent at which metastatic dissemination of a human cancer occurs is reported; it is based on highly sensitive, direct detection of DCCs rather than being inferred from tumor growth rates (Engel (2003) European journal of cancer 39, 1794-1806; Friberg (1997) Journal of surgical oncology 65, 284-297; and Yachida (2010) Nature 467, 1114-1117}. The median thickness of seeding melanomas was 0.4 mm (95% CI 0.04-0.75 mm), much earlier than previously thought. However, the 9-year death rate for T1 melanomas was 11%, which was much lower than the seeding rate at this stage (46%), whereas seeding and death rates in T4 melanomas were similar (59% vs. 54%). This observation indicates that, while dissemination might occur early, additional factors are needed to generate lethal metastatic disease.

To address the discrepancy between seeding and death rates of thin melanomas primary tumors and matched DCCs were compared, which were clearly different for CNAs independent of tumor thickness. Primary tumors displayed a differential loss of chromosomal material strongly suggesting that DCCs disseminated before these losses had occurred. This conclusion is unaffected by potential limitations of the used technology, i.e. CGH as compared to next-generation sequencing (NGS). Extensive controls (FIG. 3C and FIG. 8) demonstrate that the applied single cell technology retrieves cellular karyo- and genotypes from clinical samples with much higher reliability and robustness (Polzer (2014) EMBO molecular medicine 6, 1371-1386} than NGS approaches for single cells which are prone for random allelic dropouts (Lohr (2014) Nature biotechnology 32, 479-484; Ni (2013) PNAS 110, 21083-21088}. Thus, it was shown that melanoma cells disseminated before specific CNAs and specific mutations (such as BRAF, discussed below) were acquired in the primary irrespective of the notion that some aberrations (shared or not shared) remained undetected by our approach. CNAs were analyzed as they best reflect cancerous progression as opposed to point mutations (Bauer (2006) Dermatologic therapy 19, 40-49; Shain (2015) The New England journal of medicine 373, 1926-1936}, which are frequently detected also in benign lesions in contrast to CNAs (Hafner (2010) PNAS 107, 20780-20785; Klein (2013) Nature 501, 365-372; Shain (2015) The New England journal of medicine 373, 1926-1936). For this reason, the study did not address dissemination relative to the acquisition of non-CNA alterations except of BRAF or NRAS.

The conclusion of cancer cell spread occurring early in the somatic progression of a melanoma is also consistent with the possibility that minor sub-clones exist in the primary tumor that are more similar to DCCs but escaped detection by analysis of microdissected samples. Such subclones, if existing, are genomically immature as compared to the analyzed predominant clone; existence and dissemination (even if occurring at high T stage) of such subclones would then indicate that genomically immature cells display a higher propensity to spread than parallel existing mature cells. However, combined with the documented early seeding at 400 µm, it is more likely that melanomas often disseminate early in tumor formation and early in genomic maturation.

It was tested whether late-disseminating, genetically more mature cells are detected that may be more successful founder cells of a metastasis than early-disseminating cancer cells. For this, DCCs were analyzed before colony formation from patients with thick melanomas. They were compared with pre-colonizing DCCs from thin melanomas, but no differentiating CNAs could be identified. Also the number of CNAs did not differ between pre-colonizing DCCs from thin vs. thick melanomas.

This led to the conclusion that DCCs acquired critical alterations within lymph nodes. Indeed, growth beyond a DCCD of 77-95 was associated with losses on chromosome 9p, comprising the region of p16, and acquisition of BRAF mutations. Before that point, at DCCD=19 there was enrichment for the gain of chromosome 7q, comprising the MET oncogene. DCCD-100 was further associated with colony formation in the lymph node and significant increase in mean Ki-67 proliferation index from 11% (DCCD≤100) to 22% (DCCD>100), confirming basal proliferation and indicating the acquisition of advantageous changes. Interestingly, the mean proliferation index of 11% before colonization resembles that of T1 melanomas at transition to the tumorigenic vertical growth phase (VGP) previously found to range between 9-13% (Gimotty (2005) Journal of clinical oncology: official journal of the American Society of Clinical Oncology 23, 8048-8056). Thus, early lymph node-DCCs are non-dormant and display progression-enabling growth rates.

Taken together, a striking difference between early, pre-colonizing DCCs and matured, colonizing DCCs was identified. Survival data and xenotransplantation support the conclusion that DCCs form metastasis only after acquisition of critical colonization-enabling alterations. Therefore, metastases will genomically differ from early DCCs. These findings are fully supported by the largest sequencing study comparing primary tumors and matched metastasis from various cancers (Brastianos (2015) Cancer discovery). In all 86 cases (including melanoma), primary tumors and metastasis differed to a large degree and had acquired mutations private to both the primary and the distant sites. No example was found where the metastasis-founding clone could be identified within the primary tumor, as would be expected from linear progression. Another study, confined to melanoma, also supports branching evolution, however postulated ("deduced") ancestor mutations that were not sequenced in the primary lesion in an attempt to rescue the late dissemination model (Sanborn (2015) PNAS 112, 10995-11000). It should be noted that mathematical models for cancer phylogeny apply the "infinite sites assumption" (Deshwar (2015) Genome biology 16, 35; Jiao (2014) BMC bioinformatics 15, 35; Strino (2013) Nucleic acids research 41, e165) stating that each mutation is generated maximally once (Ma (2008) PNAS 105, 14254-14261). However, this assumption is not justified in cancer, as opposed to its original application to genome evolution of species (Ma (2008) PNAS 105, 14254-14261), because, for example, melanoma of unrelated patients converge on the classical BRAF-V660E mutation in 40% of cases. Therefore, it is unreasonable to exclude a priori that two clones of the same cancer acquire the BRAF V600E mutation independently. The herein presented single cell analysis indicates that current models of branching evolution as deduced from sequencing studies of bulk tumors underestimate the complexity of cancer evolution because they rely on the infinite sites model.

BRAF mutations are found in DCCs at colony formation in sentinel lymph nodes but rarely before. Although benign nevi harbor BRAF mutant cells in 70-88% (Pollock (2003) Nature genetics 33, 19-20; Shain (2015) The New England journal of medicine 373, 1926-1936), it is unclear whether BRAF mutations (or generally MAPK pathway mutations) initiate melanoma and are transmitted linearly. Several reasons argue against this scenario for many melanomas. First, primary tumors display generally lower rates of BRAF mutations than benign nevi (40% vs. 80%, (Platz (2008) Molecular oncology 1, 395-405; Pollock (2003) Nature genetics 33, 19-20), indicating different routes to malignancy; second, between 0 and 10% of in situ and early radial growth phase (RGP) melanomas harbor BRAF mutations (Dong (2003) Cancer research 63, 3883-3885; Verlinden (2014) Medicine 93, e285). A higher rate of BRAF mutations in such lesions is only seen in studies using samples with neighboring advanced melanoma (Omholt (2003) Clinical cancer research: an official journal of the American Association for Cancer Research 9, 6483-6488; Shain (2015) The New England journal of medicine 373, 1926-1936), but not when in situ melanomas were resected before invasive growth (Dong (2003) Cancer research 63, 3883-3885; Verlinden (2014) Medicine 93, e285), suggesting that contamination may have occurred in the former. Fourth, among patients with BRAF mutant melanoma DCCs, readily cancer cells without this mutation could be identified, disproving full clonality for this alteration in primary lesions as well.

The herein presented genetic findings cohere with the patient data suggesting that dissemination often occurs at the beginning of the VGP (0.04-0.75 mm depth). When VGP melanomas expand in the dermis (i.e. become tumorigenic), they often acquire BRAF mutations (Dong (2003) Cancer research 63, 3883-3885; Verlinden (2014) Medicine 93, e285), and increase their proliferation rate—with Ki-67 frequencies of >20% being a marker of poor outcome (Gimotty (2005) Journal of clinical oncology: official journal of the American Society of Clinical Oncology 23, 8048-8056). DCCs in SLN and possibly other metastatic sites re-capitulate this process during colonization. The herein presented genetic data and mathematical progression modeling indicate that after acquisition of a proliferative phenotype, dissemination becomes increasingly unlikely. Hazard rates for dissemination diminished with increasing tumor thickness and BRAF and NRAS mutations in primary tumors were rarely shared by matched DCCs, indicating that BRAF/NRAS mutant clones were less likely to seed. Together, dissemination from early lesions, published data of BRAF mutations in primary melanoma progression and the selection of specific alterations during lymph node colonization all cohere to a model of a largely parallel passage through the "Vogelgram" (Fearon (1990) Cell 61, 759-767) of melanoma cells at the primary and secondary sites (FIG. 7). It is tempting to speculate that melanoma cells receive cues to disseminate from the stromal compartment as they invade the dermis (FIG. 7) and continue to evolve after lodging to distant sites. Finally, the initial disparity between primary tumors and DCCs regarding BRAF mutations in addition to the strong selective advantage the mutations endow during colony formation, explain both the observed disparity for BRAF mutations between primary tumors and metastases in our and other studies (Colombino (2012) Journal of clinical oncology: official journal of the American Society of Clinical Oncology 30, 2522-2529; Saint-Jean (2013) J Invest Dermatol; Yancovitz (2012) PloS one 7, e29336; Verlinden (2014) Medicine 93, e285) as well as the increased frequency of BRAF mutations in metastases compared to early RGP melanomas.

It remains to be explored in more detail why high T stage is a risk factor in melanoma. The correlation between tumor thickness and colonization (as opposed to dissemination) may either reflect the lead-time (DCCs in patients with thick melanomas had more time to grow within the node than DCCs from thin melanomas) or suggest that primary tumors facilitate colonization by secreted factors (Peinado (2012) Nature medicine 18, 883-891). Such factors may act in a dose-dependent manner either directly upon DCCs or indirectly by altering the microenvironment locally or systemically. The fact that T1 melanomas are mostly cured by surgery (Balch (2009) Journal of clinical oncology: official journal of the American Society of Clinical Oncology 27, 6199-6206) strongly supports proliferation-stimulating factors secreted more abundantly by thick melanomas, which then promote the acquisition of genetic changes required for colony formation. Formal proof of this scenario would require model systems that enable genomic in vitro progression of immature to mature cancer cells triggered by supporting factors. Such models are currently not available. Unstimulated and consequently slow in vivo progression over years as observed in some patients may account for late recurrences (Ossowski (2010) Pigment cell & melanoma research 23, 41-56) and argue at least partially for a lead-time effect.

The lack of adequate supporting signals from the primary tumor may explain why the study failed to observe engraftment of pre-colonizing cells in NSG mice. Pre-colonizing DCCs rarely thrive, either in mice or in humans after early melanoma removal. On the other hand, colonizing DCCs engrafted in about 60% of cases, which is in agreement with the reported engraftment rate of 16%-75% for tumor cells from primary melanomas (Boiko (2010) Nature 466, 133-137; Quintana (2008) Nature 456, 593-598). DCCs generally needed between 20 and 50 weeks to form xenografts, which is much longer than cell line cells or primary tumor cells took to do so (Quintana (2008) Nature 456, 593-598}. This suggests that additional, including non-genetic, differences exist between primary tumor cells and DCCs with newly-acquired colonizing ability.

Analysis of the immune cell microenvironment of lymph nodes revealed a loss of CD8 T cell and NK cell function as well as recruitment of immunosuppressive immature MDSCs, which altogether impair the execution of an antitumoral response and result in a failure in tumor surveillance which otherwise could possibly limit metastatic growth. The functional impairment of tumor surveillance occurs at a DCCD>2000 and follows the acquisition of genetic aberrations at a DCCD>100. Furthermore it is dependent on the local tumor cell load in the lymph node, i.e. the DCCD and therefore can only be deduced from the target organ of dissemination, but not from corresponding parameters in the primary tumor.

The herein presented findings have implications for the development of adjuvant therapies. First, although the classical approach has been to determine the molecular characteristics of advanced cancer cells (for example by comparing low and high T stages) and then target progression-associated alterations, this may be irrelevant to early systemic disease and therefore unproductive at best. Rather, it may become critically relevant to determine whether systemically spread cancer cells have already formed. If yes, there is a greater chance that genetic alterations supporting colony formation are shared with primary tumors and may be targeted. Secondly, novel drugs may be required to eradicate the metastatic seed prior to colonization as pre-colonizing DCCs lack typical drug targets. Finally, molecular evolution necessitates novel tools for monitoring latent disease activity. As colonization-associated alterations in DCCs were found in all but one of nine patients dying from melanoma during follow-up, diagnosis of this colonization signature before manifestation of metastasis may present novel opportunities for adjuvant therapy selection and timing. Administering agents targeting mutant BRAF in patients lacking mutant BRAF not only lacks benefit, but could stimulate the MAPK pathway to promote tumor growth (Poulikakos (2010) Nature 464, 427-430). Therefore, the risk of unintended disease promotion in patients with BRAF mutant primary tumors but wild type DCCs in stage IIC and stage III patients might be higher than previously thought. On the other hand, given the recently appreciated importance of neo-antigen diversity for the success of immune-checkpoint blockade therapies (Snyder (2014) The New England journal of medicine 371, 2189-2199), the continuing evolution of DCCs argues that the identification of these mutations and antigens in DCCs is imperative to enable and prevent lethal metastasis. With regard to immune-checkpoint blockade and other immunotherapies, the dependency of the local impairment of tumor surveillance mechanisms on the local colonization calls for its implementation in therapeutic decision making and patient-stratification.

The invention claimed is:

1. A method for treating a patient having melanoma, said method comprising the following steps:
   (a) obtaining one or more disseminated cancer cell(s) (DCC(s)) from one or more lymph node(s) of the patient diagnosed with melanoma, wherein the DCC(s) has not developed into a metastasis;
   (b) detecting somatic alterations in the DNA of the one or more DCC(s);
   (c) determining the somatic evolution of the DCC(s) based on the somatic alterations detected in step (b);
   (d) identifying the DCC(s) as having a metastasis signature based on the somatic evolution of the DCC(s) determined in step (c); and
   (e) administering an effective amount of one or more cancer treatment to the patient with DCC(s) identified as having a metastasis signature in step (d), wherein the cancer treatment is a chemotherapy or immunotherapy.

2. The method of claim 1, wherein the DCC(s) are obtained from a sentinel lymph node.

3. The method of claim 1, further comprising determination of the DCC density (DCCD), wherein the DCCD is the number of DCCs per million cells in the lymph node used to obtain the DCCs, wherein the DCCD is indicative of the stage/type of the melanoma.

4. The method of claim 3, wherein a DCCD between 50 and 100 is indicative for the development of metastases.

5. The method of claim 1, wherein the somatic alterations comprise at least one of the somatic alterations selected from the group consisting of a BRAF mutation, a loss of chromosome 9p11-13, a loss of chromosome 9p21-24, a gain of chromosome 7q21-36, and a NRAS mutation.

6. The method of claim 1, wherein a BRAF mutation, a loss of chromosome 9p11-13, a loss of chromosome 9p21-24, a gain of chromosome 7q21-36, and/or a NRAS mutation indicates that the DCC(s) will develop to metastases.

7. The method of claim 1, further comprising evaluating the proliferation of the DCC(s), wherein a proliferation rate of at least 11% indicates that the DCC(s) will develop to metastases.

8. The method of claim 1, wherein if the DCC(s) are found to carry a BRAF mutation, the cancer treatment comprises a BRAF inhibitor.

9. The method of claim 8, wherein the BRAF inhibitor is sorafenib or vemurafenib.

10. The method of claim 1, wherein the patient's melanoma has been resected.

11. The method of claim 1, further comprising resecting the patient's melanoma.

12. The method of claim 1, wherein step (b) comprises sequencing at least a portion of the DCC(s) genomic DNA.

\* \* \* \* \*